United States Patent
Inoue et al.

(10) Patent No.: US 10,230,057 B2
(45) Date of Patent: *Mar. 12, 2019

(54) BISCARBAZOLE DERIVATIVES AND ORGANIC ELECTROLUMINESCENCE DEVICE EMPLOYING THE SAME

(71) Applicant: IDEMITSU KOSAN CO., LTD., Chiyoda-ku (JP)

(72) Inventors: Tetsuya Inoue, Chiba (JP); Mitsunori Ito, Chiba (JP); Tomoki Kato, Chiba (JP); Kumiko Gorai, Chiba (JP); Kazuki Nishimura, Chiba (JP); Takayasu Sado, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,667

(22) Filed: Oct. 9, 2017

(65) Prior Publication Data

US 2018/0047917 A1    Feb. 15, 2018

Related U.S. Application Data

(63) Continuation of application No. 15/139,508, filed on Apr. 27, 2016, now Pat. No. 9,818,958, which is a
(Continued)

(30) Foreign Application Priority Data

| Feb. 7, 2011 | (JP) | 2011-024452 |
| Oct. 18, 2011 | (JP) | 2011-229112 |
| Oct. 18, 2011 | (JP) | 2011-229117 |

(51) Int. Cl.
*H01L 51/00* (2006.01)
*C09K 11/06* (2006.01)
(Continued)

(52) U.S. Cl.
CPC ........ *H01L 51/0072* (2013.01); *C07D 403/14* (2013.01); *C07D 405/14* (2013.01);
(Continued)

(58) Field of Classification Search
CPC ............. H01L 51/5016; H01L 51/0545; H01L 51/0073; H01L 51/0067
(Continued)

(56) References Cited

U.S. PATENT DOCUMENTS

| 7,329,722 B2 | 2/2008 | Vaitkeviciene et al. |
| 7,723,722 B2 | 5/2010 | Kawakami et al. |

(Continued)

FOREIGN PATENT DOCUMENTS

| CN | 101126020 A | 2/2008 |
| EP | 1 972 619 A1 | 9/2008 |

(Continued)

OTHER PUBLICATIONS

International Search Report dated Mar. 27, 2012 in PCT/JP2012/052639 filed Feb. 6, 2012.

(Continued)

*Primary Examiner* — Anthony Ho
(74) *Attorney, Agent, or Firm* — Oblon, McClelland, Maier & Neustadt, L.L.P.

(57) ABSTRACT

Provided are an organic electroluminescence device having high current efficiency and a long lifetime, and a biscarbazole derivative for realizing the device. The biscarbazole derivative has a specific substituent. The organic EL device has a plurality of organic thin-film layers including a light emitting layer between a cathode and an anode, and at least one layer of the organic thin-film layers contains the biscarbazole derivative.

31 Claims, 1 Drawing Sheet

Related U.S. Application Data continuation of application No. 14/318,738, filed on Jun. 30, 2014, now Pat. No. 9,373,802, which is a continuation of application No. 13/366,891, filed on Feb. 6, 2012, now Pat. No. 8,803,134.

(60) Provisional application No. 61/548,469, filed on Oct. 18, 2011.

(51) Int. Cl.

| | | |
|---|---|---|
| *H01L 51/50* | (2006.01) | |
| *H05B 33/14* | (2006.01) | |
| *C07D 405/14* | (2006.01) | |
| *C07D 403/14* | (2006.01) | |
| *H01L 51/05* | (2006.01) | |
| *C09K 11/02* | (2006.01) | |
| *B82Y 10/00* | (2011.01) | |

(52) U.S. Cl.
CPC ........... *C09K 11/025* (2013.01); *C09K 11/06* (2013.01); *H01L 51/0067* (2013.01); *H01L 51/0073* (2013.01); *H01L 51/0545* (2013.01); *H01L 51/5016* (2013.01); *H05B 33/14* (2013.01); *B82Y 10/00* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0036* (2013.01); *H01L 51/0054* (2013.01); *H01L 51/0541* (2013.01); *H01L 51/5012* (2013.01); *H01L 51/5056* (2013.01)

(58) Field of Classification Search
USPC .......................................... 544/212
See application file for complete search history.

(56) References Cited

U.S. PATENT DOCUMENTS

| | | | |
|---|---|---|---|
| 8,040,047 B2 | 10/2011 | Ushikubo et al. | |
| 8,251,765 B2 | 8/2012 | Ushikubo et al. | |
| 8,283,856 B2 | 10/2012 | Ushikubo | |
| 8,362,466 B2 | 1/2013 | Ushikubo et al. | |
| 8,803,134 B2 | 8/2014 | Inoue et al. | |
| 9,373,802 B2 | 6/2016 | Inoue | |
| 9,818,958 B2 * | 11/2017 | Inoue | C09K 11/06 |
| 2005/0067955 A1 | 3/2005 | Cho et al. | |
| 2006/0046172 A1 | 3/2006 | Vaitkeviciene et al. | |
| 2006/0051611 A1 | 3/2006 | Brunner et al. | |
| 2006/0073357 A1 | 4/2006 | Brunner et al. | |
| 2006/0088728 A1 | 4/2006 | Kwong et al. | |
| 2006/0180806 A1 | 8/2006 | Arakane et al. | |
| 2009/0017330 A1 | 1/2009 | Iwakuma et al. | |
| 2009/0017331 A1 | 1/2009 | Iwakuma et al. | |
| 2009/0030202 A1 | 1/2009 | Iwakuma et al. | |
| 2009/0072732 A1 | 3/2009 | Arakane et al. | |
| 2009/0085479 A1 | 4/2009 | Ushikubo | |
| 2009/0096360 A1 | 4/2009 | Tanaka et al. | |
| 2009/0102366 A1 | 4/2009 | Ushikubo et al. | |
| 2009/0131673 A1 | 5/2009 | Tanabe et al. | |
| 2009/0236980 A1 | 9/2009 | Ohsawa | |
| 2009/0284138 A1 | 11/2009 | Yasukawa et al. | |
| 2009/0284139 A1 | 11/2009 | Ushikubo et al. | |
| 2009/0302745 A1 | 12/2009 | Otsu et al. | |
| 2010/0051106 A1 | 3/2010 | Kim et al. | |
| 2010/0141126 A1 | 6/2010 | Otsu et al. | |
| 2010/0148165 A1 | 6/2010 | Ushikubo et al. | |
| 2010/0148166 A1 | 6/2010 | Ushikubo et al. | |
| 2010/0231123 A1 | 9/2010 | Otsu et al. | |
| 2010/0237339 A1 | 9/2010 | Nomura et al. | |
| 2010/0237773 A1 | 9/2010 | Nomura et al. | |
| 2011/0031482 A1 | 2/2011 | Furukawa et al. | |
| 2011/0063485 A1 | 3/2011 | Nomura et al. | |
| 2011/0260138 A1 | 10/2011 | Xia et al. | |
| 2011/0260152 A1 | 10/2011 | Nakayama et al. | |
| 2011/0272687 A1 | 11/2011 | Katakura et al. | |
| 2011/0278552 A1 | 11/2011 | Numata et al. | |
| 2011/0278555 A1 | 11/2011 | Inoue et al. | |
| 2011/0279020 A1 | 11/2011 | Inoue et al. | |
| 2011/0297924 A1 | 12/2011 | Yabunouchi et al. | |
| 2011/0309346 A1 | 12/2011 | Watanabe et al. | |
| 2012/0007498 A1 | 1/2012 | Otsu et al. | |
| 2012/0068164 A1 | 3/2012 | Iwakuma et al. | |
| 2012/0097937 A1 | 4/2012 | Iwakuma et al. | |
| 2012/0126205 A1 | 5/2012 | Kawamura et al. | |
| 2012/0126208 A1 | 5/2012 | Kawamura et al. | |
| 2012/0138911 A1 | 6/2012 | Inoue et al. | |
| 2012/0138912 A1 | 6/2012 | Inoue et al. | |
| 2012/0175599 A1 | 7/2012 | Yokoyama et al. | |
| 2012/0181524 A1 | 7/2012 | Kato et al. | |
| 2012/0205642 A1 | 8/2012 | Yokoyama et al. | |
| 2012/0211736 A1 | 8/2012 | Kim et al. | |
| 2012/0223276 A1 | 9/2012 | Parham et al. | |
| 2012/0223295 A1 | 9/2012 | Inoue et al. | |
| 2012/0235123 A1 | 9/2012 | Lee et al. | |
| 2012/0235136 A1 | 9/2012 | Ogawa et al. | |
| 2012/0273766 A1 | 11/2012 | Kato et al. | |
| 2012/0273767 A1 | 11/2012 | Yokoyama et al. | |
| 2012/0302751 A1 | 11/2012 | Nomura et al. | |
| 2012/0305900 A1 | 12/2012 | Kim et al. | |
| 2012/0326141 A1 | 12/2012 | Pflumm et al. | |
| 2012/0326601 A1 | 12/2012 | Yasukawa et al. | |
| 2013/0009140 A1 | 1/2013 | Ushikubo | |
| 2013/0020565 A1 | 1/2013 | Numata et al. | |
| 2013/0056720 A1 | 3/2013 | Kim et al. | |
| 2013/0075716 A1 | 3/2013 | Nishimura et al. | |
| 2013/0087776 A1 | 4/2013 | Lee et al. | |
| 2013/0087778 A1 | 4/2013 | Konuma et al. | |
| 2013/0092905 A1 | 4/2013 | Numata et al. | |
| 2013/0092913 A1 | 4/2013 | Nishimura et al. | |
| 2013/0105787 A1 | 5/2013 | Tanaka et al. | |
| 2013/0112950 A1 | 5/2013 | Yokoyama et al. | |
| 2013/0134406 A1 | 5/2013 | Ushikubo et al. | |
| 2013/0234119 A1 | 9/2013 | Mizuki et al. | |
| 2013/0256644 A1 | 10/2013 | Kim et al. | |
| 2013/0264548 A1 | 10/2013 | Mizuki et al. | |
| 2013/0270540 A1 | 10/2013 | Numata | |
| 2013/0292664 A1 | 11/2013 | Nishimura et al. | |
| 2013/0306959 A1 | 11/2013 | Ikeda et al. | |
| 2014/0001446 A1 | 1/2014 | Mizuki et al. | |
| 2014/0054564 A1 | 2/2014 | Kim et al. | |
| 2014/0084271 A1 | 3/2014 | Lee et al. | |
| 2014/0151647 A1 | 6/2014 | Mizuki et al. | |
| 2015/0021574 A1 | 1/2015 | Itoi | |
| 2015/0021585 A1 | 1/2015 | Yu et al. | |
| 2015/0053933 A1 | 2/2015 | Lee et al. | |
| 2015/0228915 A1 | 8/2015 | Cho et al. | |

FOREIGN PATENT DOCUMENTS

| | | |
|---|---|---|
| EP | 2 051 310 A1 | 4/2009 |
| EP | 2 120 275 A2 | 11/2009 |
| EP | 2 141 214 A2 | 1/2010 |
| EP | 2 166 584 A1 | 3/2010 |
| EP | 2 182 039 A2 | 5/2010 |
| EP | 2 256 176 A1 | 12/2010 |
| EP | 2 423 209 A1 | 2/2012 |
| EP | 2 471 771 A1 | 7/2012 |
| EP | 2 492 985 A1 | 8/2012 |
| EP | 2 492 986 A1 | 8/2012 |
| EP | 2 497 811 | 9/2012 |
| EP | 2 555 272 A1 | 2/2013 |
| EP | 2 568 030 A2 | 3/2013 |
| EP | 2 582 769 A1 | 4/2013 |
| EP | 2 595 208 A1 | 5/2013 |
| EP | 2 617 712 A1 | 7/2013 |
| EP | 2 640 806 | 9/2013 |
| EP | 2 660 890 A1 | 11/2013 |
| EP | 2 674 418 | 12/2013 |

(56) References Cited

FOREIGN PATENT DOCUMENTS

| | | |
|---|---|---|
| JP | 8-3547 | 1/1996 |
| JP | 11-074084 | 3/1999 |
| JP | 11-135260 | 5/1999 |
| JP | 11-144873 A | 5/1999 |
| JP | 11-149987 | 6/1999 |
| JP | 11-329737 | 11/1999 |
| JP | 2002-69044 | 3/2002 |
| JP | 2003-133075 | 5/2003 |
| JP | 2003-151774 | 5/2003 |
| JP | 2003-151774 A | 5/2003 |
| JP | 2003-238534 | 8/2003 |
| JP | 2004-79265 A | 3/2004 |
| JP | 2004-171808 A | 6/2004 |
| JP | 2004-342391 A | 12/2004 |
| JP | 2005-289914 A | 10/2005 |
| JP | 2006-143845 A | 6/2006 |
| JP | 2007-194241 | 8/2007 |
| JP | 2007-201189 | 8/2007 |
| JP | 2007-201193 | 8/2007 |
| JP | 2007-201194 | 8/2007 |
| JP | A-2007-288035 | 11/2007 |
| JP | 2008-74939 A | 4/2008 |
| JP | 2008-135498 | 6/2008 |
| JP | 2008-181937 A | 8/2008 |
| JP | 2008-205488 A | 9/2008 |
| JP | 2008-252094 A | 10/2008 |
| JP | 2008-294161 | 12/2008 |
| JP | 2009-59767 A | 3/2009 |
| JP | 2009-267255 A | 11/2009 |
| JP | 2009-267257 A | 11/2009 |
| JP | 2010-114180 A | 5/2010 |
| JP | 2010-135467 | 6/2010 |
| JP | 2010-278287 A | 12/2010 |
| JP | 2011-86442 A | 4/2011 |
| JP | 2012-23127 A | 2/2012 |
| JP | 2012-94898 A | 5/2012 |
| JP | 5562970 B2 | 6/2014 |
| JP | 2015-065248 | 4/2015 |
| KR | 2009-0028943 | 3/2009 |
| KR | 10-2010-0079458 A | 7/2010 |
| KR | 10-2010-0099460 A | 9/2010 |
| KR | 10-2011-0043270 A | 4/2011 |
| KR | 10-2011-0088898 A | 8/2011 |
| KR | 10-2011-0138596 A | 12/2011 |
| KR | 10-1170666 | 8/2012 |
| KR | 10-2014-0141951 | 12/2014 |
| KR | 10-2015-0006199 | 1/2015 |
| KR | 10-2015-0006722 | 1/2015 |
| KR | 10-2015-0007476 | 1/2015 |
| KR | 10-2015-0030511 | 3/2015 |
| KR | 10-2015-0001101 | 1/2016 |
| WO | WO 2004/055129 A1 | 7/2004 |
| WO | WO 2004/066685 A1 | 8/2004 |
| WO | WO 2004/072205 A2 | 8/2004 |
| WO | WO 2007/119816 A1 | 10/2007 |
| WO | WO 2009/008100 A1 | 1/2009 |
| WO | WO 2009/060742 A1 | 5/2009 |
| WO | WO 2009/060779 | 5/2009 |
| WO | WO 2009/060780 A1 | 5/2009 |
| WO | WO 2009/084413 A1 | 7/2009 |
| WO | WO 2009/116605 A1 | 9/2009 |
| WO | WO 2010/004877 A1 | 1/2010 |
| WO | WO 2010/004887 A1 | 1/2010 |
| WO | WO 2010/044342 A1 | 4/2010 |
| WO | WO 2010/095621 A1 | 8/2010 |
| WO | WO 2011/024451 | 3/2011 |
| WO | WO 2011/037429 A2 | 3/2011 |
| WO | WO 2011-048821 A1 | 4/2011 |
| WO | WO 2011/048822 | 4/2011 |
| WO | WO 2011/055934 | 5/2011 |
| WO | WO 2011/081423 A2 | 7/2011 |
| WO | WO 2011/122132 A1 | 10/2011 |
| WO | WO 2011-125680 A1 | 10/2011 |
| WO | WO 2011/137072 | 11/2011 |
| WO | WO 2011/139055 | 11/2011 |
| WO | WO 2011/149240 A2 | 12/2011 |
| WO | WO 2011/155507 A1 | 12/2011 |
| WO | WO 2011/155508 A1 | 12/2011 |
| WO | WO 2011/157790 A1 | 12/2011 |
| WO | WO 2011/162162 | 12/2011 |
| WO | WO 2012/001986 A1 | 1/2012 |
| WO | WO 2012/023947 | 2/2012 |
| WO | WO 2012/029253 A1 | 3/2012 |
| WO | WO 2012/036482 A1 | 3/2012 |
| WO | WO 2012/063691 A1 | 5/2012 |
| WO | WO 2012/077714 A1 | 6/2012 |
| WO | WO 2012/086170 A1 | 6/2012 |
| WO | WO 2012/087007 A1 | 6/2012 |
| WO | WO 2012/108389 A1 | 8/2012 |
| WO | WO 2015/029354 | 3/2015 |
| WO | WO 2015/050173 | 4/2015 |

OTHER PUBLICATIONS

International Search Report dated Mar. 27, 2012 in PCT/JP2012/052640 filed Feb. 6, 2012.
Extended European Search Report dated Jun. 27, 2014, in European Patent Application No. 12744512.0.
Extended European Search Report dated Jun. 30, 2014, in European Patent Application No. 12744393.5.
Japanese Office Action dated Apr. 21, 2015 in corresponding Japanese Patent Application No. 2012-556880.
Office Action dated Nov. 1, 2016 in Japanese Patent Application No. 2016-084843.

* cited by examiner

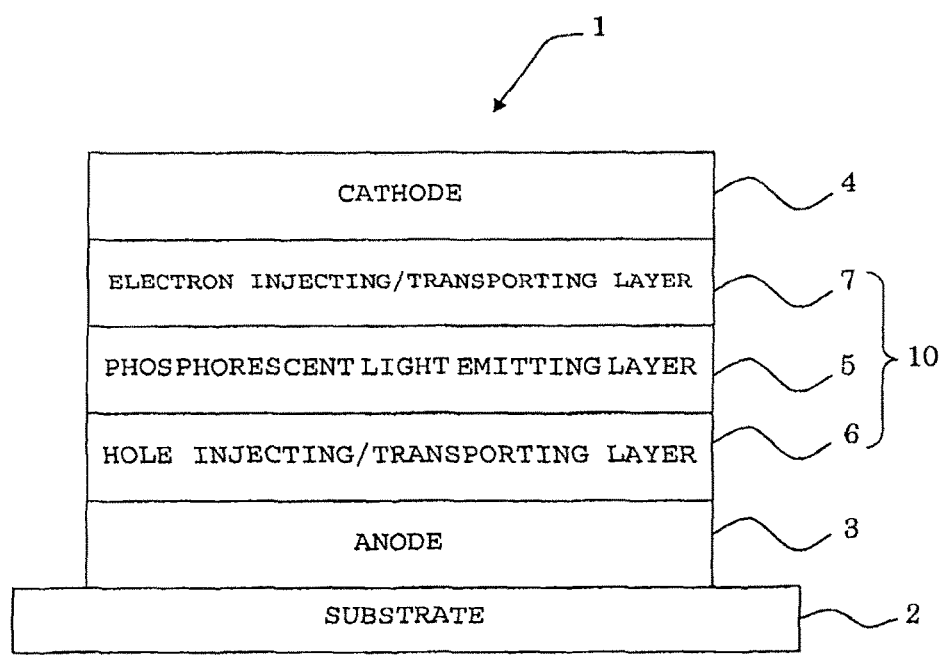

BISCARBAZOLE DERIVATIVES AND ORGANIC ELECTROLUMINESCENCE DEVICE EMPLOYING THE SAME

CROSS REFERENCE TO RELATED APPLICATIONS

This application is a continuation of U.S. patent application Ser. No. 15/139,508, filed Apr. 27, 2016, now allowed, which is a continuation of U.S. patent application Ser. No. 14/318,738, filed Jun. 30, 2014, now U.S. Pat. No. 9,373,802, which is a continuation of U.S. patent application Ser. No. 13/366,891, filed Feb. 6, 2012, now U.S. Pat. No. 8,803,134, the disclosures of which are incorporated herein by reference in their entireties. This application claims priority to Provisional U.S. patent application Ser. No. 61/548,469, filed Oct. 18, 2011, Japanese Patent Application No. 2011-024452, filed Feb. 7, 2011, Japanese Patent Application No. 2011-229112, filed Oct. 18, 2011, and Japanese Patent Application No. 2011-229117, filed Oct. 18, 2011, the disclosures of which are incorporated herein by reference in their entireties.

TECHNICAL FIELD

The present invention relates to a biscarbazole derivative and an organic electroluminescence device using the derivative, in particular, an organic electroluminescence device having high current efficiency and a long lifetime, and a biscarbazole derivative for realizing the device.

BACKGROUND ART

In recent years, research has been vigorously conducted on an organic thin-film light emitting device that emits light upon recombination of an electron injected from a cathode and a hole injected from an anode in an organic light emitting body interposed between both the electrodes. The light emitting device has been attracting attention because of the following features. The device is thin and emits light having high luminance under a low driving voltage, and the selection of its light emitting material allows the device to emit light beams of various colors.

When a voltage is applied to an organic electroluminescence device (hereinafter referred to as "organic EL device"), a hole and an electron are injected into a light emitting layer from an anode and a cathode, respectively. Then, the hole and the electron thus injected recombine in the light emitting layer to form an exciton. At this time, singlet excitons and triplet excitons are produced at a ratio of 25%:75% according to the statistical law of electron spins. When the organic EL devices are classified in accordance with their light emission principles, the internal quantum efficiency of a fluorescence-type organic EL device is said to be at most 25% because the device uses light emission based on a singlet exciton. On the other hand, it has been known that as a phosphorescence-type organic EL device uses light emission based on a triplet exciton, its internal quantum efficiency is enhanced to 100% when intersystem crossing from a singlet exciton is efficiently performed.

Optimum device design has been conventionally performed in the organic EL devices depending on their fluorescence- and phosphorescence-type light emission mechanisms. In particular, it has been known that when a fluorescent device technology is simply diverted for the phosphorescence-type organic EL device, owing to its light emitting characteristic, a high-performance device is not obtained. The reason for the foregoing is generally considered to be as described below.

First, phosphorescent emission is light emission utilizing a triplet exciton and hence a compound to be used in the light emitting layer must have a large energy gap. This is because a value for the energy gap of a certain compound (hereinafter, sometimes referred to as "singlet energy") is typically larger than a value for the triplet energy of the compound (which refers to an energy difference between its lowest excited triplet state and ground state in the present invention).

Therefore, in order that the triplet energy of a phosphorescent emitting dopant material may be efficiently trapped in the device, first, a host material having a larger triplet energy than the triplet energy of the phosphorescent emitting dopant material must be used in the light emitting layer. Further, an electron transporting layer and a hole transporting layer adjacent to the light emitting layer must be provided, and a compound having a larger triplet energy than that of the phosphorescent emitting dopant material must be used in each of the electron transporting layer and the hole transporting layer. Designing an organic EL device on the basis of a conventional device design idea as described above leads to a situation where a compound having a larger energy gap than that of a compound to be used in the fluorescence-type organic EL device is used in the phosphorescence-type organic EL device. As a result, the driving voltage of the entire organic EL device increases.

In addition, a hydrocarbon-based compound having high oxidation resistance or high reduction resistance that has been useful in a fluorescent device has a small energy gap because of large expansion of its $\pi$-electron cloud. Accordingly, such hydrocarbon-based compound is hardly selected in the phosphorescence-type organic EL device, and an organic compound containing a heteroatom such as oxygen or nitrogen is selected. As a result, the phosphorescence-type organic EL device involves a problem in that its lifetime is short as compared with that of the fluorescence-type organic EL device.

Further, device performance is largely affected by the fact that the exciton relaxation rate of a triplet exciton of the phosphorescent emitting dopant material is extremely long as compared with that of a singlet exciton. That is, light emission from a singlet exciton has a fast relaxation rate leading to the light emission, and hence the diffusion of the exciton into a peripheral layer of the light emitting layer (such as the hole transporting layer or the electron transporting layer) hardly occurs and efficient light emission is expected. On the other hand, light emission from a triplet exciton is spin-forbidden and has a slow relaxation rate. Accordingly, the exciton is apt to diffuse into the peripheral layer, and thermal energy deactivation occurs from a compound except a specific phosphorescent emitting compound. In other words, the control of a region where an electron and a hole recombine is more important in such device than in the fluorescence-type organic EL device.

By such reason as described above, an improvement in the performance of the phosphorescence-type organic EL device requires material selection and device design different from those in the case of the fluorescence-type organic EL device.

One of the most serious problems in the organic thin-film light emitting device is compatibility between high current efficiency and a low driving voltage. A method involving doping a host material with several percent of a dopant material to form a light emitting layer has been known as means for obtaining a high-efficiency light emitting device (see Patent Literature 1). The host material is requested to have a high carrier mobility, uniform film formability, and the like, and the dopant material is requested to have a high fluorescent quantum yield, uniform dispersibility, and the like.

Although a fluorescent (singlet light emission) material has been conventionally used as the dopant material in general, an attempt has been made to use a phosphorescent (triplet light emission) material for enhancing current efficiency since the past, and a group of Princeton University has shown that the material provides much higher current efficiency than the conventional fluorescent material does (See Non Patent Literature 1). There has been disclosed a technology involving using, as the phosphorescent dopant material, a metal complex containing iridium, osmium, rhodium, palladium, platinum, or the like as a central metal (see Patent Literatures 2 to 4). In addition, there has been disclosed a technology involving using, for example, a carbazole derivative, an aromatic amine derivative, or a quinolinol metal complex as the host material to be combined with the phosphorescent dopant material (see Patent Literatures 2 to 6). However, none of the materials has shown sufficient current efficiency and a low driving voltage.

Meanwhile, a technology involving using a biscarbazole derivative as a hole transporting material for a fluorescent device has been disclosed (Patent Literature 7). Some technologies each involving using a biscarbazole derivative as a phosphorescent host material have also been disclosed. For example, Patent Literature 8 describes an example of a biscarbazole derivative as a host material to be combined with a specific metal complex dopant. However, no biscarbazole derivative compound that causes the expression of a high light emitting characteristic has been disclosed. In addition, Patent Literature 9 describes that a biscarbazole derivative is used as a host material. In Patent Literature 9 described above, a substituent for improving the carrier transportability of the host material such as an amino substituent-containing phenyl group, a naphthyl group, or a fluorenyl group is introduced into the N-position of a carbazole structure. Although a reduction in the driving voltage of a light emitting device has been achieved by the introduction, a specific effect of the introduction on the lifetime of the device has been unclear.

Meanwhile, several technologies each involving extracting light emission from a triplet exciton, which have not been effectively exploited so far, have been disclosed in relation to a technology for enhancing the efficiency of a fluorescence-type device. For example, Non Patent Literature 2 discloses the following mechanism by analyzing a non-doped device using an anthracene-based compound as a host. Two triplet excitons collide and fuse with each other to produce a singlet exciton, and as a result, the intensity of fluorescent emission is increased. The phenomenon in which the two triplet excitons collide and fuse with each other to produce a singlet exciton as described above is hereinafter called a triplet-triplet fusion (TTF) phenomenon.

In addition, Non Patent Literature 3 discloses a blue light emission fluorescence-type OLED including a layer formed of an aromatic compound (efficiency-enhancement layer referred to as "EEL") between a light emitting layer containing a host and a dopant, and an electron transporting layer. It has been shown that an OLED using a compound EEL-1 in its EEL is driven at a low voltage, shows high external quantum efficiency, and has a long lifetime as compared with an OLED using BPhen or BCP in its EEL. It can be said that the EEL functions as a barrier layer for causing the TTF phenomenon.

Further, an organic EL device using an EEL that causes the TTF phenomenon requires a hole transporting layer for adjusting a carrier balance.

CITATION LIST

Patent Literature

[PTL 1] JP 2814435 B2
[PTL 2] JP 2003-526876 W
[PTL 3] JP 2003-515897 W
[PTL 4] JP 2003-81988 A
[PTL 5] JP 2003-133075 A
[PTL 6] JP 2002-540572 W
[PTL 7] JP 3139321 B2
[PTL 8] JP 4357781 B2
[PTL 9] JP 2008-135498 A

Non Patent Literature

[NPL 1] Applied Physics Letters (US), 1999, Vol. 75, No. 1, p. 4
[NPL 2] Journal of Applied Physics, 102, 114504 (2007)
[NPL 3] SID10 DIGEST, 560 (2010)

SUMMARY OF INVENTION

Technical Problem

The present invention has been made under such circumstances, and an object of the present invention is to provide an organic electroluminescence device having high current efficiency and a long lifetime, and a biscarbazole derivative for realizing the device.

Solution to Problem

The inventors of the present invention have made extensive studies to achieve the object, and as a result, have found that the object can be achieved with a biscarbazole derivative having a specific substituent. The present invention has been completed on the basis of such finding.

That is, the present invention provides the following biscarbazole derivative, material for an organic electroluminescence device, and organic electroluminescence device. It should be noted that the term "hydrogen" as used herein comprehends deuterium as well.

[1] A biscarbazole derivative, which is represented by the following formula (1):

[Chem. 1]

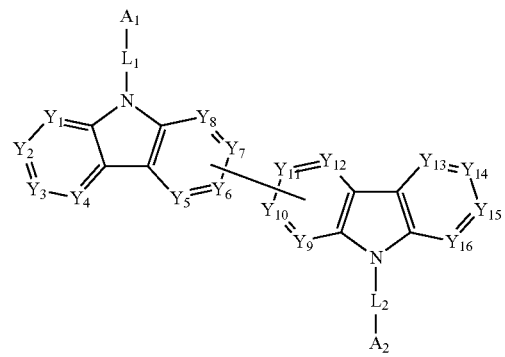

in the formula (1):

A$_1$ and A$_2$ each independently represent a substituted or unsubstituted aromatic hydrocarbon group having 6 to 30 ring carbon atoms, or a substituted or unsubstituted aromatic heterocyclic group having 2 to 30 ring carbon atoms;

Y$_1$ to Y$_{16}$ each independently represent C(R) or a nitrogen atom, and R's each independently represent a hydrogen atom, a substituent, or a bond to a carbazole skeleton; and L$_1$ and L$_2$ each independently represent a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that:

at least one of A$_1$ and A$_2$ represents a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group;

when one of A$_1$ and A$_2$ represents a dibenzofuranyl group or a dibenzothiophenyl group, the other represents a substituted or unsubstituted aromatic hydrocarbon group having 6 to 30 ring carbon atoms, or a substituted or unsubstituted benzofuranyl group, a substituted or unsubstituted benzothiophenyl group, a substituted or unsubstituted benzonaphthofuranyl group, or a substituted or unsubstituted benzonaphthothiophenyl group; and when Y$_6$ and Y$_{11}$ are bonded to each other, the following conditions (i) and (ii) are satisfied:

(i) when A$_1$ represents a dibenzofuranyl group or a dibenzothiophenyl group, L$_1$ represents a substituted or unsubstituted, divalent aromatic hydrocarbon group having 6 to 30 ring carbon atoms, or a substituted or unsubstituted, divalent aromatic heterocyclic group having 2 to 30 ring carbon atoms; and (ii) when A$_2$ represents a dibenzofuranyl group or a dibenzothiophenyl group, L$_2$ represents a substituted or unsubstituted, divalent aromatic hydrocarbon group having 6 to 30 ring carbon atoms, or a substituted or unsubstituted, divalent aromatic heterocyclic group having 2 to 30 ring carbon atoms.

[2] The biscarbazole derivative according to the above-mentioned item [1], in which the derivative is represented by the following formula (2):

[Chem. 2]

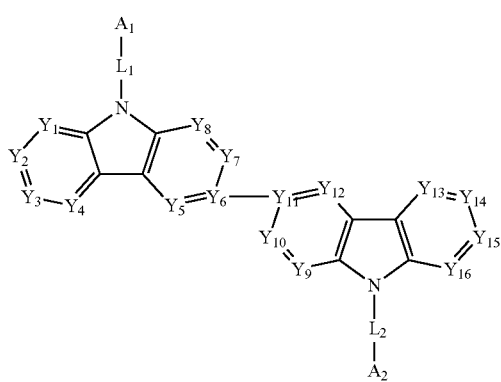

(2)

in the formula (2), A$_1$, A$_2$, Y$_1$ to Y$_{16}$, L$_1$, and L$_2$ each have the same meaning as that in the formula (1).

[3] The biscarbazole derivative according to the above-mentioned item [1], in which the derivative is represented by the following formula (3) or (4)

[Chem. 3]

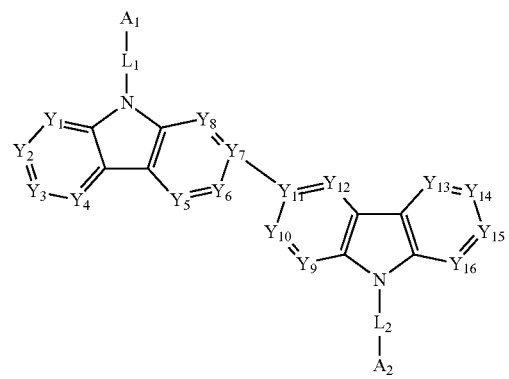

(3)

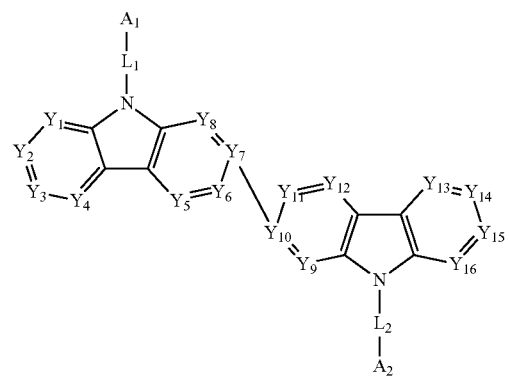

(4)

in the formula (3) or the formula (4), A$_1$, A$_2$, Y$_1$ to Y$_{16}$, L$_1$, and L$_2$ each have the same meaning as that in the formula (1).

[4] The biscarbazole derivative according to any one of the above-mentioned items [1] to [3], in which the -L$_1$-A$_1$ and the -L$_2$-A$_2$ are different from each other.

[5] The biscarbazole derivative according to any one of the above-mentioned items [1] to [4], in which the A$_1$ represents a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group.

[6] The biscarbazole derivative according to any one of the above-mentioned items [1] to [4], in which the L$_1$ represents a substituted or unsubstituted, divalent aromatic hydrocarbon group having 6 to 30 ring carbon atoms, or a substituted or unsubstituted, divalent aromatic heterocyclic group having 2 to 30 ring carbon atoms, and the A$_1$ represents a 1-dibenzofuranyl group, a 3-dibenzofuranyl group, a 4-dibenzofuranyl group, or a dibenzothiophenyl group.

[7] The biscarbazole derivative according to any one of the above-mentioned items [1] to [6], in which at least one of the $L_1$ and the $L_2$ represents a divalent aromatic heterocyclic group represented by the following general formula (a):

[Chem. 4]

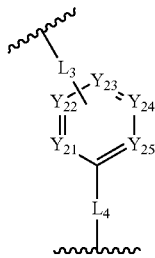

(a)

in the formula (a):

$Y_{21}$ to $Y_{25}$ each independently represent $C(R_a)$ or a nitrogen atom, and $R_a$'s each independently represent a hydrogen atom, a substituent, or a bond to $L_3$; and $L_3$ and $L_4$ each independently represent a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that one or more of $Y_{21}$ to $Y_{25}$ each represent a nitrogen atom.

[8] A material for an organic electroluminescence device, including the biscarbazole derivative according to any one of the above-mentioned items [1] to [7].

[9] An organic electroluminescence device, including a plurality of organic thin-film layers including a light emitting layer between a cathode and an anode, in which at least one of the plurality of organic thin-film layers contains the biscarbazole derivative according to any one of the above-mentioned items [1] to [8].

[10] The organic electroluminescence device according to the above-mentioned item [9], in which the light emitting layer contains the biscarbazole derivative as a host material.

[11] The organic electroluminescence device according to the above-mentioned item [10], in which the light emitting layer contains a phosphorescent material.

[12] The organic electroluminescence device according to the above-mentioned item [11], in which the phosphorescent material includes an ortho-metalated complex of a metal atom selected from iridium (Ir), osmium (Os), and platinum (Pt).

[13] The organic electroluminescence device according to the above-mentioned item [12], in which an electron injecting layer is provided between the cathode and the light emitting layer, and the electron injecting layer contains a nitrogen-containing ring derivative.

[14] The organic electroluminescence device according to the above-mentioned item [13], in which an electron transporting layer is provided between the cathode and the light emitting layer, and the electron transporting layer contains the biscarbazole derivative.

[15] The organic electroluminescence device according to the above-mentioned item [14], in which a hole transporting layer is provided between the anode and the light emitting layer, and the hole transporting layer contains the biscarbazole derivative.

[16] The organic electroluminescence device according to the above-mentioned item [15], further including a electron-donating dopant at an interface between the cathode and the plurality of organic thin-film layers.

[17] The organic electroluminescence device according to any one of the above-mentioned items [9], [10], and [13] to [16], in which the device is used for fluorescent emission.

[18] The organic electroluminescence device according to the above-mentioned item [17], in which a hole injecting layer is provided between the anode and a hole transporting layer.

[19] The organic electroluminescence device according to the above-mentioned item [18], in which at least one of the hole transporting layer and the hole injecting layer contains an acceptor material.

[20] The organic electroluminescence device according to any one of the above-mentioned items [17] to [19], in which the light emitting layer contains at least one kind selected from an anthracene derivative, a fluoranthene derivative, a styrylamine derivative, and an arylamine derivative.

[21] A lighting apparatus, including the organic electroluminescence device according to any one of the above-mentioned items [9] to [20].

[22] A display apparatus, including the organic electroluminescence device according to any one of the above-mentioned items [9] to [20].

Advantageous Effects of Invention

According to the present invention, it is possible to provide the organic electroluminescence device having high current efficiency and a long lifetime, and the biscarbazole derivative for realizing the device.

BRIEF DESCRIPTION OF DRAWINGS

FIG. 1 is a view illustrating the schematic construction of an example of an organic electroluminescence device (hereinafter, sometimes abbreviated as "organic EL device") according to an embodiment of the present invention.

DESCRIPTION OF EMBODIMENTS

Hereinafter, the present invention is specifically described.

(Construction of Organic EL Device)

First, the device construction of an organic EL device is described.

Typical examples of the device construction of the organic EL device may include the following structures.

(1) Anode/light emitting layer/cathode
(2) Anode/hole injectng layer/light emitting layer/cathode
(3) Anode/light emitting layer/electron injecting/transporting layer/cathode
(4) Anode/hole injecting layer/light emitting layer/electron injecting/transporting layer/cathode
(5) Anode/organic semiconductor layer/light emitting layer/cathode
(6) Anode/organic semiconductor layer/electron barrier layer/light emitting layer/cathode (7) Anode/organic semiconductor layer/light emitting layer/adhesion improving layer/cathode
(8) Anode/hole injecting/transporting layer/light emitting layer/electron injecting/transporting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting/transporting layer/light emitting layer/insulating layer/cathode
(13) Anode/insulating layer/hole injecting/transporting layer/light emitting layer/electron injecting/transporting layer/cathode Of those, the construction (8) is preferably used, and as a matter of course, the device construction is not limited to the above-mentioned constructions.

In addition, a space layer may be provided between the respective light emitting layers for the purpose of preventing an exciton produced in a phosphorescent light emitting layer from diffusing into a fluorescent light emitting layer.

FIG. 1 illustrates the schematic construction of an example of an organic EL device in an embodiment of the present invention.

An organic EL device 1 includes a transparent substrate 2, an anode 3, a cathode 4, and an organic thin-film layer 10 disposed between the anode 3 and the cathode 4.

The organic thin-film layer 10 includes a phosphorescent light emitting layer 5 containing a phosphorescent host as a host material and a phosphorescent dopant as a phosphorescent material. A layer such as a hole injecting/transporting layer 6 may be provided between the phosphorescent light emitting layer 5 and the anode 3 while a layer such as an electron injecting/transporting layer 7 may be provided between the phosphorescent light emitting layer 5 and the cathode 4.

In addition, an electron blocking layer may be provided on the anode 3 side of the phosphorescent light emitting layer 5 while a hole blocking layer may be provided on the cathode 4 side of the phosphorescent light emitting layer 5.

With this construction, electrons and holes can be trapped in the phosphorescent light emitting layer 5, thereby enhancing probability of exciton generation in the phosphorescent light emitting layer 5.

In addition, the organic EL device of the present invention may be a fluorescent or phosphorescent emission-type, monochromatic light emitting device, or may be a fluorescence/phosphorescence hybrid-type, white light emitting device, and the device may be of a simple type having a single light emitting unit, or may be of a tandem type having a plurality of light emitting units. Here, the term "light emitting unit" refers to the minimum unit including one or more organic layers one layer of which is a light emitting layer, the minimum unit being capable of emitting light through the recombination of a hole and an electron that have been injected. A representative layer construction of the light emitting unit is described below.

(a) Hole transporting layer/light emitting layer(/electron transporting layer)
(b) Hole transporting layer/first phosphorescent light emitting layer/second phosphorescent light emitting layer(/electron transporting layer)
(c) Hole transporting layer/phosphorescent light emitting layer/space layer/fluorescent light emitting layer(/electron transporting layer)
(d) Hole transporting layer/first phosphorescent light emitting layer/second phosphorescent light emitting layer/space layer/fluorescent light emitting layer(/electron transporting layer)
(e) Hole transporting layer/first phosphorescent light emitting layer/space layer/second phosphorescent light emitting layer/space layer/fluorescent light emitting layer(/electron transporting layer)
(f) Hole transporting layer/phosphorescent light emitting layer/space layer/first fluorescent light emitting layer/second fluorescent light emitting layer(/electron transporting layer)

The respective phosphorescent or fluorescent light emitting layers can be adapted to show luminescent colors different from each other. Specifically, for example, the following layer construction is adopted for the laminated light emitting layer (d): hole transporting layer/first phosphorescent light emitting layer (emitting red light)/second phosphorescent light emitting layer (emitting green light)/space layer/fluorescent light emitting layer (emitting blue light)/electron transporting layer.

It should be noted that an electron barrier layer may be appropriately provided between each light emitting layer and the hole transporting layer or the space layer. In addition, a hole barrier layer may be appropriately provided between each light emitting layer and the electron transporting layer. When the electron barrier layer or the hole barrier layer is provided, an electron or a hole is trapped in the light emitting layer, and hence the probability that charge recombination occurs in the light emitting layer can be increased and current efficiency can be enhanced, The following device construction can be given as an example of a representative device construction of a tandem-type organic EL device.

Anode/first light emitting unit/intermediate layer/second light emitting unit/cathode Here, the first light emitting unit and the second light emitting unit can each independently be selected from, for example, units similar to the light emitting unit.

The intermediate layer is generally called an intermediate electrode, intermediate conductive layer, charge generating layer, electron withdrawing layer, connection layer, or intermediate insulating layer as well, and such a known material constitution as to supply an electron and a hole to the first light emitting unit and the second light emitting unit, respectively can be used.

It should be noted that, with regard to the terms "fluorescent host" and "phosphorescent host" as used herein, a host is referred to as "fluorescent host" when combined with a fluorescent dopant or is referred to as "phosphorescent host" when combined with a phosphorescent dopant, and is not uniquely categorized into the fluorescent host or the phosphorescent host in a limitative fashion only in terms of its molecular structure.

In other words, the term "fluorescent host" as used herein refers to a material constituting a fluorescent light emitting layer containing a fluorescent dopant, and does not refer to a material that can be utilized only as a host for a fluorescent material.

Similarly, the term "phosphorescent host" refers to a material constituting a phosphorescent light emitting layer containing a phosphorescent dopant, and does not refer to a material that can be utilized only as a host for a phosphorescent material.

In addition, the term "hole injecting/transporting layer" as used herein refers to "at least one of a hole injecting layer and a hole transporting layer," and the term "electron injecting/transporting layer" as used herein refers to "at least one of an electron injecting layer and an electron transporting layer."

(Translucent Substrate)

The organic EL device of the present invention is produced on a translucent substrate. The term "translucent substrate" as used herein refers to a substrate for supporting the organic EL device, and the substrate is preferably a smooth substrate having a transmittance for light in the visible region from 400 nm to 700 nm of 50% or more.

Specifically, there are given a glass plate, a polymer plate, and the like.

Particular examples of the glass plate include those formed by using, as raw materials, a soda-lime glass, a barium/strontium-containing glass, a lead glass, an aluminosilicate glass, a borosilicate glass, a barium borosilicate glass, and quartz.

In addition, examples of the polymer plate include those formed by using, as raw materials, a polycarbonate, an acrylic, a polyethylene terephthalate, a polyether sulfide, and a polysulfone.

(Anode and Cathode)

The anode of the organic EL device has a role in injecting holes into the hole injecting layer, the hole transporting layer, or the light emitting layer. It is effective that the anode has a work function of 4.5 eV or more.

An indium tin oxide alloy (ITO), tin oxide (NESA), indium oxide-zinc oxide, gold, silver, platinum, copper, and the like are given as specific examples of a material for the anode.

The anode can be produced by forming a thin film with any such material for electrodes by, for example, a vapor deposition method or a sputtering method.

As in the case of this embodiment, when the light emitted from the light emitting layer is extracted through the anode, it is preferred that the anode have a transmittance of more than 10% with respect to the light in the visible region. It is also preferred that the sheet resistance of the anode be several hundred $\Omega/\square$ or less. The thickness of the anode is, in general, selected in the range of 10 nm to 1 µm, preferably in the range of 10 nm to 200 nm although the preferred range may be different depending on the used material.

As the cathode, a material having a small work function is preferred for the purpose of injecting an electron into the electron injecting layer, the electron transporting layer, or the light emitting layer.

A material for the cathode is not particularly limited, and specifically, indium, aluminum, magnesium, an magnesium-indium alloy, a magnesium-aluminum alloy, an aluminum-lithium alloy, an aluminum-scandium-lithium alloy, a magnesium-silver alloy, or the like can be used.

As in the case of the anode, the cathode can be produced by forming a thin film according to a method such as a vapor deposition method or a sputtering method. Such a mode that emitted light is extracted from a cathode side can also be adopted.

(Light Emitting Layer)

The light emitting layer of the organic EL device brings together the following functions.

That is, (i) The injecting function: the function of injecting holes from the anode or the hole injecting layer and injecting electrons from the cathode or the electron injecting layer when an electric field is applied;

(ii) The transporting function: the function of transporting injected charges (i.e., electrons and holes) by the force of the electric field; and (iii) The light emitting function: the function of providing the field for recombination of electrons and holes and leading the recombination to the emission of light.

It should be noted that the ease with which holes are injected and the ease with which electrons are injected may differ from each other, and transporting abilities represented by the mobilities of the holes and the electrons may vary.

For example, a known method such as a vapor deposition method, a spin coating method, or an LB method is applicable as a method of forming the light emitting layer.

Here, a double host (also referred to as "host/co-host") that adjusts a carrier balance in the light emitting layer, the double host being obtained by, for example, combining an electron transportable host and a hole transportable host, may be adopted for the light emitting layer.

In addition, the following double dopant may be adopted. Two or more kinds of dopant materials having high quantum yields are incorporated so that each dopant may emit light. Specifically, the following mode is given. A host, a red dopant, and a green dopant are co-deposited from the vapor so that a light emitting layer common to the materials may be formed to realize yellow light emission.

When the light emitting layer is a laminate obtained by laminating a plurality of light emitting layers, an electron and a hole are accumulated at an interface between the light emitting layers, and a recombination region is converged on the interface between the light emitting layers. As a result, quantum efficiency can be enhanced.

The light emitting layer is preferably a molecular deposit film.

The term "molecular deposit film" as used herein refers to a thin film formed by the deposition of a material compound in a vapor phase state, or a film formed by the solidification of a material compound in a solution state or a liquid phase state. The molecular deposit film can be typically distinguished from a thin film formed by the LB method (molecular accumulation film) on the basis of differences between the films in aggregation structure and higher order structure, and functional differences between the films caused by the foregoing differences.

In addition, the light emitting layer can also be formed by preparing a solution of a binder such as a resin and a material compound dissolved in a solvent, and then forming the solution into a thin film by the spin coating method or the like.

The organic EL device of the present invention includes an organic thin-film layer formed of one or more layers between the cathode and the anode, the organic thin-film layer has at least one light emitting layer, and at least one layer of the organic thin-film layer contains at least one kind of phosphorescent material and at least one kind of material for an organic electroluminescence device of the present invention to be described later. In addition, at least one of the light emitting layers preferably contains the material for an organic electroluminescence device of the present invention and the at least one kind of phosphorescent material.

(Biscarbazole Derivative)

The organic EL device of the present invention has a plurality of organic thin-film layers including a light emitting layer between the cathode and the anode, and at least one layer of the organic thin-film layers contains a biscarbazole derivative. It should be noted that the term "hydrogen" as used herein comprehends deuterium as well. In addition, the biscarbazole derivative of the present invention preferably has only two carbazole structures in a molecule thereof.

The biscarbazole derivative of the present invention has, at a specific position, a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group, and is specifically represented by any one of the following formulae (1) to (4).

[Chem. 5]

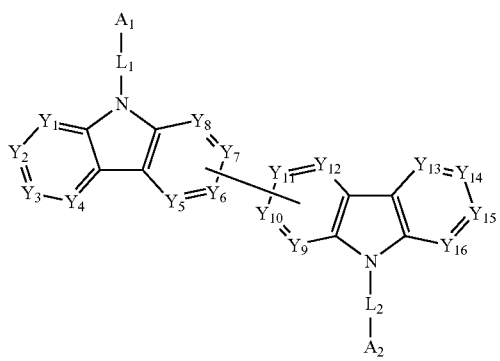

(1)

(In the formula (1):

$A_1$ and $A_2$ each independently represent a substituted or unsubstituted aromatic hydrocarbon group having 6 to 30 ring carbon atoms, or a substituted or unsubstituted aromatic heterocyclic group having 2 to 30 ring carbon atoms;

$Y_1$ to $Y_{16}$ each independently represent $C(R)$ or a nitrogen atom, and R's each independently represent a hydrogen atom, a substituent, or a bond to a carbazole skeleton; and $L_1$ and $L_2$ each independently represent a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that: at least one of $L_1$ and $L_2$ represents a substituted or unsubstituted, divalent aromatic hydrocarbon group having 6 to 30 ring carbon atoms, or a substituted or unsubstituted, divalent aromatic heterocyclic group having 2 to 30 ring carbon atoms; at least one of $A_1$ and $A_2$ represents a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group; and when one of $A_1$ and $A_2$ represents a dibenzofuranyl group or a dibenzothiophenyl group, the other represents a substituted or unsubstituted aromatic hydrocarbon group having 6 to 30 ring carbon atoms, or a substituted or unsubstituted benzofuranyl group, a substituted or unsubstituted benzothiophenyl group, a substituted or unsubstituted benzonaphthofuranyl group, or a substituted or unsubstituted benzonaphthothiophenyl group.)

It should be noted that in the formula (1), at least one of $Y_1$ to $Y_4$ represents $C(R)$, at least one of $Y_5$ to $Y_8$ represents $C(R)$, at least one of $Y_9$ to $Y_{12}$ represents $C(R)$, and at least one of $Y_{13}$ to $Y_{16}$ represents $C(R)$.

In addition, one of $Y_5$ to $Y_8$ represents $C(R)$, one of $Y_9$ to $Y_{12}$ represents $C(R)$, and these R's represent bond to each other.

The plurality of R's in the formula (1) may be identical to or different from each other.

[Chem. 6]

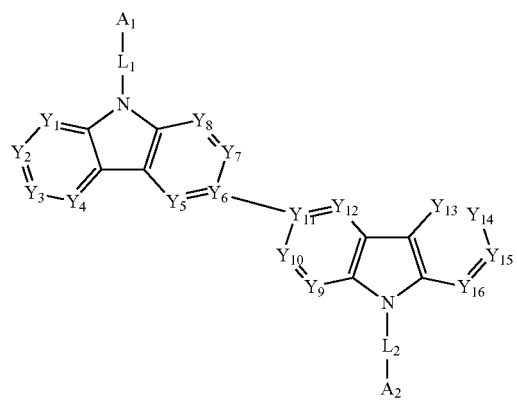

(2)

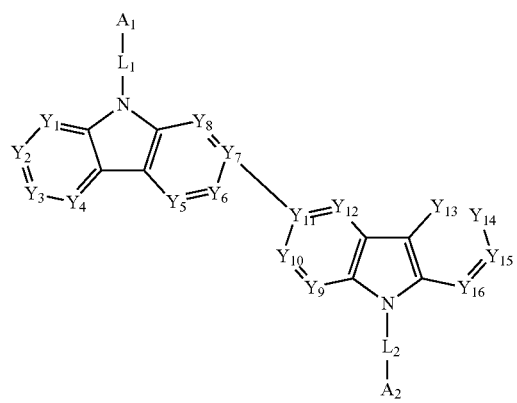

(3)

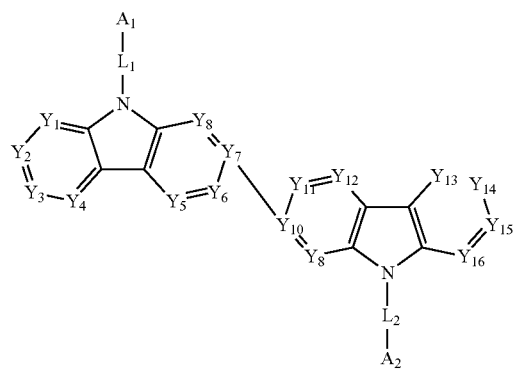

(4)

(In each of the formulae (2) to (4), $A_1$, $A_2$, $Y_1$ to $Y_{16}$, $L_1$, and $L_2$ each have the same meaning as that in the formula (1).)

In each of the formulae (1) to (4), at least one of $A_1$ and $A_2$ represents a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group, and when one of $A_1$ and $A_2$ represents a dibenzofuranyl group or a dibenzothiophenyl group, the other represents a substituted or unsubstituted aromatic hydrocarbon group having 6 to 30 ring carbon atoms, or a substituted or unsubstituted benzofuranyl group, a substituted or unsubstituted benzothiophenyl group, a substituted or unsubstituted benzonaphthofuranyl group, or a substituted or unsubstituted benzonaphthothiophenyl group.

The substituted or unsubstituted dibenzofuranyl group represented by each of the $A_1$ and the $A_2$ is particularly preferably a substituted or unsubstituted 4-dibenzofuranyl group, and the substituted or unsubstituted dibenzothiophenyl group represented by each of the $A_1$ and the $A_2$ is particularly preferably a substituted or unsubstituted 4-dibenzothiophenyl group.

Further, -$L_1$-$A_1$ and -$L_2$-$A_2$ in each of the formulae (1) to (4) are preferably different from each other.

It should be noted that a substituted or unsubstituted phenyl group represented by any one of $A_1$, $A_2$, and R is preferably a phenyl group substituted with an aromatic hydrocarbon group having 10 to 30 carbon atoms, particularly preferably a naphthylphenyl group.

When at least one of $L_1$ and $L_2$ in each of the formulae (1) to (4) represents a divalent aromatic heterocyclic group represented by the following formula (a), the biscarbazole derivative is particularly preferred as a host material to be used in combination with a green light emitting dopant.

[Chem. 7]

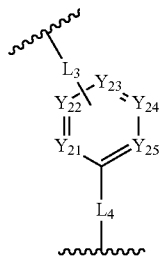

(a)

(In the formula (a):

$Y_{21}$ to $Y_{25}$ each independently represent $C(R_a)$ or a nitrogen atom, and $R_a$'s each independently represent a hydrogen atom, a substituent, or a bond to $L_3$; and $L_3$ and $L_4$ each independently represent a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that one or more of $Y_{21}$ to $Y_{25}$ each represent a nitrogen atom.)

In the formula (a), $Y_{21}$ and $Y_{25}$ each preferably represent a nitrogen atom, and $Y_{22}$ and $Y_{24}$ each more preferably represent $C(R_a)$.

Further, when $A_1$ in each of the formulae (1) to (4) represents a substituted or unsubstituted dibenzofuranyl group, or a substituted or unsubstituted dibenzothiophenyl group, $L_2$ preferably represents a divalent aromatic heterocyclic group represented by the general formula (a), and when $A_2$ in each of the formulae represents a substituted or unsubstituted dibenzofuranyl group, or a substituted or unsubstituted dibenzothiophenyl group, $L_1$ preferably represents a divalent aromatic heterocyclic group represented by the general formula (a).

Specific examples of the substituent which $A_1$ and $A_2$ in each of the general formulae (1) to (4) each have, and the substituent represented by each of R and $R_a$ include: a fluorine atom; a cyano group; a substituted or unsubstituted, linear, branched, or cyclic alkyl group having 1 to 20 carbon atoms; a linear, branched, or cyclic alkylene group having 1 to 20 carbon atoms; a linear, branched, or cyclic, divalent, unsaturated hydrocarbon group having 1 to 20 carbon atoms; a substituted or unsubstituted, linear, branched, or cyclic alkoxy group having 1 to 20 carbon atoms; a substituted or unsubstituted, linear, branched, or cyclic haloalkyl group having 1 to 20 carbon atoms; a substituted or unsubstituted, linear, branched, or cyclic haloalkoxy group having 1 to 20 carbon atoms; a substituted or unsubstituted, linear, branched, or cyclic alkylsilyl group having 1 to 10 carbon atoms; a substituted or unsubstituted arylsilyl group having 6 to 30 carbon atoms; a substituted or unsubstituted aromatic hydrocarbon group having 6 to 30 ring carbon atoms; and a substituted or unsubstituted aromatic heterocyclic group having 2 to 30 ring carbon atoms. In addition, a plurality of substituents of any such kind may exist, and when the plurality of substituents exist, the substituents may be identical to or different from each other.

It should be noted that R's on adjacent ring carbon atoms may be bonded to each other to form a ring structure together with the ring carbon atoms.

Examples of the linear, branched, or cyclic alkyl group having 1 to 20 carbon atoms include, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a cyclopentyl group, a cyclohexyl group, a cyclooctyl group, a 3,5-tetramethylcyclohexyl group, a trifluoromethyl group, a 2,2,2-trifluoroethyl group, and a 1,1,1,3,3,3-hexafluoro-2-propyl group.

Examples of the linear, branched, or cyclic alkylene group having 1 to 20 carbon atoms include an ethylene group, a propylene group, and a butylene group.

Examples of the linear, branched, or cyclic, divalent unsaturated hydrocarbon group having 1 to 20 carbon atoms include a 1,3-butadiene-1,4-diyl group.

Examples of the linear, branched, or cyclic alkylsilyl group having 1 to 10 carbon atoms include a trimethylsilyl group, a triethylsilyl group, a tributylsilyl group, a dimethylethylsilyl group, a dimethylisopropylsilyl group, a dimethylpropylsilyl group, a dimethylbutylsilyl group, a dimethyltertiarybutylsilyl group, and a diethylisopropylsilyl group.

Examples of the arylsilyl group having 6 to 30 carbon atoms include a phenyldimethylsilyl group, a diphenylmethylsilyl group, a diphenyltertiarybutylsilyl group, and a triphenylsilyl group.

Examples of the halogen atom include a fluorine atom.

Examples of the aromatic heterocyclic group having 2 to 30 ring carbon atoms include non-fused aromatic heterocyclic and fused aromatic heterocyclic groups, more specifically, a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a thienyl group, and groups formed from a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, and a benzo[c]dibenzofuran ring.

Examples of the aromatic hydrocarbon group having 6 to 30 ring carbon atoms include non-fused aromatic hydrocarbon groups and fused aromatic hydrocarbon groups, more specifically, a phenyl group, a naphthyl group, a phenanthryl group, a biphenyl group, a terphenyl group, a quaterphenyl group, a fluoranthenyl group, a triphenylenyl group, a phenanthrenyl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl group.

$L_1$ and $L_2$ in each of the general formulae (1) to (4) each represent, for example, a substituted or unsubstituted, divalent aromatic hydrocarbon group having 6 to 30 ring carbon atoms, or a substituted or unsubstituted, divalent aromatic heterocyclic group having 2 to 30 ring carbon atoms.

Specific examples of the divalent aromatic hydrocarbon group having 6 to 30 ring carbon atoms include groups obtained by making the examples of the aromatic hydrocarbon group having 6 to 30 ring carbon atoms divalent.

In addition, specific examples of the divalent aromatic heterocyclic group having 2 to 30 ring carbon atoms include groups obtained by making the examples of the aromatic heterocyclic group having 2 to 30 ring carbon atoms divalent.

In each of the general formulae (1) to (4), all of $Y_1$ to $Y_{16}$ each preferably represent C(R).

In each of the general formulae (1) to (4), the number of substituents each represented by R in each of $Y_1$ to $Y_8$ and $Y_9$ to $Y_{16}$ is preferably 0 to 2, more preferably 0 or 1.

Specific examples of the biscarbazole derivative of the present invention represented by any one of the general formulae (1) to (4) include the following compounds. It should be noted that in the following structural formulae, D represents deuterium.

[Chem. 8]

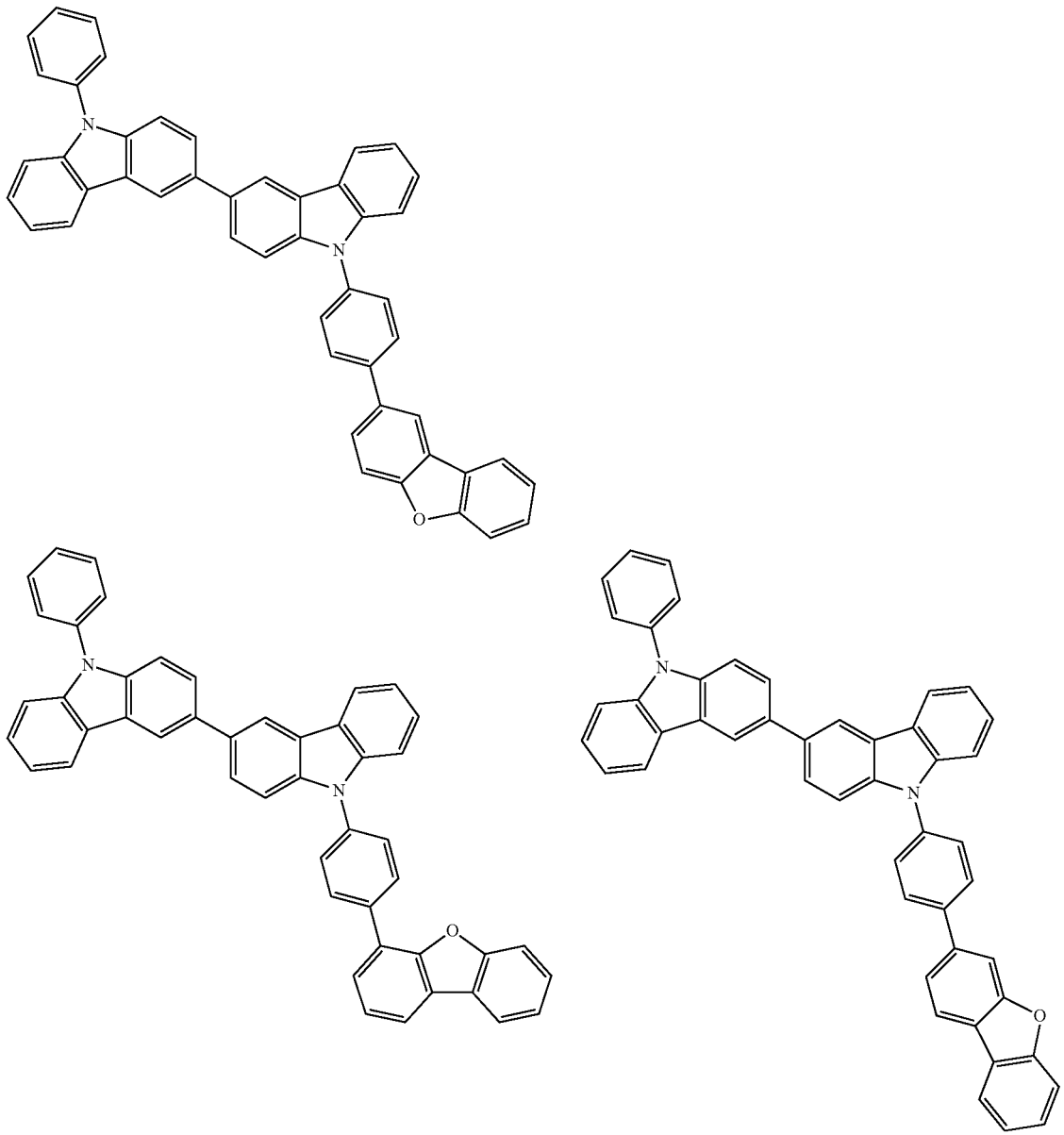

-continued
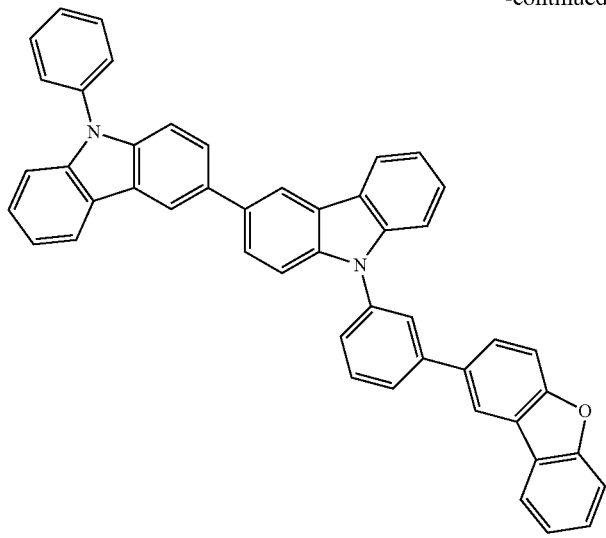
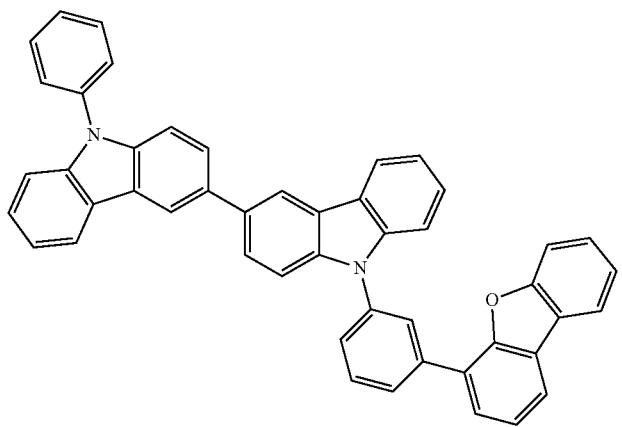
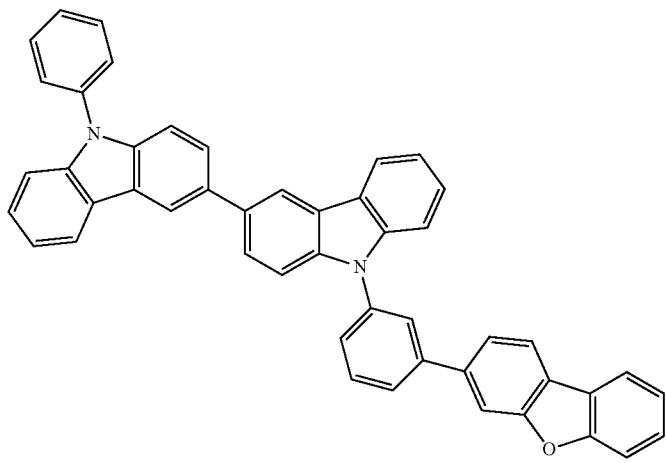

-continued
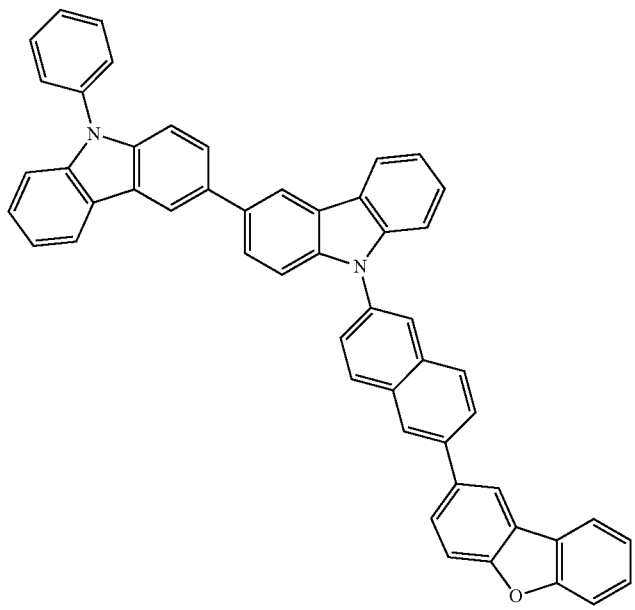
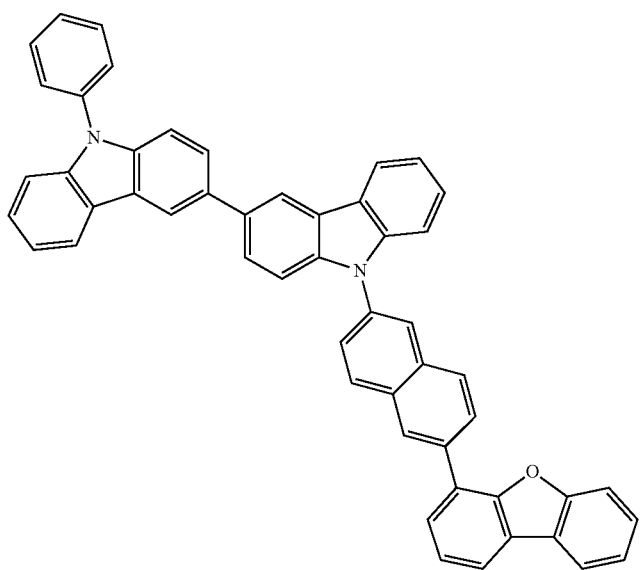

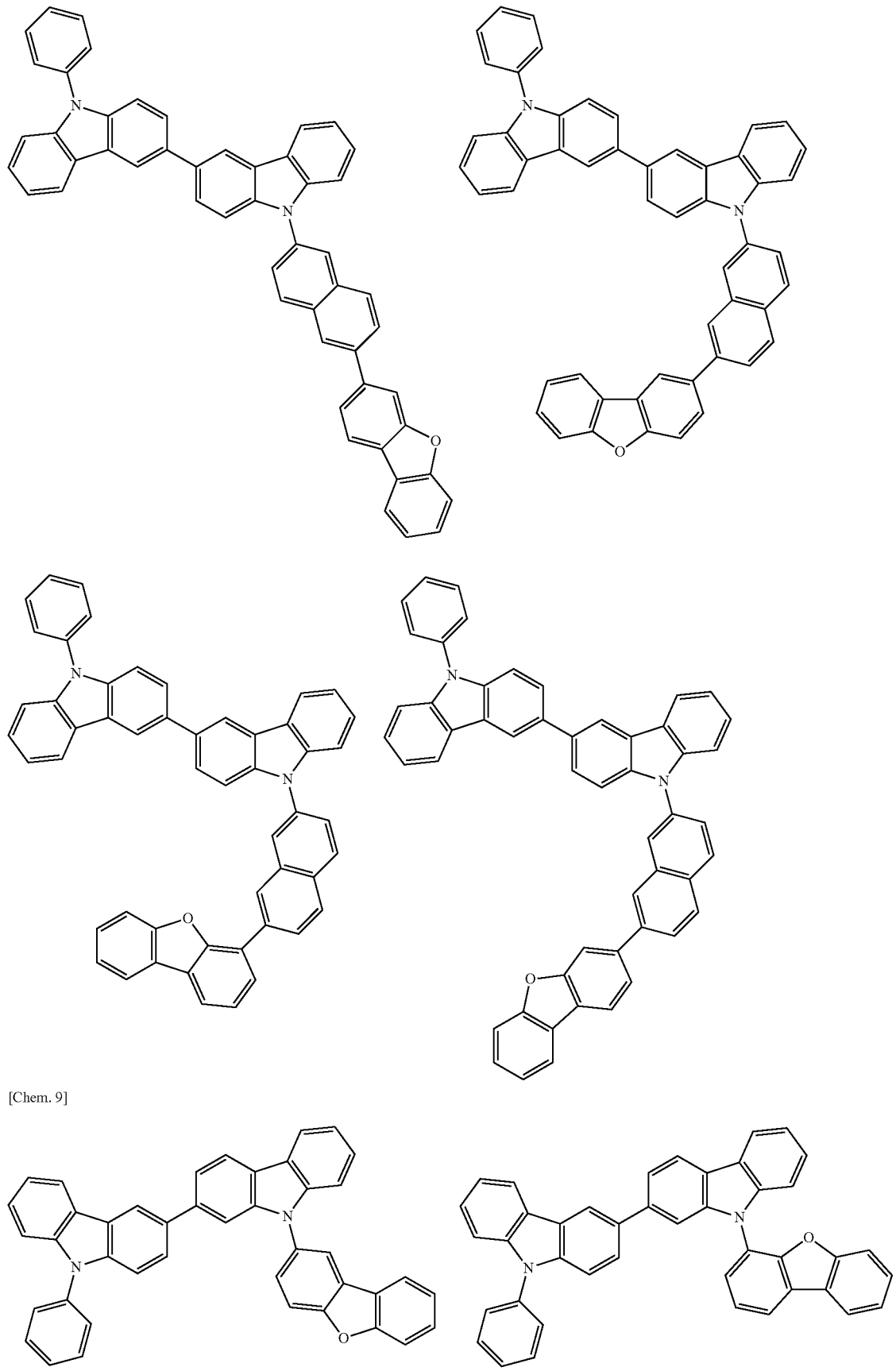
[Chem. 9]

-continued
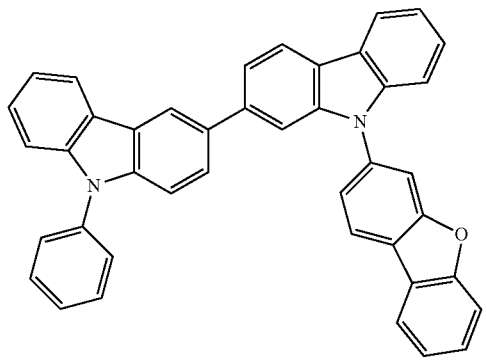
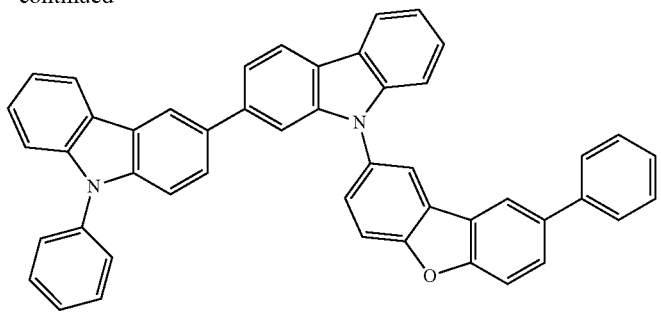
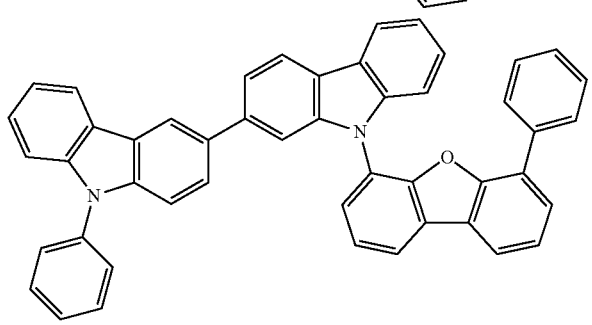
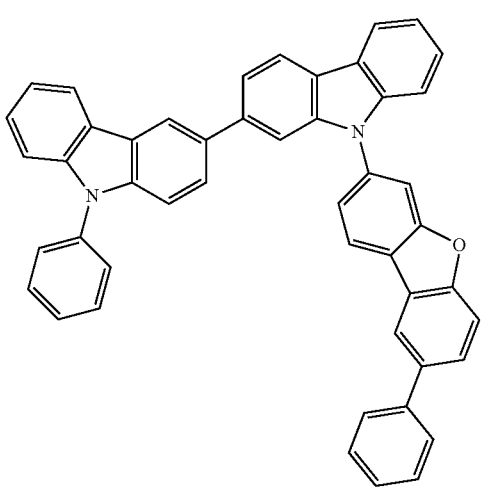
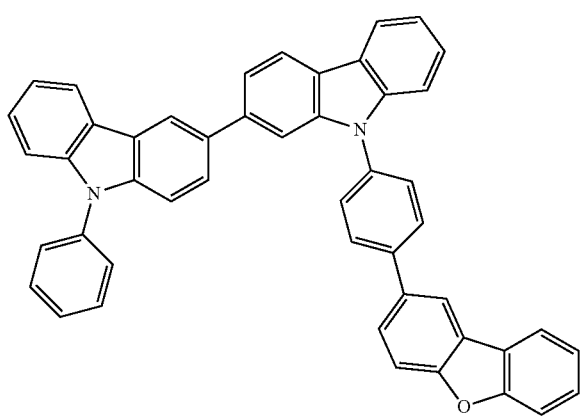
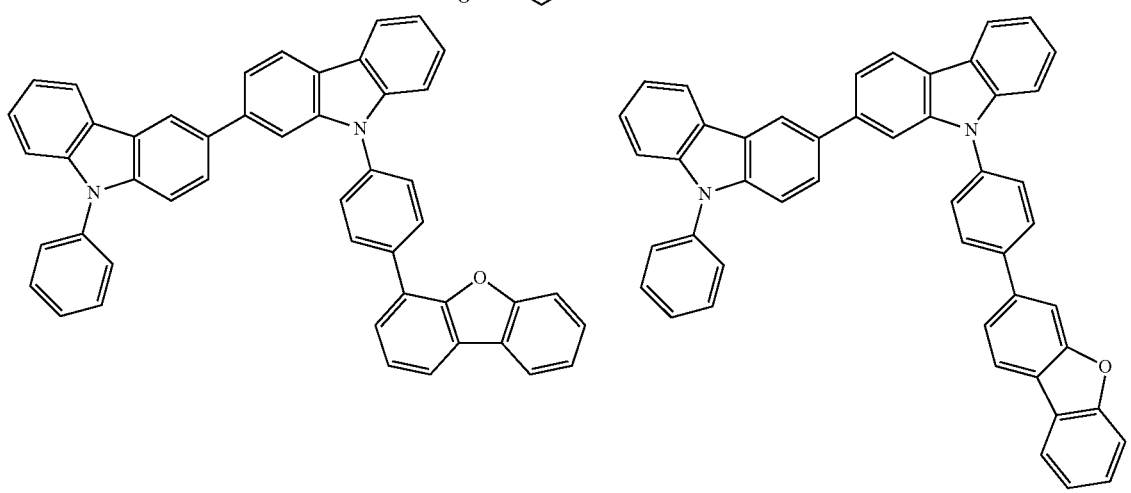

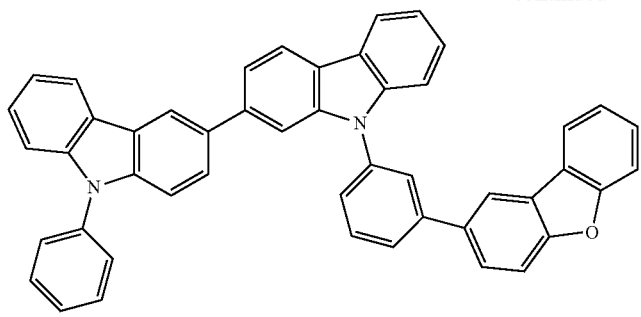
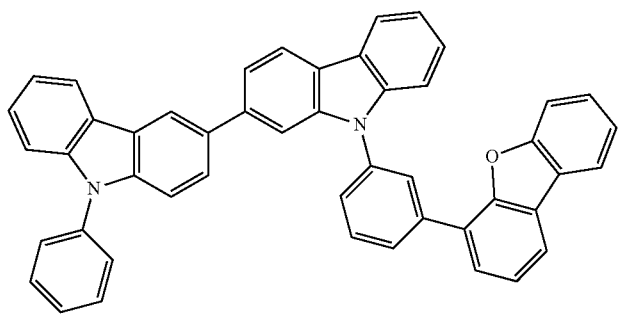
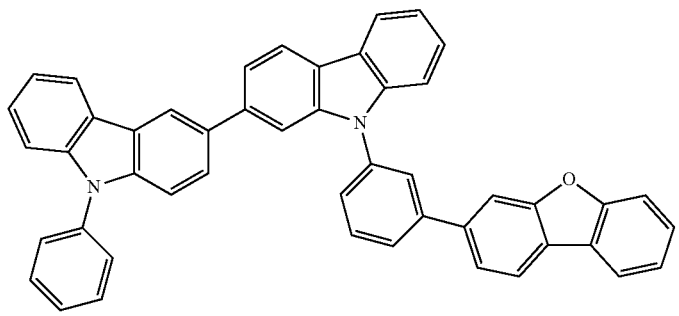
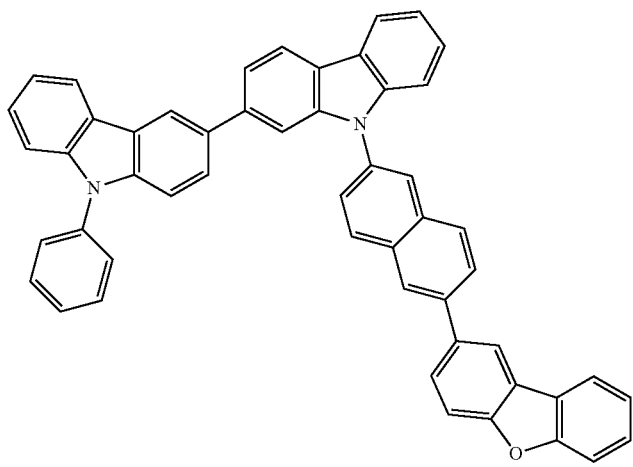

-continued
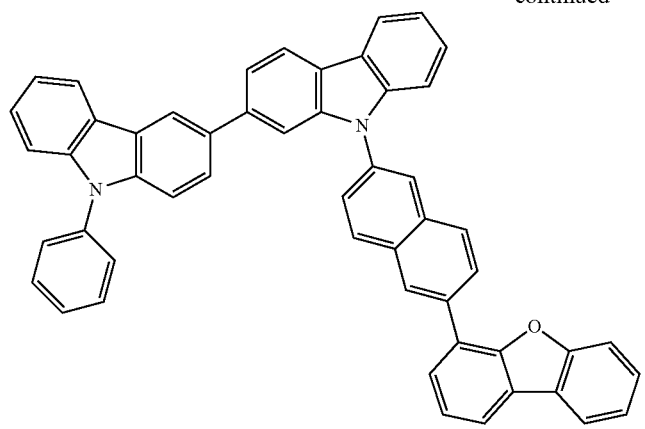

[Chem. 10]
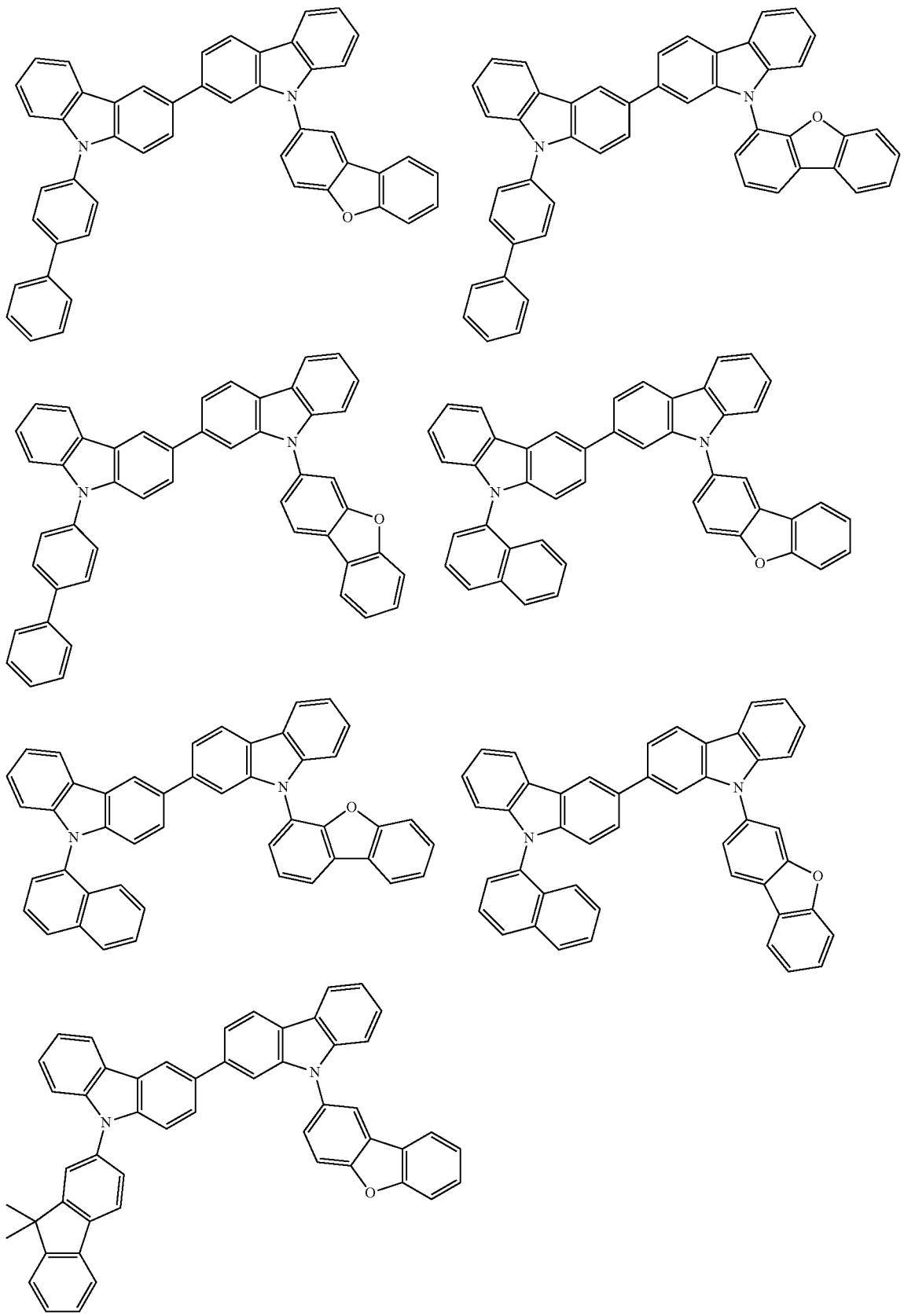

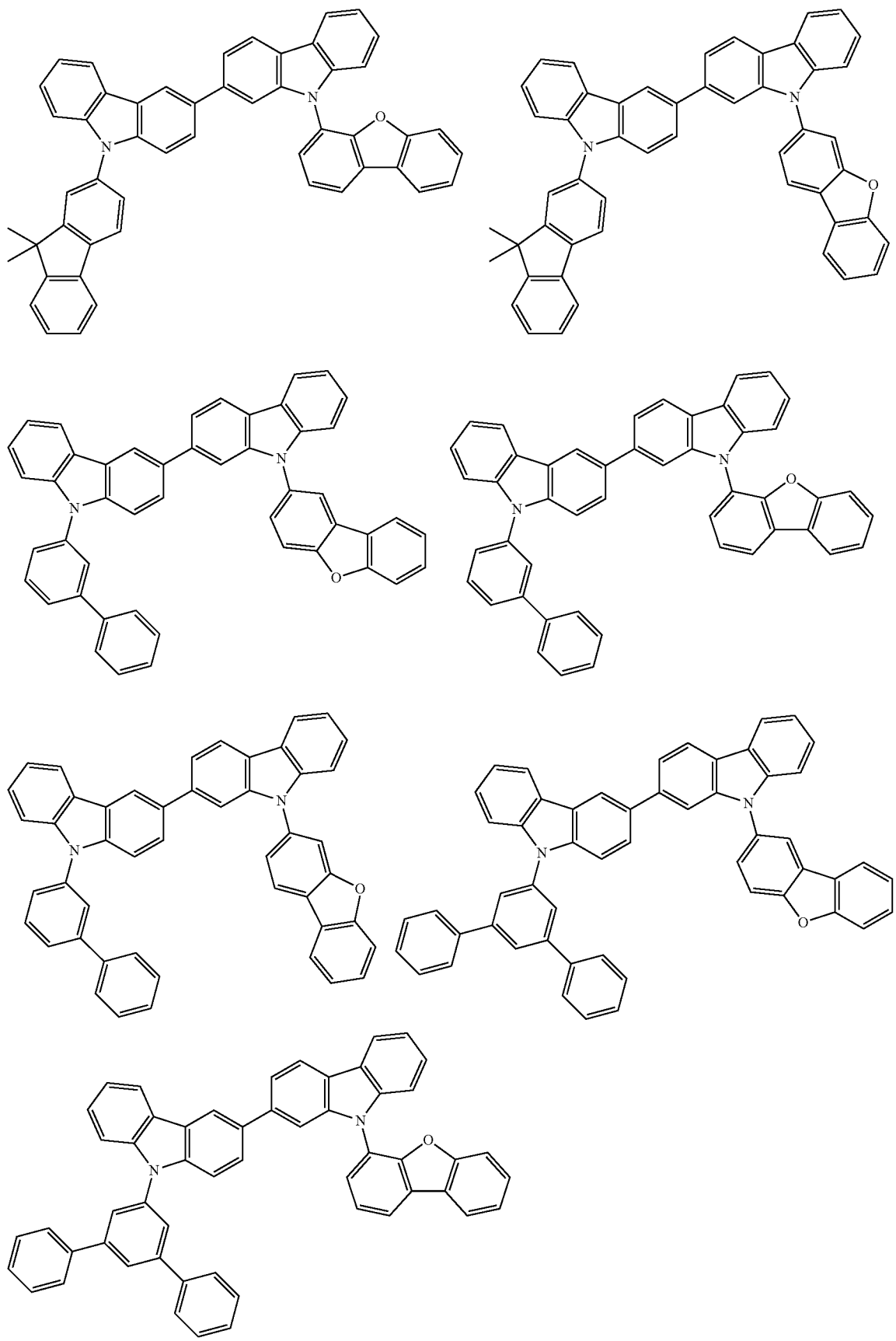

-continued
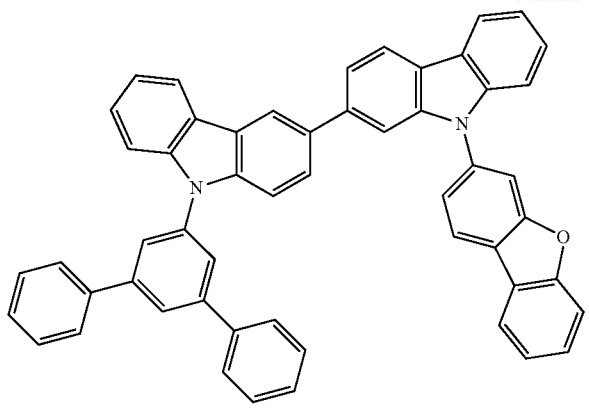
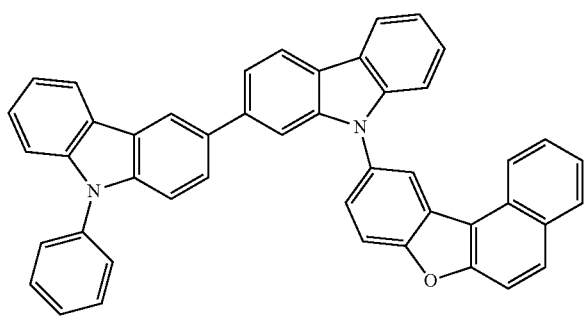
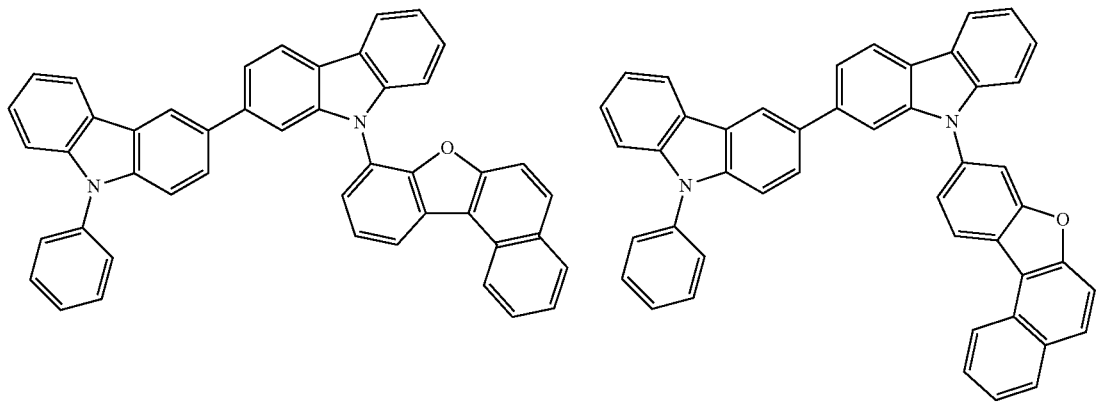
[Chem. 11]
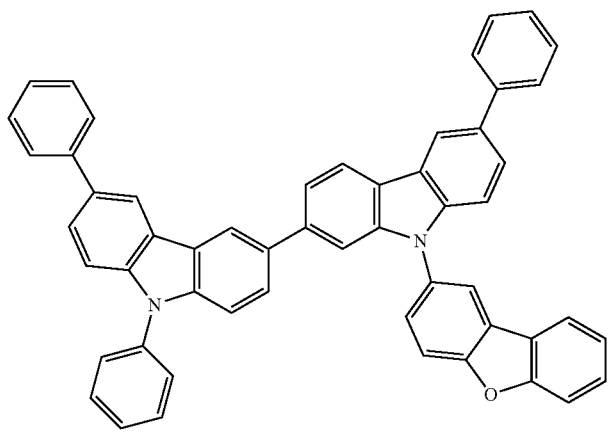

-continued
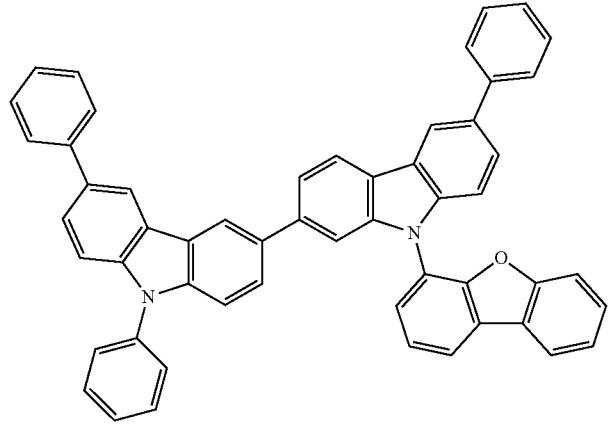
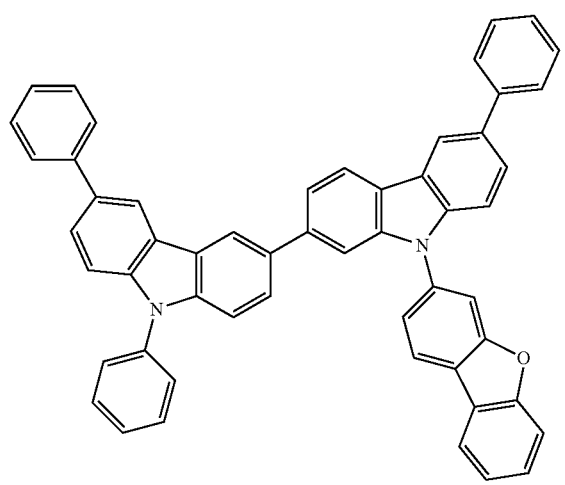
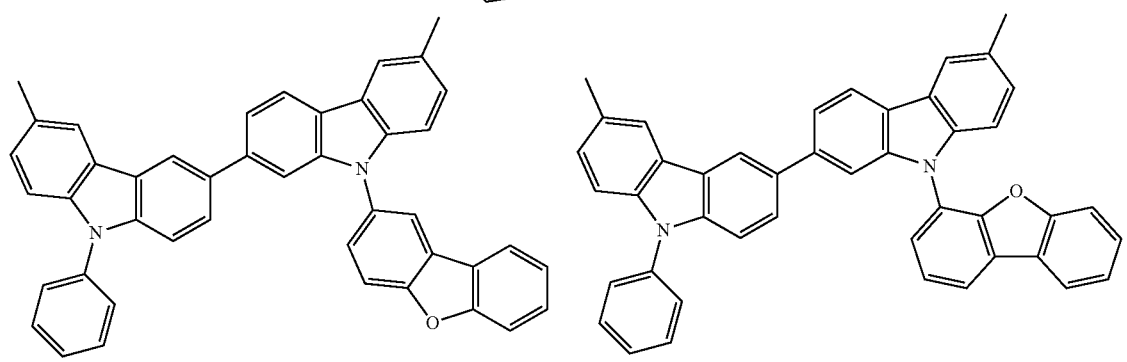
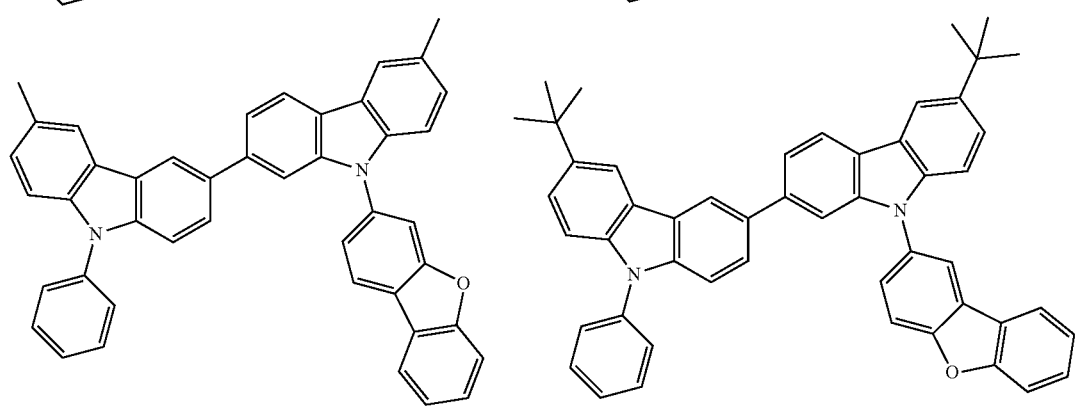

-continued
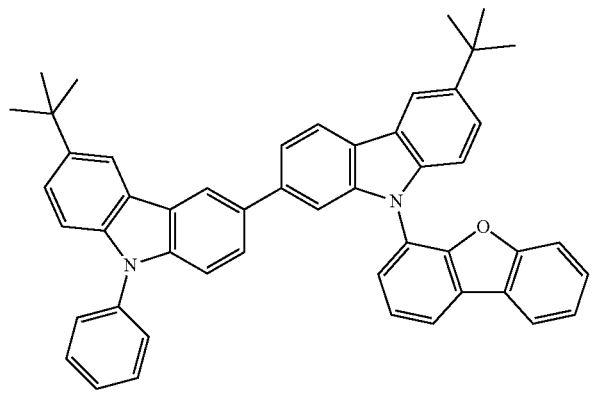
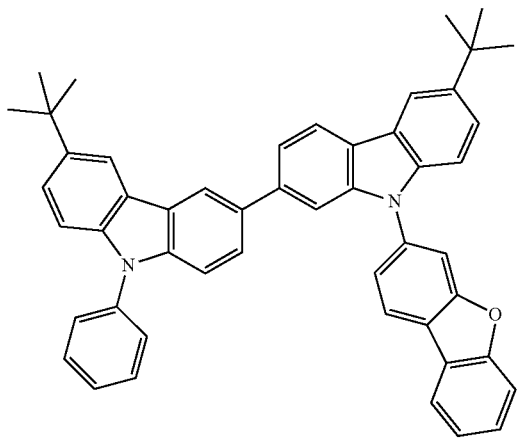
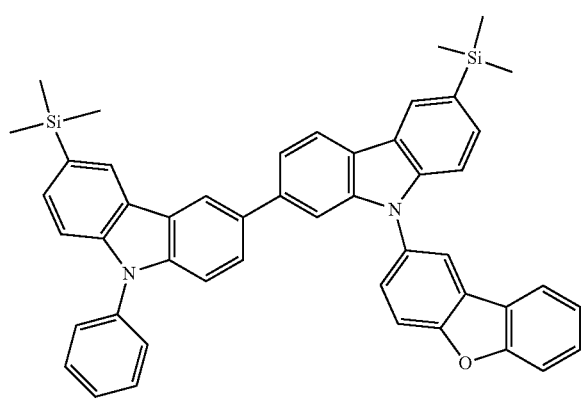
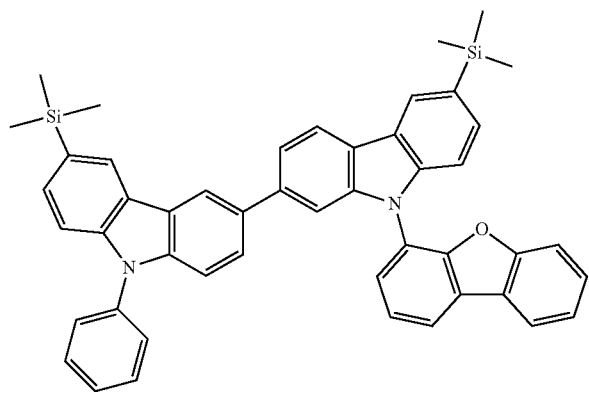
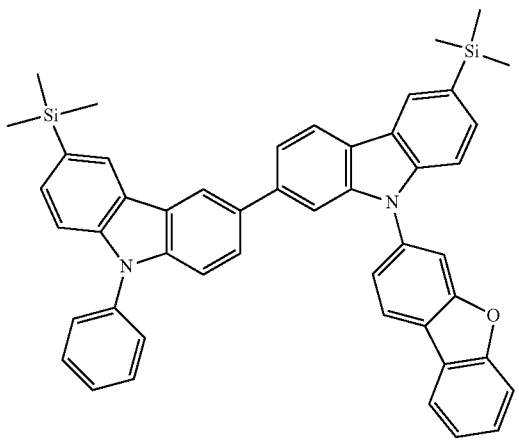
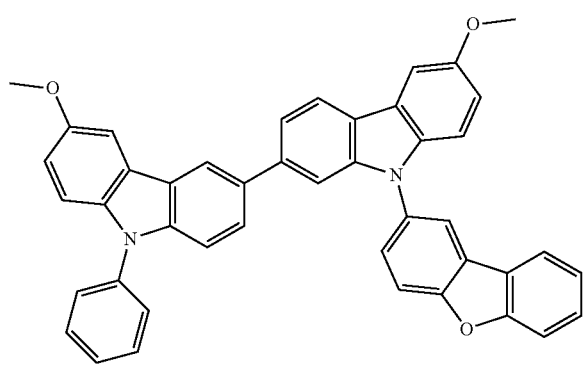

41 42
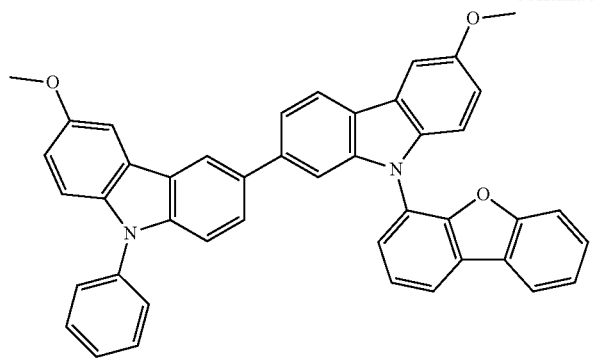
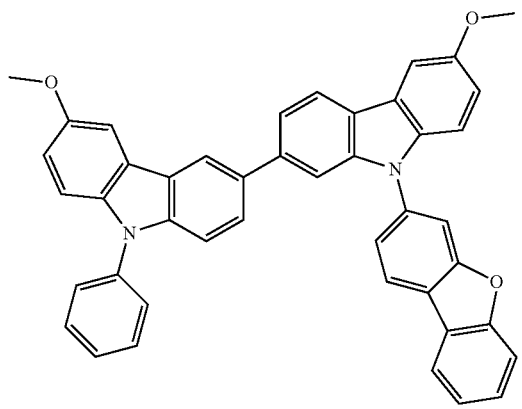
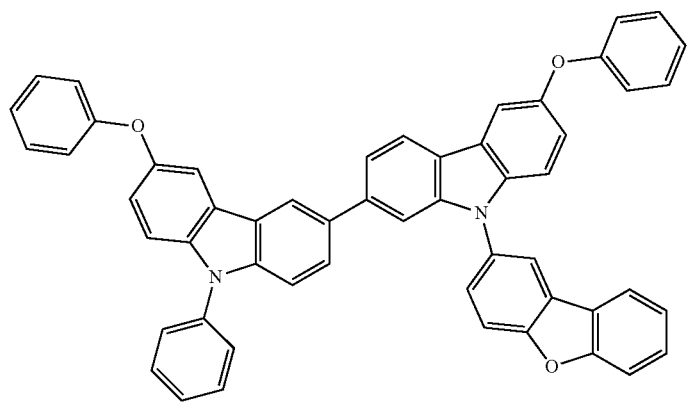
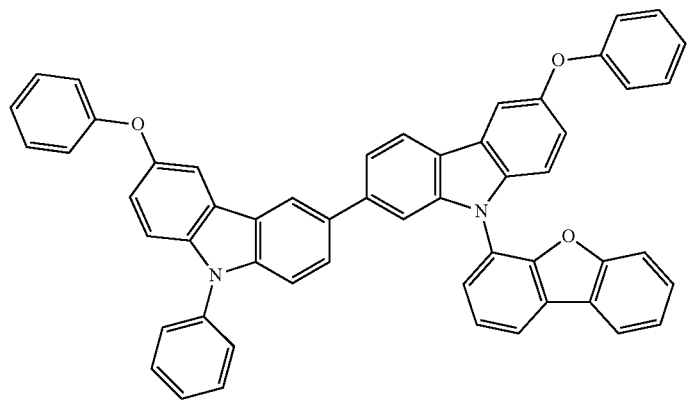
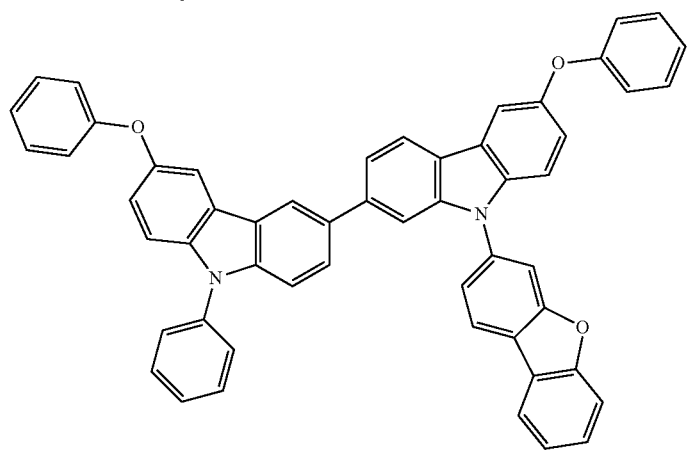

-continued
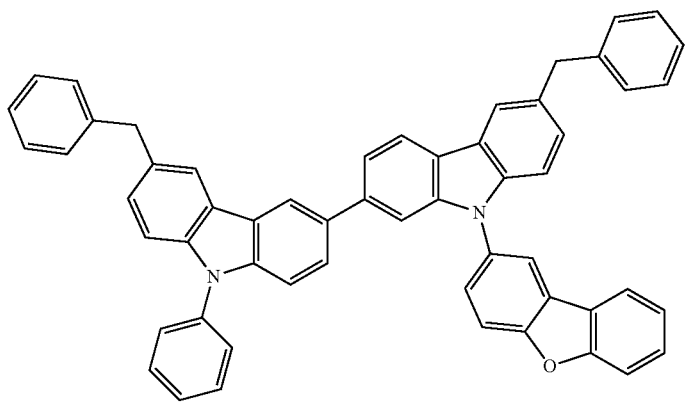
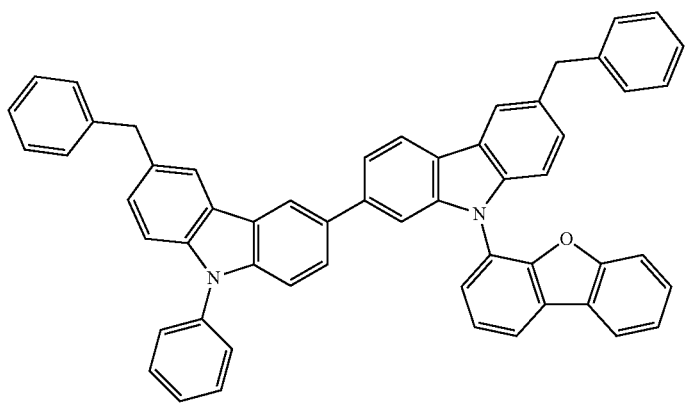
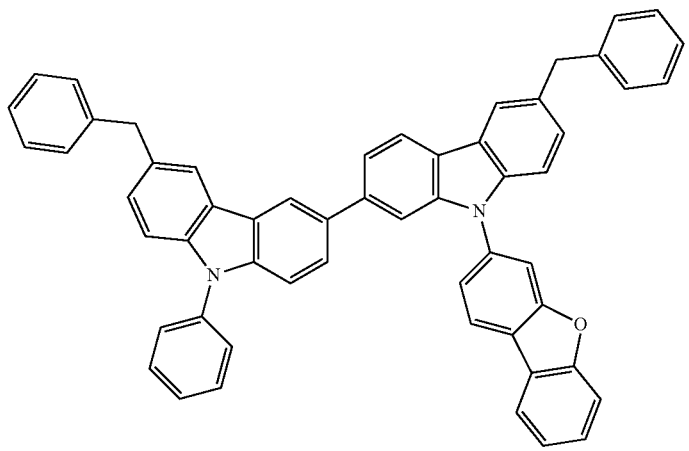

[Chem. 12]
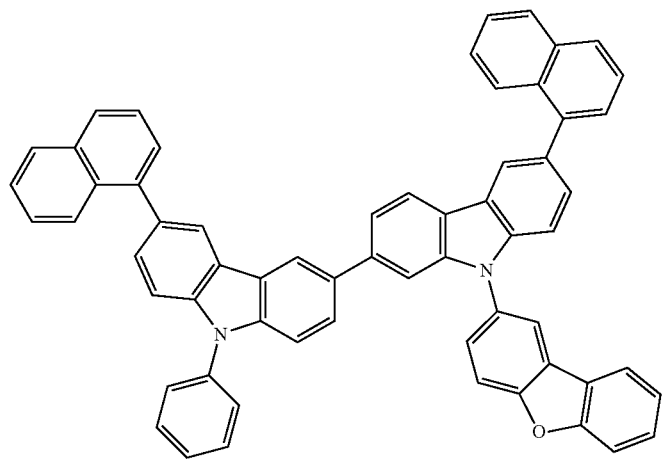
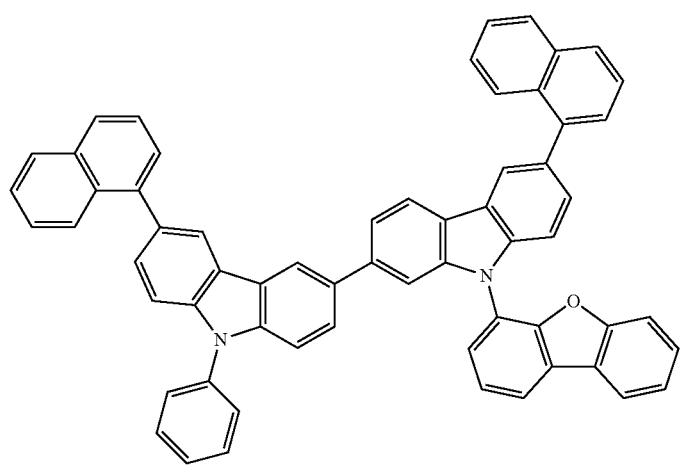
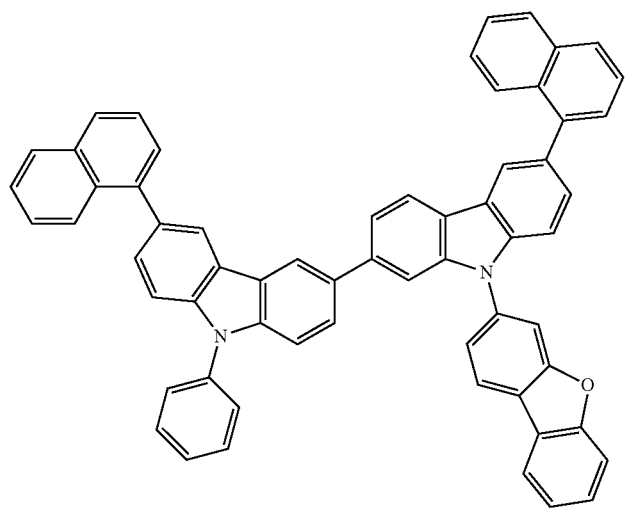

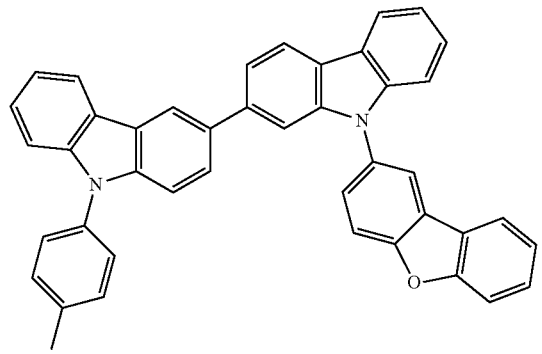
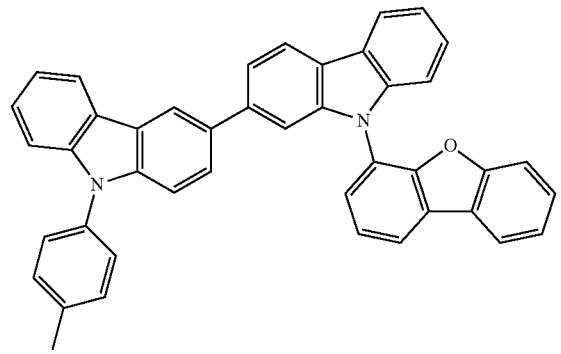
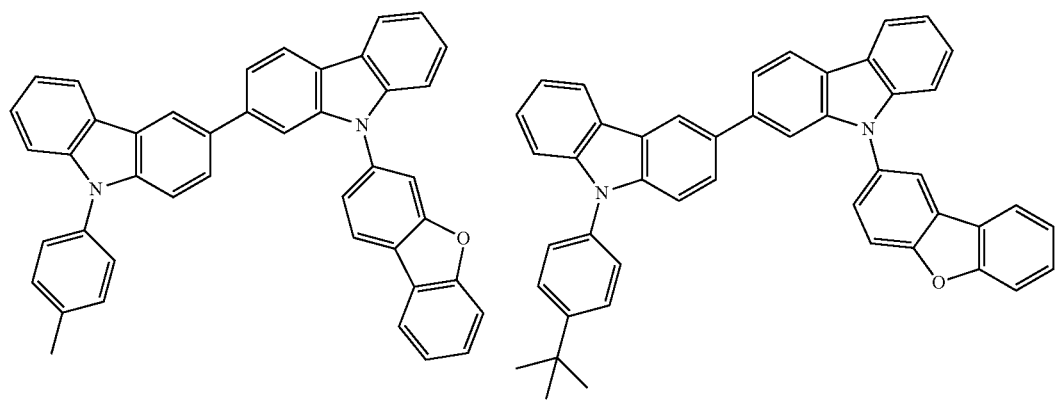
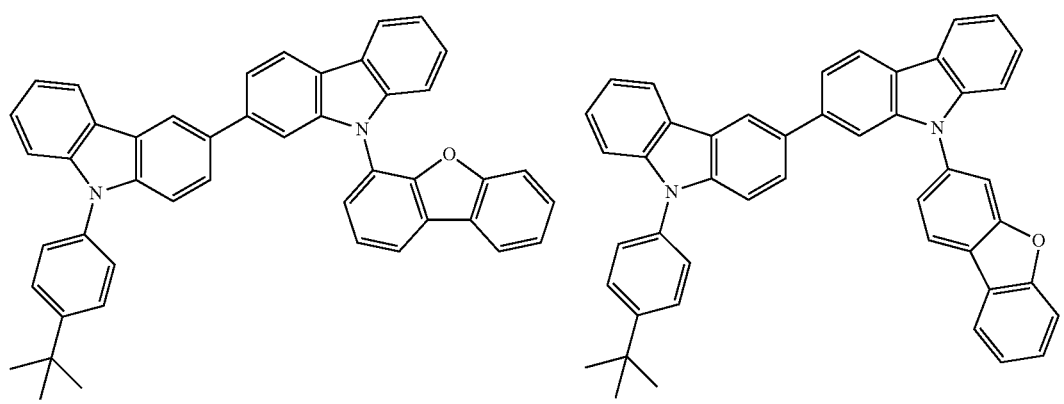
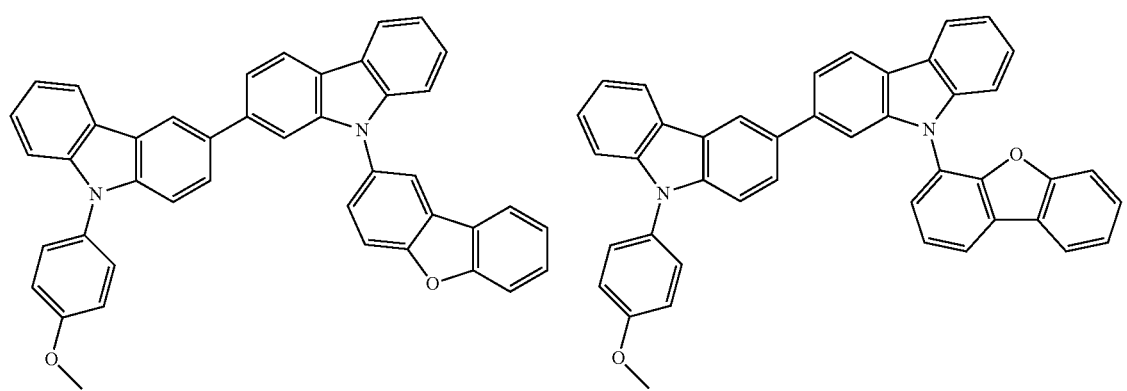

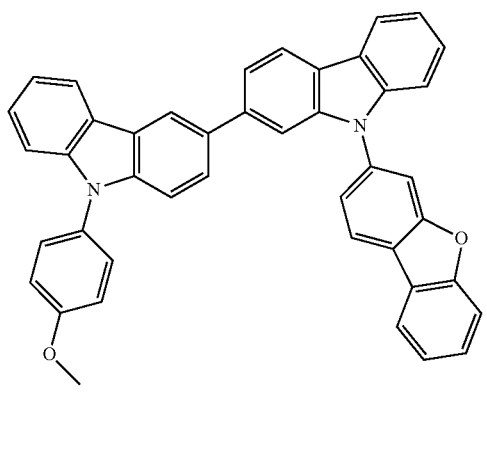
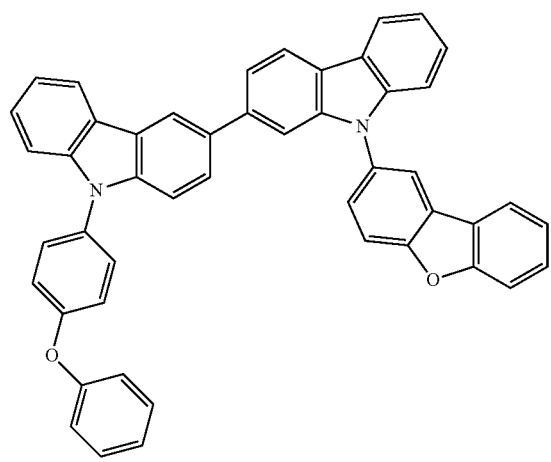
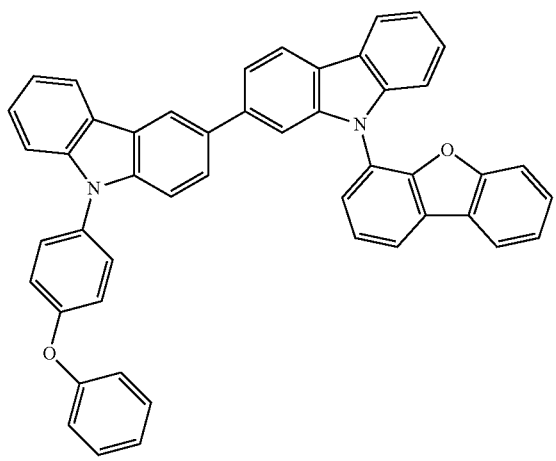
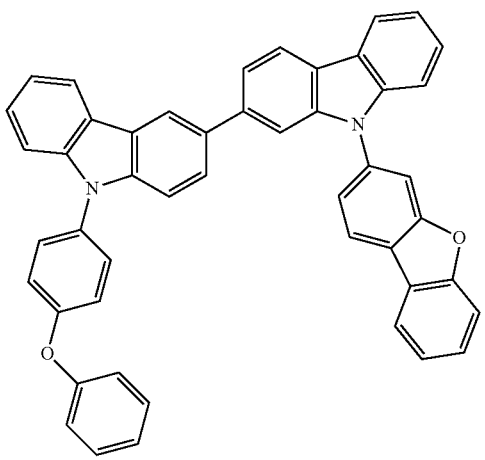
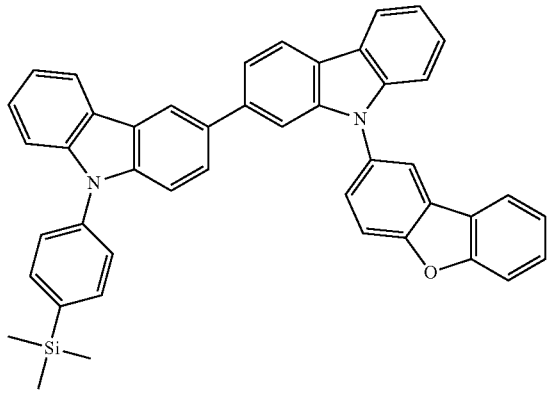
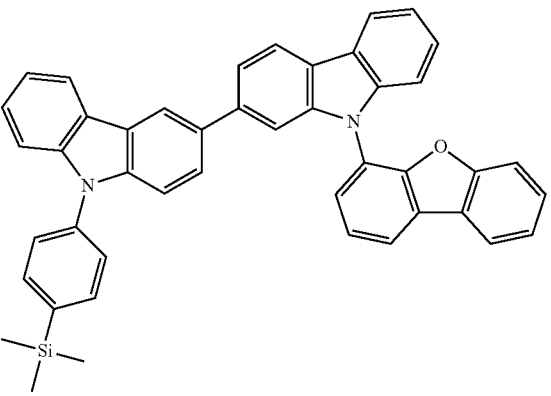
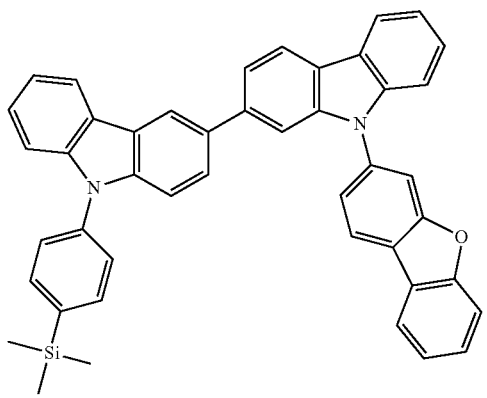

[Chem. 13]
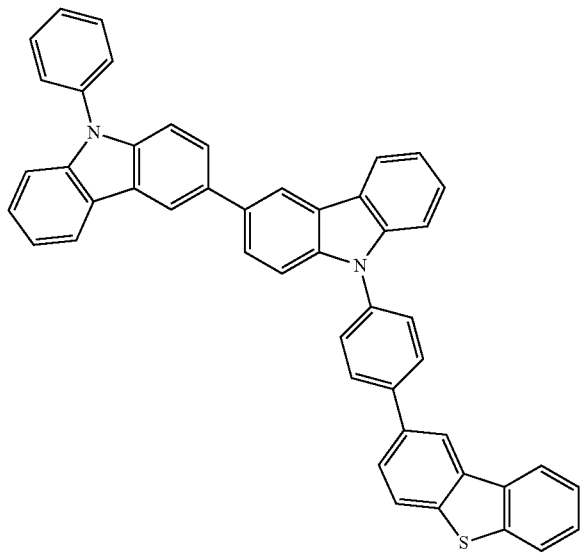
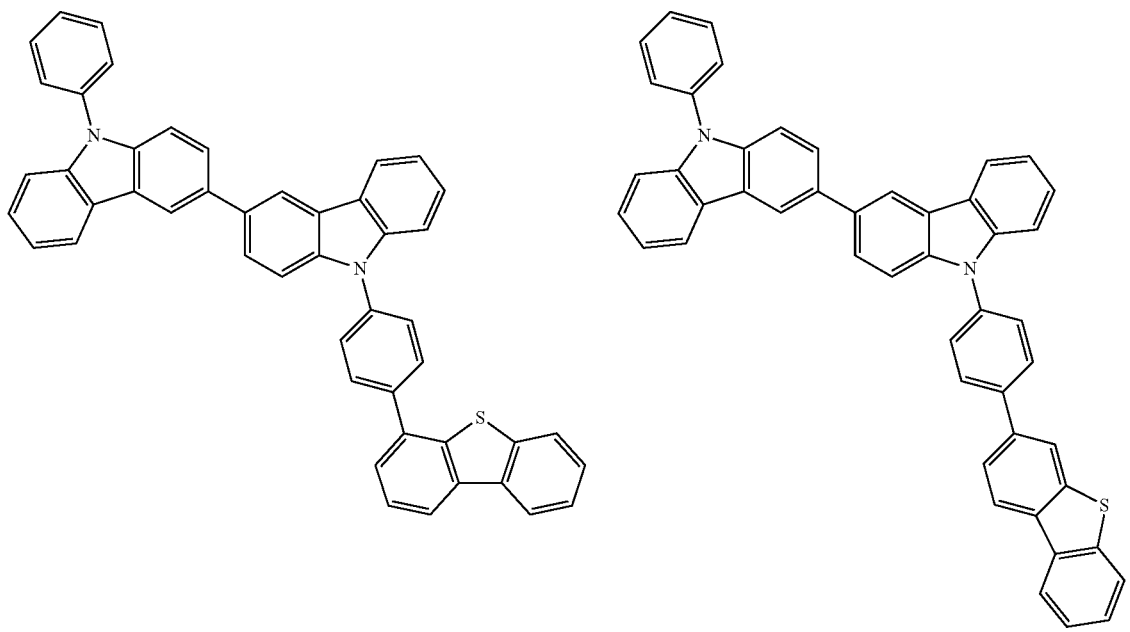
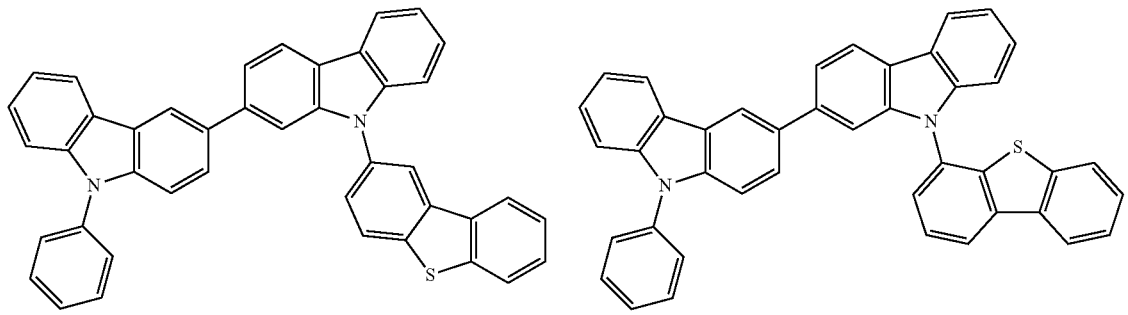

-continued
| 53 | 54 |
|---|---|
| 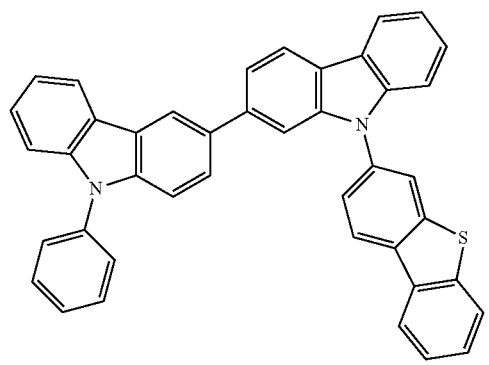 | 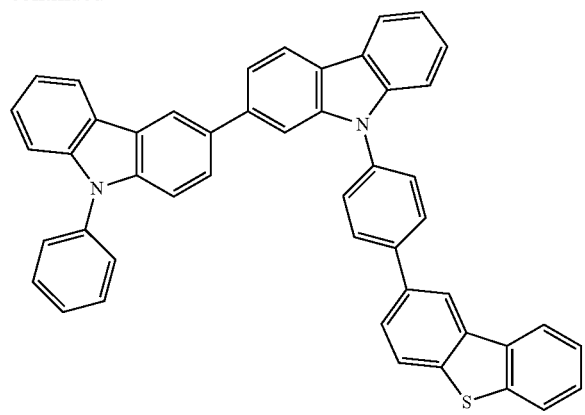 |
| 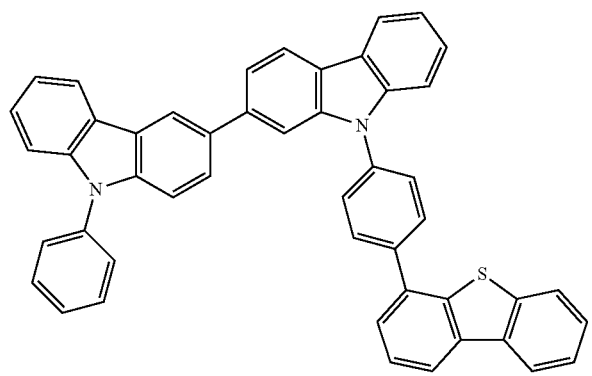 | 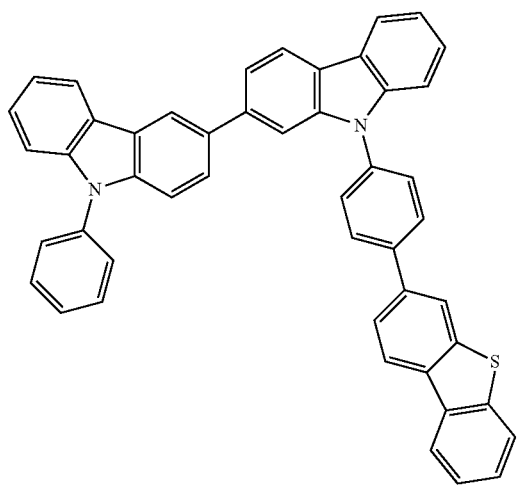 |
| 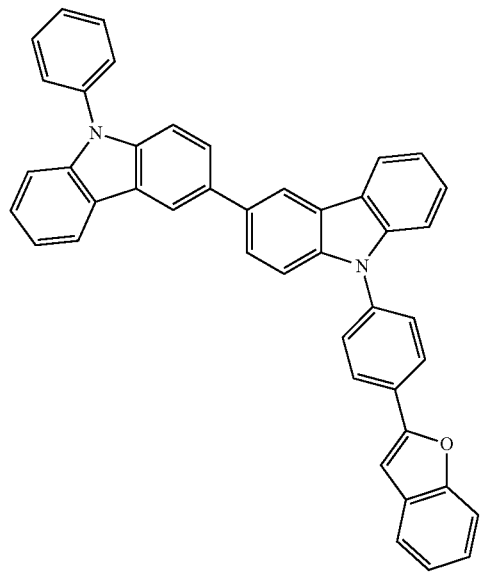 | 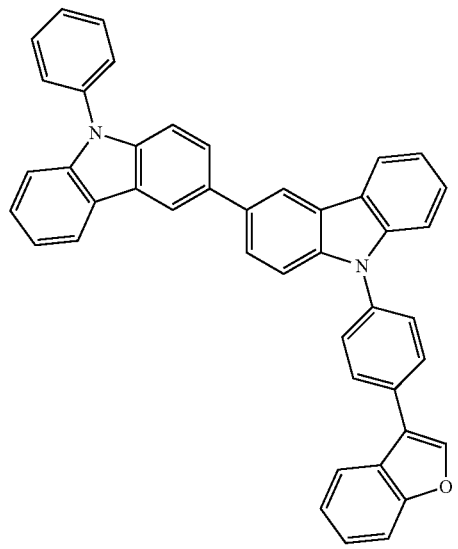 |

-continued
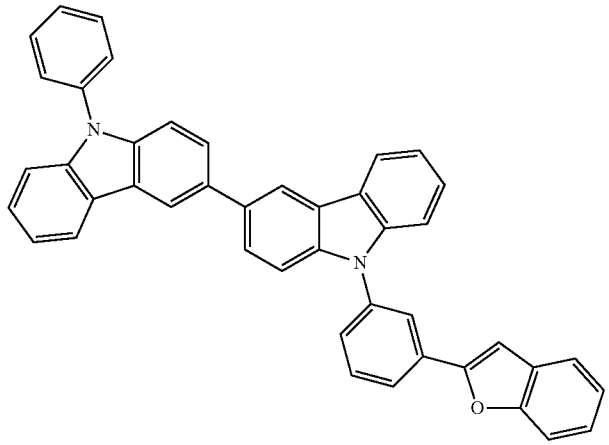
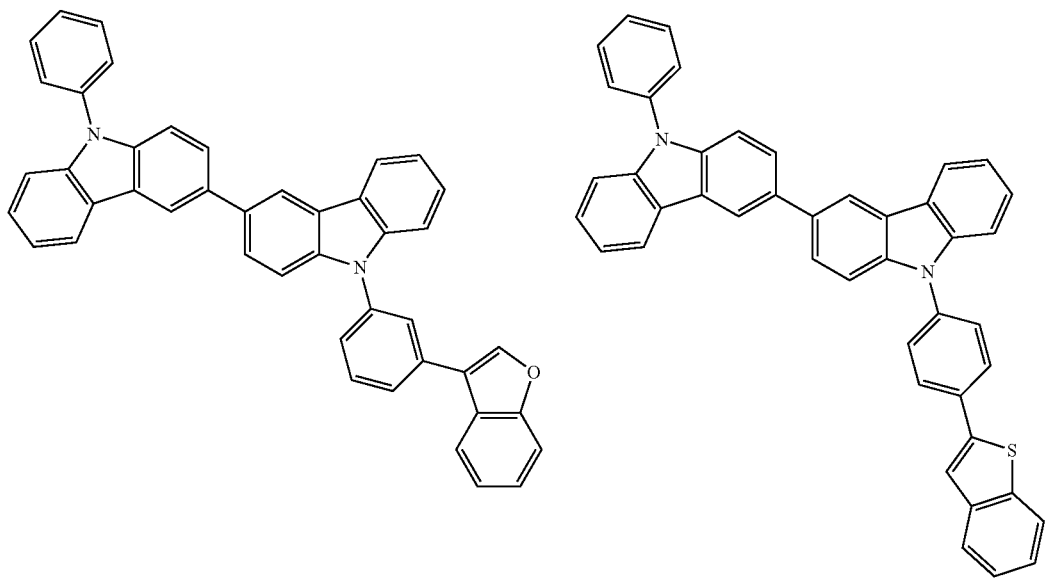
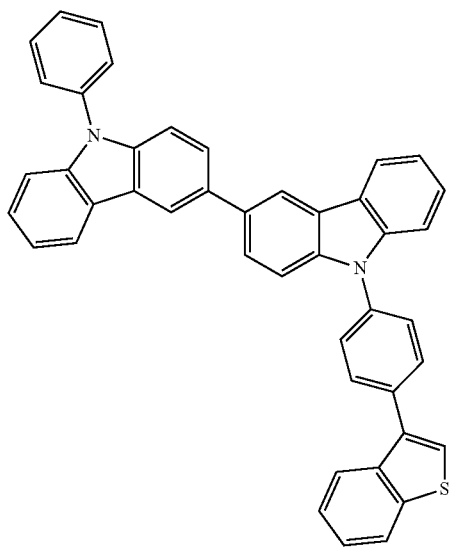

-continued
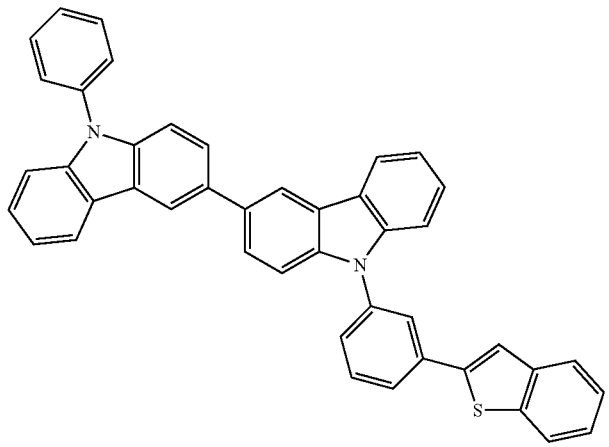
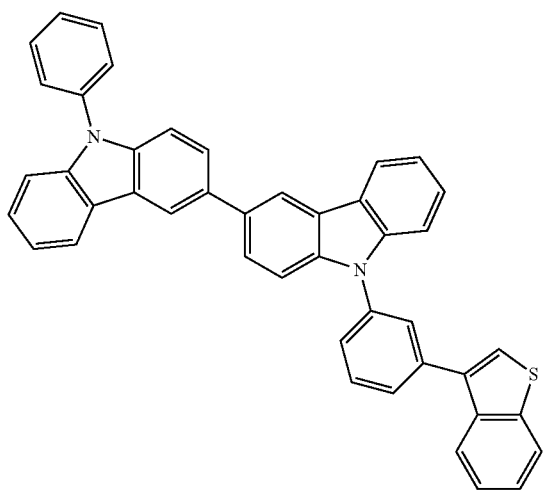
[Chem. 14]
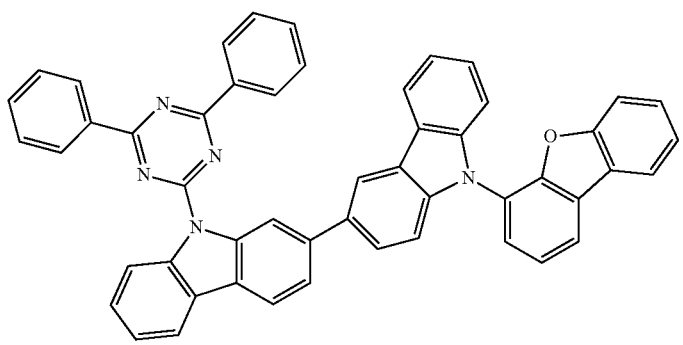
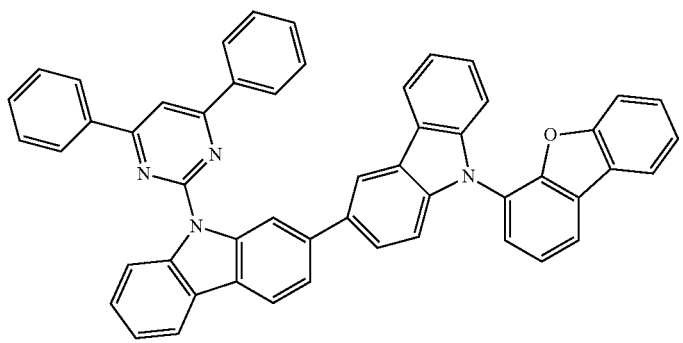

-continued
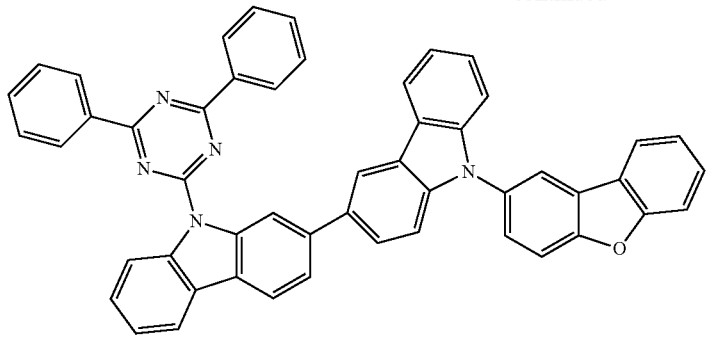
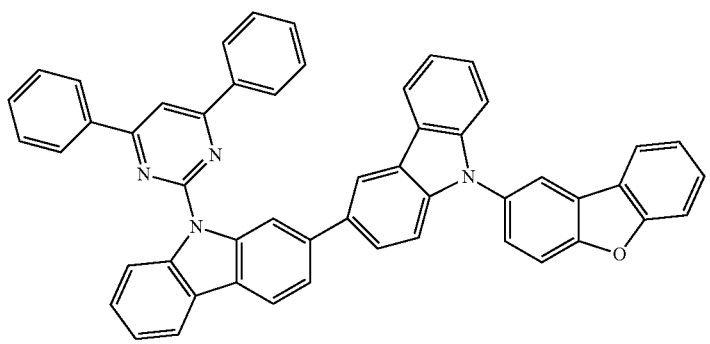
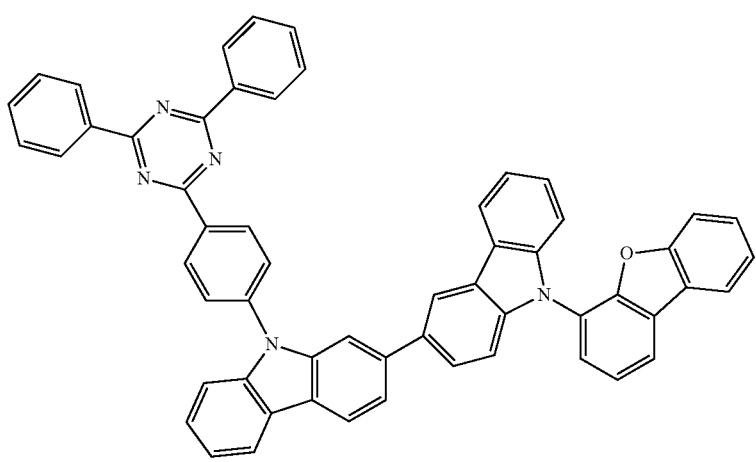
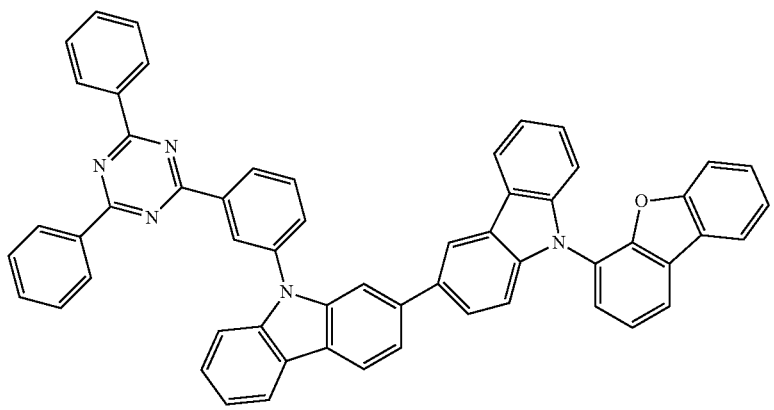

-continued
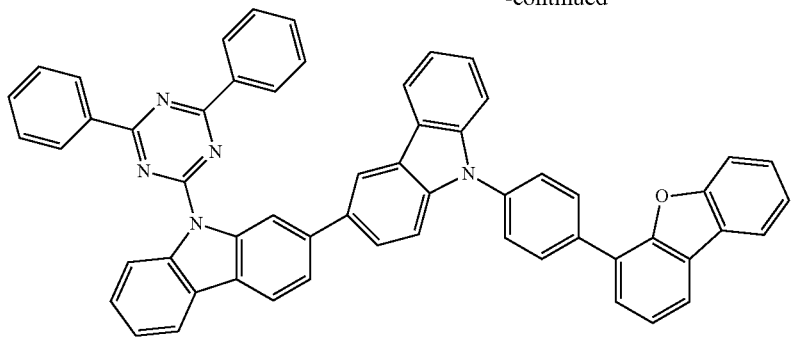
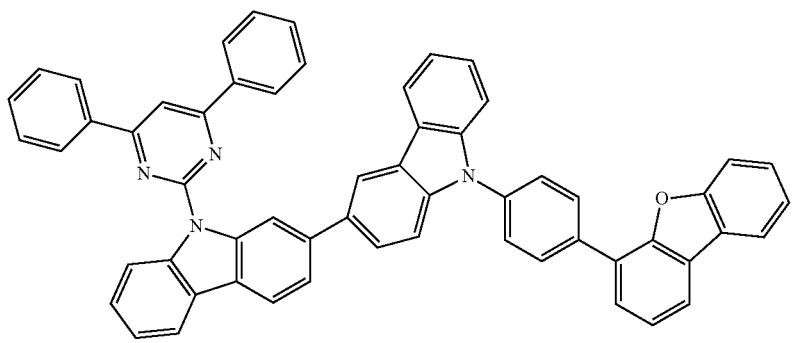
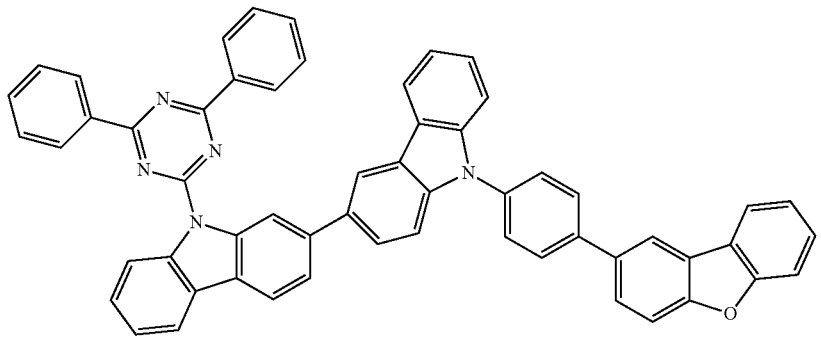
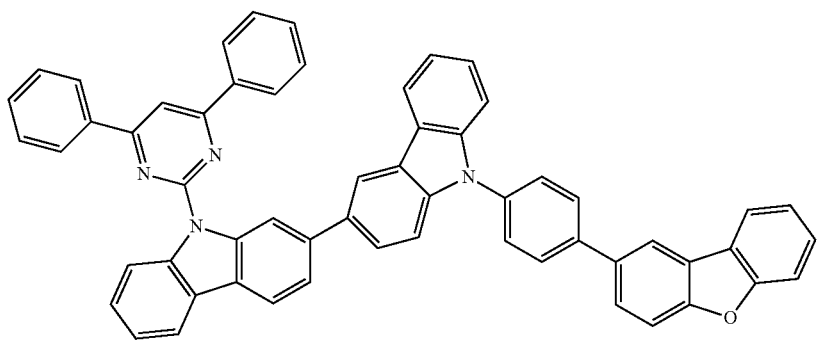

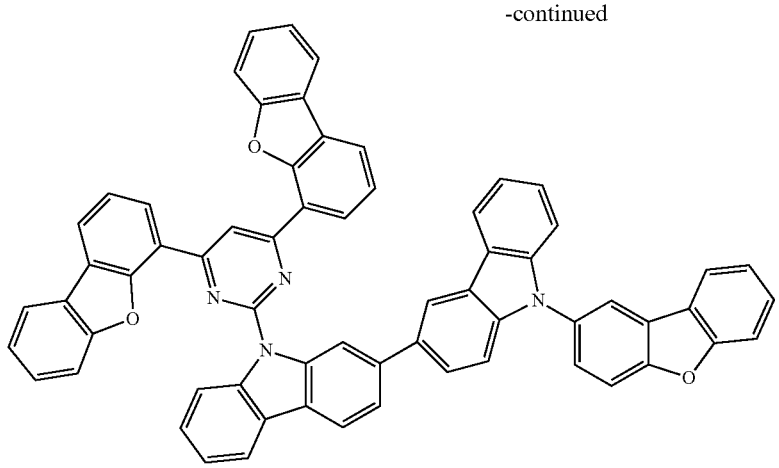
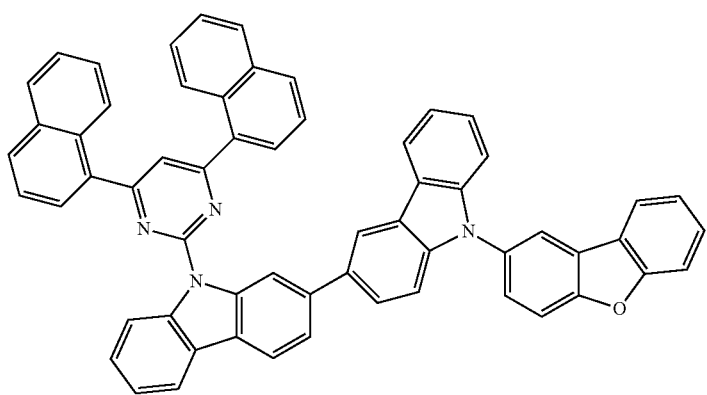
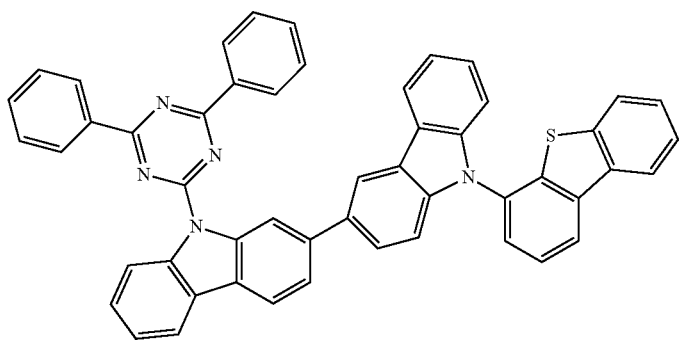
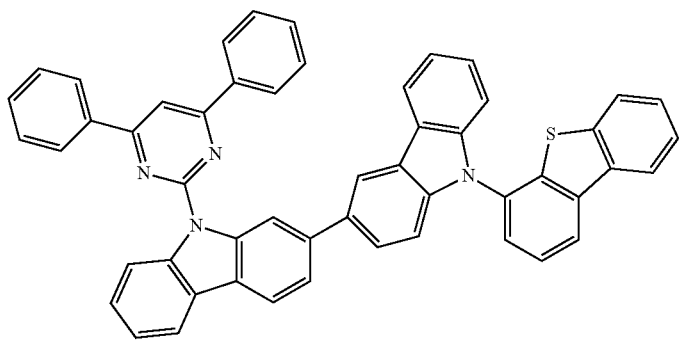

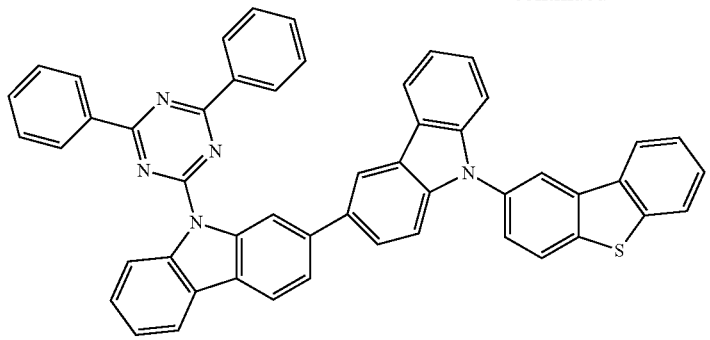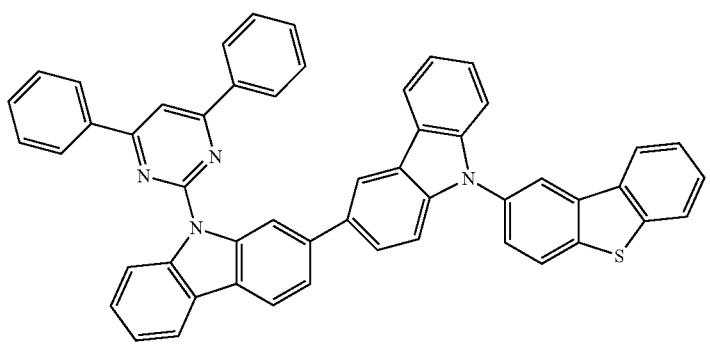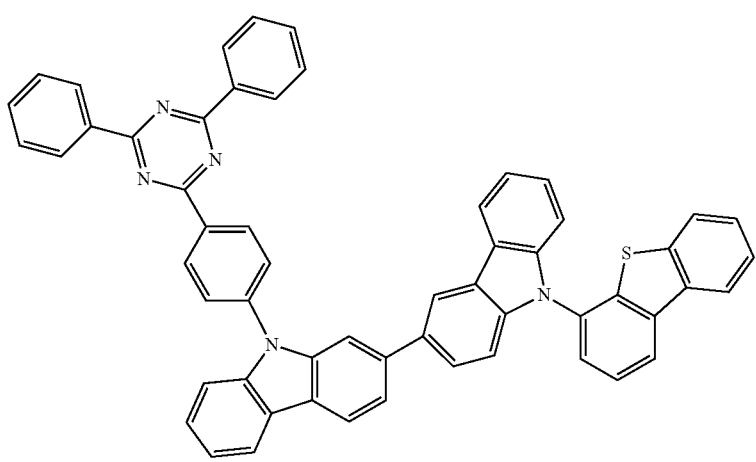 [SMILES: c1ccc(-c2nc(-c3ccccc3)nc(-c3ccc(-n4c5ccccc5c5ccc(-c6ccc7c(c6)c6ccccc6n7-c6cccc7c6sc6ccccc67)cc54)cc3)n2)cc1]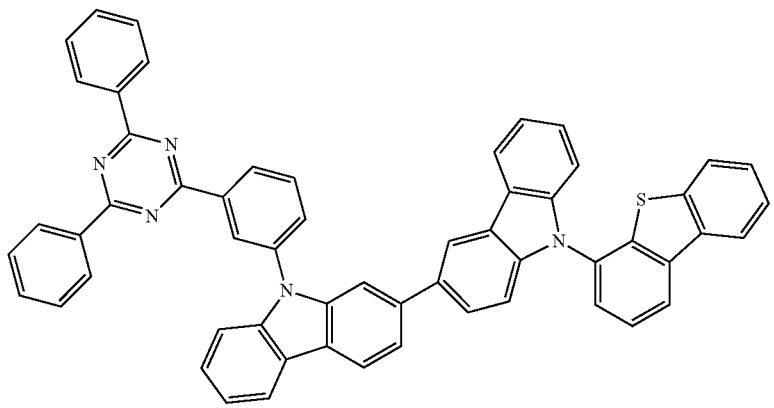

[Chem. 15]
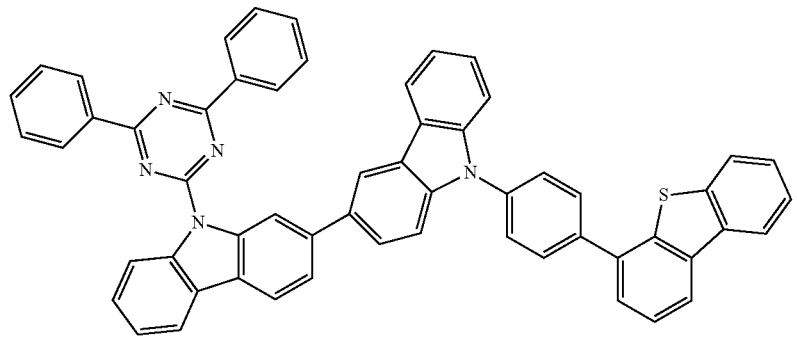
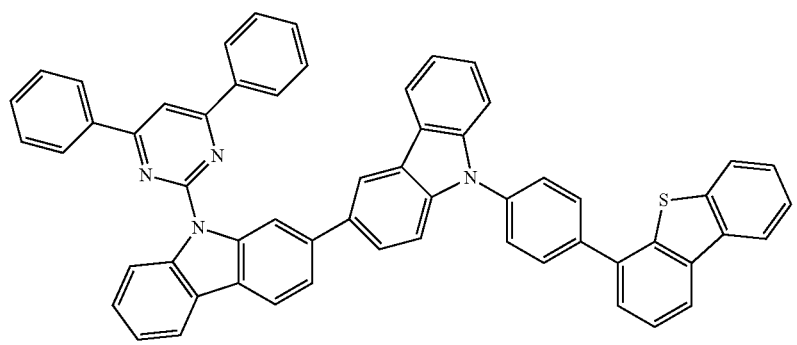
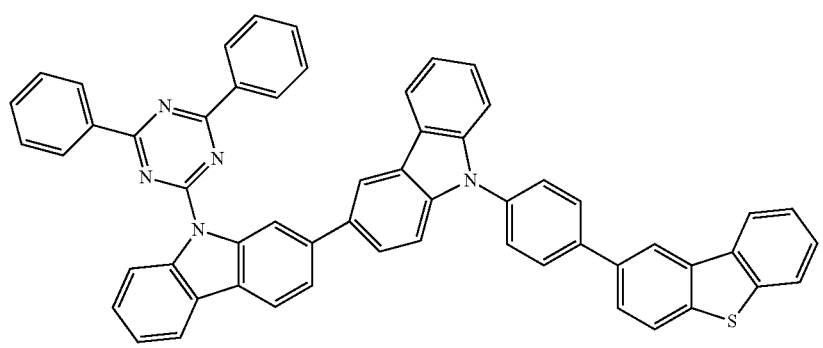
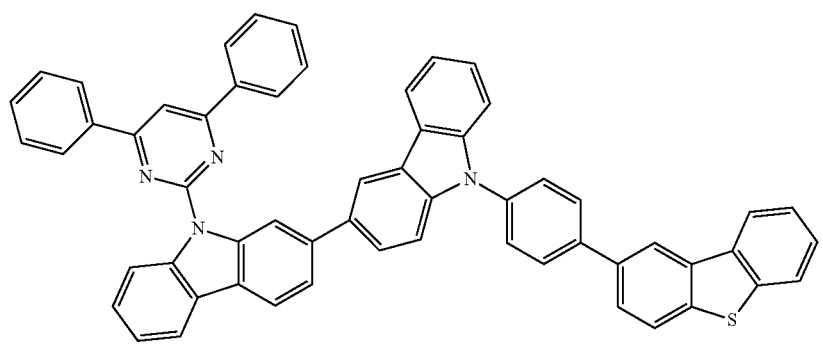

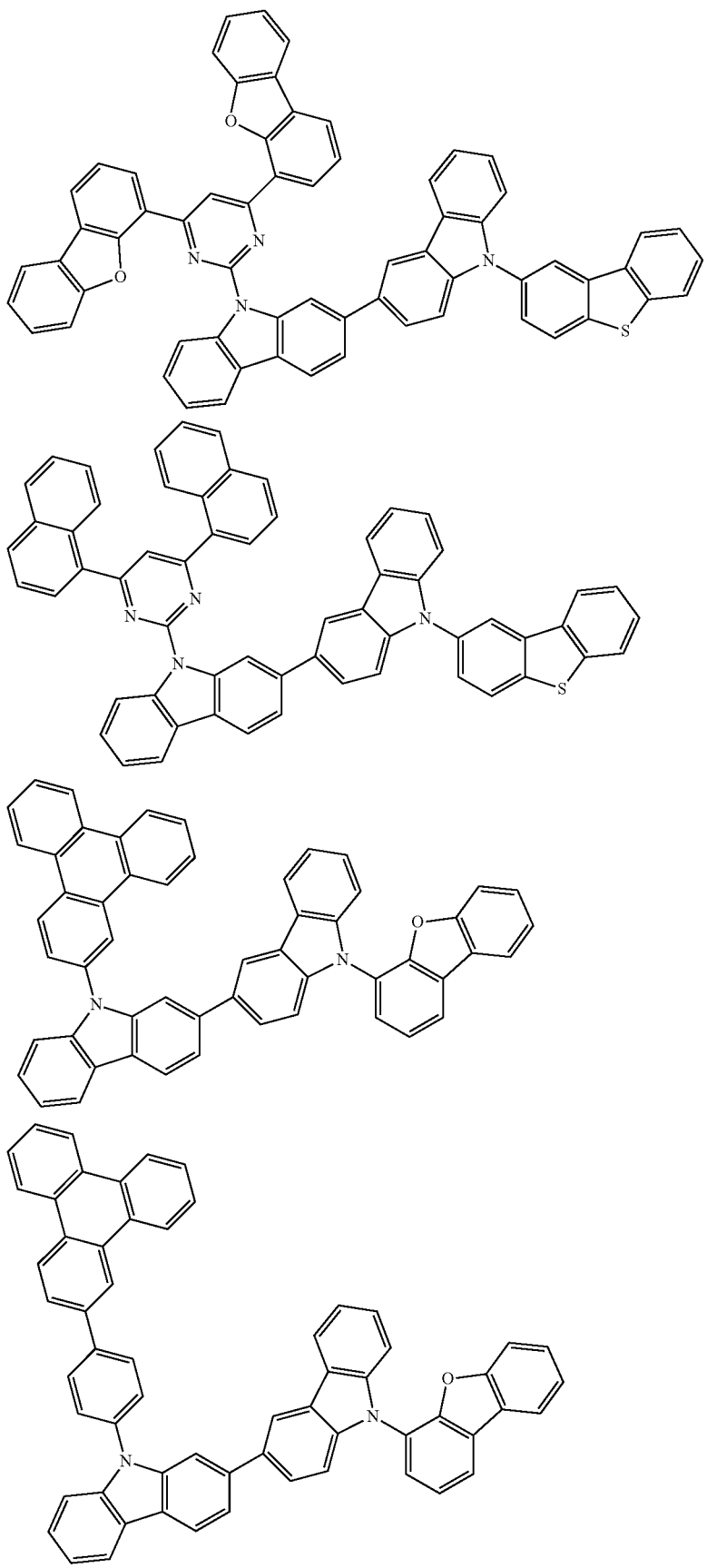

-continued
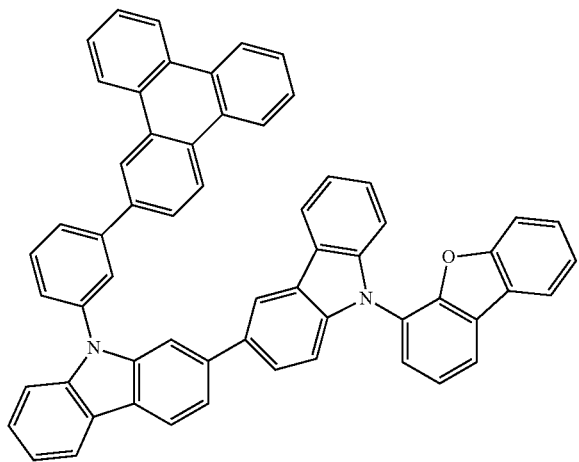
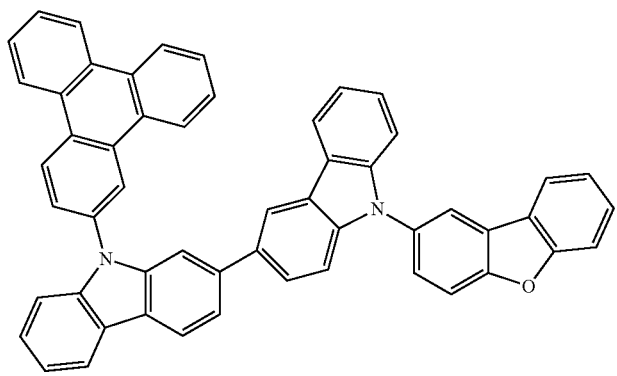
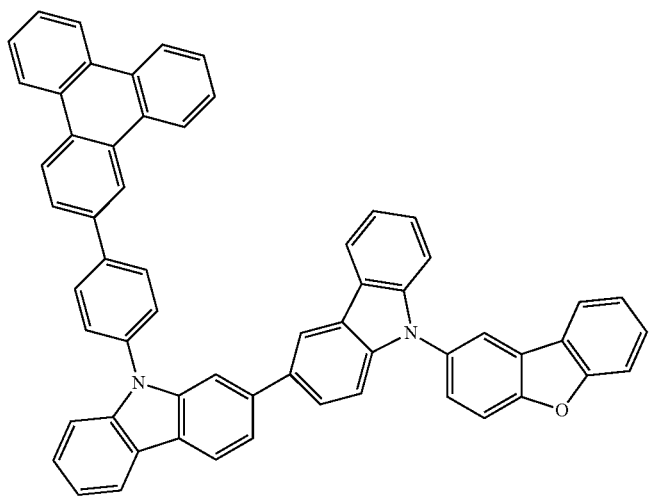

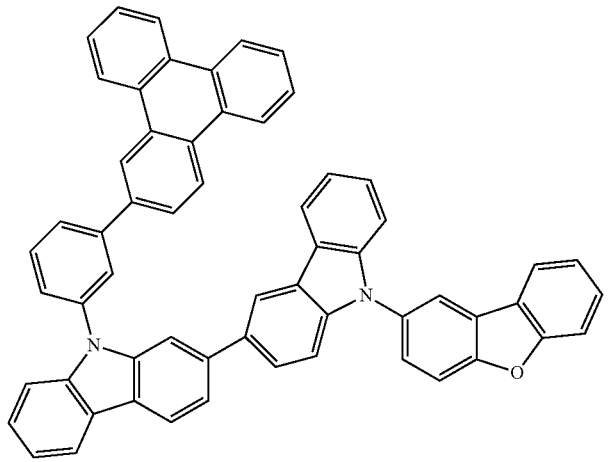
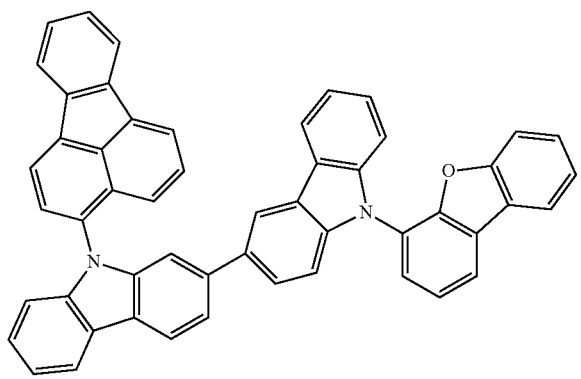
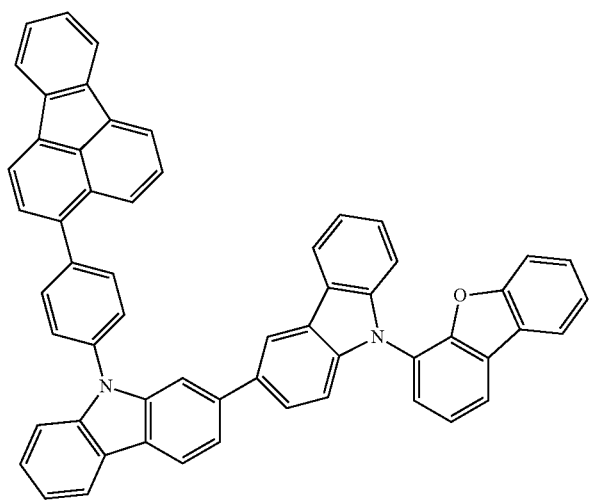

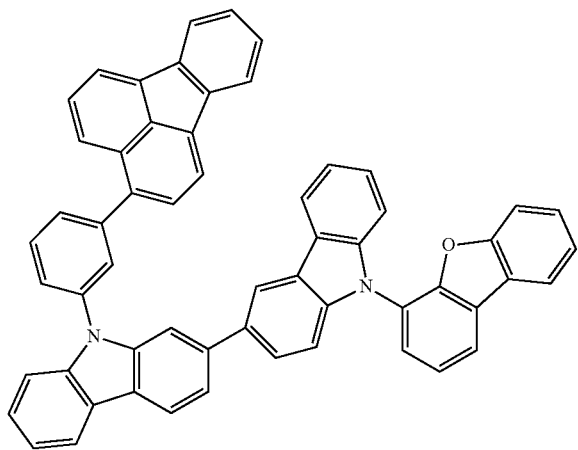
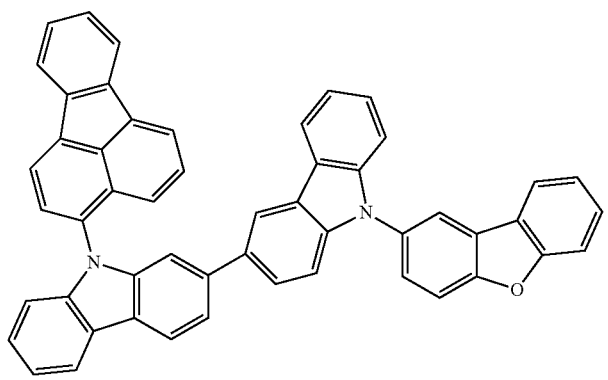
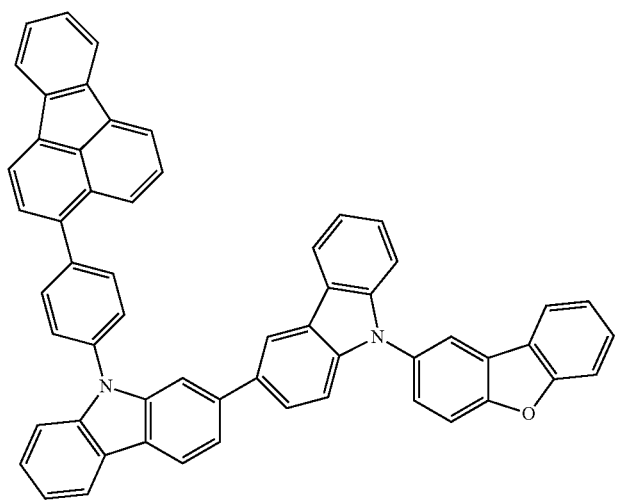

-continued
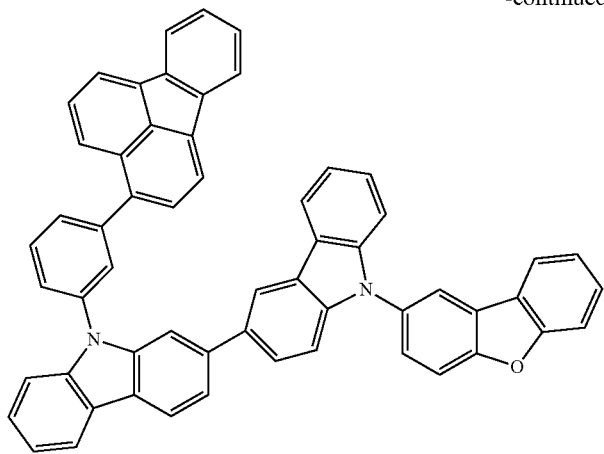
[Chem. 16]
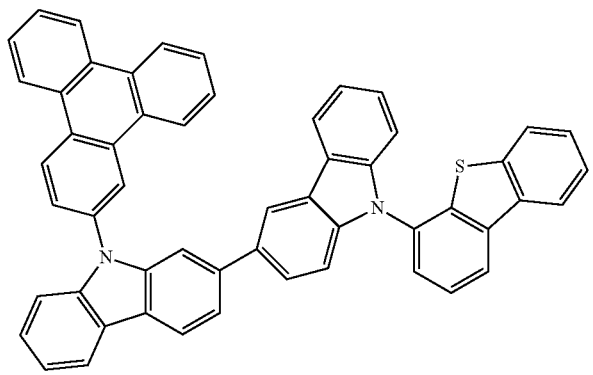
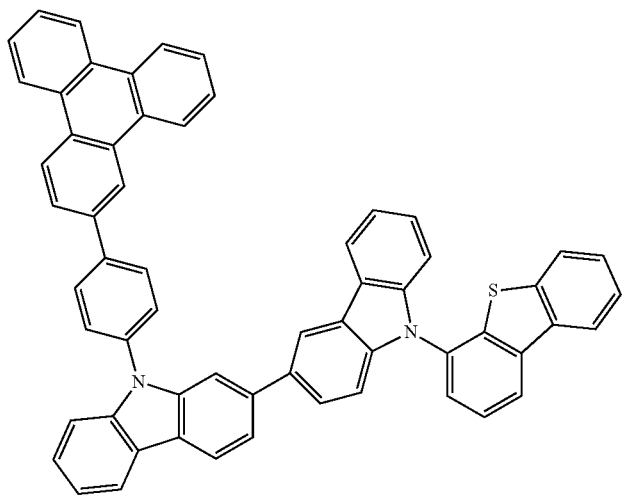

-continued
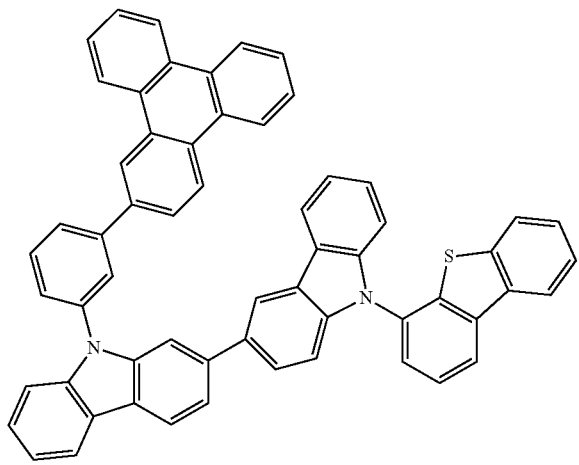
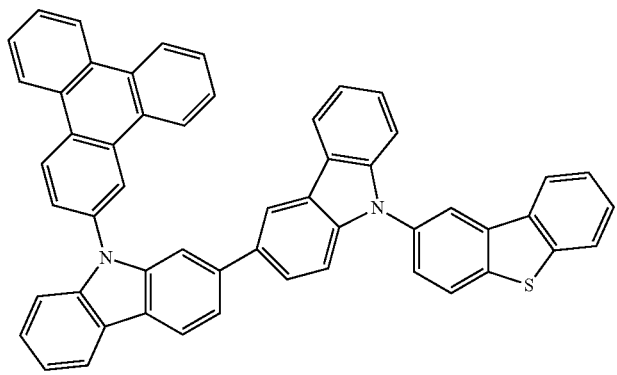
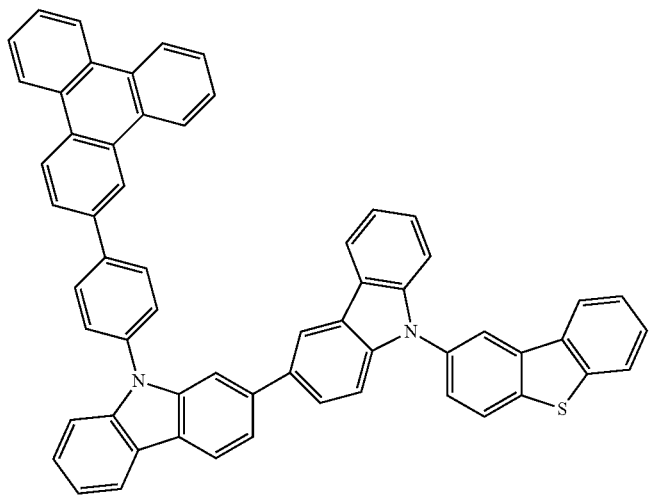

-continued
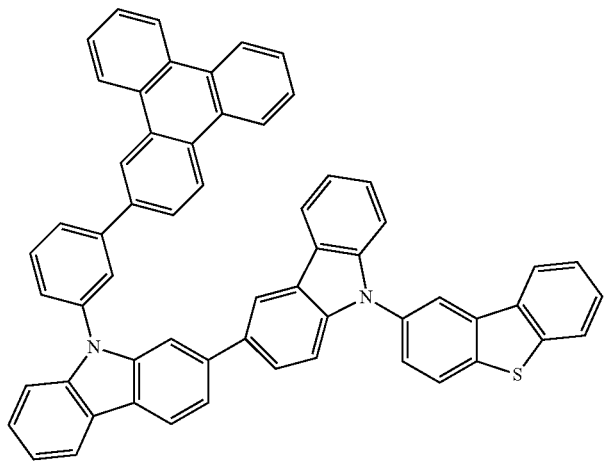
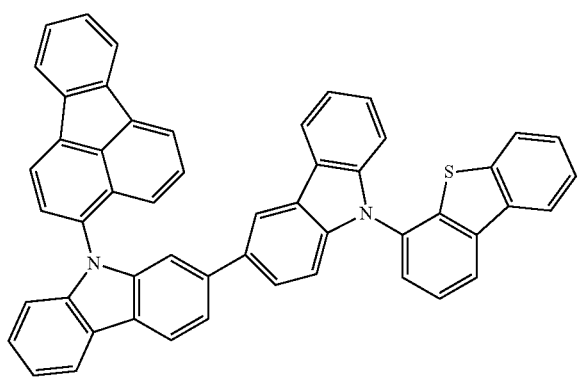
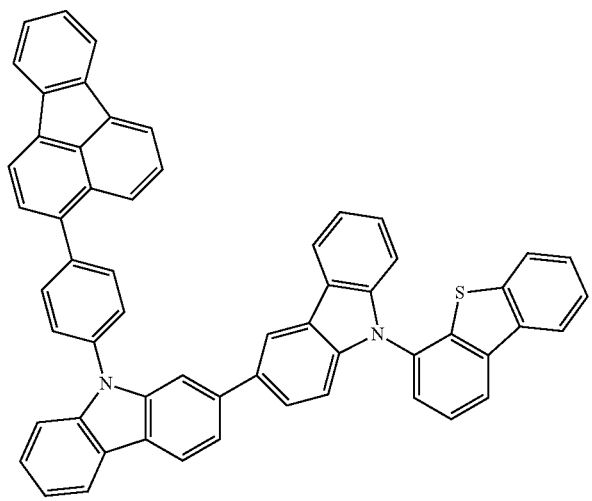

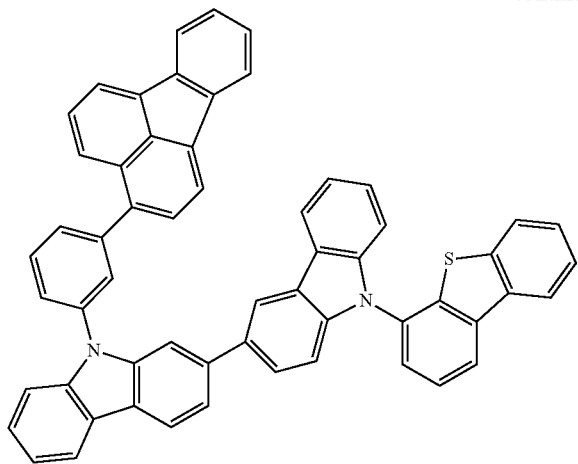
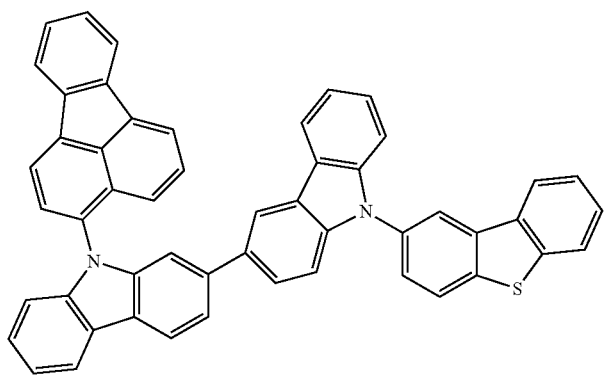
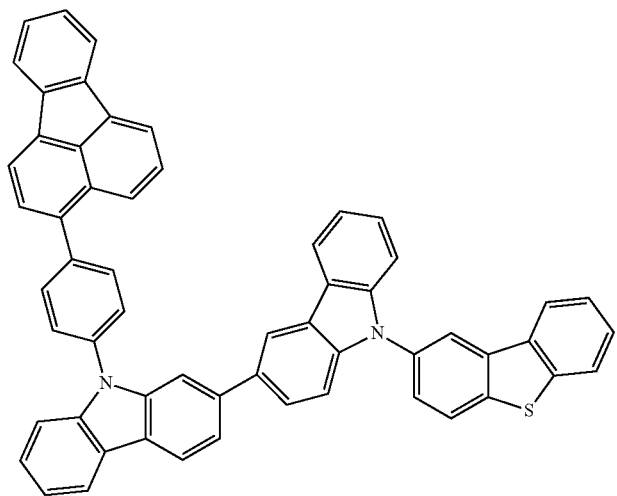

-continued
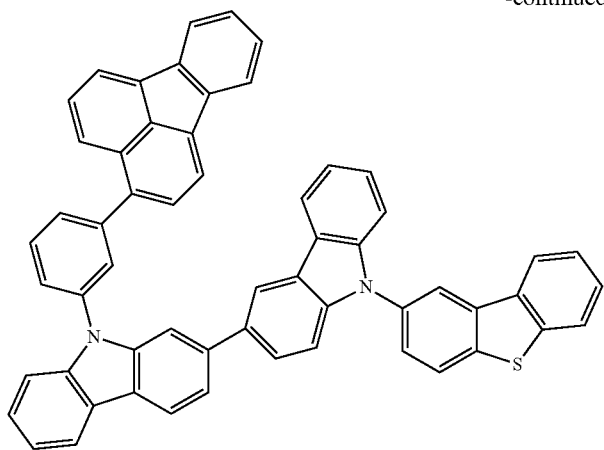
[Chem. 17]
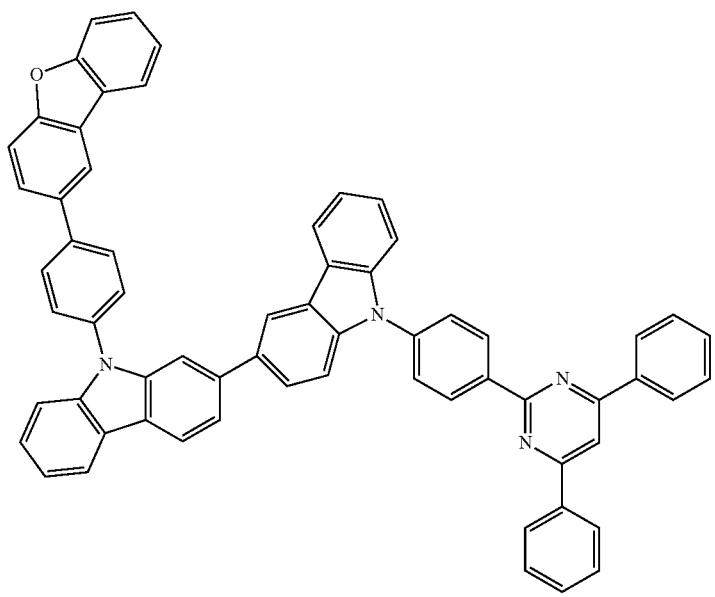
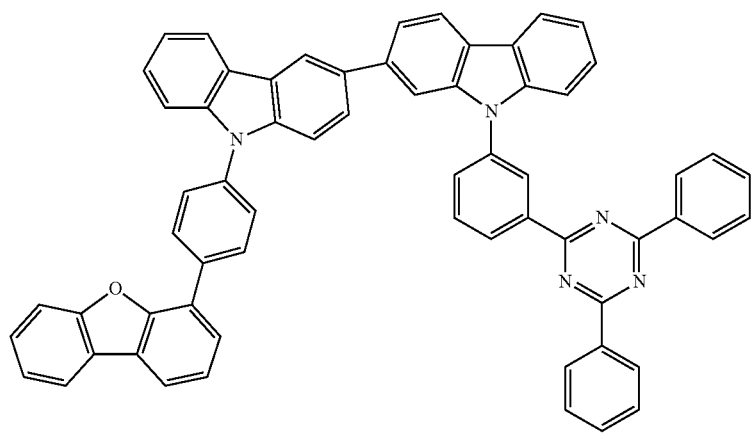

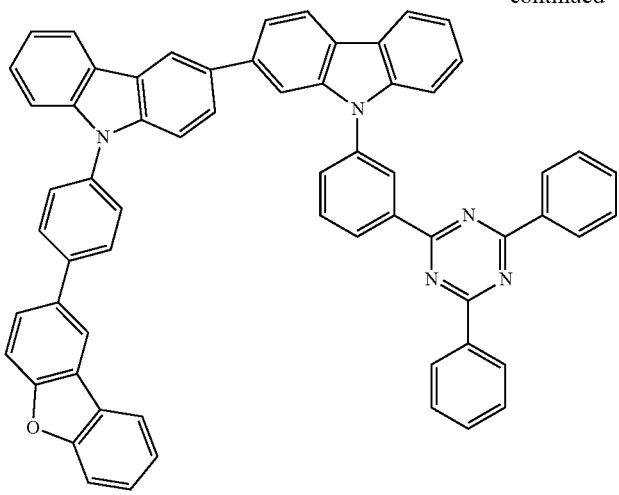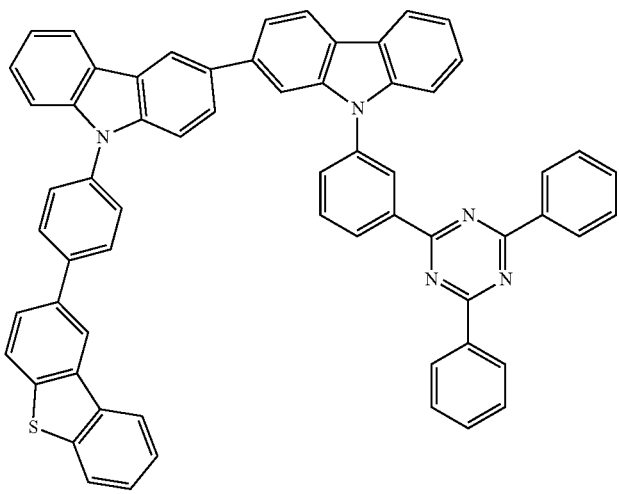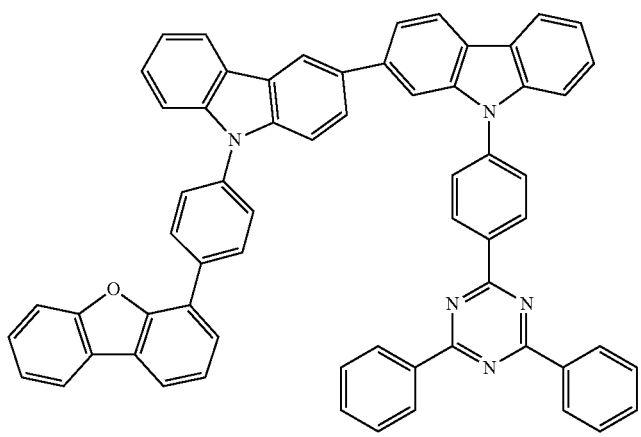

89
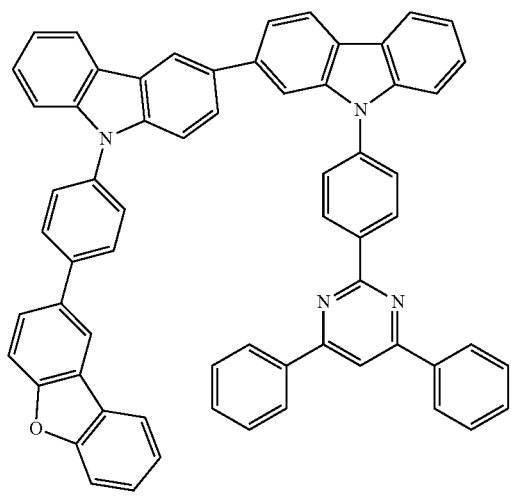
90
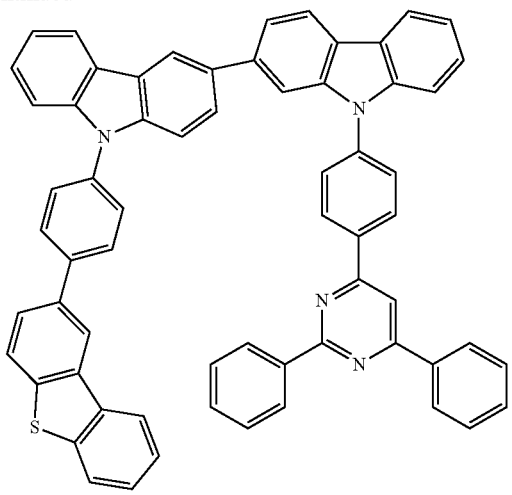
[Chem. 18]
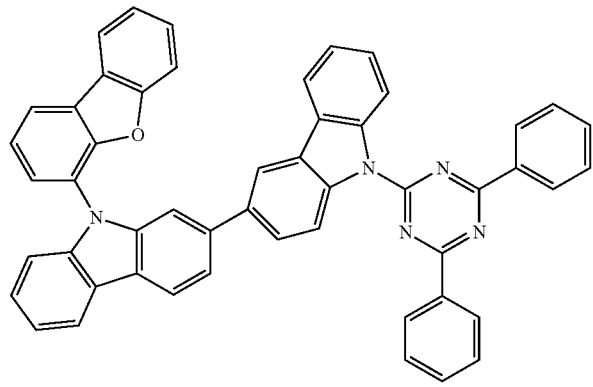
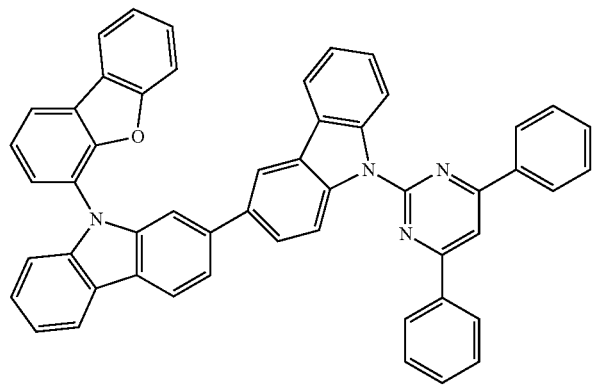
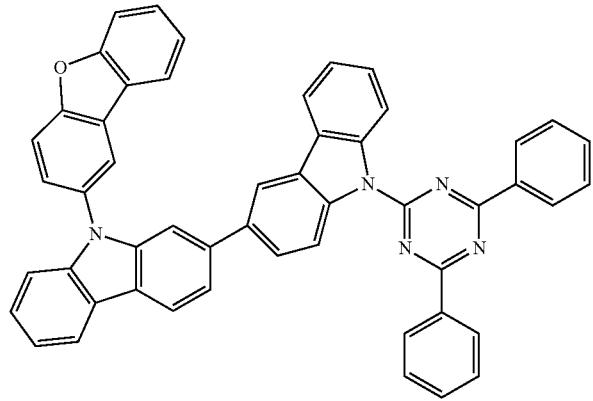

-continued
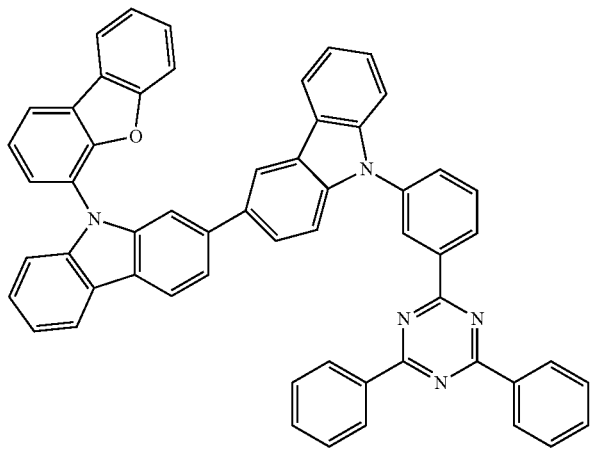
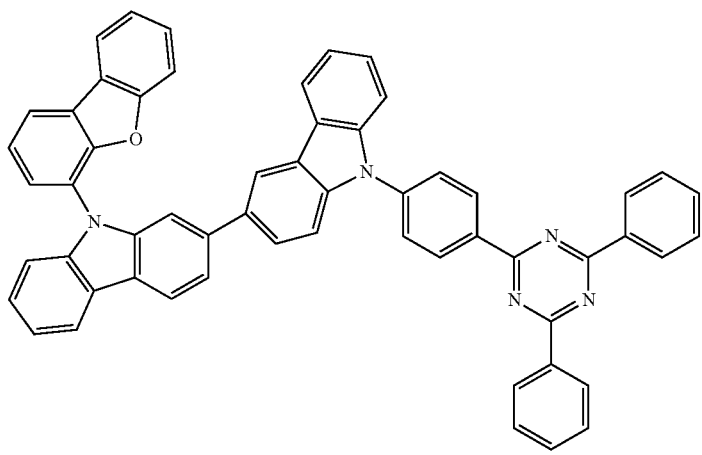
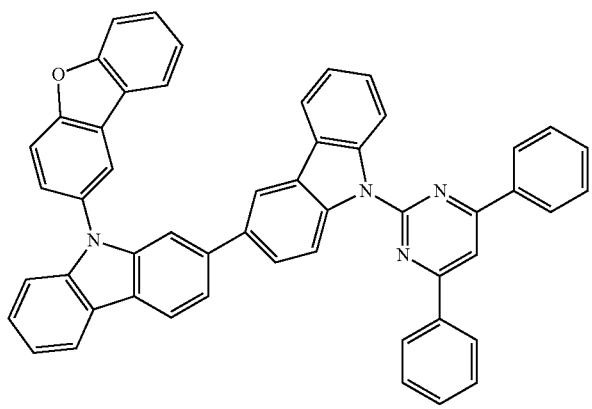
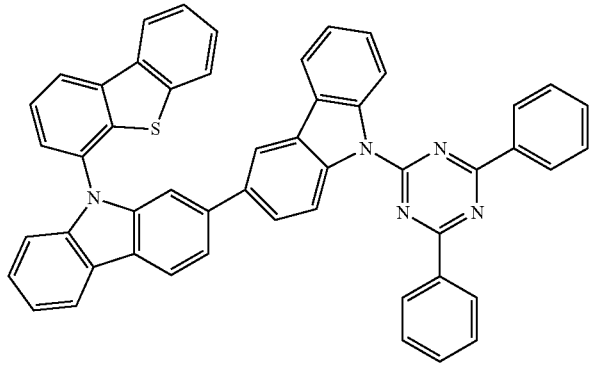

-continued
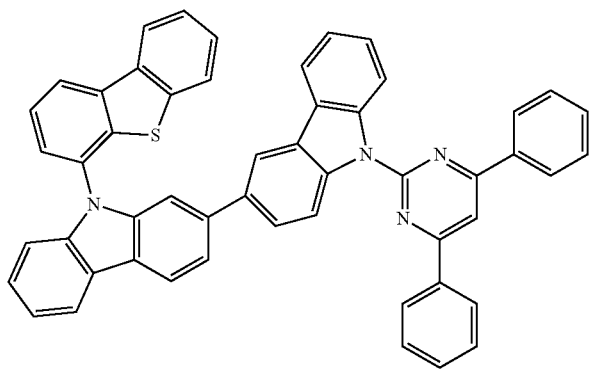
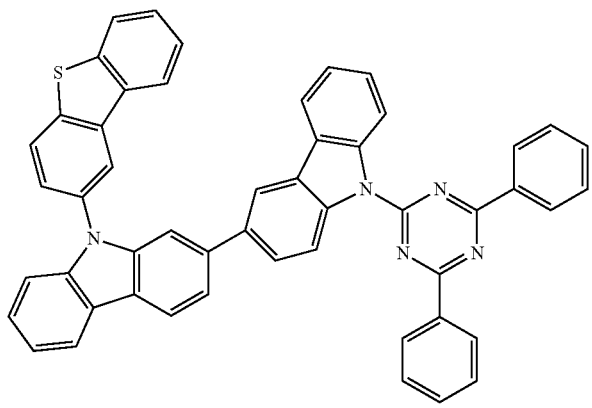
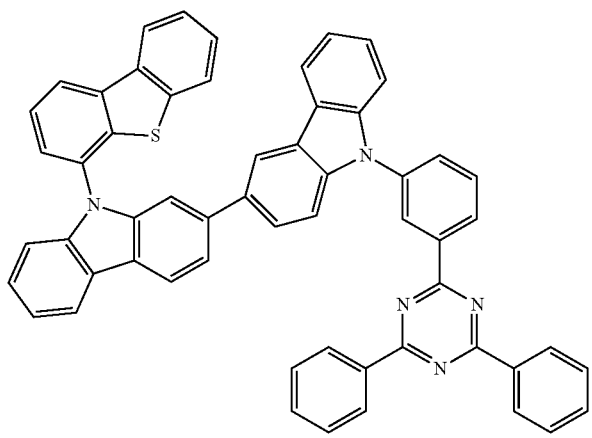
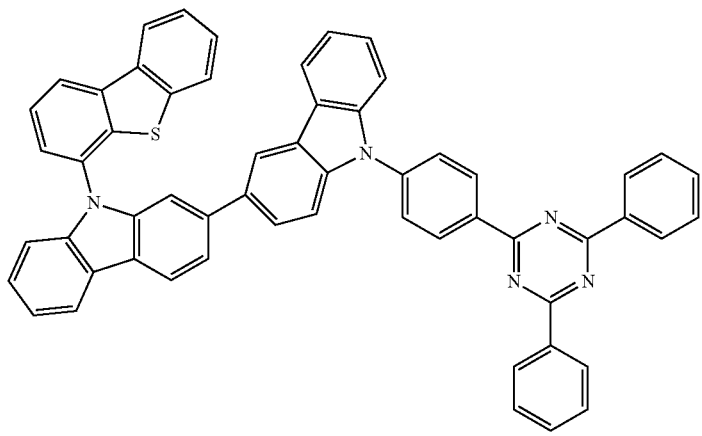

-continued
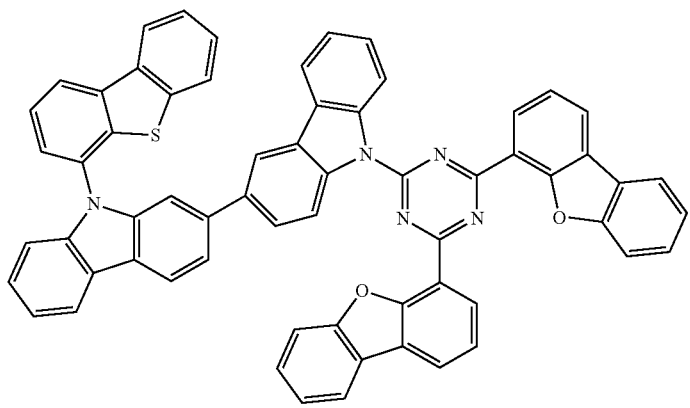
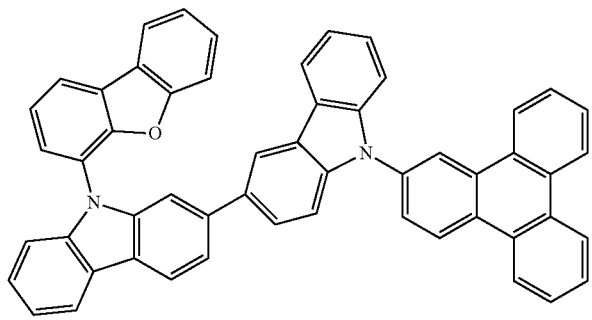
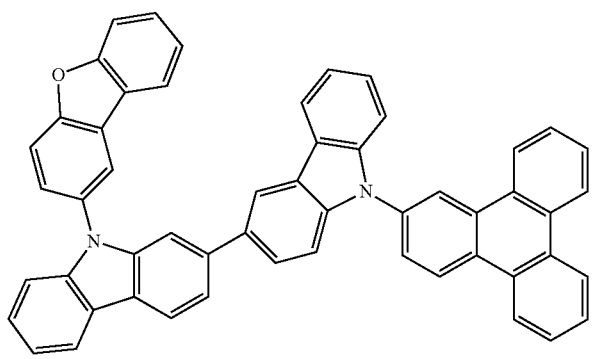
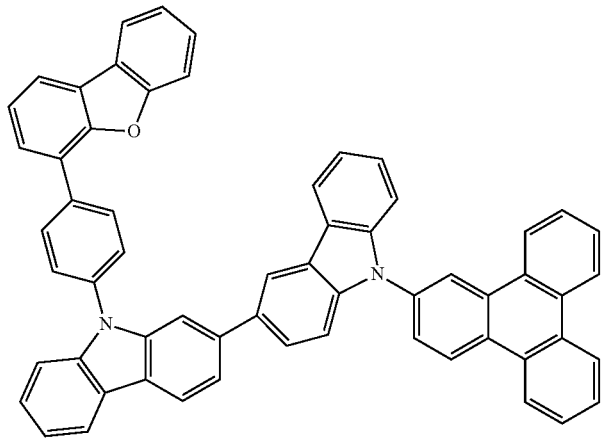

-continued
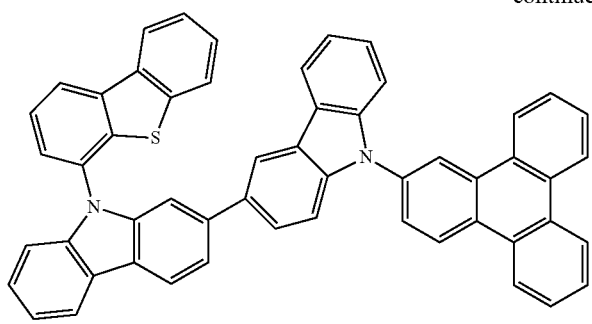
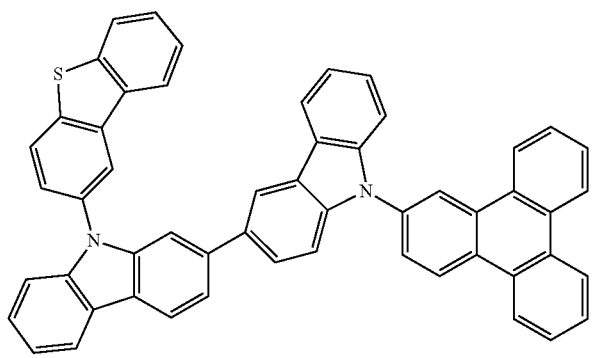
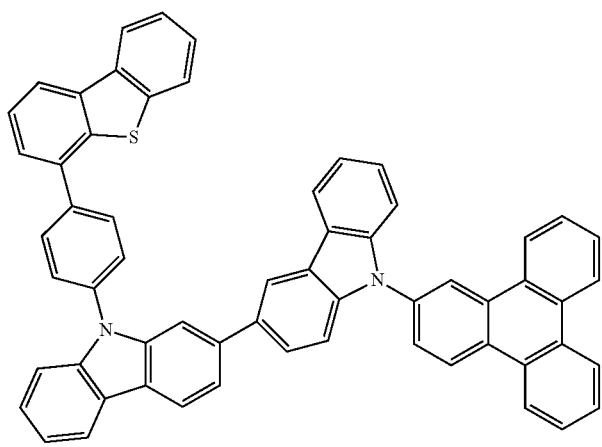

[Chem. 19]
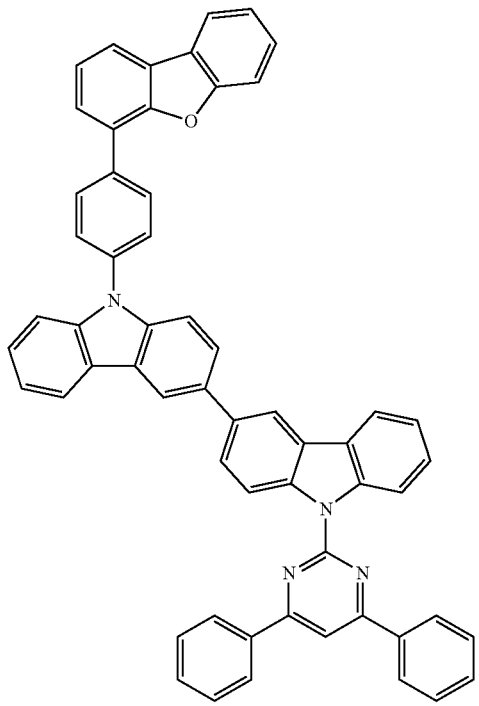
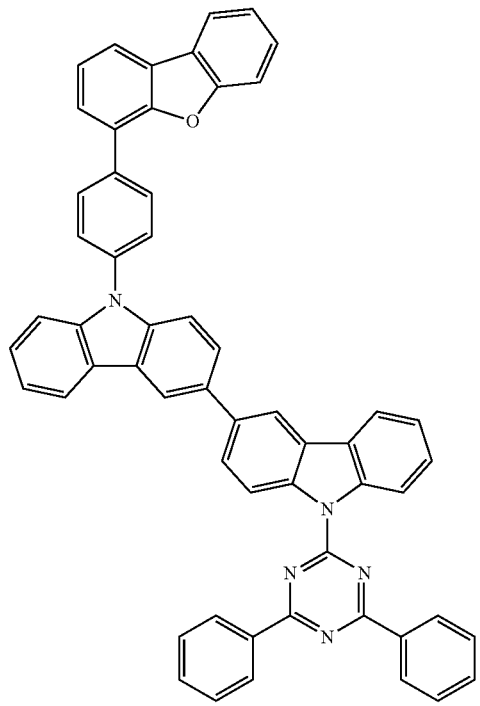
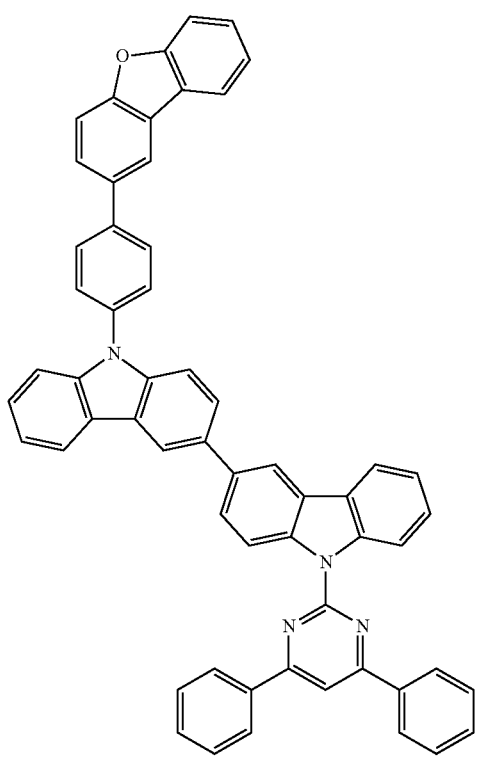
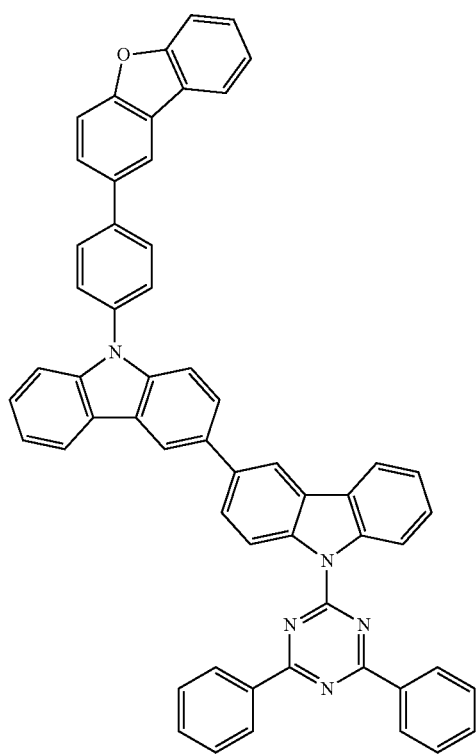

101 102
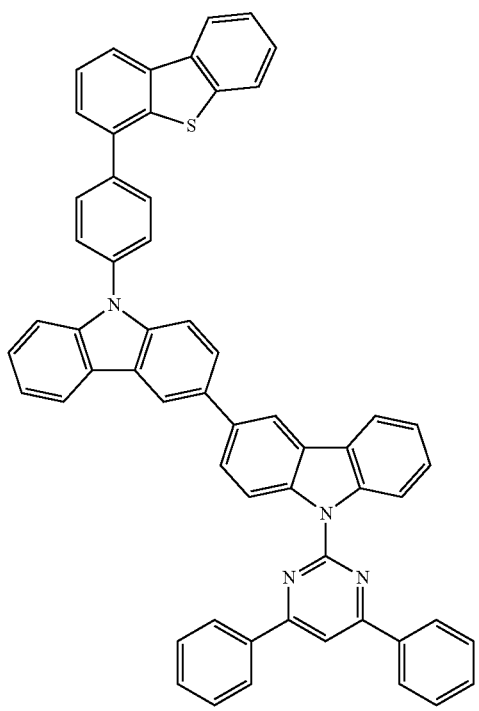
-continued

-continued
103
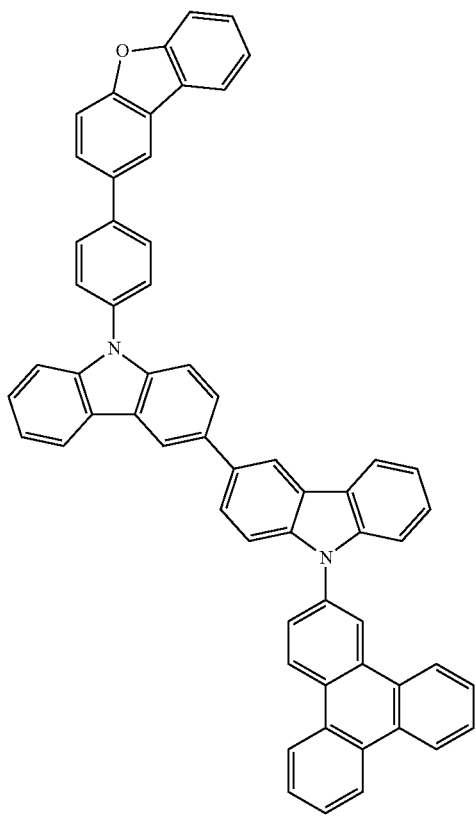
104
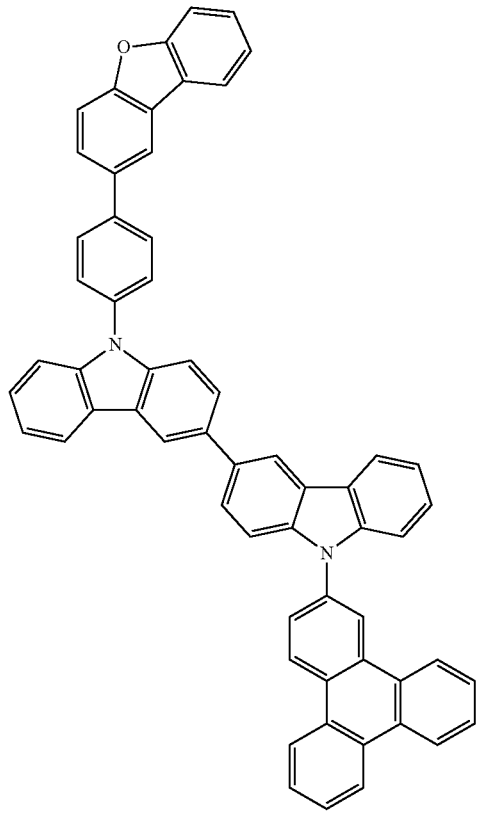
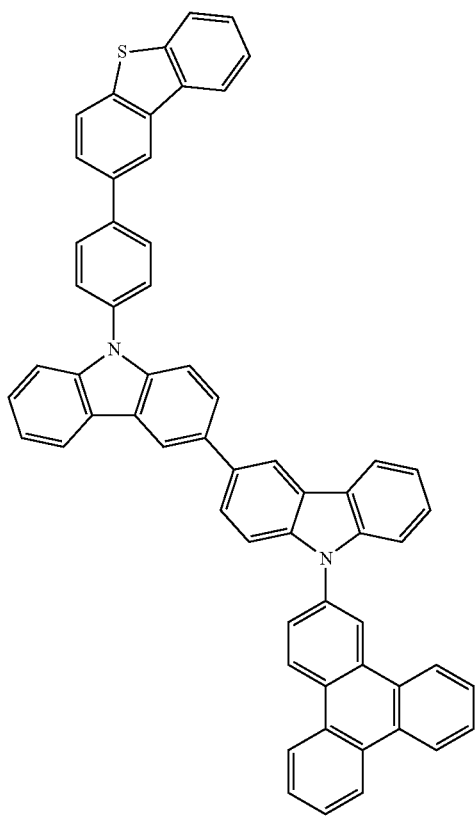
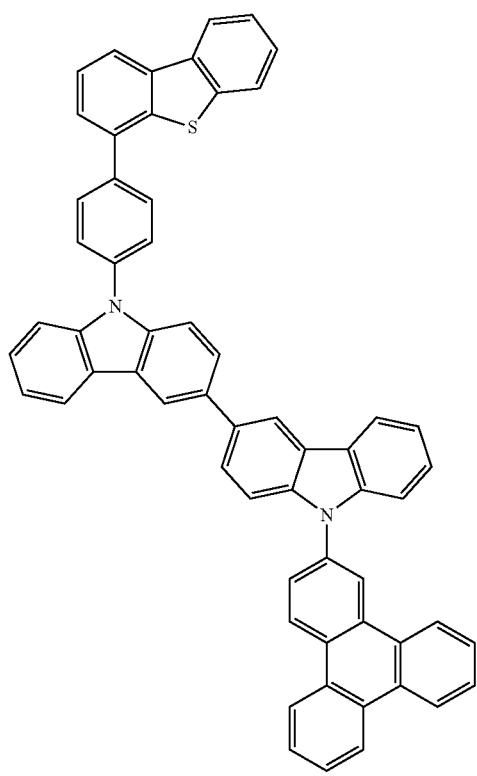

[Chem. 20]
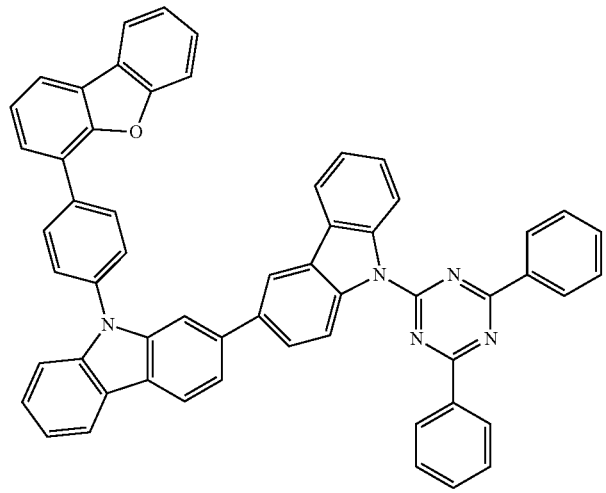
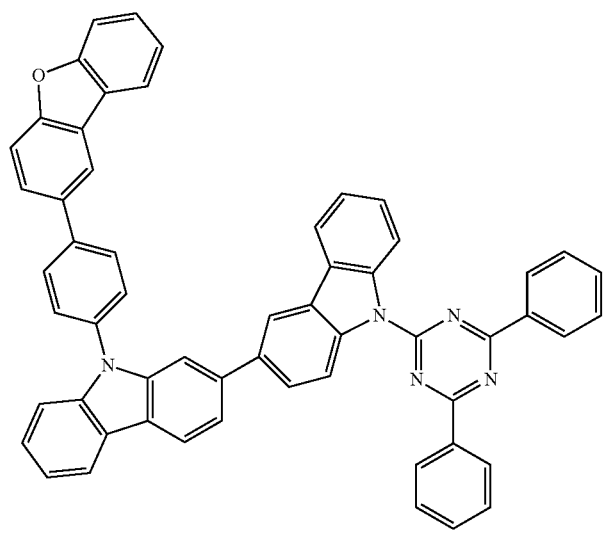
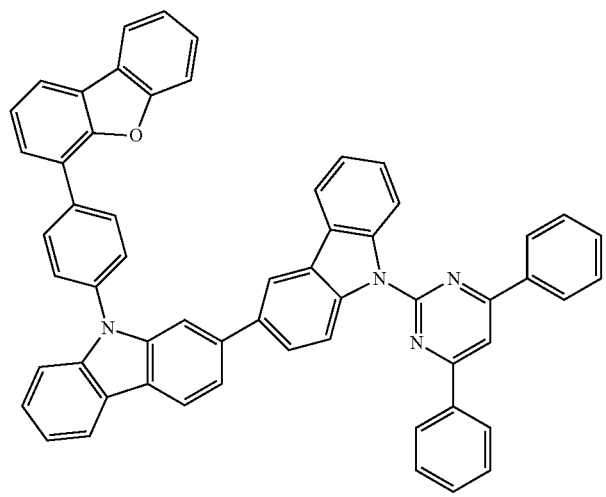

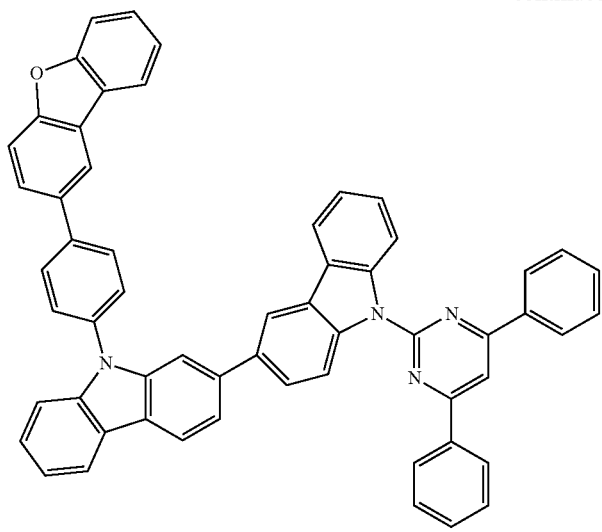
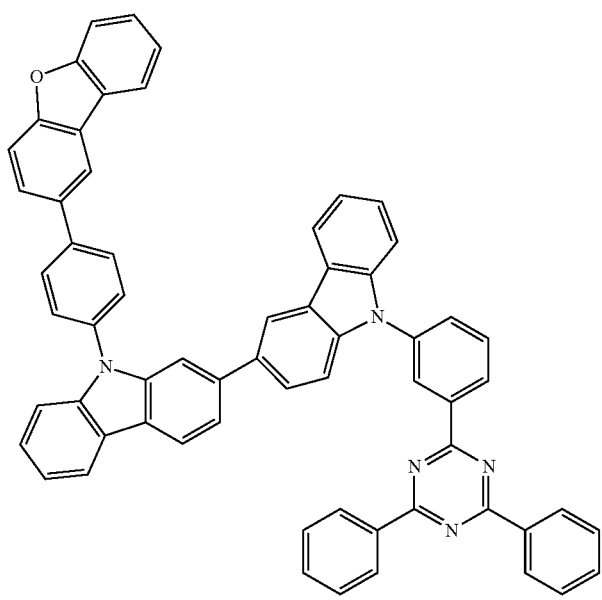
[Chem. 21]
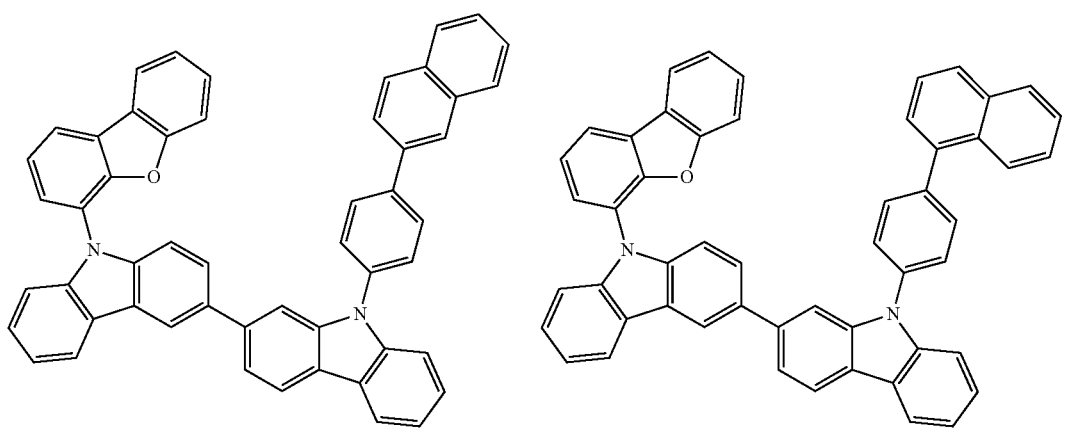

-continued
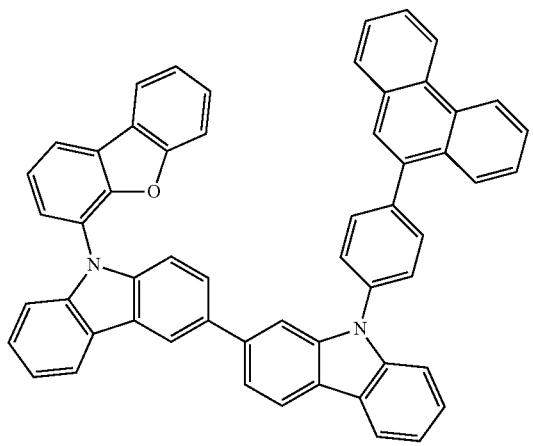
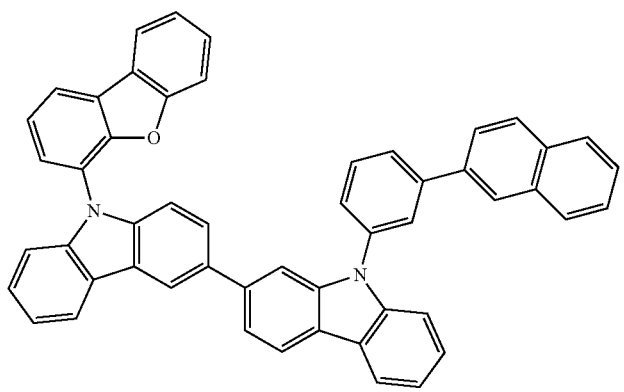
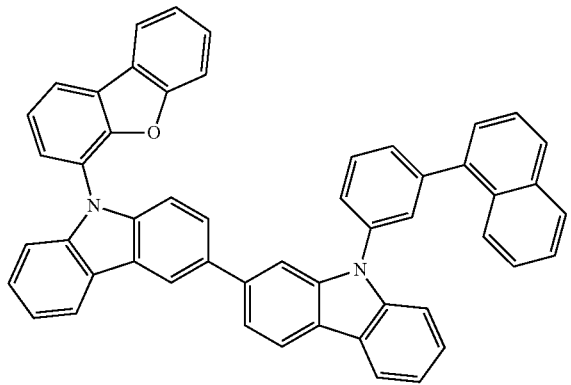
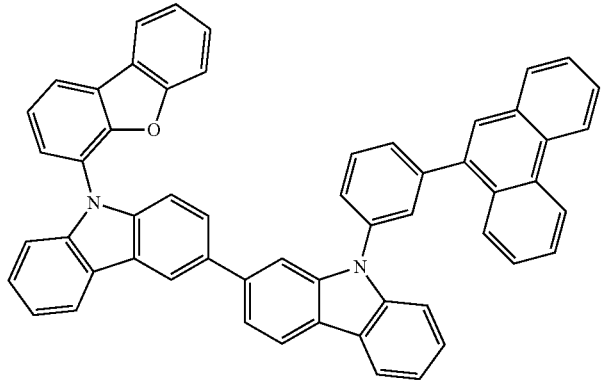

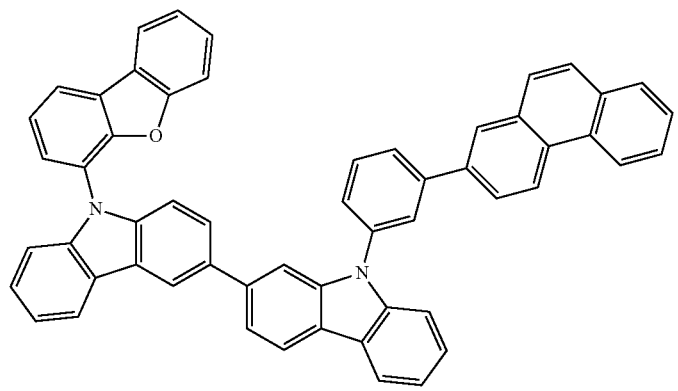
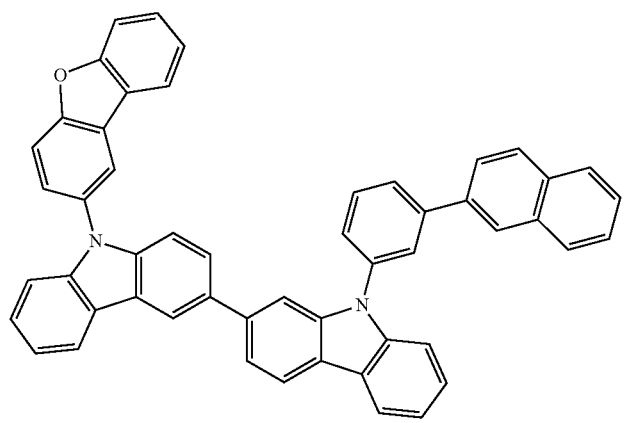
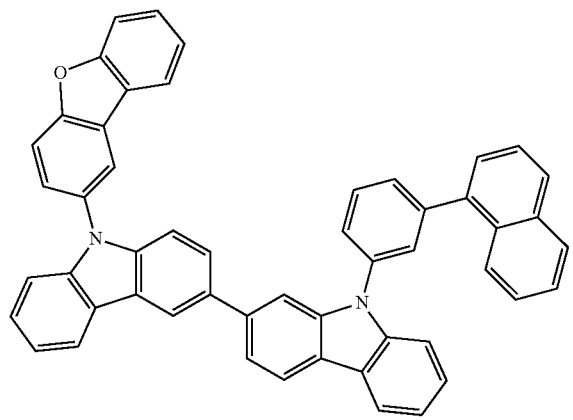
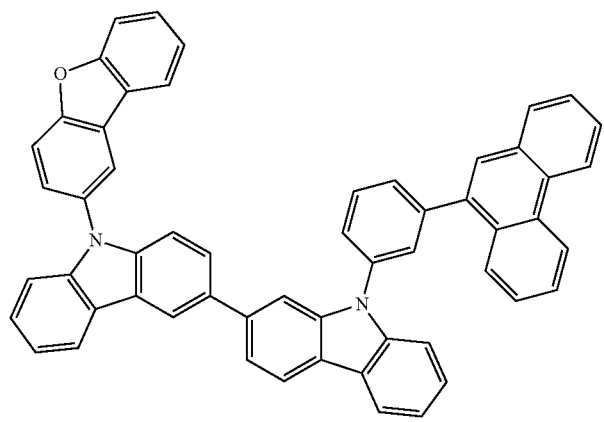

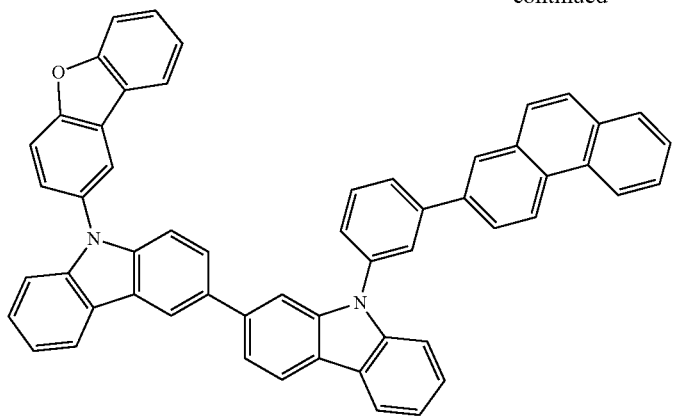
[Chem. 22]
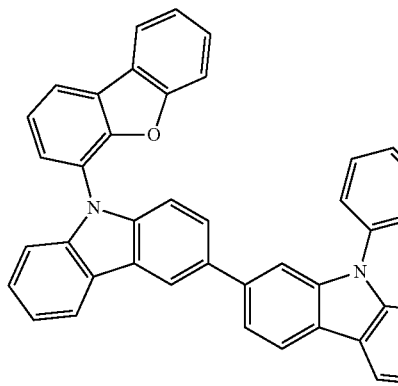 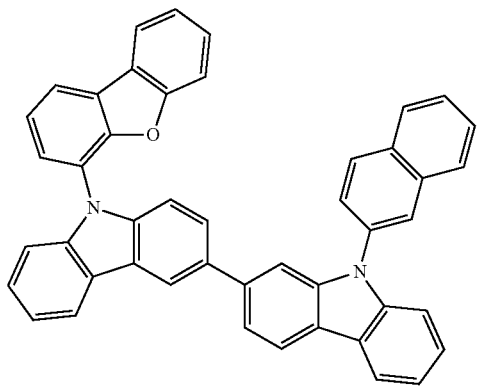
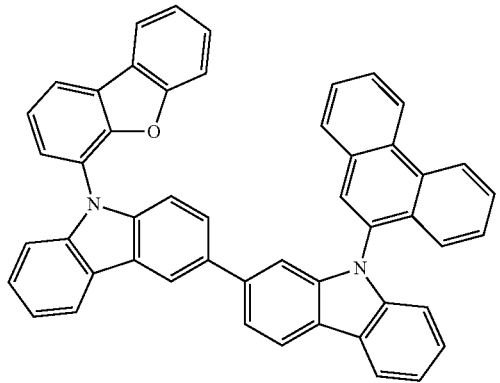 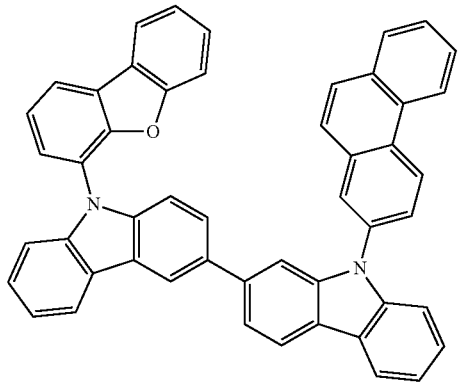
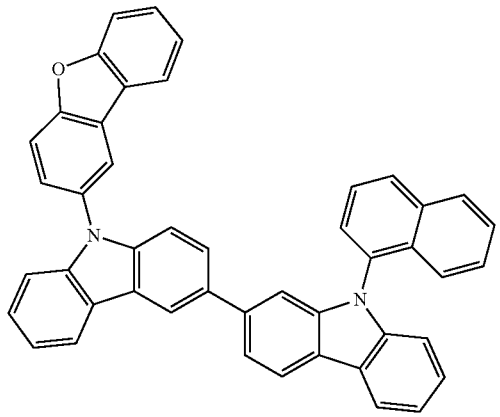 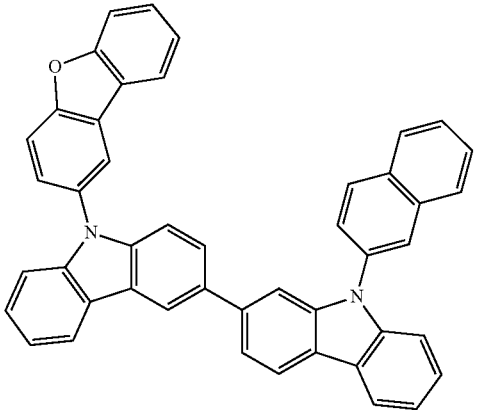

-continued
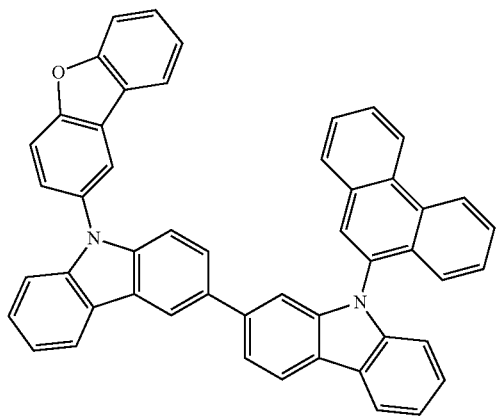
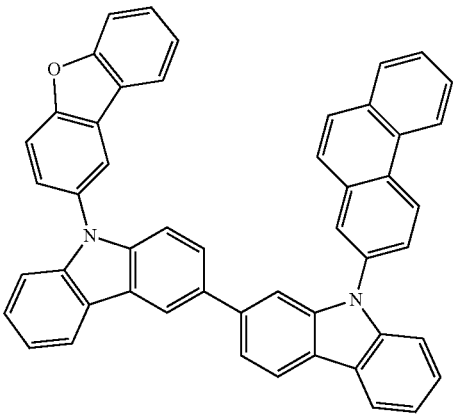
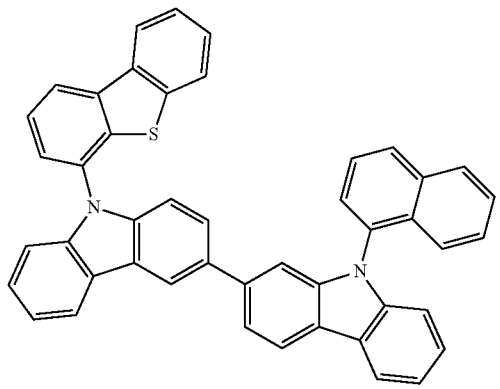
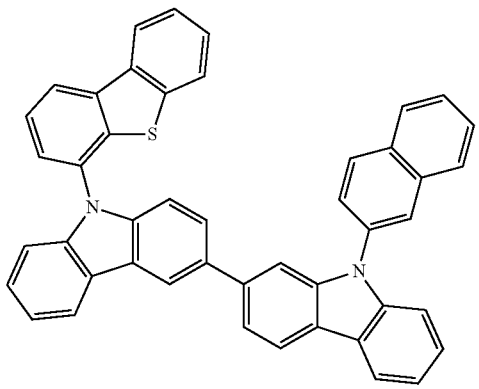
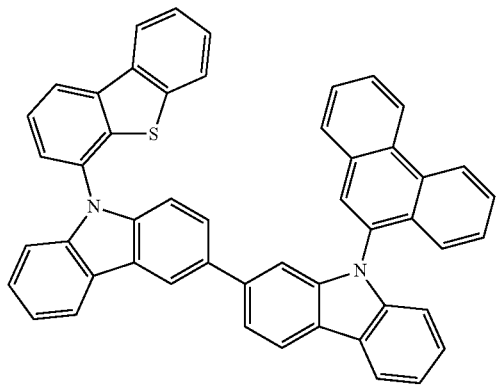
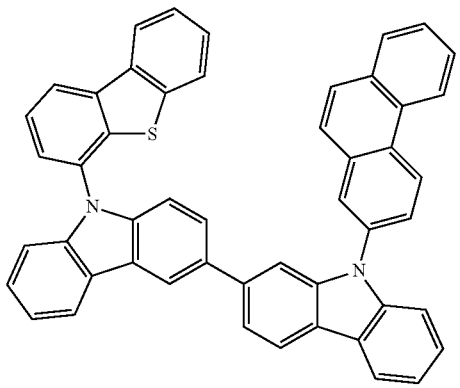
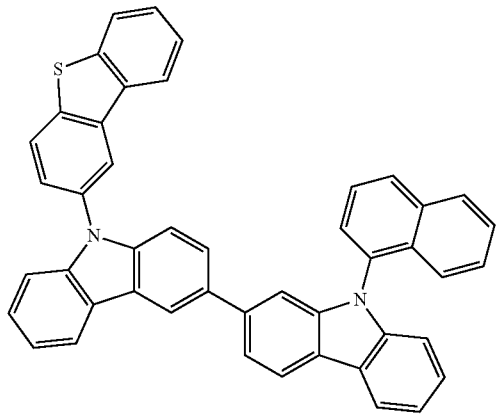
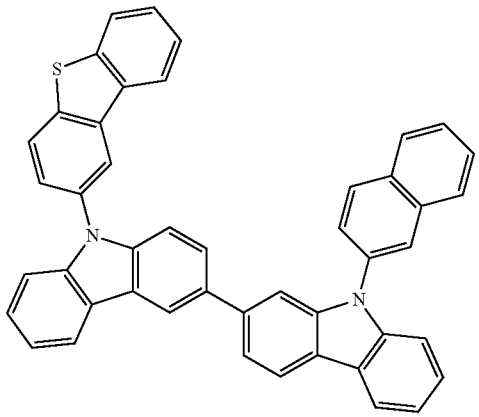

-continued
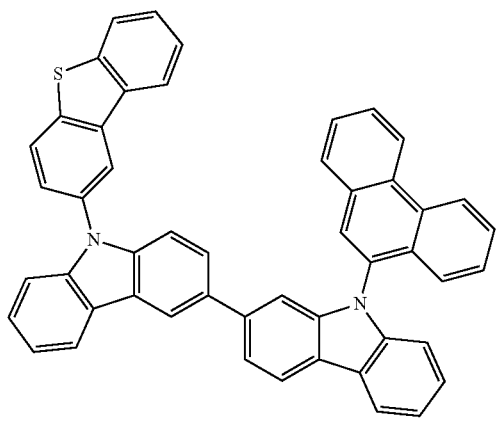
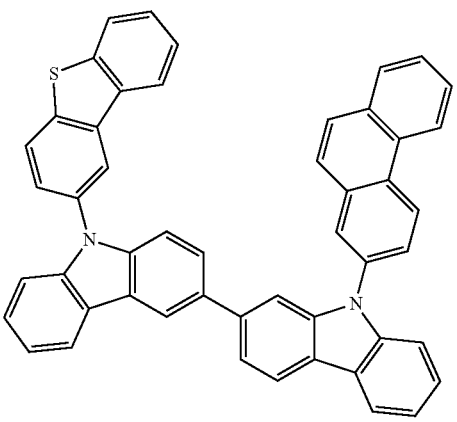
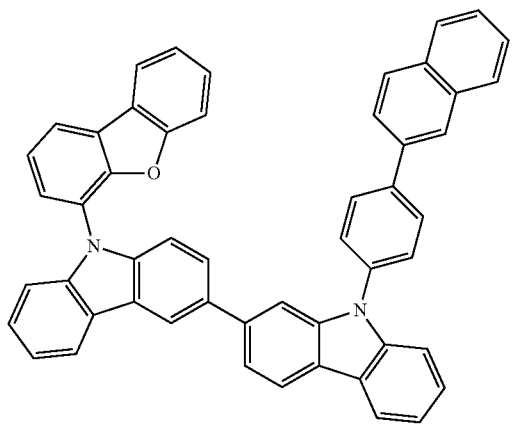
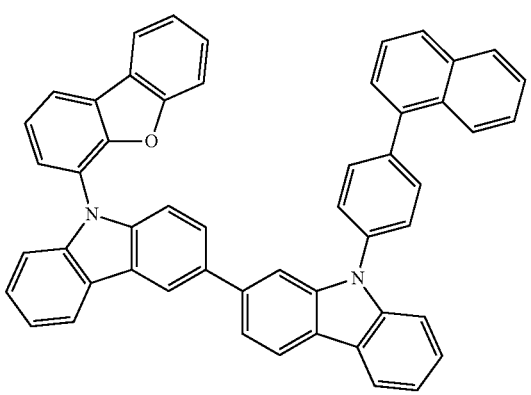
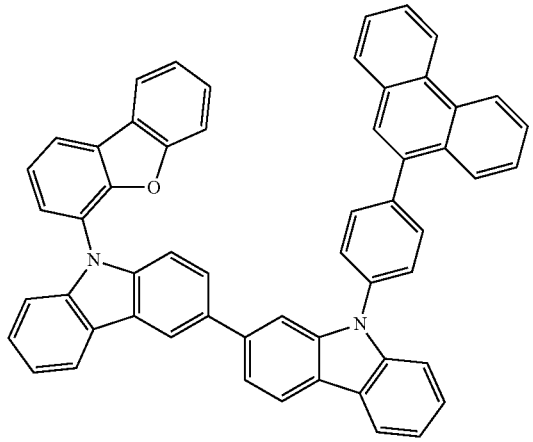
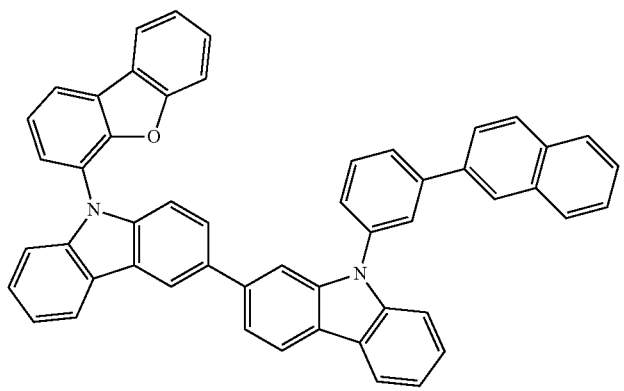

-continued
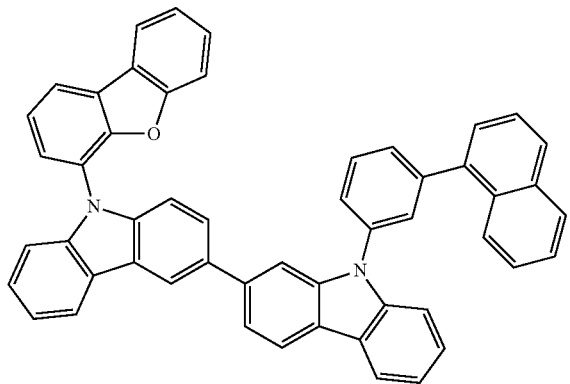
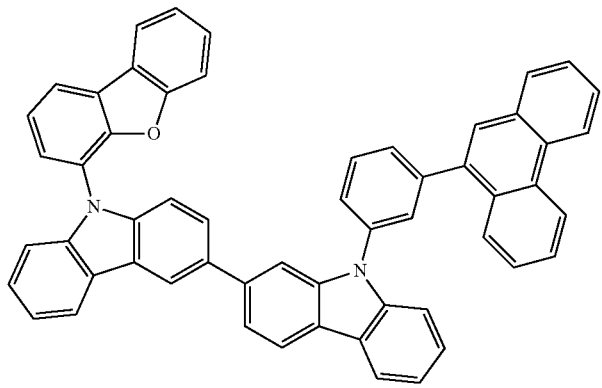
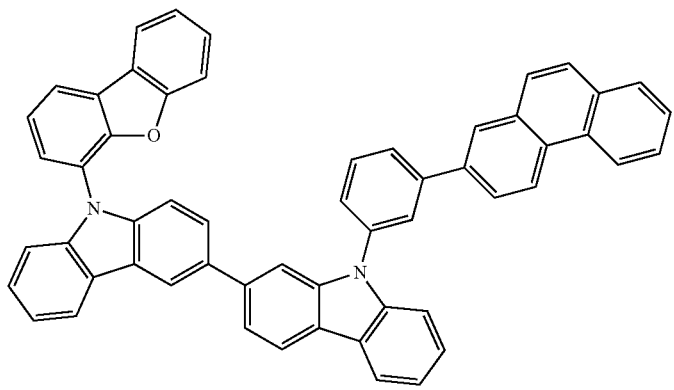
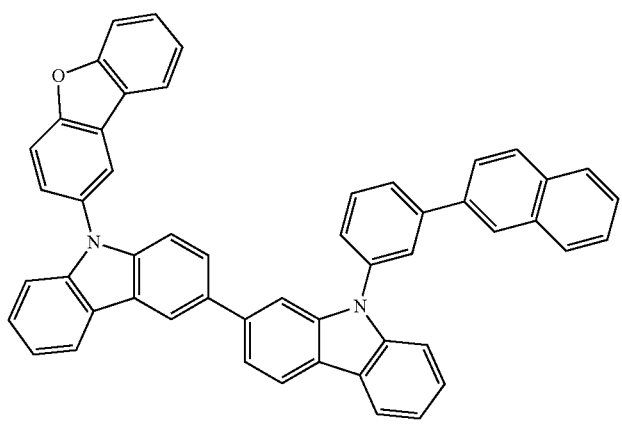

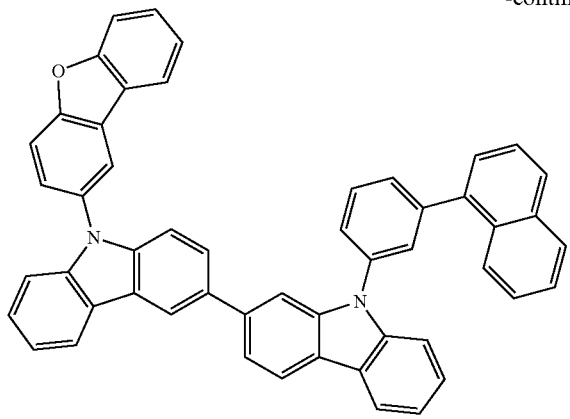

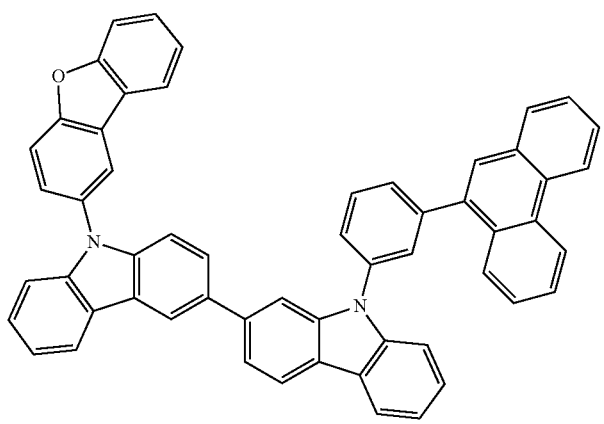

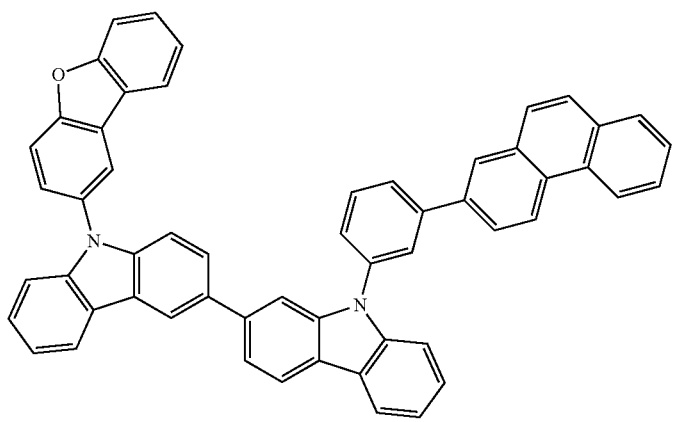

The organic EL device of the present invention is preferably such that its light emitting layer contains the biscarbazole derivative of the present invention.

It is also preferred that the organic EL device of the present invention have a hole transporting layer (hole injecting layer) and the hole transporting layer (hole injecting layer) contain the biscarbazole derivative of the present invention.

(Host)

A host of the light emitting layer is exemplified by the biscarbazole derivative of the present invention, an anthracene derivative, a polycyclic aromatic skeleton-containing compound, and the like, and is preferably the biscarbazole derivative of the present invention or an anthracene derivative.

The following compounds can, for example, be used as a host of a blue light emitting layer.

[Chem. 23]
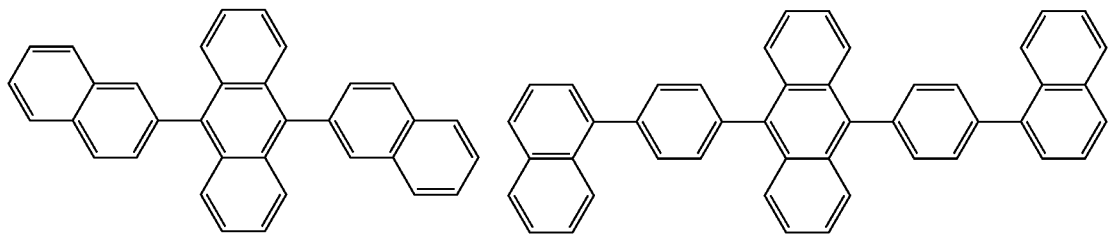
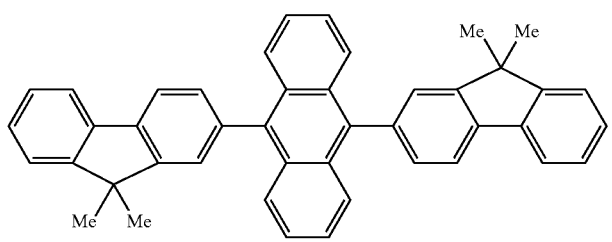
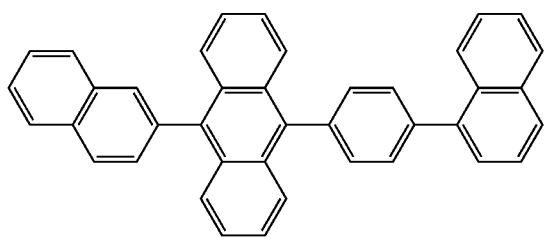
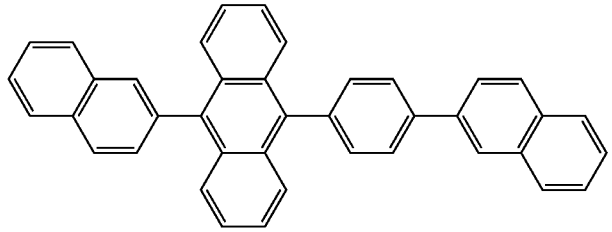
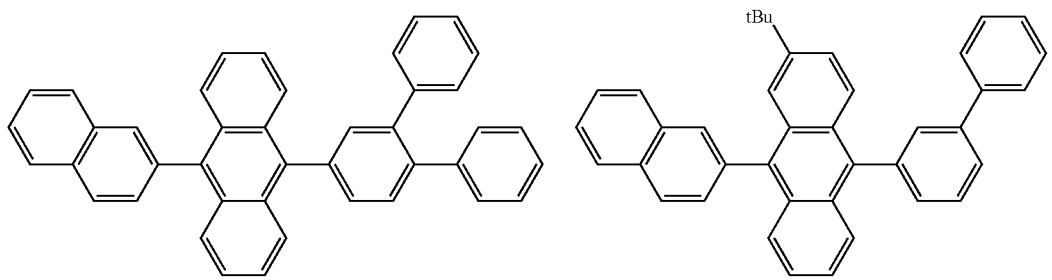
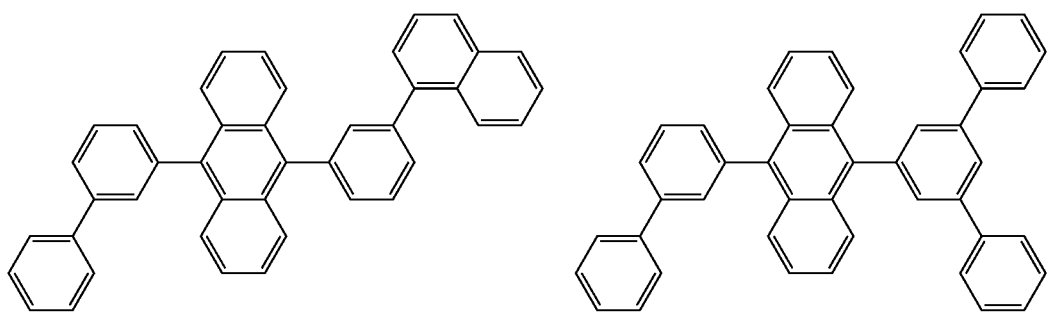

-continued
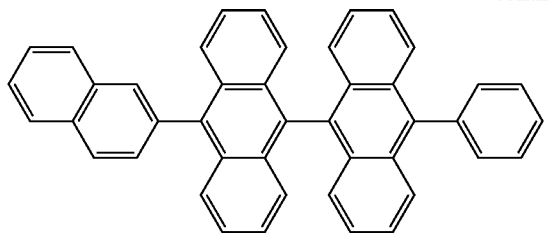
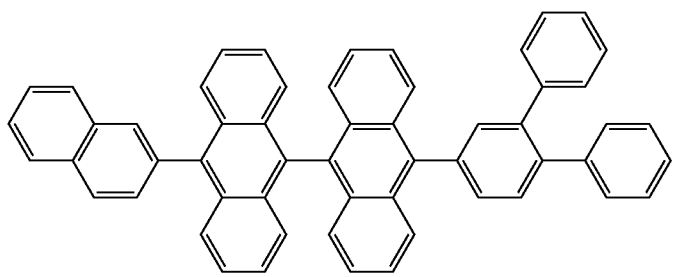
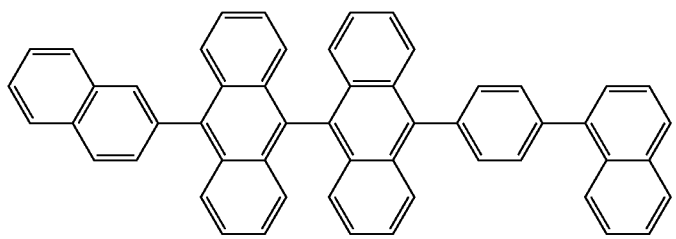
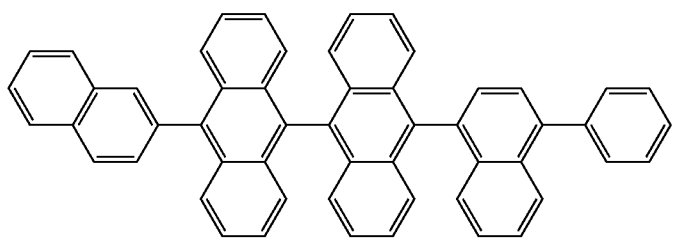
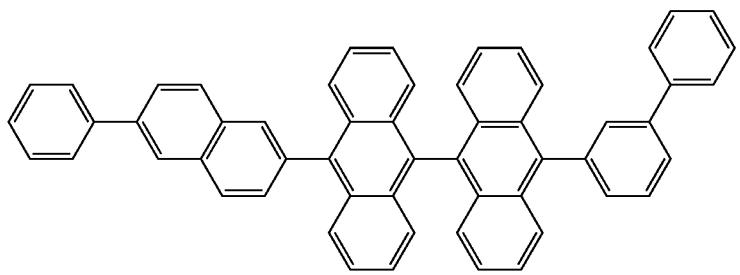
[Chem. 24]
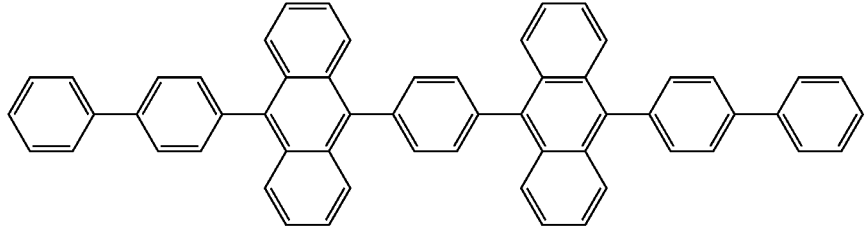

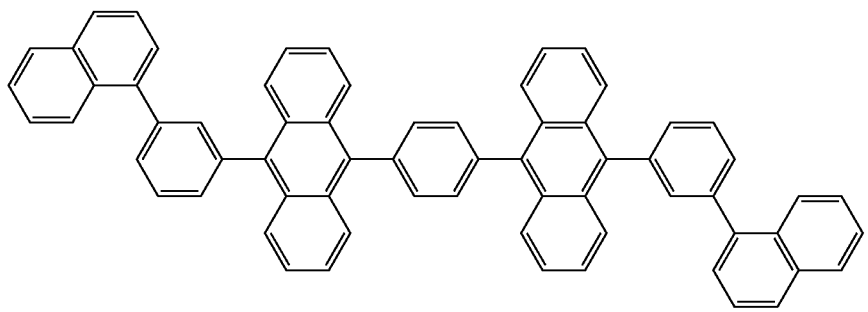
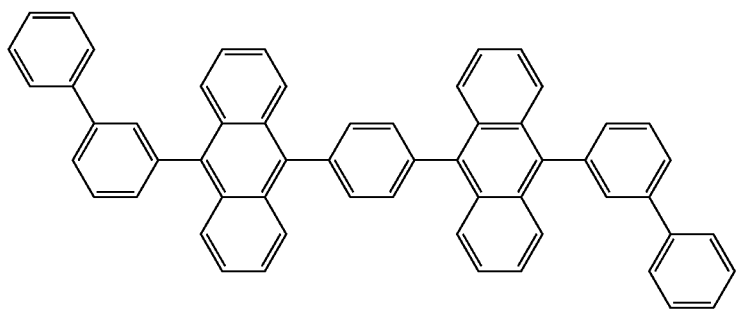
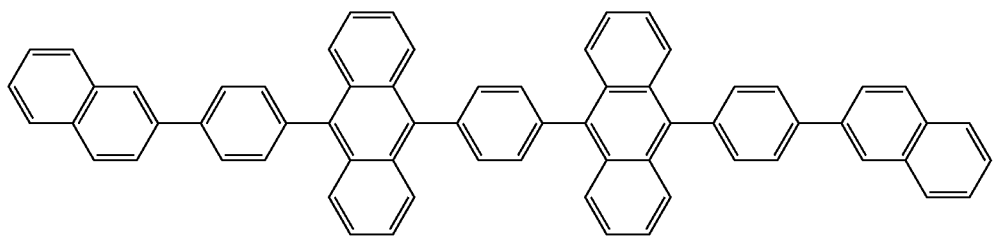
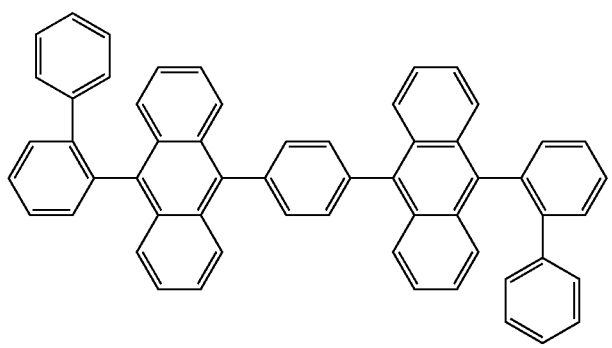
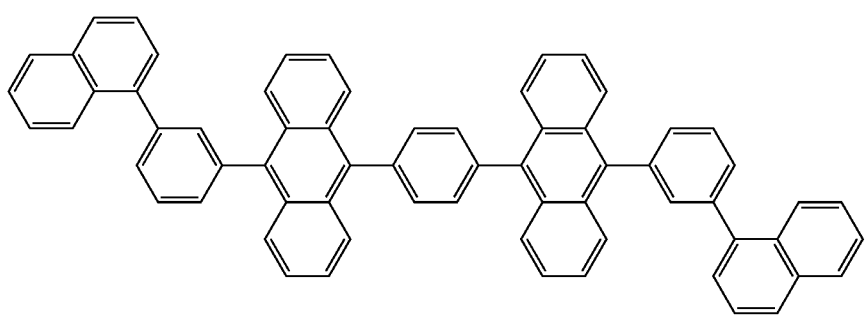

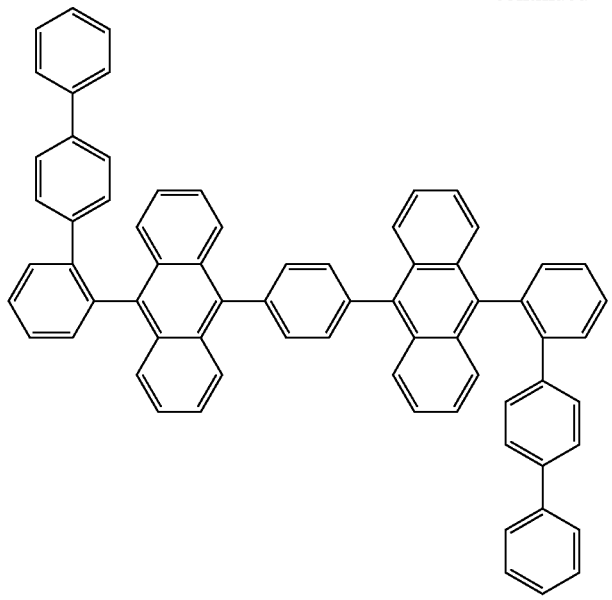
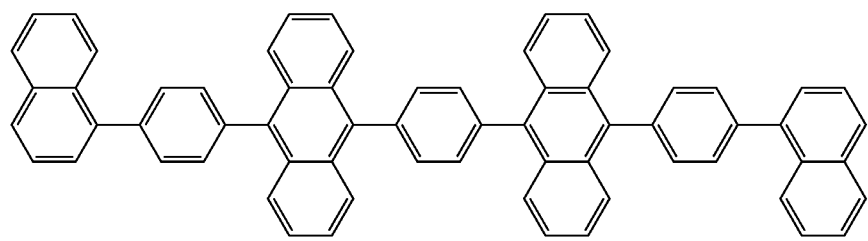
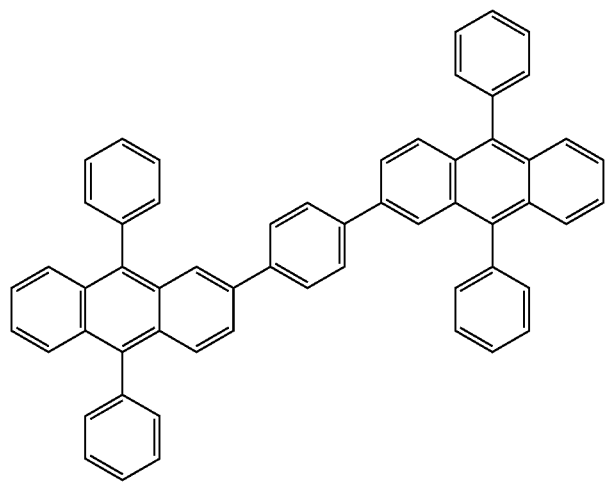

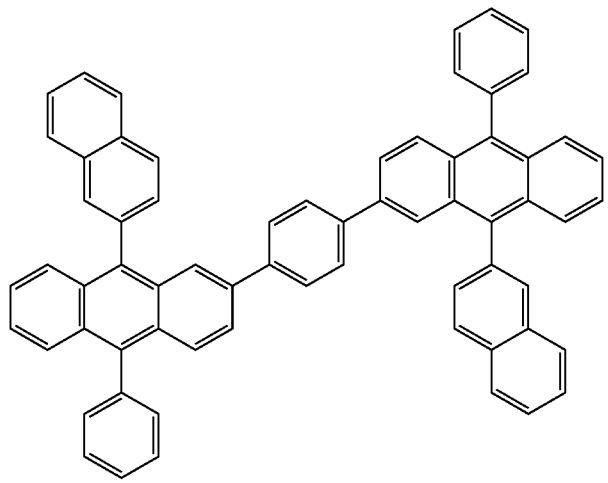
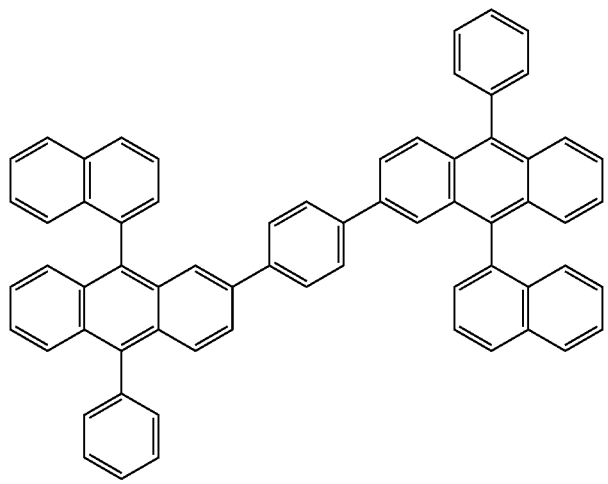
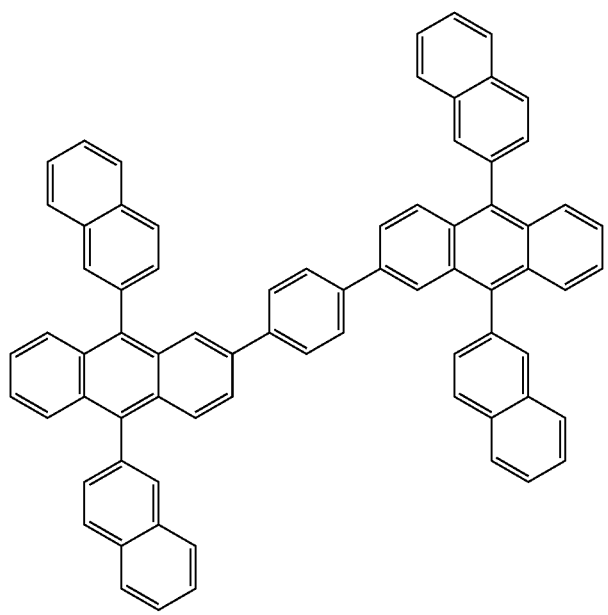

[Chem. 25]

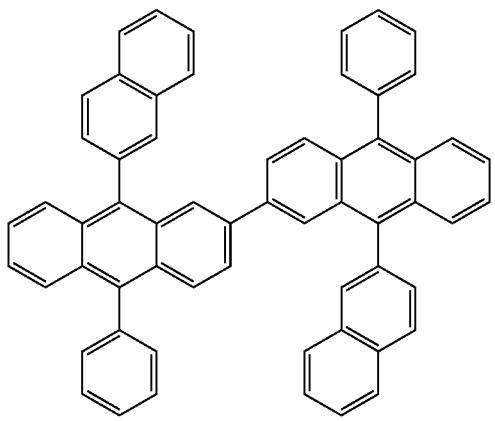

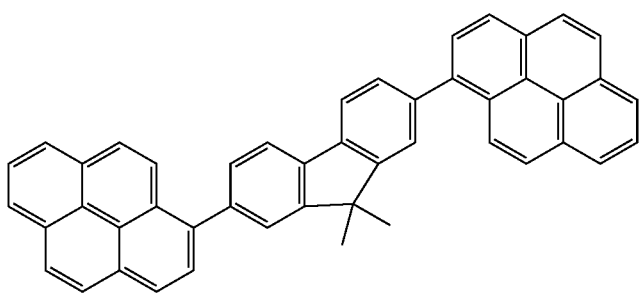

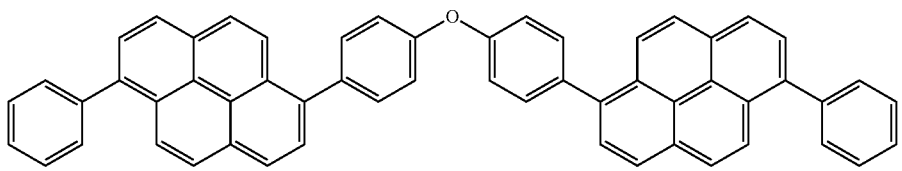 [SMILES: c1ccc(-c2ccc3ccc4c(-c5ccc(Oc6ccc(-c7ccc8ccc9c(-c%10ccccc%10)ccc%10ccc7c8c%109)cc6)cc5)ccc5ccc2c3c54)cc1]

The thickness of the light emitting layer is preferably 5 to 50 nm, more preferably 7 to 50 nm, still more preferably 10 to 50 nm. When the thickness is 5 nm or more, it is easy to form the light emitting layer. When the thickness is 50 nm or less, the driving voltage can be prevented from increasing.

(Phosphorescent Material)

In the present invention, the phosphorescent material contains a metal complex. The metal complex preferably has a metal atom selected from Ir, Pt, Os, Au, Cu, Re, and Ru, and a ligand. In particular, the ligand preferably has an ortho-metal bond.

A compound containing a metal atom selected from Ir, Os, and Pt is preferred from the viewpoints that the phosphorescent quantum yield is high and the external quantum efficiency of the light emitting device can be additionally improved. A metal complex such as an iridium complex, an osmium complex, or a platinum complex is more preferred. Of those, an iridium complex and a platinum complex are still more preferred and an orthometalated iridium complex is most preferred.

Specific examples of the preferred metal complex are shown below.

[Chem. 26]

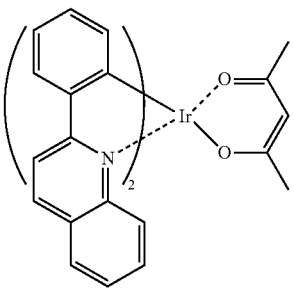

PQIr

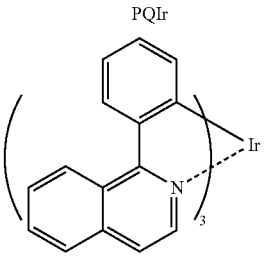

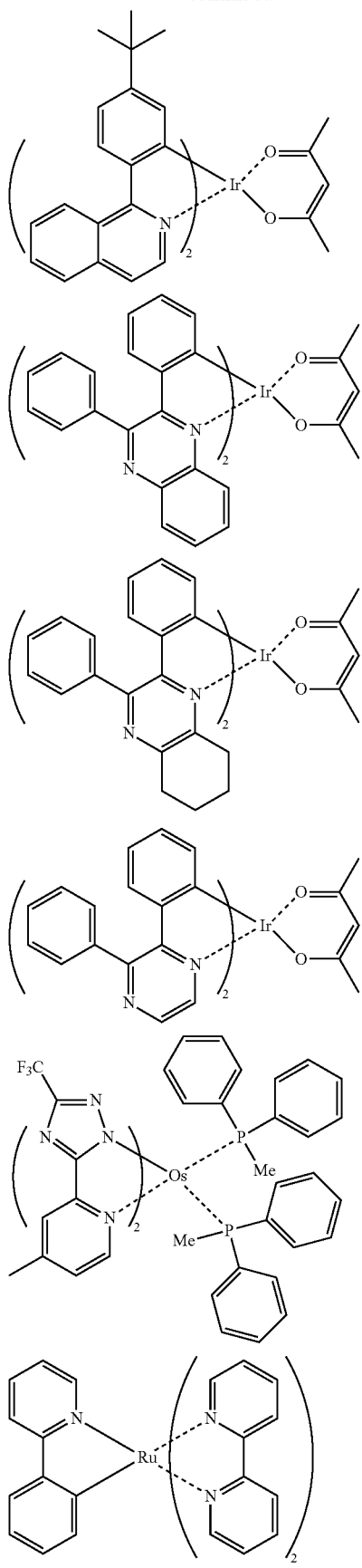
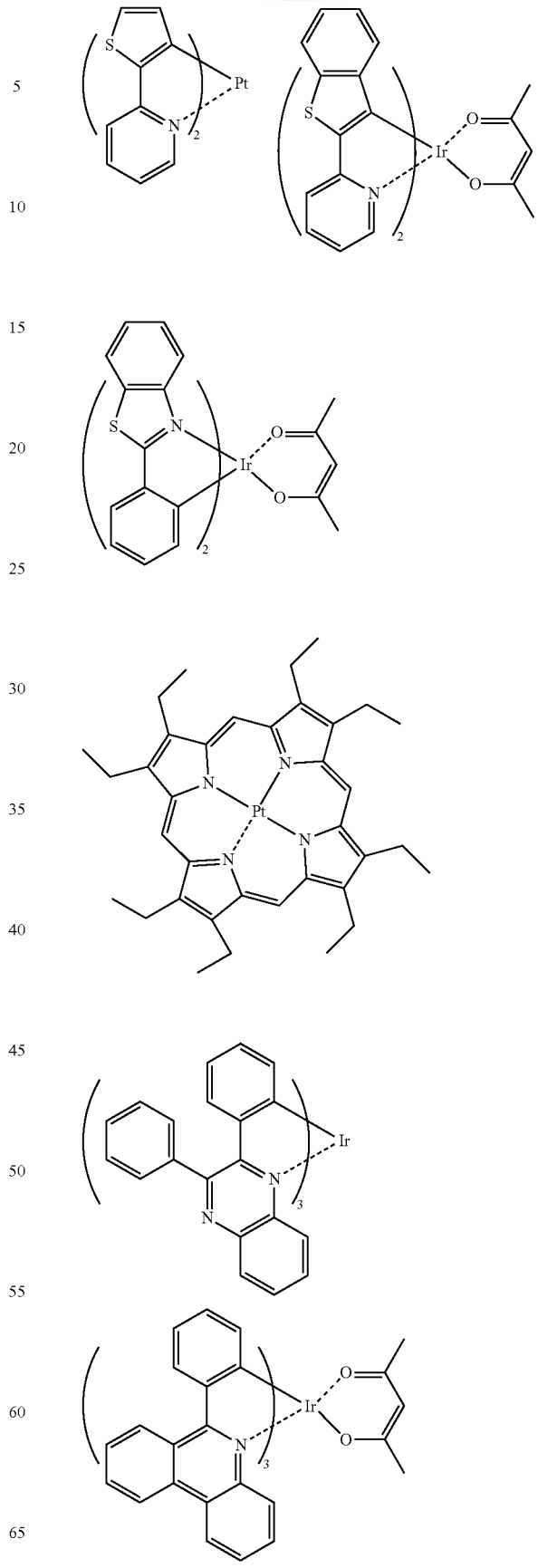

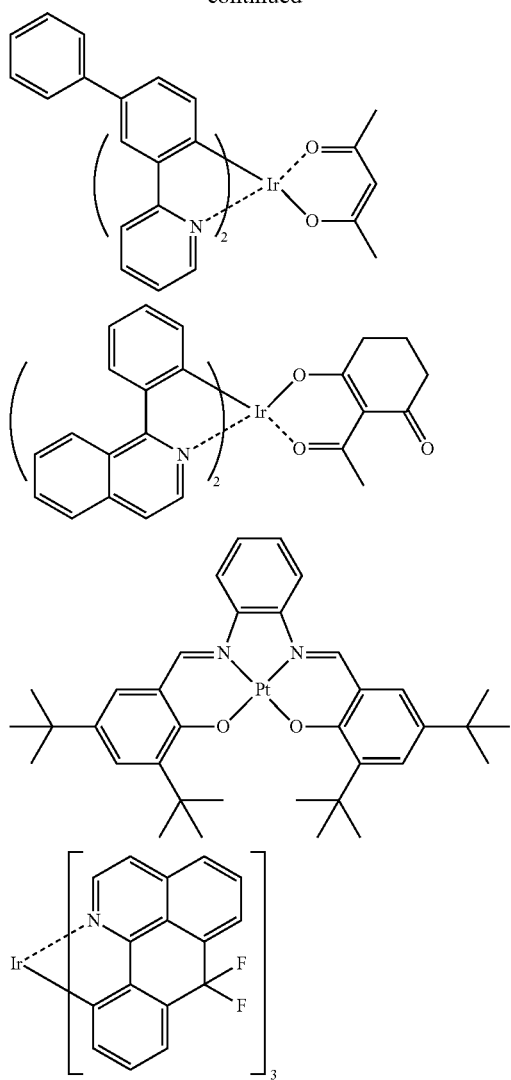
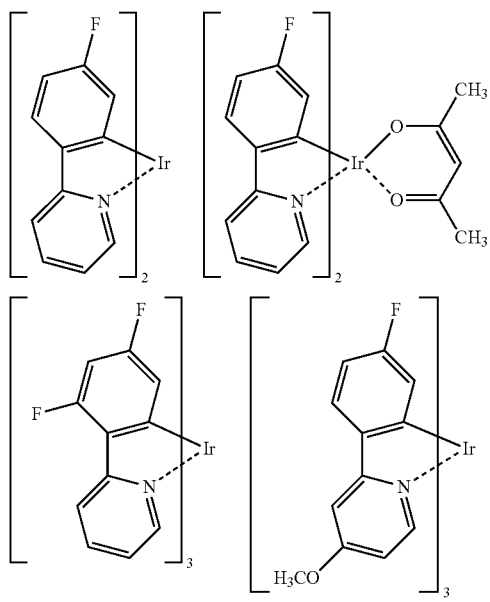
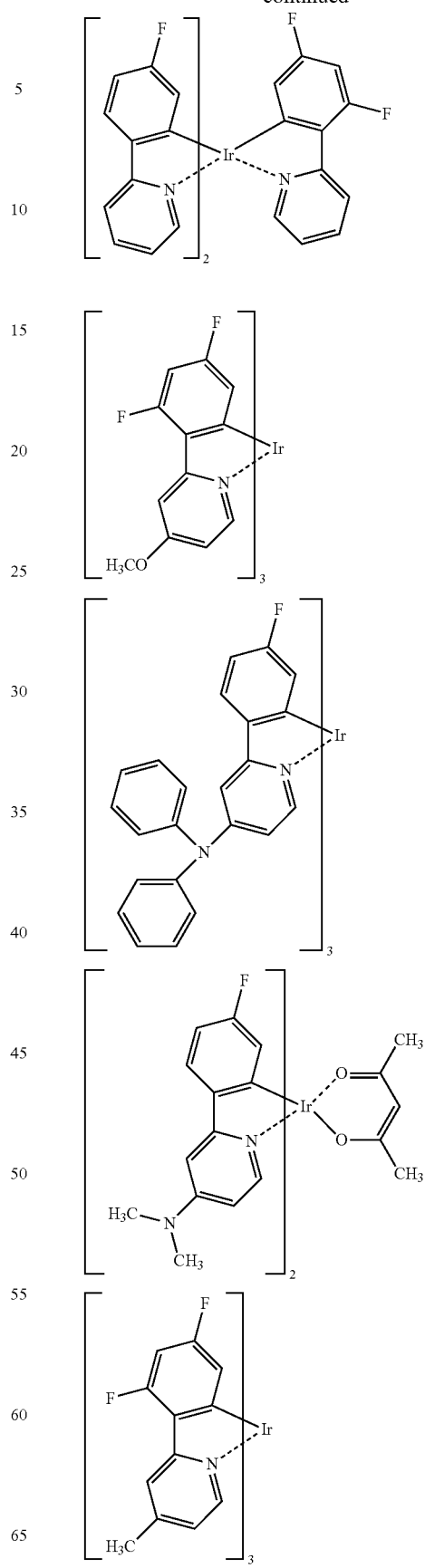
[Chem. 27]

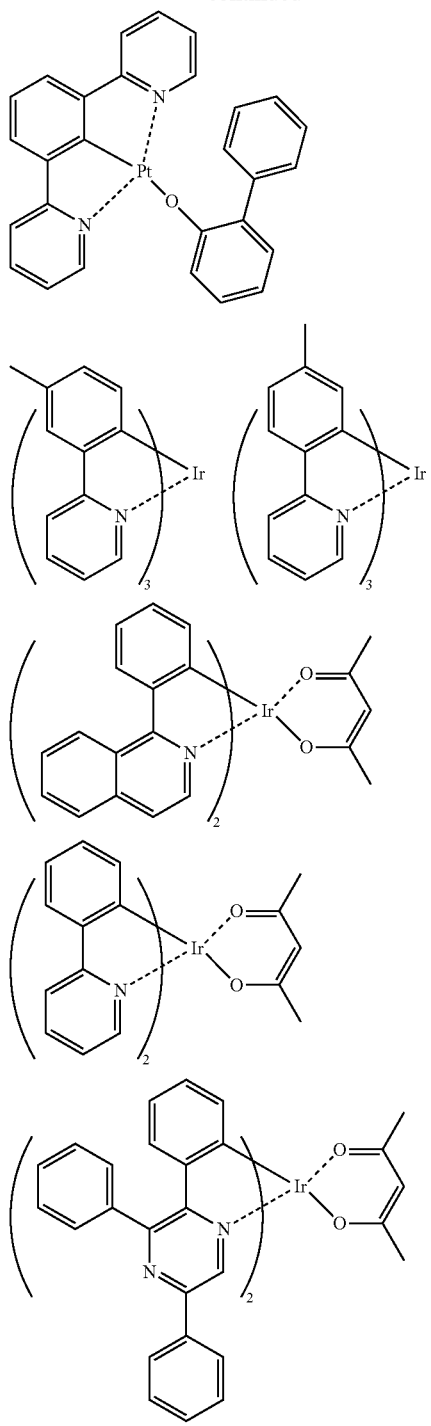
[Chem. 28]
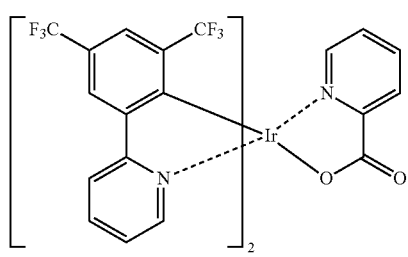
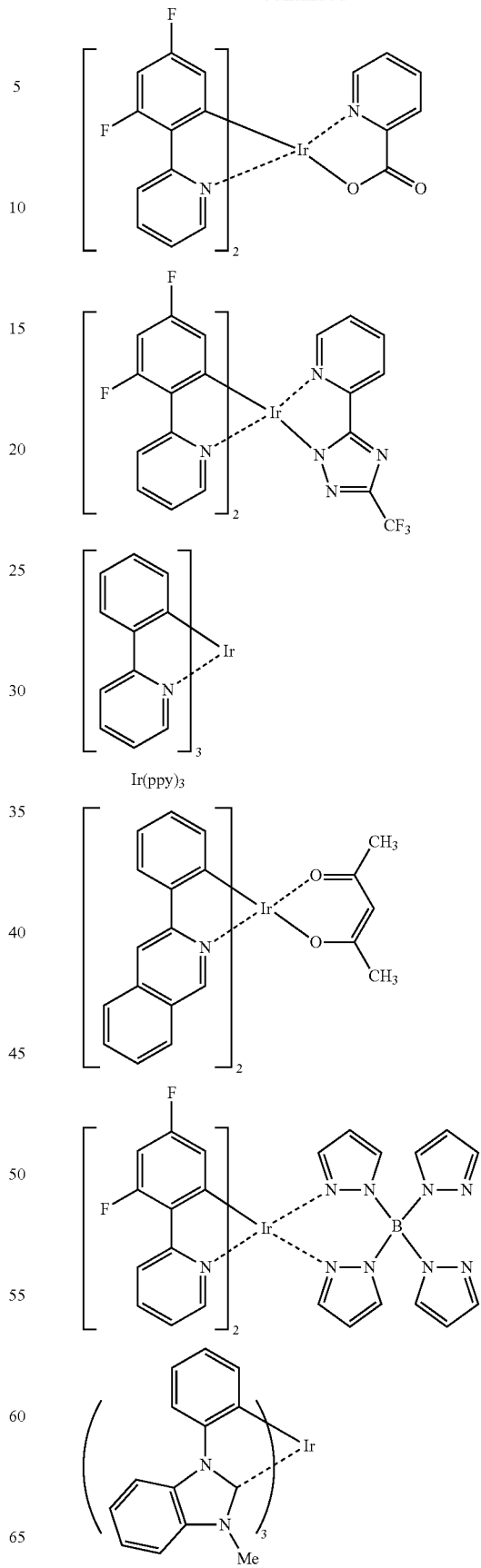
Ir(ppy)₃

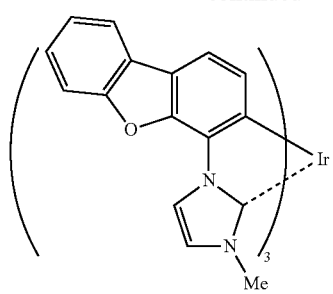
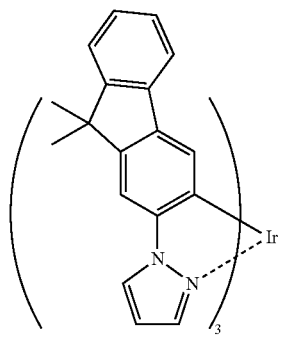
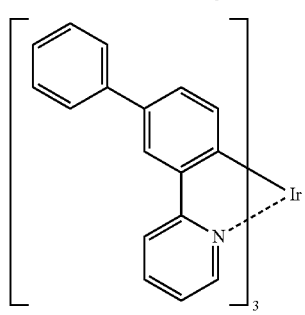
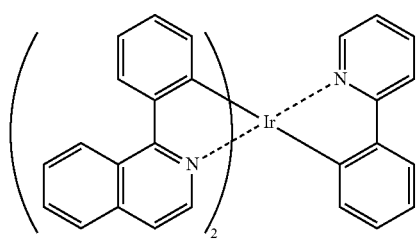
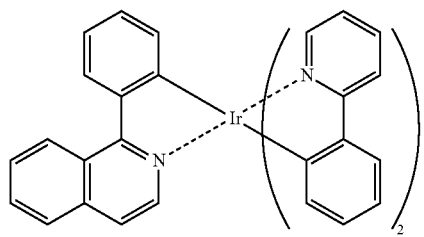
[Chem. 29]
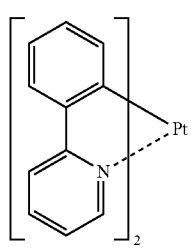
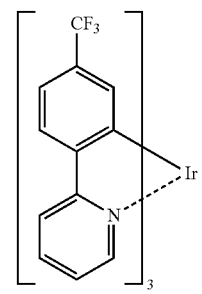
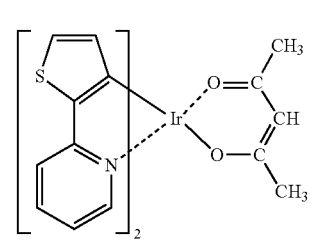
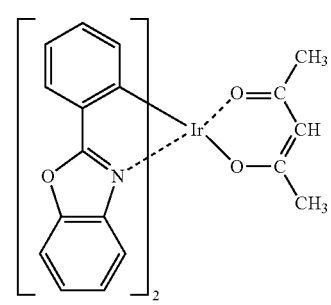
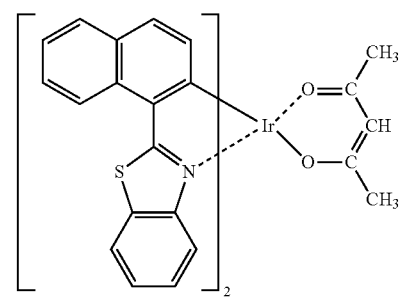
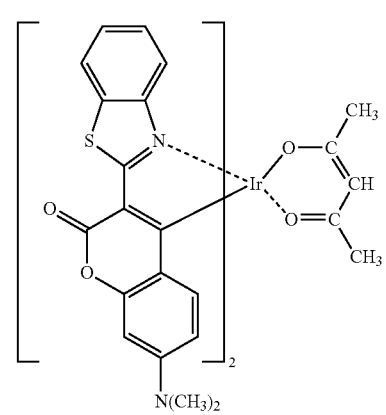

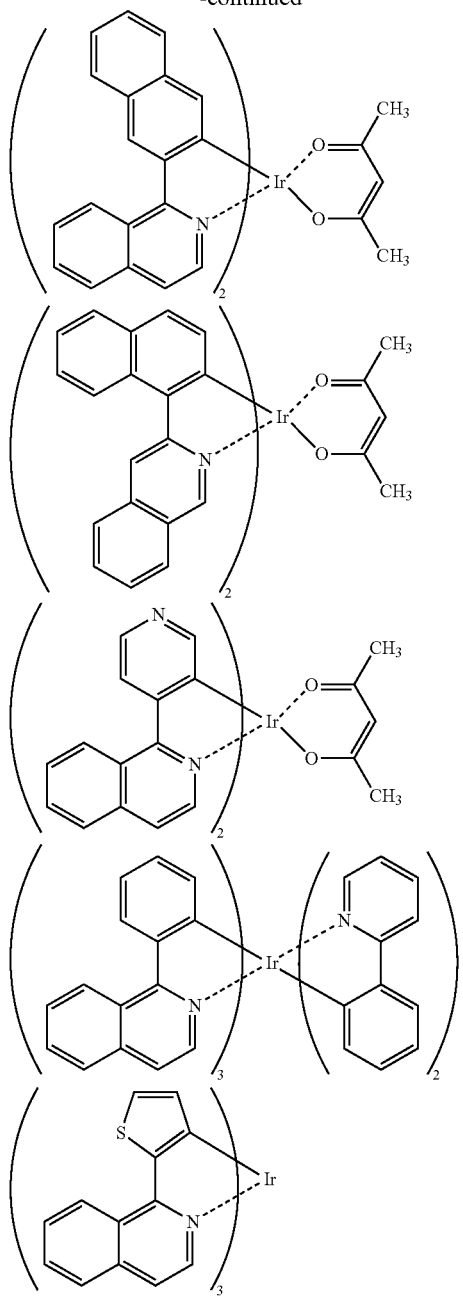

In the present invention, the luminous wavelength of at least one kind of the phosphorescent materials in the light emitting layer has a local maximum of preferably 450 nm or more and 750 nm or less. The local maximum is suitably, for example, 450 nm or more and 495 nm or less, 495 nm or more and 590 nm or less, 590 nm or more and 750 nm or less.

When the light emitting layer is constructed by doping a specific host material used in the present invention with the phosphorescent material (phosphorescent dopant) having such luminous wavelength, a high-efficiency organic EL device can be obtained.

(Fluorescent Dopant)

A fluorescent dopant (fluorescent emitting material) to be incorporated into the light emitting layer as necessary is a compound that can emit light from a singlet excited state and is not particularly limited to as long as light is emitted from a singlet excited state. Examples thereof include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative. Of those, preferred are an anthracene derivative, a fluoranthene derivative, a styrylamine derivative, an arylamine derivative, a styrylarylene derivative, a pyrene derivative, and a boron complex, and more preferred are an anthracene derivative, a fluoranthene derivative, a styrylamine derivative, an arylamine derivative, and a boron complex compound.

The fluoranthene derivative is specifically, for example, the following compound.

[Chem. 30]

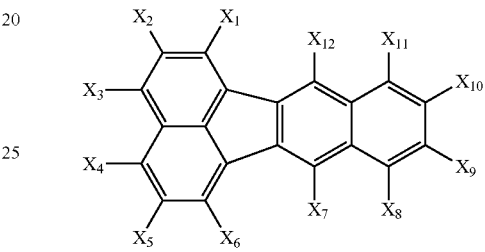

In the formula, $X_1$ to $X_{12}$ each represent hydrogen or a substituent. The compound is preferably such that $X_1$ and $X_2$, $X_4$ to $X_6$, and $X_8$ to $X_{11}$ each represent a hydrogen atom, and $X_3$, $X_7$, and $X_{12}$ each represent a substituted or unsubstituted aryl group having 5 to 50 ring forming atoms. The compound is more preferably such that $X_1$ and $X_2$, $X_4$ to $X_6$, and $X_8$ to $X_{11}$ each represent a hydrogen atom, $X_7$ and $X_{12}$ each represent a substituted or unsubstituted aryl group having 5 to 50 ring forming atoms, and $X_3$ represents —$Ar_1$—$Ar_2$ (where $Ar_1$ represents a substituted or unsubstituted arylene group having 5 to 50 ring forming atoms and $Ar_2$ represents a substituted or unsubstituted aryl group having 5 to 50 ring forming atoms). The compound is also preferably such that $X_1$ and $X_2$, $X_4$ to $X_6$, and $X_8$ to $X_{11}$ each represent a hydrogen atom, $X_7$ and $X_{12}$ each represent a substituted or unsubstituted aryl group having 5 to 50 ring forming atoms, and $X_3$ represents —$Ar_1$—$Ar_2$—$Ar_3$ (where $Ar_1$ and $Ar_3$ each represent a substituted or unsubstituted arylene group having 5 to 50 ring forming atoms, and $Ar_2$ represents a substituted or unsubstituted aryl group having 5 to 50 ring forming atoms).

The boron complex compound is specifically, for example, the following compound.

[Chem. 31]

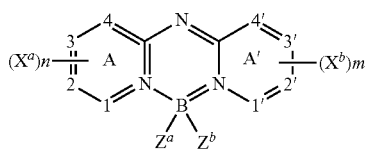

In the formula, A and A' each represent an independent azine ring system corresponding to a six-membered aromatic ring system containing at least one nitrogen, $X^a$ and $X^b$ each independently represent a substituent, $X^a$ and $X^b$ are linked to the ring A and the ring A', respectively to form fused rings together with the ring A and the ring A', and at the time of the formation, the fused rings each contain an aryl or heteroaryl substituent, m and n each independently represent 0 to 4, $Z^a$ and $Z^b$ are each independently selected from halides, and 1, 2, 3, 4, 1', 2', 3', and 4' are each independently selected from a carbon atom and a nitrogen atom.

The azine rings are desirably such quinolinyl or isoquinolinyl rings that all of 1, 2, 3, 4, 1', 2', 3', and 4' represent carbon atoms, m and n each represent 2 or more, and $X^a$ and $X^b$ each represent the following substituent having 2 or more carbon atoms. The substituents are linked to each other to form an aromatic ring. $Z^a$ and $Z^b$ each desirably represent a fluorine atom.

The anthracene derivative is specifically, for example, the following compound.

[Chem. 32]

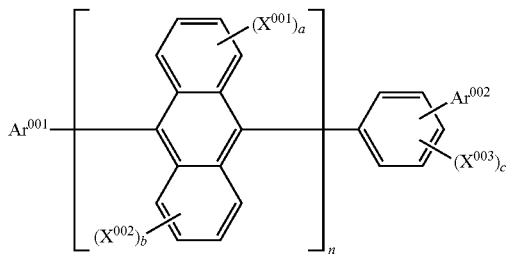

In the formula: $Ar^{001}$ represents a substituted or unsubstituted, fused aromatic group having 10 to 50 ring carbon atoms; $Ar^{002}$ represents a substituted or unsubstituted aromatic group having 6 to 50 ring carbon atoms; $X^{001}$ to $X^{003}$ each independently represent a substituted or unsubstituted aromatic group having 6 to 50 ring carbon atoms, a substituted or unsubstituted aromatic heterocyclic group having 5 to 50 ring forming atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring forming atoms, a substituted or unsubstituted arylthio group having 5 to 50 ring forming atoms, a substituted or unsubstituted alkoxycarbonyl group having 1 to 50 carbon atoms, a carboxyl group, a halogen atom, a cyano group, a nitro group, or a hydroxy group; a, b, and c each represent an integer of 0 to 4; and n represents an integer of 1 to 3, and when n represents 2 or more, structures in [ ] may be identical to or different from each other. n preferably represents 1. a, b, and c each preferably represent 0.

Although the content of the fluorescent dopant in the light emitting layer is not particularly limited and can be appropriately selected depending on purposes, for example, the content is preferably 0.1 to 70 mass, more preferably 1 to 30 mass %. When the content of the fluorescent dopant is 0.1 mass % or more, sufficient light emission is obtained, and when the content is 70 mass % or less, concentration quenching can be avoided.

(Electron-Donating Dopant)

The organic EL device of the present invention preferably has a electron-donating dopant at an interfacial region between the cathode and the organic thin-film layer.

Such construction achieves an improvement in the current efficiency, and the lengthening of the lifetime, in the organic EL device.

Examples of the electron-donating dopant include at least one kind selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV). Of those, an alkali metal having a work function of 2.9 eV or less is particularly preferred. Of those, preferred are K, Rb, and Cs, more preferred are Rb and Cs, and most preferred is Cs.

Examples of the alkaline earth metal include Ca (work function: 2.9 eV), Sr (work function: 2.0 eV to 2.5 eV), and Ba (work function: 2.52 eV). An alkaline earth metal having a work function of 2.9 eV or less is particularly preferred.

Examples of the rare earth metal include Sc, Y, Ce, Tb, and Yb. A rare earth metal having a work function of 2.9 eV or less is particularly preferred.

Of those metals, a preferred metal has a particularly high reductive ability, and hence an improvement in the current efficiency, and the lengthening of the lifetime, in the organic EL device can be attained by adding a relatively small amount of the metal to an electron injecting region.

Examples of the alkali metal compound include an alkali oxide such as $Li_2O$, $Cs_2O$, or $K_2O$, and an alkali halide such as LiF, NaF, CsF, or KF. Of those, LiF, $Li_2O$, and NaF are preferred.

Examples of the alkaline earth metal compound include BaO, SrO, CaO, and mixtures thereof such as $Ba_xSr_{1-x}O$ (0<x<1) and $Ba_xCa_{1-x}O$ (0<x<1). Of those, BaO, SrO, and CaO are preferred.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferred.

The alkali metal complex, alkaline earth metal complex, and rare earth metal complex are not particularly limited as long as the complexes each contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the electron-donating dopant, it is preferred that the electron-donating dopant be formed in a shape of a layer or an island in the interfacial region. A preferred method for the formation is a method in which an organic substance as a light emitting material or an electron injecting material for forming the interfacial region is deposited at the same time as the electron-donating dopant is deposited by a resistant heating deposition method, thereby dispersing the electron-donating dopant in the organic substance. The disperse concentration by molar ratio of the organic substance to the electron-donating dopant is 100:1 to 1:100, preferably 5:1 to 1:5.

In a case where the electron-donating dopant is formed into the shape of a layer, the light emitting material or electron injecting material which serves as an organic layer in the interface is formed into the shape of a layer. After that, the electron-donating dopant is solely deposited by the resistant heating deposition method to form a layer preferably having a thickness of 0.1 nm to 15 nm.

In a case where the electron-donating dopant is formed into the shape of an island, the light emitting material or electron injecting material which serves as an organic layer in the interface is formed into the shape of an island. After that, the electron-donating dopant is solely deposited by the resistant heating deposition method to form an island preferably having a thickness of 0.05 nm to 1 nm.

In addition, a ratio "main component:electron-donating dopant" between the main component and the electron-donating dopant in the organic EL device of the present invention is preferably 5:1 to 1:5, more preferably 2:1 to 1:2 in terms of a molar ratio.

(Electron Injecting Layer and Electron Transporting Layer)

The electron injecting layer or the electron transporting layer is a layer that aids the injection of electrons into the light emitting layer, and has a large electron mobility. The electron injecting layer is provided for the adjustment of an energy level such as the alleviation of an abrupt change in energy level.

It is preferred that the organic EL device of the present invention have an electron injecting layer between the light emitting layer and the cathode, and the electron injecting layer contain a nitrogen-containing ring derivative as a main component. Here, the electron injecting layer may be a layer that functions as the electron transporting layer.

It should be noted that the phrase "as a main component" means that the electron injecting layer contains 50 mass % or more of the nitrogen-containing ring derivative.

An aromatic heterocyclic compound containing one or more heteroatoms in a molecule thereof is preferably used as an electron transportable material used in the electron injecting layer, and a nitrogen-containing ring derivative is particularly preferred. In addition, the nitrogen-containing ring derivative is preferably an aromatic ring having a nitrogen-containing, six- or five-membered ring skeleton, or a fused aromatic ring compound having a nitrogen-containing, six- or five-membered ring skeleton.

The nitrogen-containing ring derivative is preferably, for example, a nitrogen-containing ring metal chelate complex represented by the following formula (A).

[Chem. 33]

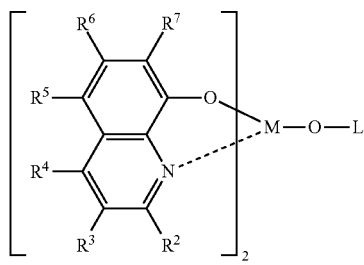

(A)

$R^2$ to $R^7$ in the general formula (A) each independently represent a hydrogen atom, a deuterium atom, a halogen atom, an oxy group, an amino group, a hydrocarbon group having 1 to 40 carbon atoms, an alkoxy group, an aryloxy group, an alkoxycarbonyl group, or an aromatic heterocyclic group, each of which may be substituted.

Examples of the halogen atom include fluorine, chlorine, bromine, and iodine. Further, examples of the amino group that may be substituted include an alkylamino group, an arylamino group, and an aralkylamino group.

The alkoxycarbonyl group is represented by —COOY', and examples of Y' include the same groups as those of the alkyl group. The alkylamino group and the aralkylamino group are each represented by —NQ$^1$Q$^2$. Specifically, Q$^1$ and Q$^2$ each independently represent, for example, any one of the same groups as those described for the alkyl group and the aralkyl group, and the same holds true for preferred examples of Q$^1$ and Q$^2$. One of Q$^1$ and Q$^2$ may represent a hydrogen atom or a deuterium atom.

The arylamino group is represented by —NAr$^1$Ar$^2$, and specifically, Ar$^1$ and Ar$^2$ each independently represent, for example, any one of the same groups as those described for the non-fused aromatic hydrocarbon group and the fused aromatic hydrocarbon group. One of Ar$^1$ and Ar$^2$ may represent a hydrogen atom or a deuterium atom.

M represents aluminum (Al), gallium (Ga), or indium (In), preferably In.

L in the formula (A) is a group represented by the following formula (A') or (A").

[Chem. 34]

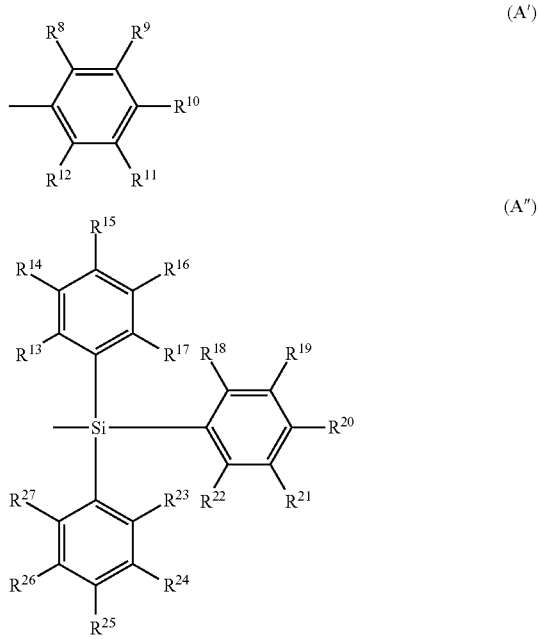

In the formula (A'), $R^8$ to $R^{12}$ each independently represent a hydrogen atom, a deuterium atom, or a substituted or unsubstituted hydrocarbon group having 1 to 40 carbon atoms, and adjacent groups may form a cyclic structure. In addition, in the formula (A"), $R^{13}$ to $R^{27}$ each independently represent a hydrogen atom, a deuterium atom, or a substituted or unsubstituted hydrocarbon group having 1 to 40 carbon atoms, and adjacent groups may form a cyclic structure.

Examples of the hydrocarbon group having 1 to 40 carbon atoms and represented by $R^8$ to $R^{12}$ in the formula (A') and $R^{13}$ to $R^{27}$ in the formula (A") include the same specific examples as those of $R^2$ to $R^7$ in the formula (A).

In addition, examples of the divalent group in $R^8$ to $R^{12}$ and $R^{13}$ to $R^{27}$ in the case where adjacent groups form a cyclic structure include a tetramethylene group, a pentamethylene group, a hexamethylene group, a diphenylmethane- 2,2'-diyl group, a diphenylethane-3,3'-diyl group, and a diphenylpropane-4,4'-diyl group.

An electron transferable compound used in the electron injecting layer or the electron transporting layer is suitably a metal complex of 8-hydroxyquinoline or of a derivative thereof, an oxadiazole derivative, or a nitrogen-containing heterocyclic derivative. Specifically, for example, a metal chelate oxynoid compound containing a chelate of oxine (generally, 8-quinolinol or 8-hydroxyquinoline) such as tris (8-quinolinol)aluminum can be used as the metal complex of 8-hydroxyquinoline or of a derivative thereof. In addition, examples of the oxadiazole derivative include the following compounds.

[Chem. 35]

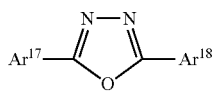

[Chem. 36]

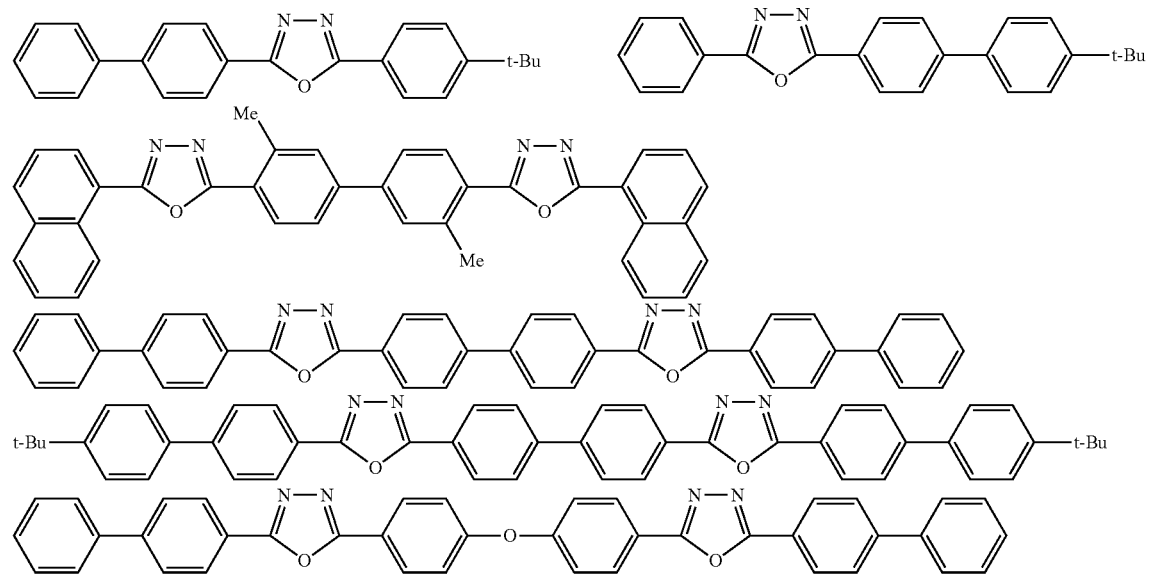

-continued

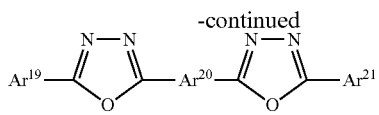

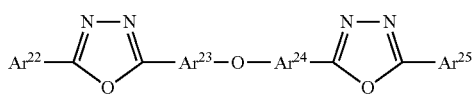

In the formulae $Ar^{17}$, $Ar^{18}$, $Ar^{19}$, $Ar^{21}$, $Ar^{22}$, and $Ar^{25}$ each represent an aromatic hydrocarbon group or fused aromatic hydrocarbon group that has, or does not have, a substituent, and $Ar^{17}$ and $Ar^{18}$, $Ar^{19}$ and $Ar^{21}$, or $Ar^{22}$ and $Ar^{25}$ may be identical to or different from each other. Examples of the aromatic hydrocarbon group or the fused aromatic hydrocarbon group include a phenyl group, a naphthyl group, a biphenyl group, an anthranyl group, a perylenyl group, and a pyrenyl group. In addition, examples of the substituent for any such group include an alkyl group having 1 to 10 carbon atoms, an alkoxy group having 1 to 10 carbon atoms, and a cyano group.

$Ar^{20}$, $Ar^{23}$, and $Ar^{24}$ each represent a divalent aromatic hydrocarbon group or fused aromatic hydrocarbon group that has, or does not have, a substituent, and $Ar^{23}$ and $Ar^{24}$ may be identical to or different from each other.

Examples of the divalent aromatic hydrocarbon group or the fused aromatic hydrocarbon group include a phenylene group, a naphthylene group, a biphenylene group, an anthranylene group, a perylenylene group, and a pyrenylene group. In addition, examples of the substituent for any such group include an alkyl group having 1 to 10 carbon atoms, an alkoxy group having 1 to 10 carbon atoms, or a cyano group.

A compound having good thin film formability is preferably used as the electron transferable compound. In addition, specific examples of the electron transferable compound include the following compounds.

The nitrogen-containing heterocyclic derivative as the electron transferable compound is a nitrogen-containing heterocyclic derivative formed of an organic compound having the following general formula, and there is given a nitrogen-containing compound which is not a metal complex. Examples of the derivative include a five- or six-membered ring containing a skeleton represented by the following formula (B) and a compound having a structure represented by the following formula (C).

[Chem. 37]

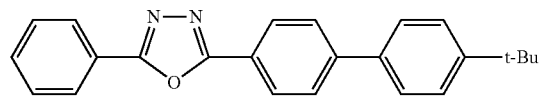 (A)

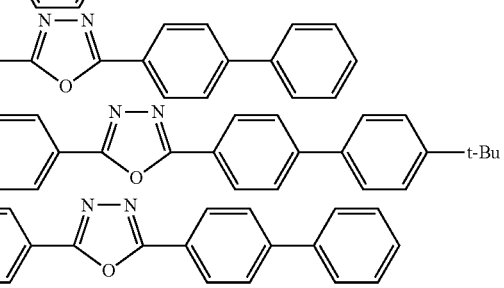 (B)

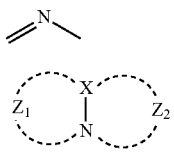

In the formula (C), X represents a carbon atom or a nitrogen atom. $Z_1$ and $Z_2$ each independently represent an atomic group capable of forming a nitrogen-containing heterocycle.

The nitrogen-containing heterocyclic derivative is more preferably an organic compound having a nitrogen-containing aromatic polycycle formed of a five- or six-membered ring. Further, in the case of such nitrogen-containing aromatic polycycle having multiple nitrogen atoms, a nitrogen-containing aromatic polycyclic organic compound having a skeleton obtained by combining the formulae (B) and (C) or the formula (B) and the following formula (D) is preferred.

[Chem. 38]

(C)

The nitrogen-containing group of the nitrogen-containing aromatic polycyclic organic compound is selected from, for example, nitrogen-containing heterocyclic groups represented by the following general formulae.

[Chem. 39]

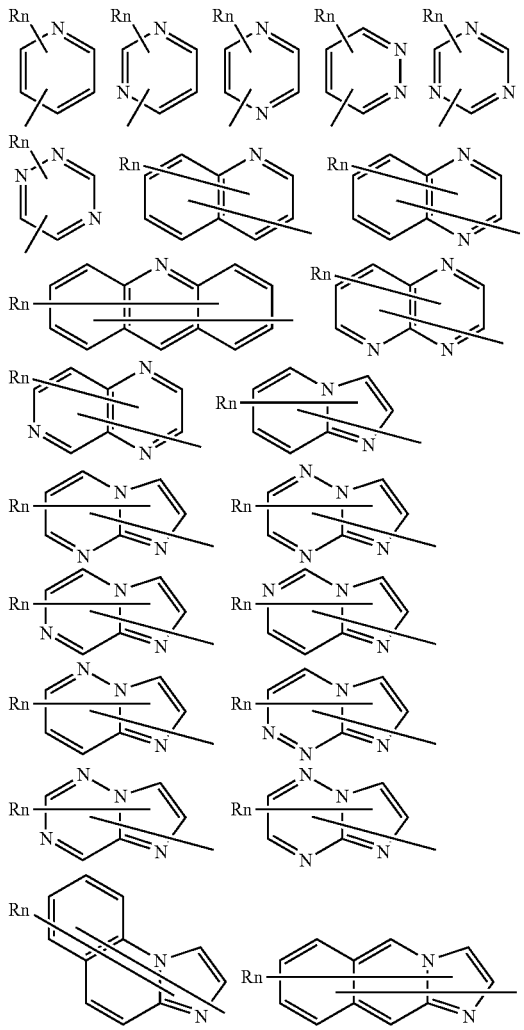

In each of the formulae, R represents an aromatic hydrocarbon group or fused aromatic hydrocarbon group having 6 to 40 carbon atoms, an aromatic heterocyclic group or fused aromatic heterocyclic group having 3 to 40 carbon atoms, an alkyl group having 1 to 20 carbon atoms, or an alkoxy group having 1 to 20 carbon atoms, n represents an integer of 0 to 5, and, when n represents an integer of 2 or more, multiple R's may be identical to or different from each other.

Further, a preferred specific compound is, for example, a nitrogen-containing heterocyclic derivative represented by the following formula.

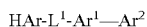

HAr-$L^1$-$Ar^1$—$Ar^2$

In the formula, HAr represents a nitrogen-containing heterocyclic group which has 3 to 40 carbon atoms and may have a substituent, $L^1$ represents a single bond, an aromatic hydrocarbon group or fused aromatic hydrocarbon group which has 6 to 40 carbon atoms and may have a substituent, or an aromatic heterocyclic group or fused aromatic heterocyclic group which has 3 to 40 carbon atoms and may have a substituent, $Ar^1$ represents a divalent aromatic hydrocarbon group which has 6 to 40 carbon atoms and may have a substituent, and $Ar^2$ represents an aromatic hydrocarbon group or fused aromatic hydrocarbon group which has 6 to 40 carbon atoms and may have a substituent, or an aromatic heterocyclic group or fused aromatic heterocyclic group which has 3 to 40 carbon atoms and may have a substituent.

HAr is selected from, for example, the following group.

[Chem. 40]

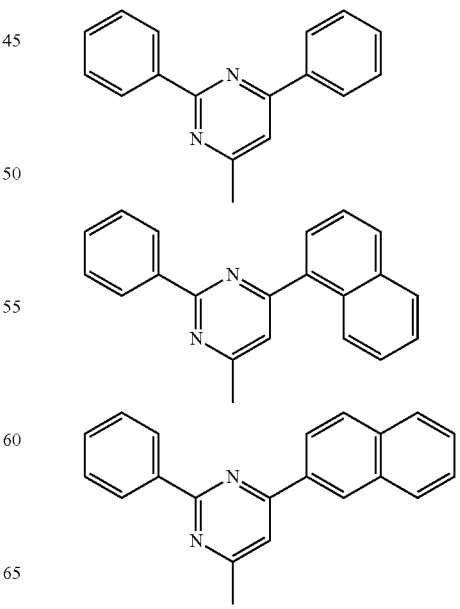

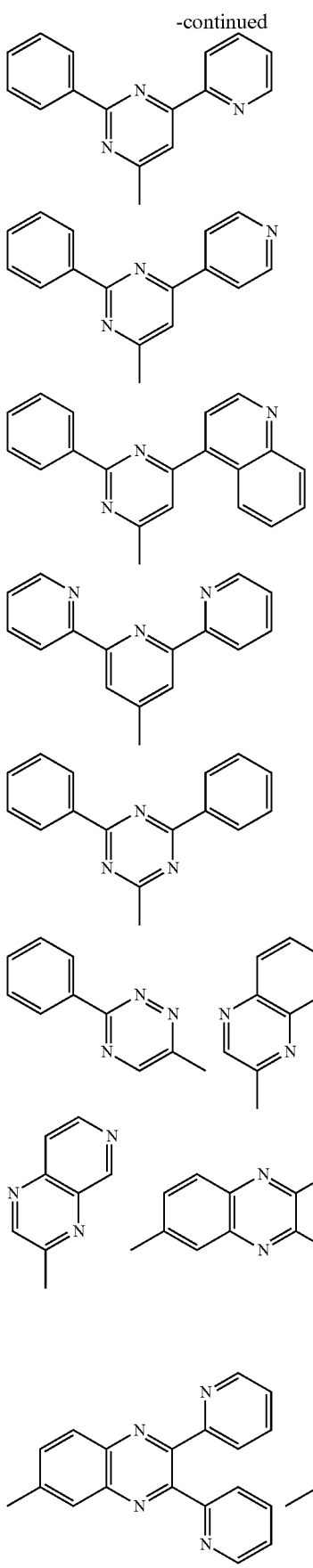

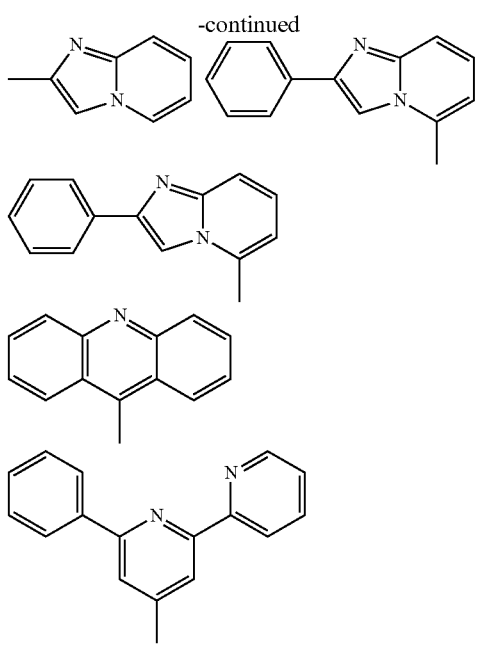

$L^1$ is selected from, for example, the following group.

[Chem. 41]

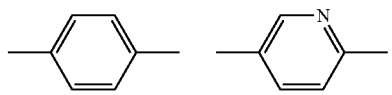

$Ar^1$ is selected from, for example, the following arylanthranil groups.

[Chem. 42]

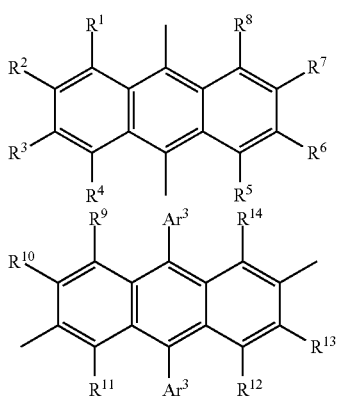

In the formulae, $R^1$ to $R^{14}$ each independently represent a hydrogen atom, a deuterium atom, a halogen atom, an alkyl group having 1 to 20 carbon atoms, an alkoxy group having 1 to 20 carbon atoms, an aryloxy group having 6 to 40 carbon atoms, an aromatic hydrocarbon group or fused aromatic hydrocarbon group which has 6 to 40 carbon atoms and may have a substituent, or an aromatic heterocyclic group or fused aromatic heterocyclic group having 3 to 40 carbon atoms, and $Ar^3$ represents an aromatic hydrocarbon group or fused aromatic hydrocarbon group which has 6 to 40 carbon atoms and may have a substituent, or an aromatic heterocyclic group or fused aromatic heterocyclic group having 3 to 40 carbon atoms.

In addition, the nitrogen-containing heterocyclic derivative may be such that $R^1$ to $R^8$ each represent a hydrogen atom or a deuterium atom.

$Ar^2$ is selected from, for example, the following group.

[Chem. 43]

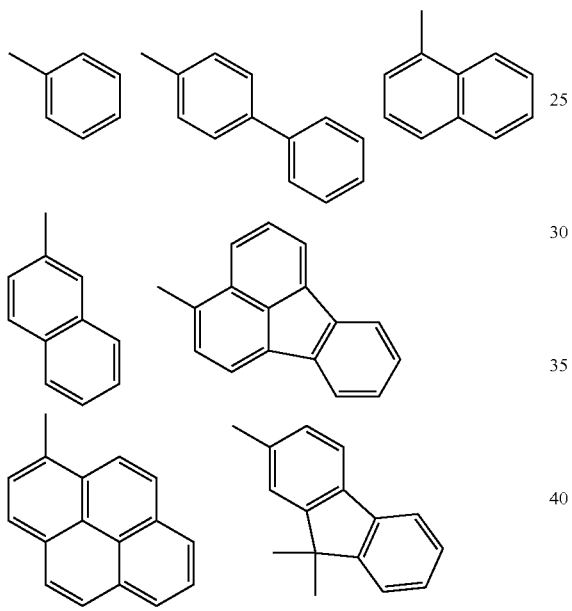

In addition to the foregoing, the following compound (see JP 09-3448 A) is also suitably used as the nitrogen-containing aromatic polycyclic organic compound as the electron transferable compound.

[Chem. 44]

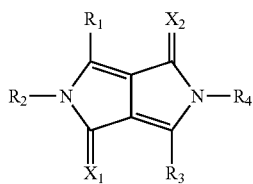

In the formula, $R_1$ to $R_4$ each independently represent a hydrogen atom, a deuterium atom, a substituted or unsubstituted aliphatic group, a substituted or unsubstituted alicyclic group, a substituted or unsubstituted carbocyclic aromatic ring group, or a substituted or unsubstituted heterocyclic group, and $X_1$ and $X_2$ each independently represent an oxygen atom, a sulfur atom, or a dicyanomethylene group.

In addition, the following compound (see JP 2000-173774 A) is also suitably used as the electron transferable compound.

[Chem. 45]

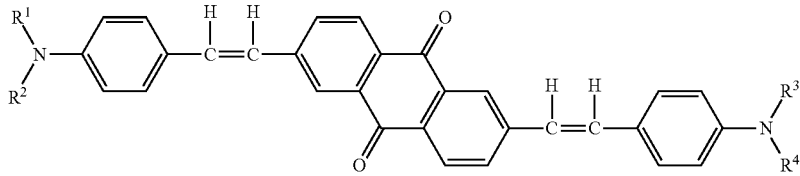

In the formula, $R^1$, $R^2$, $R^3$, and $R^4$ represent groups identical to or different from one another, and each represent an aromatic hydrocarbon group or fused aromatic hydrocarbon group represented by the following formula.

[Chem. 46]

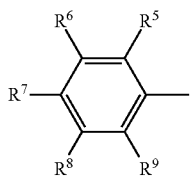

In the formula, $R^5$, $R^6$, $R^7$, $R^8$, and $R^9$ represent groups identical to or different from one another, and each represent a hydrogen atom or a deuterium atom, or at least one thereof represents a saturated or unsaturated alkoxyl, alkyl, amino, or alkylamino group.

Further, a polymer compound containing the nitrogen-containing heterocyclic group or nitrogen-containing heterocyclic derivative is also permitted as the electron transferable compound.

In addition, the electron transporting layer preferably contains at least one of the nitrogen-containing heterocyclic derivatives represented by the following formulae (201) to (203).

[Chem. 47]

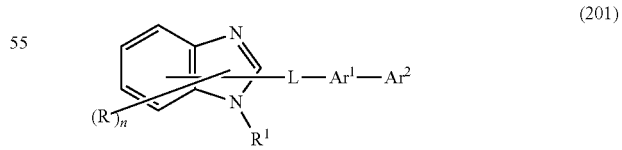
(201)

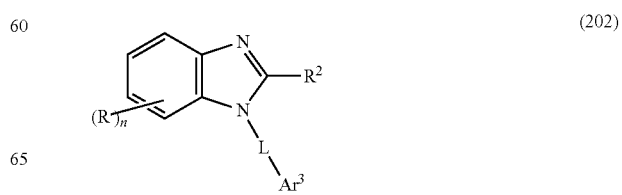
(202)

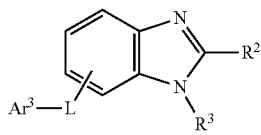

(203)

In the formulae (201) to (203), R represents a hydrogen atom, a deuterium atom, an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent, n represents an integer of 0 to 4, $R^1$ represents an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group having 1 to 20 carbon atoms, $R^2$ and $R^3$ each independently represent a hydrogen atom, a deuterium atom, an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent, L represents an aromatic hydrocarbon group or fused aromatic hydrocarbon group which has 6 to 60 carbon atoms and may have a substituent, a pyridinylene group which may have a substituent, a quinolinylene group which may have a substituent, or a fluorenylene group which may have a substituent, $Ar^1$ represents an aromatic hydrocarbon group or fused aromatic hydrocarbon group which has 6 to 60 carbon atoms and may have a substituent, a pyridinylene group which may have a substituent, or a quinolinylene group which may have a substituent, and $Ar^2$ represents an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

$Ar^3$ represents an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, an alkoxy group which has 1 to 20 carbon atoms and may have a substituent, or a group represented by —$Ar^1$—$Ar^2$ ($Ar^1$ and $Ar^2$ are each the same as that described above).

It should be noted that, in the formulae (201) to (203), R represents a hydrogen atom, a deuterium atom, an aromatic hydrocarbon group or fused aromatic hydrocarbon group which has 6 to 60 carbon atoms and may have a substituent, a pyridyl group which may have a substituent, a quinolyl group which may have a substituent, an alkyl group which has 1 to 20 carbon atoms and may have a substituent, or an alkoxy group which has 1 to 20 carbon atoms and may have a substituent.

It should be noted that the thickness of the electron injecting layer or the electron transporting layer, which is not particularly limited, is preferably 1 nm to 100 nm.

In addition, an insulator or semiconductor serving as an inorganic compound as well as the nitrogen-containing ring derivative is preferably used as a component of the electron injecting layer. When the electron injecting layer is formed of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferred that the electron injecting layer be formed of the alkali metal chalcogenide or the like because the electron injecting property can be further improved. Specifically, preferred examples of the alkali metal chalcogenide include $Li_2O$, $K_2O$, $Na_2S$, $Na_2Se$, and $Na_2O$, and preferred examples of the alkaline earth metal chalcogenide include CaO, BaO, SrO, BeO, BaS, and CaSe. Further, preferred examples of the alkali metal halide include LiF, NaF, KF, LiCl, KCl, and NaCl. In addition, preferred examples of the alkaline earth metal halide include fluorides such as $CaF_2$, $BaF_2$, $SrF_2$, $MgF_2$, and $BeF_2$ and halides other than the fluorides.

In addition, examples of the semiconductor include oxides, nitrides, and oxynitrides each containing at least one element from Ba, Ca, Sr, Yb, Al, Ga, In, Li, Na, Cd, Mg, Si, Ta, Sb, and Zn, and one kind thereof may be used alone, or two or more kinds thereof may be used in combination. Further, it is preferred that the inorganic compound for forming the electron injecting layer form a crystallite or amorphous insulating thin film. When the electron injecting layer is formed of the insulating thin film, a more uniform thin film is formed, and thus defects of pixels such as dark spots can be decreased. It should be noted that examples of the inorganic compound include alkali metal chalcogenides, alkaline earth metal chalcogenides, alkali metal halides, and alkaline earth metal halides.

When such insulator or semiconductor is used, the layer preferably has a thickness of about 0.1 nm to 15 nm. In addition, the electron injecting layer in the present invention may preferably contain the electron-donating dopant described above.

(Hole Injecting Layer and Hole Transporting Layer)

An aromatic amine compound such as an aromatic amine derivative represented by the following general formula (I) is suitably used in the hole injecting layer or hole transporting layer (the hole injecting/transporting layer is also included in this category).

[Chem. 48]

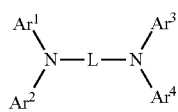

(I)

In the general formula (I), $Ar^1$ to $Ar^4$ each represent a substituted or unsubstituted aromatic hydrocarbon group or fused aromatic hydrocarbon group having 6 to 50 ring carbon atoms, a substituted or unsubstituted aromatic heterocyclic group or fused aromatic heterocyclic group having 5 to 50 ring atoms, or a group obtained by bonding any such aromatic hydrocarbon group or fused aromatic hydrocarbon group and any such aromatic heterocyclic group or fused aromatic heterocyclic group.
Specific examples of the compound represented by the general formula (I) are shown below. However, the compound is not limited to these examples.
[Chem. 49]
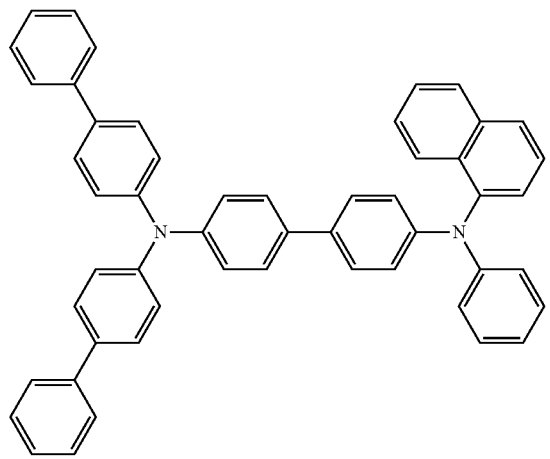
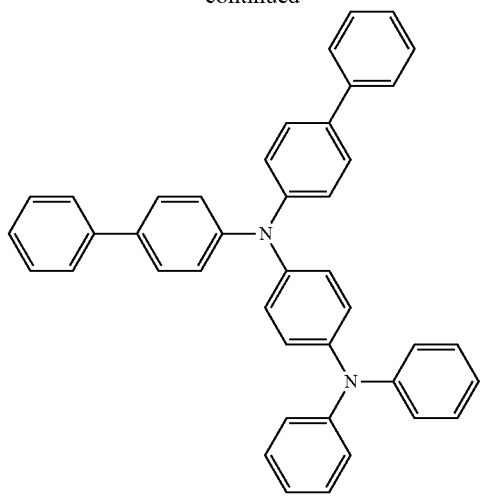
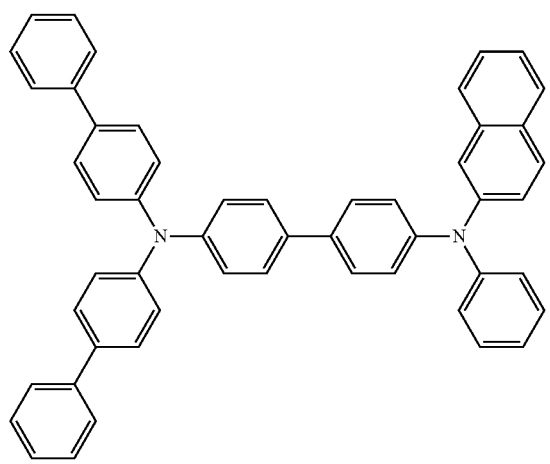
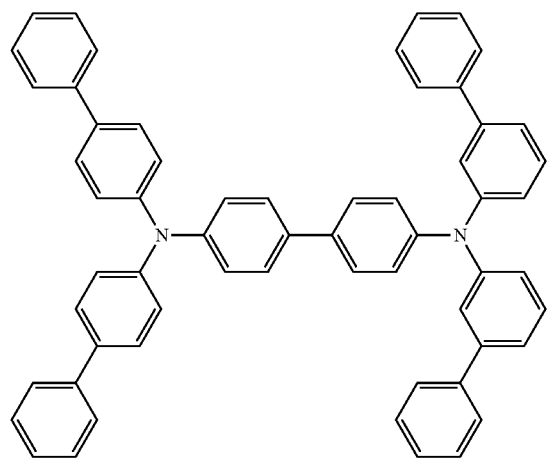
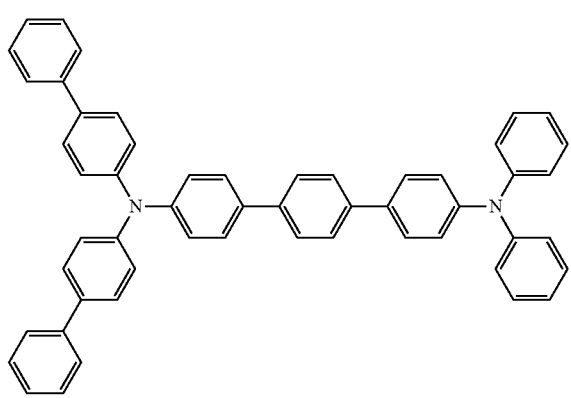
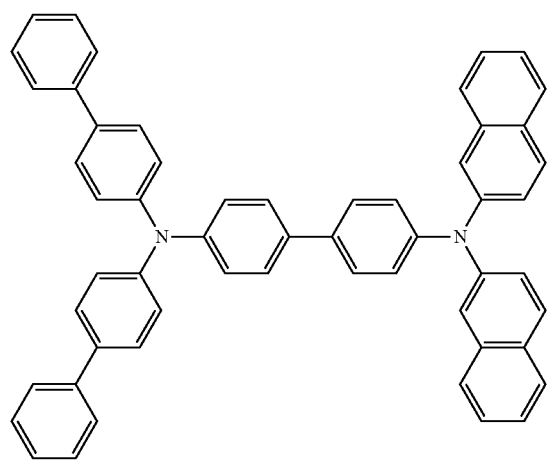

161
-continued
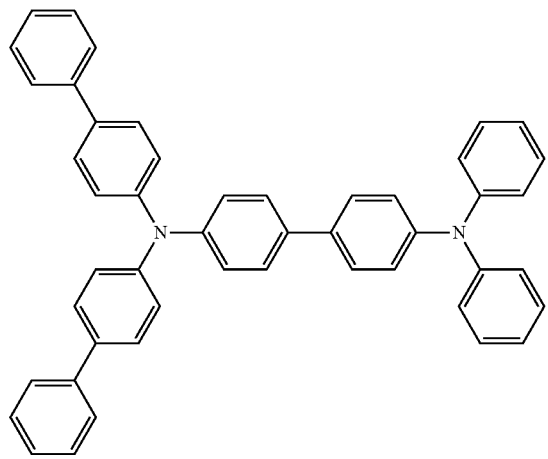
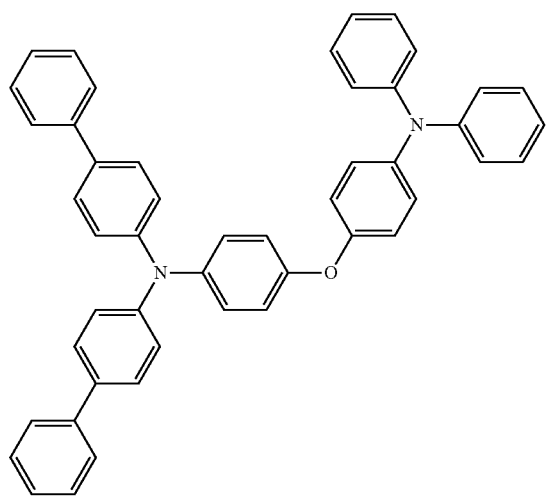
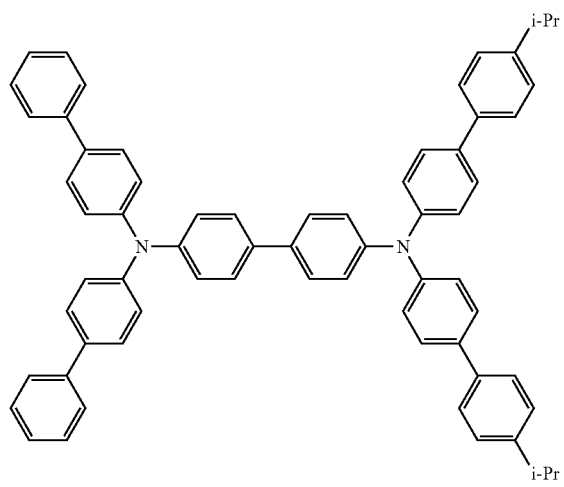
162
-continued
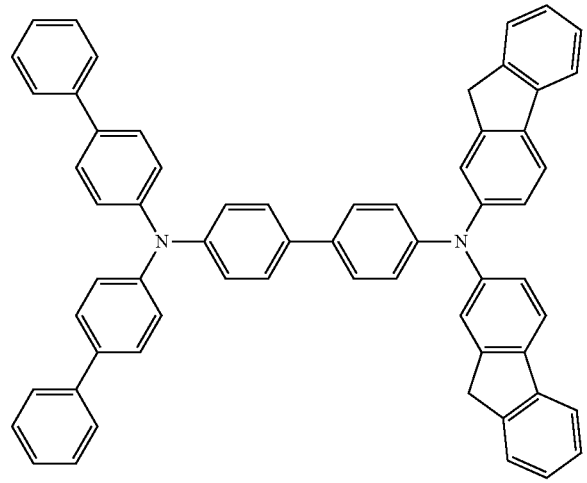
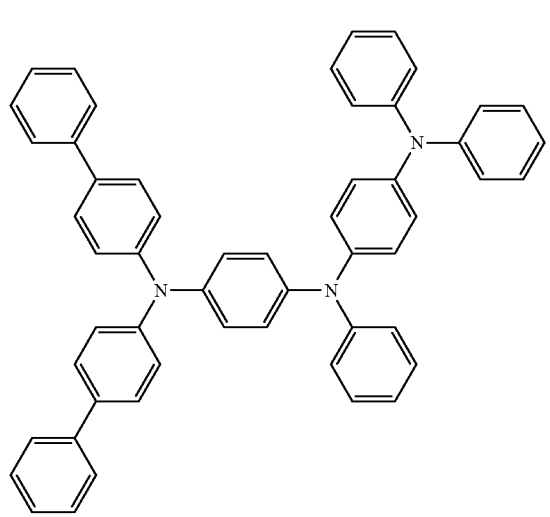
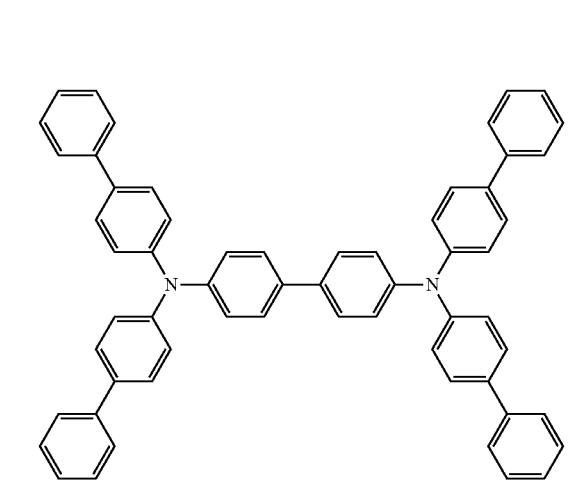

163
-continued
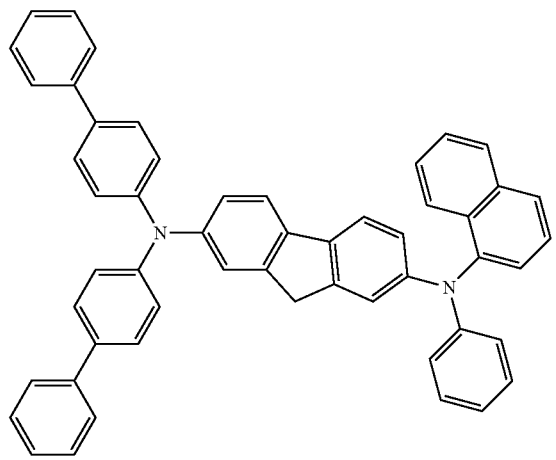
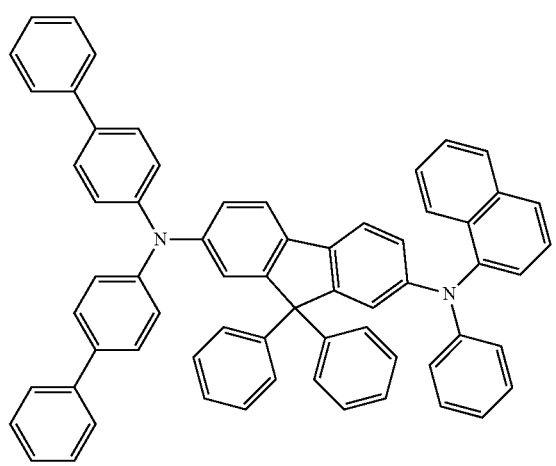
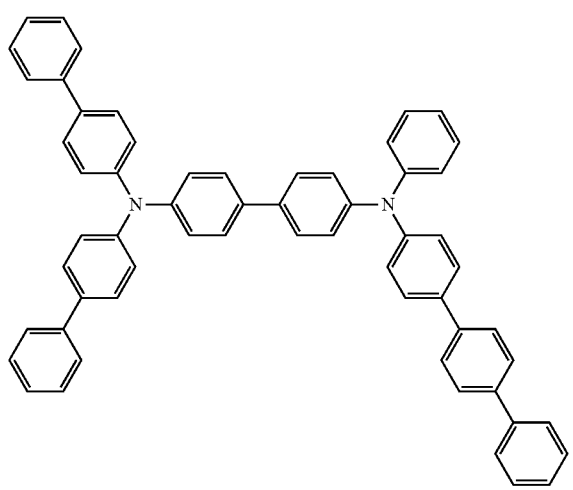
164
-continued
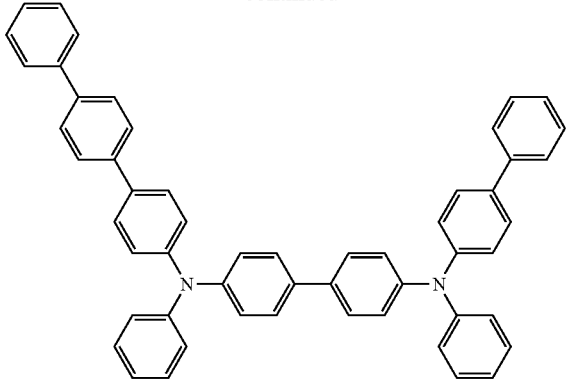
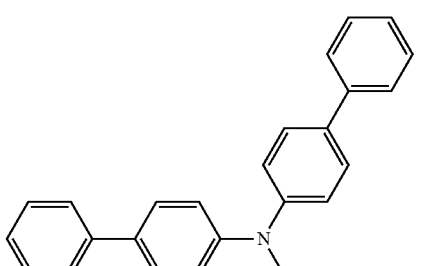
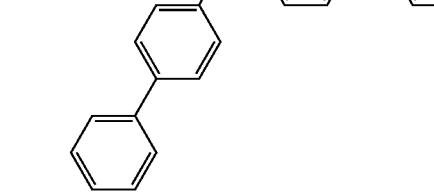

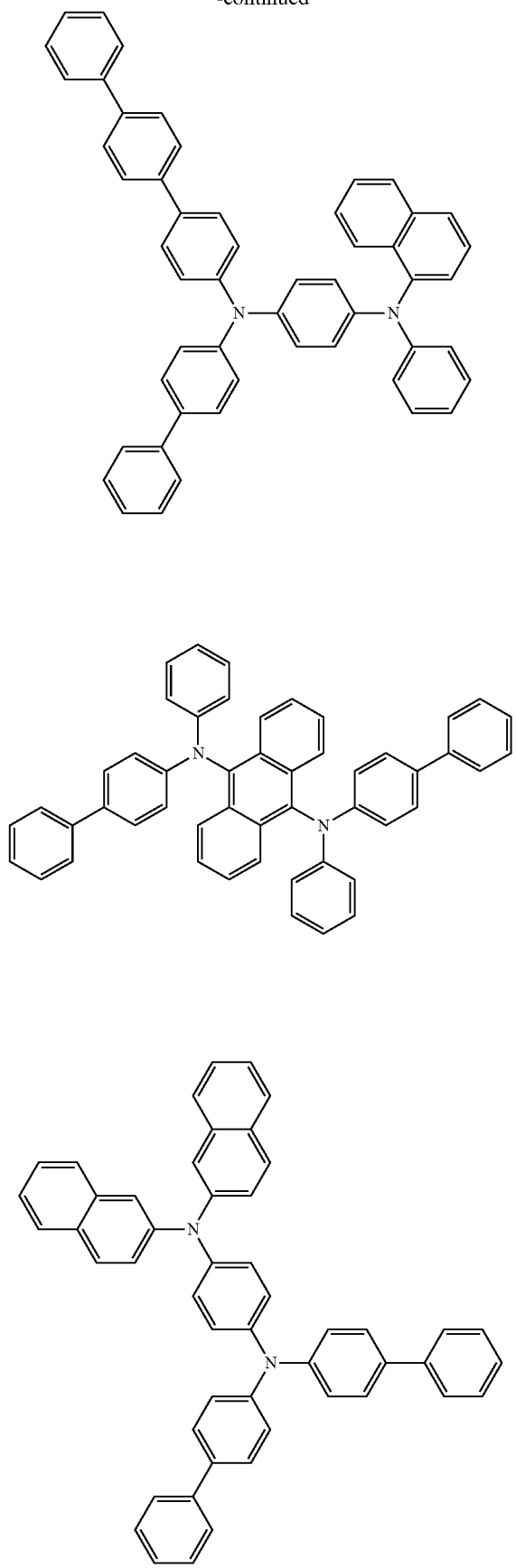
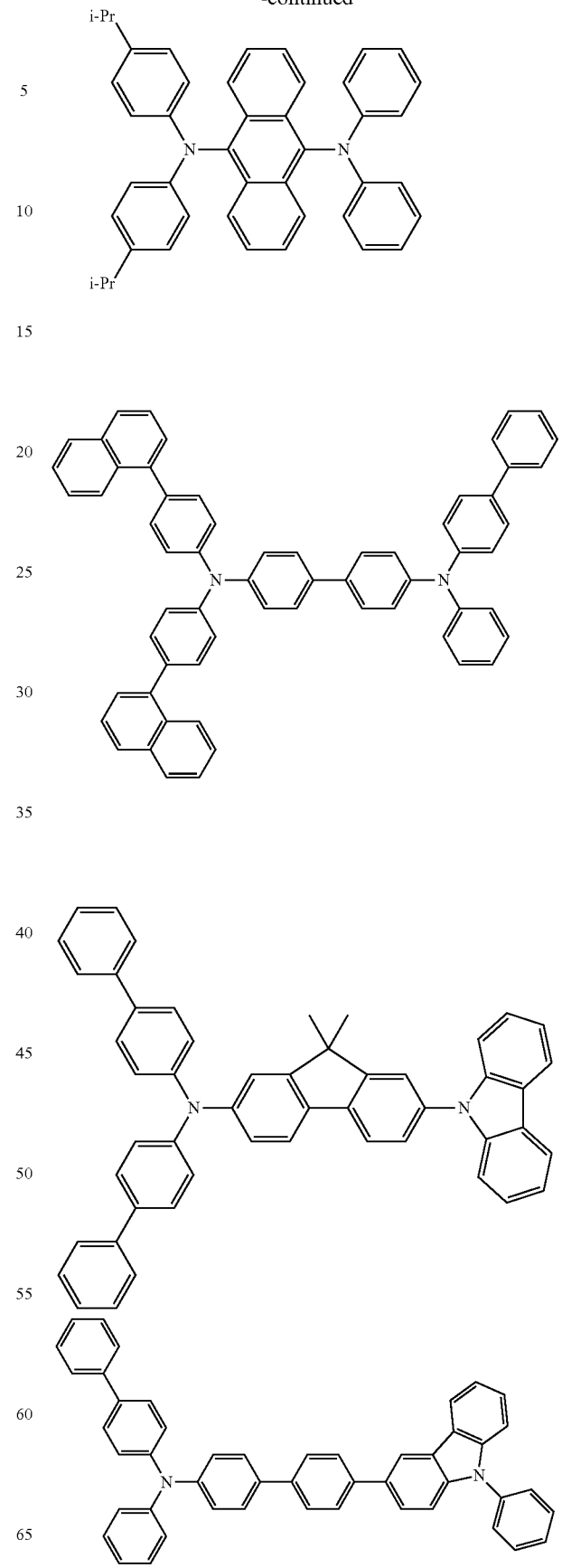

167
-continued

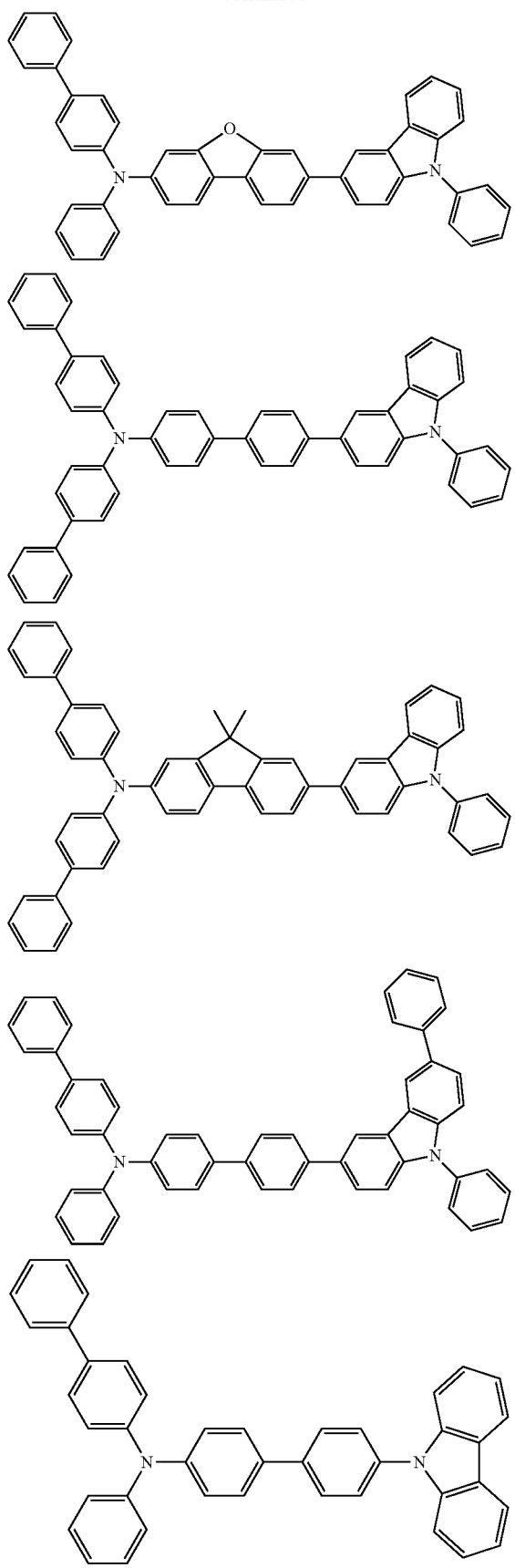

168
-continued

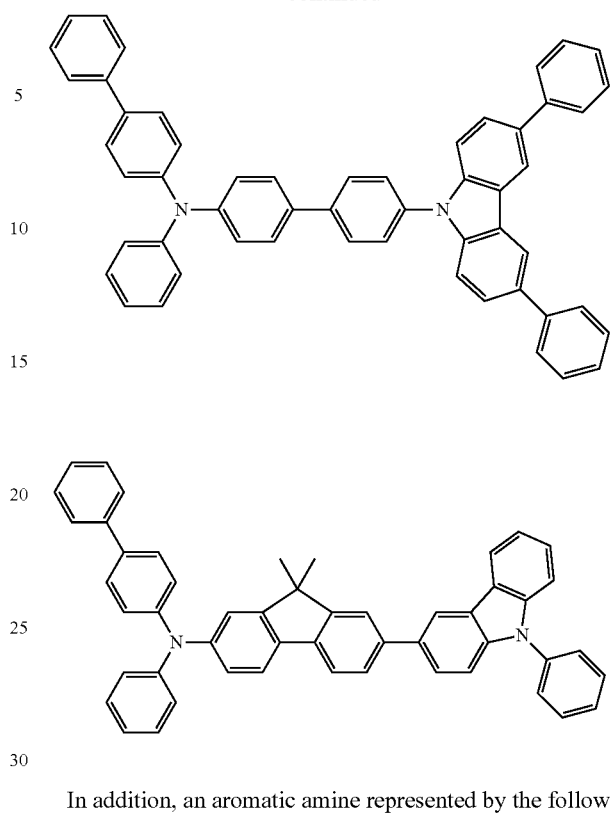

In addition, an aromatic amine represented by the following general formula (II) is also suitably used in the formation of the hole injecting layer or hole transporting layer.

[Chem. 50]

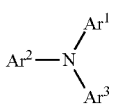

(II)

In the general formula (II), the definition of $Ar_1$ to $Ar_3$ is the same as that of $Ar^1$ to $Ar^4$ in the general formula (I). Specific examples of the compound represented by the general formula (II) are shown below. However, the compound is not limited to these examples.

[Chem. 51]

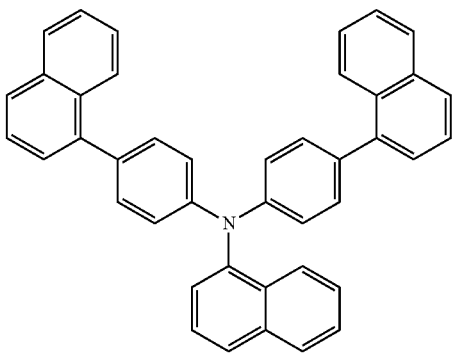

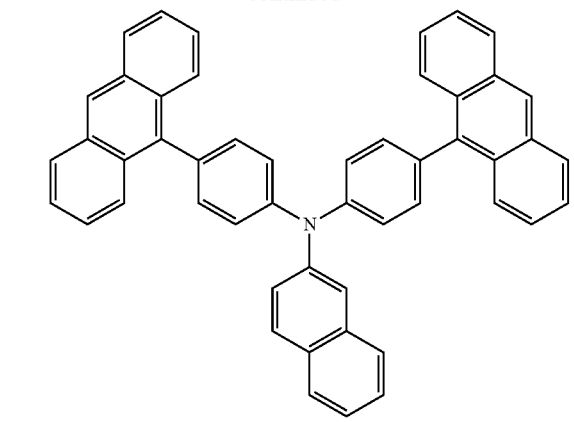
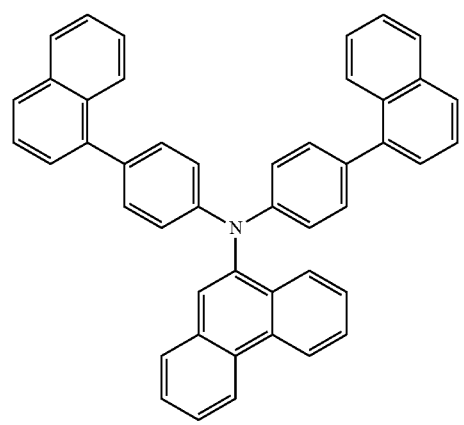
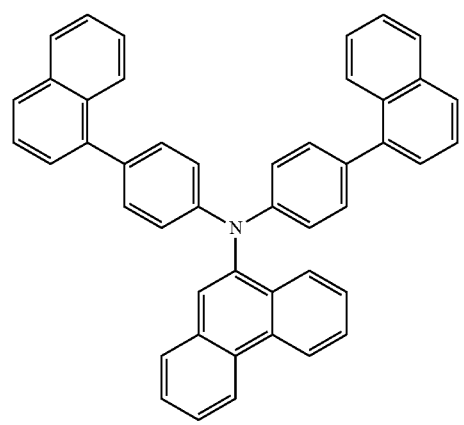
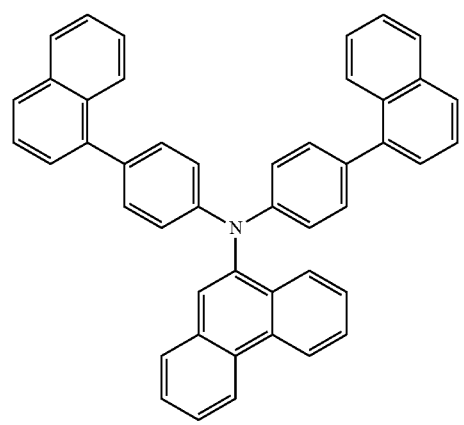
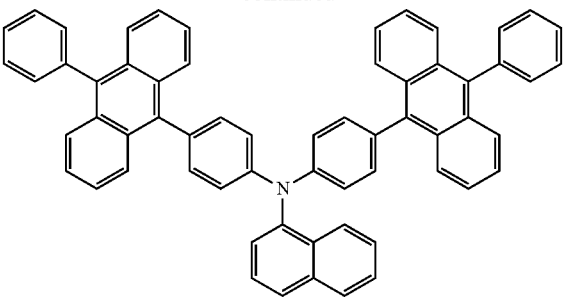
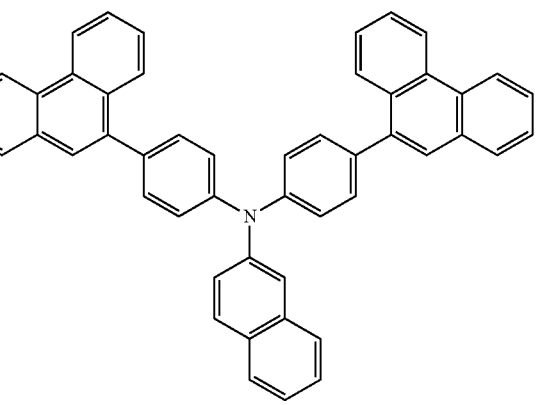
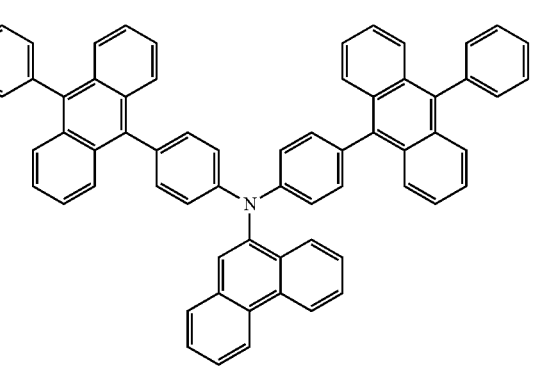
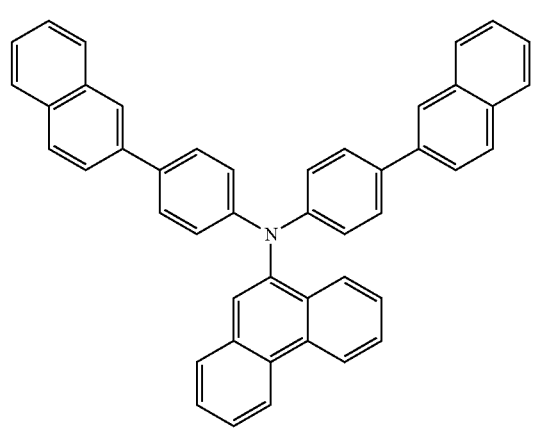

171
-continued
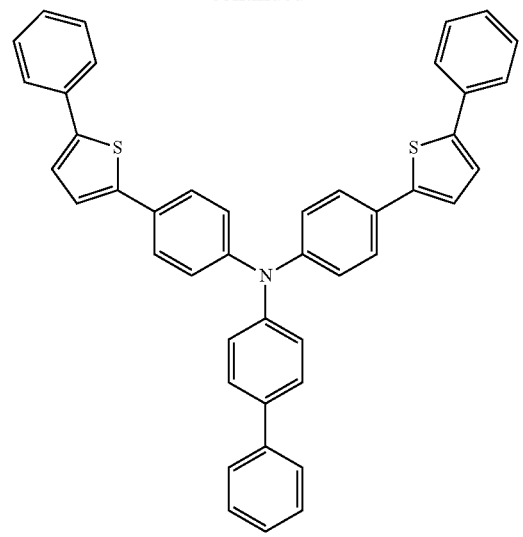
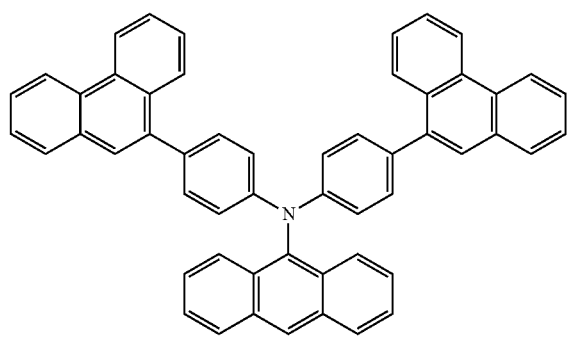
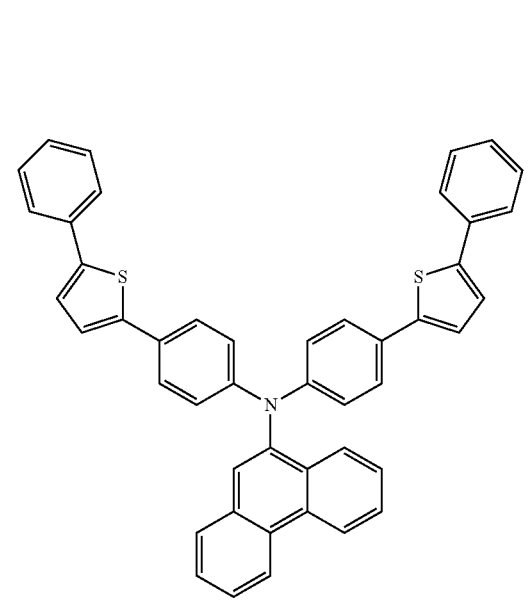
172
-continued
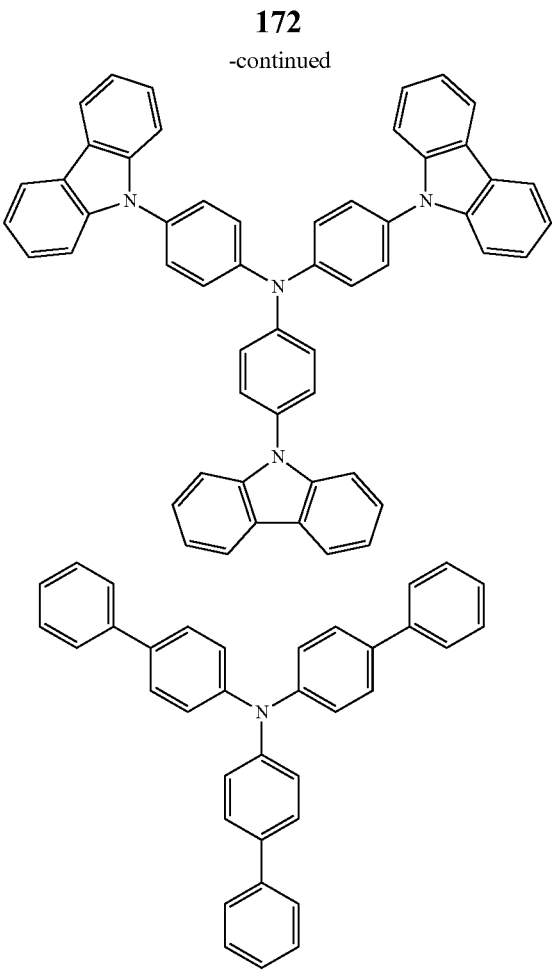
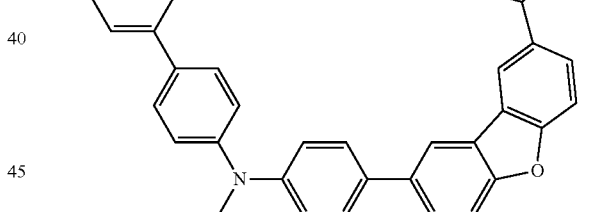
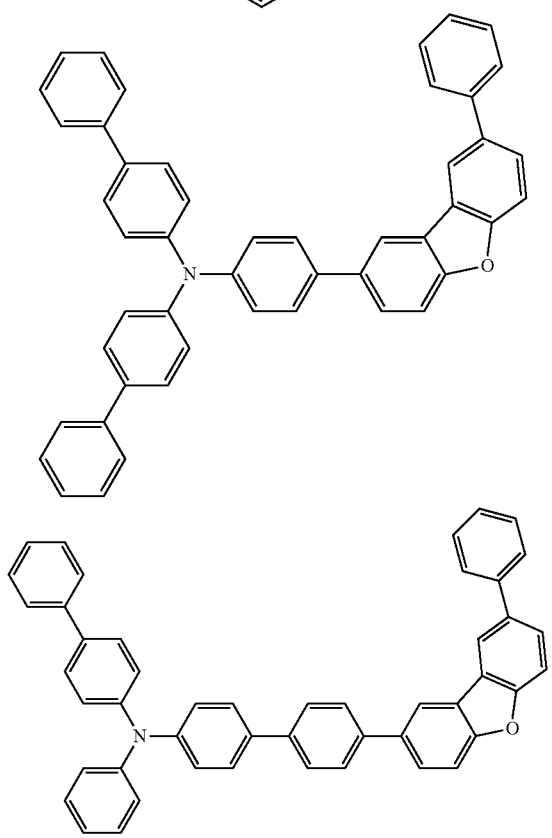

-continued

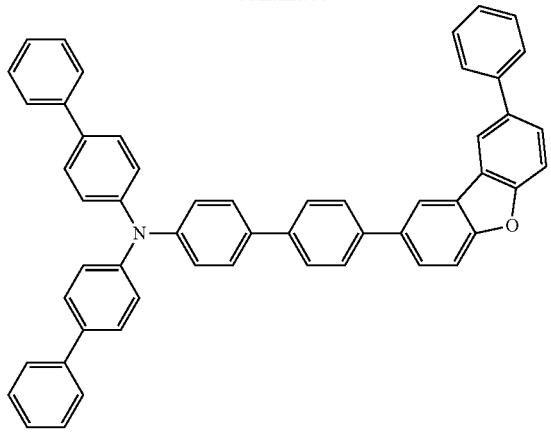

It should be noted that the present invention is not limited to the foregoing description and any modification that does not deviate from the gist of the present invention is included in the present invention.

For example, such modification as described below is a suitable modified example of the present invention.

In the present invention, the light emitting layer preferably contains a charge injection aid.

When the light emitting layer is formed with a host material having a wide energy gap, a difference between the ionization potential (Ip) of the host material and the Ip of the hole injecting/transporting layer or the like enlarges, thereby making it difficult to inject holes into the light emitting layer. As a result, a driving voltage for obtaining sufficient luminance may increase.

In such case, the incorporation of a hole injectable/transportable charge injection aid into the light emitting layer facilitates the injection of holes into the light emitting layer. As a result, the driving voltage can be reduced.

For example, a general hole injecting/transporting material can be utilized as the charge injection aid.

Specific examples thereof include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, fluorenone derivatives, hydrazone derivatives, stilbene derivatives, silazane derivatives, polysilane-based copolymers, aniline-based copolymers, and conductive high molecular oligomers (in particular, thiophene oligomer).

As a material having hole injecting property, the materials described above can be given. However, porphyrin compounds, aromatic tertiary amine compounds, and styrylamine compounds are preferred, and aromatic tertiary amine compounds are particularly preferred.

Further examples of the material include a compound having two fused aromatic rings in a molecule thereof, such as 4,4'-bis(N-(1-naphthyl)-N-phenylamino)biphenyl (hereinafter abbreviated as NPD), and a compound in which three triphenylamine units are linked together in a star-burst shape, such as 4,4',4"-tris(N-(3-methylphenyl)-N-phenylamino)triphenylamine (hereinafter abbreviated as MTDATA).

In addition, a hexaazatriphenylene derivative or the like can also be suitably used as a material having hole injecting property.

Further, an inorganic compound such as p-type Si or p-type SiC can also be used as a hole injecting material.

In the organic EL device of the present invention, a layer containing an acceptor material may be joined to the anode side of the hole transporting layer or the first hole transporting layer. Reductions in driving voltage and production cost are expected from the joining.

The acceptor material is preferably a compound represented by the following formula (10).

[Chem. 52]

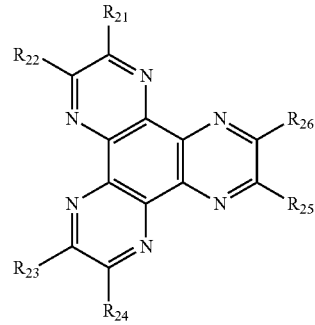

(10)

(In the formula (10), $R_{21}$ to $R_{26}$ may be identical to or different from one another, and each independently represent a cyano group, —$CONH_2$, a carboxyl group, or —$COOR_{27}$ (where $R_{27}$ represents an alkyl group having 1 to 20 carbon atoms or a cycloalkyl group having 3 to 20 carbon atoms), provided that one, or each of two or more, of the pairs of $R_{21}$ and $R_{22}$, $R_{23}$ and $R_{24}$, and $R_{25}$ and $R_{26}$ may form a group represented by —CO—O—CO— together.)

$R_{27}$ represents, for example, a methyl group, an ethyl group, an n-propyl group, an isopropyl group, an n-butyl group, an isobutyl group, a t-butyl group, a cyclopentyl group, or a cyclohexyl group.

The thickness of the layer containing the acceptor material, which is not particularly limited, is preferably 5 to 20 nm.

(n/p Doping)

As described in JP 3695714 B2, a carrier injecting ability in the hole transporting layer or the electron transporting layer can be adjusted through doping with a donor-type material (n) or doping with an acceptor-type material (p).

A representative example of the n doping is a method involving doping an electron transporting material with a metal such as Li or Cs, and a representative example of the p doping is a method involving doping a hole transporting material with an acceptor material such as $F_4TCNQ$.

(Space Layer)

The space layer is the following layer. For example, when a fluorescent light emitting layer and a phosphorescent light emitting layer are laminated, the layer is provided between the fluorescent light emitting layer and the phosphorescent light emitting layer for the purpose of: preventing an exciton produced in the phosphorescent light emitting layer from diffusing into the fluorescent light emitting layer; or adjusting a carrier balance. Alternatively, the space layer can be provided between a plurality of phosphorescent light emitting layers.

The space layer is preferably formed of a material that brings together electron transportability and hole transportability because the layer is provided between the light emitting layers. In addition, the layer preferably has a triplet energy of 2.6 eV or more for preventing the diffusion of the triplet energy in adjacent phosphorescent light emitting layers. Examples of the material to be used in the space layer include the same examples as those of the material to be used in the hole transporting layer.

(Barrier Layer)

The organic EL device of the present invention preferably has a barrier layer such as an electron barrier layer, a hole barrier layer, or a triplet barrier layer at a portion adjacent to the light emitting layer. Here, the electron barrier layer is a layer for preventing the leak of an electron from the light emitting layer to the hole transporting layer, and the hole barrier layer is a layer for preventing the leak of a hole from the light emitting layer to the electron transporting layer.

As described later, the triplet barrier layer has a function of suppressing the energy deactivation of a triplet exciton produced in the light emitting layer on a molecule in the electron transporting layer except a light emitting dopant by preventing the triplet exciton from diffusing into a peripheral layer to trap the triplet exciton in the light emitting layer.

When the triplet barrier layer is provided, as long as the energy magnitude relationship of $E^T_d < E^T_{TB}$ is established where $E^T_d$ represents the triplet energy of a phosphorescent emitting dopant in the light emitting layer and $E^T_{TB}$ represents the triplet energy of a compound to be used in the triplet barrier layer, a triplet exciton of the phosphorescent emitting dopant is trapped (prevented from moving toward any other molecule) on the basis of the energy relationship, and as a result, an energy deactivation path except light emission on the dopant is cut off. Accordingly, it is assumed that light emission can be performed with high efficiency. It should be noted that even when the relationship of $E^T_d < E^T_{TB}$ is established, in the case where the energy difference $\Delta E^T = E^T_{TB} - E^T_d$ is small, under an environment having a temperature around room temperature as an environment where the device is actually driven, the triplet exciton may be able to endothermically surmount the energy difference $\Delta E^T$ by virtue of a peripheral thermal energy to move toward the other molecule. An influence of an endothermic exciton movement process appears with relative ease particularly in the case of phosphorescent emission because the exciton lifetime of the phosphorescent emission is longer than that of fluorescent emission. The energy difference $\Delta E^T$ with respect to the thermal energy of room temperature is preferably as large as possible, more preferably 0.1 eV or more, particularly preferably 0.2 eV or more.

The triplet energy in the present invention is measured as described below.

First, a sample is dissolved in an EPA solvent (diethyl ether:isopentane:ethanol=5:5:2 (volume ratio)) at 10 µmol/L so that a sample for phosphorescence measurement may be obtained. The sample for phosphorescence measurement is loaded into a quartz cell and irradiated with excitation light at a temperature of 77 K, and then the phosphorescence spectrum of phosphorescence to be emitted is measured. The triplet energy is defined as a value determined on the basis of the spectrum from the conversion equation "$E^T$ (eV)=1,239.85/$\lambda_{edge}$." The symbol "$\lambda_{edge}$" means a wavelength value (unit: nm) for the following point of intersection. When the phosphorescence spectrum is represented with an axis of ordinate indicating a phosphorescence intensity and an axis of abscissa indicating a wavelength, a tangent is drawn to the rise of the phosphorescence spectrum on shorter wavelengths, and the point of intersection of the tangent and the axis of abscissa is adopted.

A host material for the light emitting layer preferably satisfies the relationship of $A_b - A_h \leq 0.1$ eV. Here, $A_b$ represents the affinity of a material for the barrier layer and $A_h$ represents the affinity of the host material for the light emitting layer.

An affinity Af (electron affinity) in the present invention refers to an energy to be released or absorbed when one electron is donated to a material molecule, and is defined as being positive when released or as being negative when absorbed. The affinity Af is specified with an ionization potential Ip and an optical energy gap Eg(S) as described below.

$$Af = Ip - Eg(S)$$

Here, the ionization potential Ip means an energy needed to remove an electron from the compound of each material to ionize the compound, and in the present invention, is a value having a positive sign measured with an atmospheric photoelectron spectrometer (AC-3 manufactured by Riken Keiki Co., Ltd.). The optical energy gap Eg(S) refers to a difference between a conduction level and a valence level, and in the present invention, is a value having a positive sign determined by converting a wavelength value for the point of intersection of a tangent on longer wavelengths and a baseline (zero absorption) in the ultraviolet and visible light absorption spectrum of a dilute solution of each material in dichloromethane into an energy.

In addition, the electron mobility of a material constituting the triplet barrier layer is desirably $10^{-6}$ cm$^2$/Vs or more in the electric field intensity range of 0.04 to 0.5 MV/cm. Although several methods such as a time-of-flight method have been known as methods of measuring the electron mobilities of organic materials, the electron mobility mentioned here is one determined by impedance spectroscopy.

The electron injecting layer desirably has an electron mobility of $10^{-6}$ cm$^2$/Vs or more in the electric field intensity range of 0.04 to 0.5 MV/cm. This is because of the following reason. The inject ion of an electron from the cathode into the electron transporting layer is promoted, and as a result, the injection of an electron into the adjacent barrier layer or light emitting layer is also promoted and driving at an additionally low voltage is enabled.

The forming method of each layer of the organic EL device of the present invention is not particularly limited. A conventionally known forming method such as a vacuum vapor deposition method or a spin coating method can be used. The organic thin-film layer containing the compound represented by any one of the formulae (1) to (4) to be used in the organic EL device of the present invention can be formed by a known method such as a vacuum vapor deposition method, a molecular beam epitaxy method (MBE method), or an application method involving using a solution prepared by dissolving the compound in a solvent, such as a dipping method, a spin coating method, a casting method, a bar coat method, or a roll coat method.

The thickness of each organic layer of the organic EL device of the present invention is not particularly limited. In general, however, the following problems arise. When the thickness is excessively small, defects such as pinholes are apt to occur. In contrast, when the thickness is excessively large, a high applied voltage is needed, thereby resulting in poor efficiency. Accordingly, the thickness preferably ranges from several nanometers to one micrometer in ordinary cases.

EXAMPLES

Next, the present invention is described more specifically with reference to examples and comparative examples. However, the present invention is by no means limited to the description of the examples.

Synthesis Example 1-1 (Synthesis of Compound 1)

[Chem. 53]

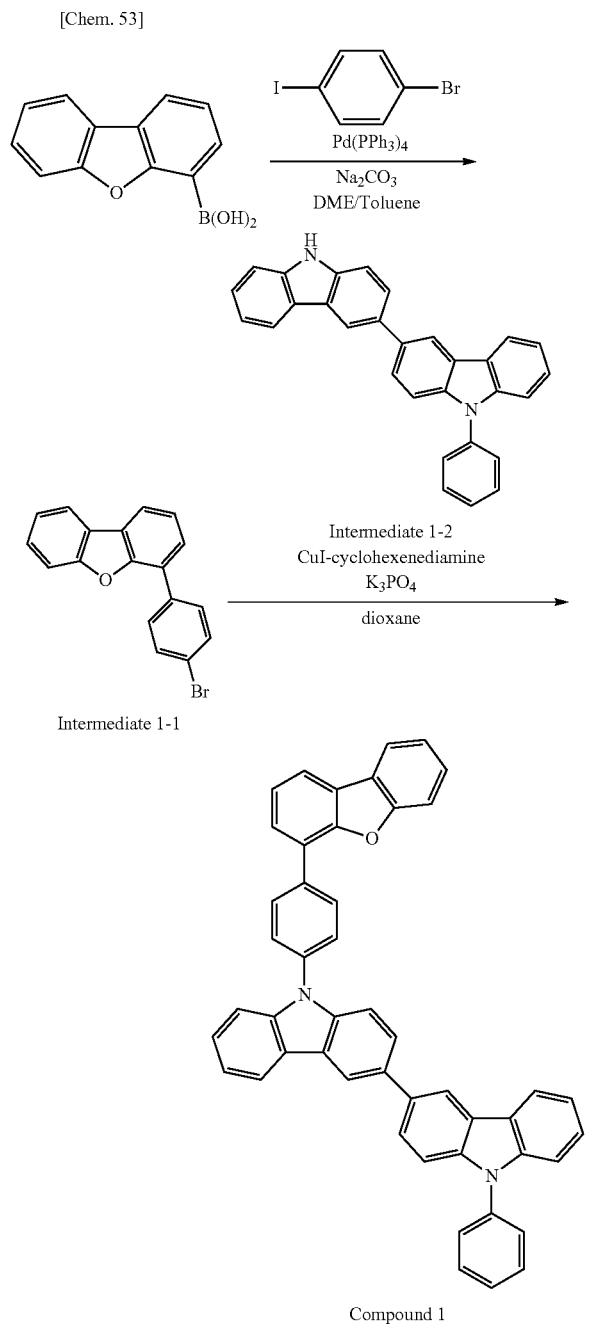

Synthesis of Intermediate 1-1

Under an argon atmosphere, toluene (150 mL), dimethoxyethane (150 mL), and an aqueous solution of sodium carbonate having a concentration of 2 M (150 mL) were added to 4-iodobromobenzene (28.3 g, 100.0 mmol), dibenzofuran-4-boronic acid (22.3 g, 105 mmol), and tetrakis(triphenylphosphine)palladium(0) (2.31 g, 2.00 mmol), and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, an intermediate 1-1 (26.2 g, 81% yield) was obtained.

FD-MS analysis confirmed that the intermediate had a ratio m/e of 322 with respect to its molecular weight, i.e., 322.

Synthesis of Compound 1

Under an argon atmosphere, the intermediate 1-1 (2.36 g, 7.3 mmol), an intermediate 1-2 (3.0 g, 7.3 mmol), CuI (1.4 g, 7.3 mmol), tripotassium phosphate (2.3 g, 11 mmol), anhydrous dioxane (30 mL), and cyclohexanediamine (0.84 g, 7.3 mmol) were loaded in the stated order into a three-necked flask, and were then stirred at 100° C. for 8 hours.

Water was added to the reaction mixture to precipitate a solid, and then the solid was washed with hexane and then with methanol. Further, the resultant solid was purified by silica gel column chromatography. Thus, a compound 1 (2.9 g, 60% yield) was obtained.

The result of FD-MS analysis confirmed that the compound had a ratio m/e of 650 with respect to its molecular weight, i.e., 650.

Synthesis Example 1-2 (Synthesis of Compound 2)

[Chem. 54]

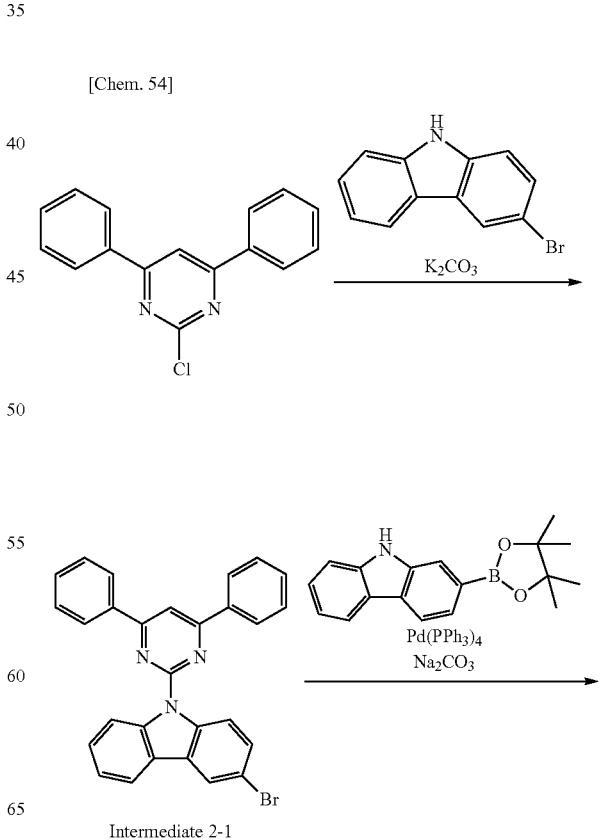

Intermediate 2-1

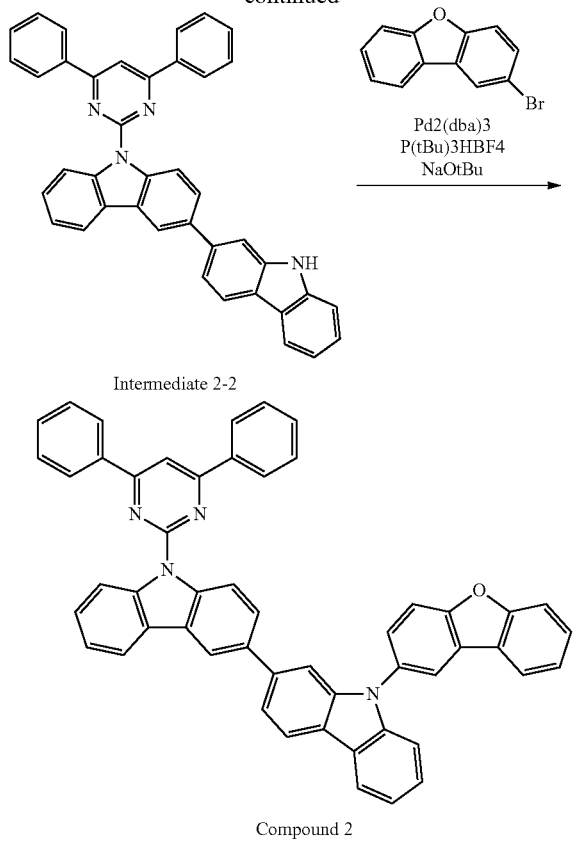

Intermediate 2-2

Compound 2

Synthesis of Intermediate 2-1

4,6-Diphenylpyrimidine-2-chloride (5.3 g, 20 mmol), 3-bromocarbazole (4.9 g, 20 mmol), and potassium carbonate (3.8 g, 28 mmol) were added to dimethylformamide (30 mL), and then the mixture was stirred under heating at 100° C. for 8 hours.

Water was added to the reaction mixture to precipitate a solid, and then the solid was washed with methanol. Thus, an intermediate 2-1 (7.6 g, 80% yield) was obtained.

Synthesis of Intermediate 2-2

Next, under an argon atmosphere, the intermediate 2-1 (5.8 g, 12.2 mmol), 9H-carbazole-2-boronic acid pinacol ester (3.6 g, 12.2 mmol), tetrakis(triphenylphosphine)palladium (0.26 g, 0.24 mmol), and a 2 M aqueous solution of sodium carbonate (20 mL) were added to toluene (40 mL), and then the mixture was stirred under heating at 80° C. for 8 hours.

The organic layer was separated, and then the organic layer was concentrated with an evaporator. After that, the resultant residue was purified by silica gel column chromatography. Thus, an intermediate 2-2 (5.3 g, 77% yield) was obtained.

Synthesis of Compound 2

Under an argon atmosphere, 2-bromodibenzofuran (2 g, 8.1 mmol), the intermediate 2-2 (4.1 g, 7.3 mmol), Pd$_2$(dba)$_3$ (0.14 g, 0.15 mmol), P(tBu)$_3$HBF$_4$ (0.17 g, 0.6 mmol), sodium t-butoxide (1.1 g, 11 mmol), and anhydrous xylene (30 mL) were loaded in the stated order into a three-necked flask, and were then heated for 8 hours while being refluxed.

Water was added to the reaction mixture to precipitate a solid, and then the solid was washed with hexane and then with methanol. Further, the resultant solid was purified by silica gel column chromatography. Thus, a compound 2 (3.6 g, 68% yield) was obtained.

The result of FD-MS analysis confirmed that the compound had a ratio m/e of 728 with respect to its molecular weight, i.e., 728.

Synthesis Example 1-3 (Synthesis of Compound 3)

[Chem. 55]

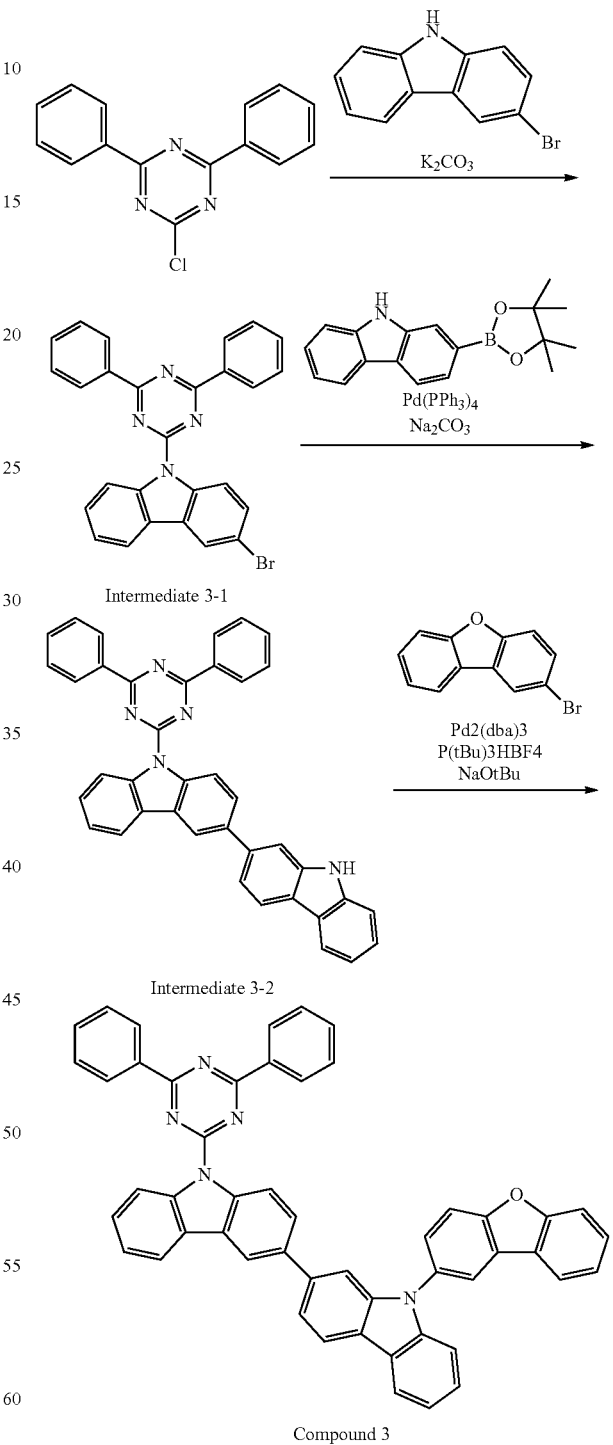

Intermediate 3-1

Intermediate 3-2

Compound 3

Synthesis of Intermediate 3-1

4,6-Diphenyltriazine-2-chloride (5.3 g, 20 mmol), 3-bromocarbazole (4.9 g, 20 mmol), and potassium carbonate (3.8 g, 28 mmol) were added to dimethylformamide (30 mL), and then the mixture was stirred under heating at 100° C. for 8 hours.

Water was added to the reaction mixture to precipitate a solid, and then the solid was washed with methanol. Thus, an intermediate 3-1 (8.1 g, 85% yield) was obtained.

Synthesis of Intermediate 3-2

Next, under an argon atmosphere, the intermediate 3-1 (5.8 g, 12.2 mmol), 9H-carbazole-2-boronic acid pinacol ester (3.6 g, 12.2 mmol), tetrakis(triphenylphosphine)palladium (0.26 g, 0.24 mmol), and a 2 M aqueous solution of sodium carbonate (20 mL) were added to toluene (40 mL), and then the mixture was stirred under heating at 80° C. for 8 hours.

The organic layer was separated, and then the organic layer was concentrated with an evaporator. After that, the resultant residue was purified by silica gel column chromatography. Thus, an intermediate 3-2 (5.0 g, 73% yield) was obtained.

Synthesis of Compound 3

Under an argon atmosphere, 2-bromodibenzofuran (2 g, 8.1 mmol), the intermediate 3-2 (4.1 g, 7.3 mmol), $Pd_2(dba)_3$ (0.14 g, 0.15 mmol) $P(tBu)_3HBF_4$ (0.17 g, 0.6 mmol), sodium t-butoxide (1.1 g, 11 mmol), and anhydrous xylene (30 mL) were loaded in the stated order into a three-necked flask, and were then heated for 8 hours while being refluxed.

Water was added to the reaction mixture to precipitate a solid, and then the solid was washed with hexane and then with methanol. Further, the resultant solid was purified by silica gel column chromatography. Thus, a compound 3 (3.2 g, 60% yield) was obtained.

The result of FD-MS analysis confirmed that the compound had a ratio m/e of 729 with respect to its molecular weight, i.e., 729.

Example 1-1 (Production of Organic EL Device)

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes, and was then subjected to UV/ozone cleaning for 30 minutes.

The glass substrate with the transparent electrode line after the cleaning was mounted on the substrate holder of a vacuum deposition apparatus. First, the following electron acceptable compound (C-1) was deposited from the vapor onto the surface on the side where the transparent electrode line was formed so as to cover the transparent electrode. Thus, a C-1 film having a thickness of 5 nm was formed. The following aromatic amine derivative (X3) as a first hole transporting material was deposited from the vapor onto the C-1 film so that a first hole transporting layer having a thickness of 157 nm was formed. Subsequently to the formation of the first hole transporting layer, the compound 1 as a second hole transporting material was deposited from the vapor so that a second hole transporting layer having a thickness of 10 nm was formed.

Further, the following compound (Y1) was deposited from the vapor onto the second hole transporting layer so that a light emitting layer having a thickness of 40 nm was formed. At the same time, the following compound (D4) as a phosphorescent emitting material was co-deposited from the vapor. The concentration of the compound D4 was 10.0 mass %. The co-deposited film functions as a light emitting layer.

Then, the compound (ET2) was formed into a film having a thickness of 20 nm subsequently to the formation of the light emitting layer. The ET2 film functions as an electron transporting layer.

Next, LiF was formed into a film having a thickness of 1 nm at a film formation rate of 0.1 Å/min so as to serve as an electron injectable electrode (cathode). Metal Al was deposited from the vapor onto the LiF film so that a metal cathode having a thickness of 80 nm was formed. Thus, an organic EL device was produced.

The resultant organic electroluminescence device was caused to emit light through DC current driving, its luminance (L) and current density were measured, and its current efficiency (cd/A) and driving voltage (V) at a current density of 10 $mA/cm^2$ were determined. Further, its half lifetime at a current density of 50 $mA/cm^2$ was determined. Table 1-1 shows the results.

Comparative Examples 1-1 to 1-3

Organic EL devices were each produced in the same manner as in Example 1-1 except that a light emitting layer was formed by using a compound described in Table 1-1 instead of using the compound 1 in Example 1-1. Table 1-1 shows the results of the measurement of their luminous efficiencies and half lifetimes.

[Chem. 56]

X3

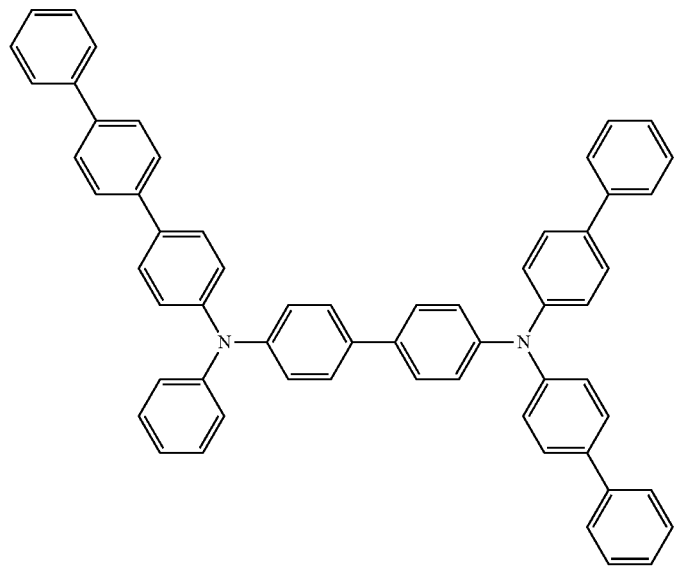

-continued
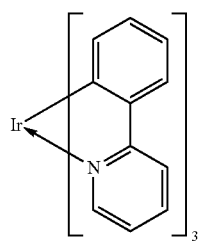
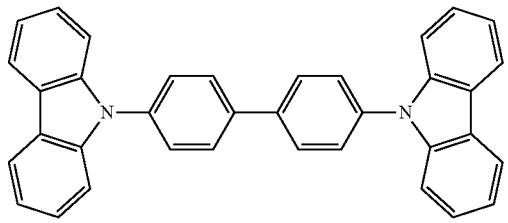
D4
Y1
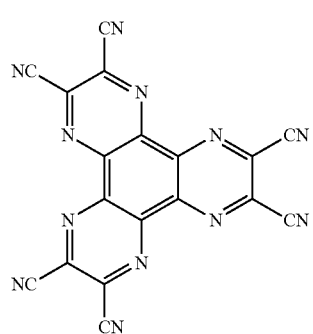
C-1
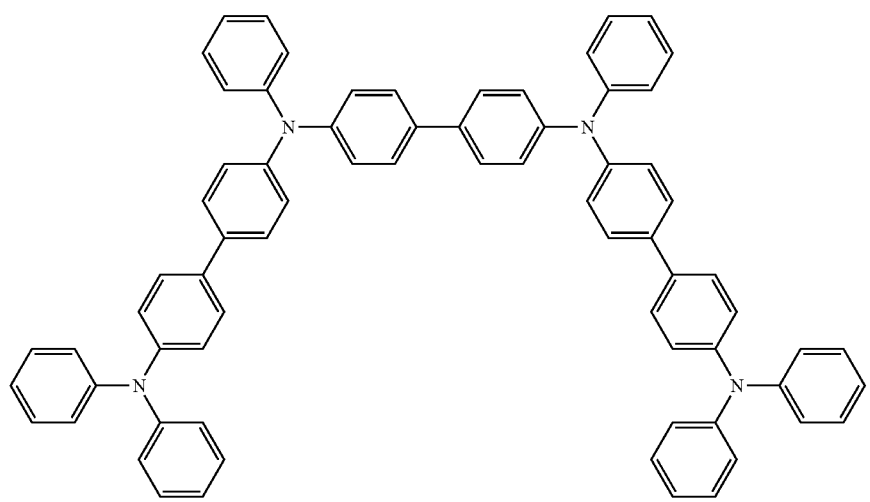
X1
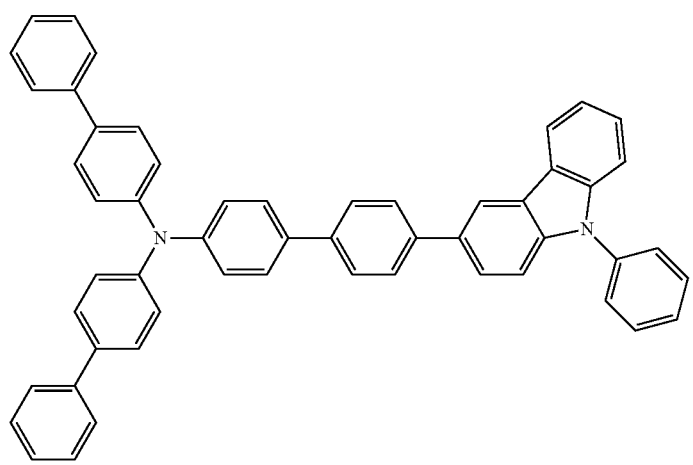
X2

-continued

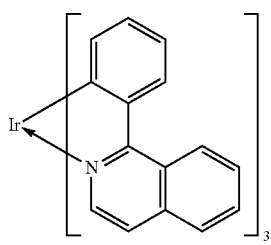

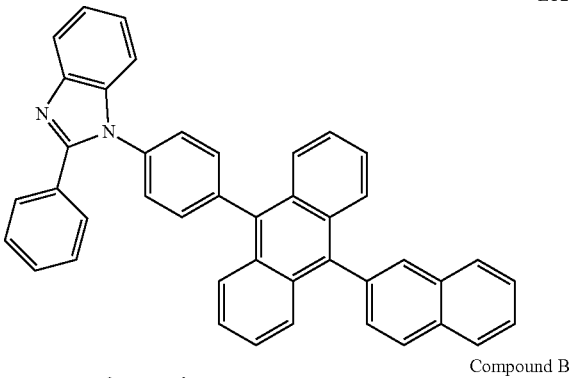

Compound A

Compound B

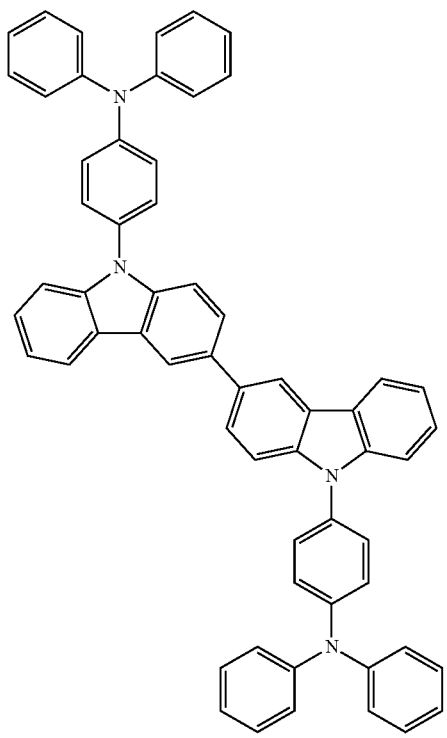

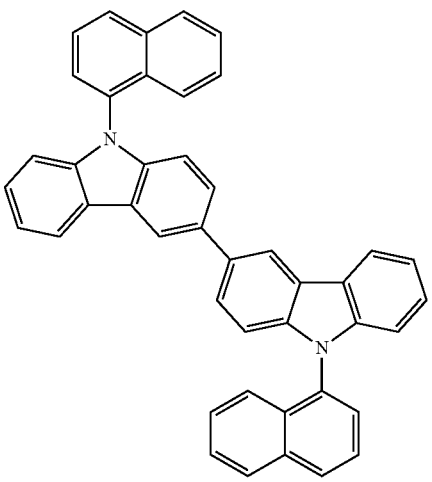

TABLE 1-1

|  | Hole transporting material | Voltage (V) | Current efficiency (cd/A) | Luminance half lifetime (hrs) |
|---|---|---|---|---|
| Example 1-1 | Compound 1 | 3.8 | 53.3 | 580 |
| Comparative Example 1-1 | Compound A | 3.6 | 49.5 | 100 |
| Comparative Example 1-2 | Compound B | 3.7 | 46.8 | 220 |
| Comparative Example 1-3 | Compound X2 | 3.6 | 47.5 | 180 |

When the compound A was used, the half lifetime reduced because the compound was inferior in electron resistance to the biscarbazole derivative of the present invention.

In addition, even when a fused ring was used as with the present invention, the efficiency of the device using the compound B having a naphthalene skeleton reduced to a large extent. This is because the extent to which a triplet exciton was trapped in the light emitting layer was insufficient owing to a small triplet energy of the compound B.

Further, when the compound X2 free of any biscarbazole derivative skeleton is used, the current efficiency similarly reduces because the triplet energy of the compound X2 is small as with the compound B.

As is apparent from the foregoing results, the biscarbazole derivative of the present invention is superior in current efficiency and lifetime to the compounds used in the comparative examples.

Example 1-2

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes, and was then subjected to ultraviolet (UV)/ozone cleaning for 30 minutes.

The glass substrate with the transparent electrode line after the cleaning was mounted on the substrate holder of a vacuum deposition apparatus. First, the following compound E was deposited from the vapor onto the surface on the side of the glass substrate where the transparent electrode line was formed so as to cover the transparent electrode. Thus, a film of the compound E having a thickness of 40 nm was formed. The film was defined as a hole injecting layer.

The following compound F was deposited from the vapor onto the film of the compound E so that a film of the compound F having a thickness of 20 nm was formed. The film was defined as a hole transporting layer.

The compound 2 obtained in Synthesis Example 1-2 was deposited from the vapor onto the hole transporting layer so that a light emitting layer having a thickness of 40 nm was formed. Simultaneously with the vapor deposition of the compound 2, the following compound D1 (Ir(Ph-ppy)$_3$ (facial body)) as a phosphorescent emitting material was co-deposited from the vapor. The concentration of the compound D1 was 20 mass %. The co-deposited film functions as a light emitting layer using the compound 2 as a phosphorescent host material and the compound D1 as a phosphorescent dopant material. It should be noted that the compound D1 is a green light emitting material.

Then, the following compound G was deposited from the vapor subsequently to the formation of the light emitting layer so that a film of the compound G having a thickness of 30 nm was formed. The film was defined as an electron transporting layer.

Next, LiF was deposited from the vapor onto the electron transporting layer at a film formation rate of 0.1 Å/min so that an LiF film having a thickness of 1 nm was formed. The film was defined as an electron injectable electrode (cathode).

Further, metal Al was deposited from the vapor onto the LiF film so that a metal cathode having a thickness of 80 nm was formed. Thus, an organic EL device was produced.

[Chem. 57]

Compound E

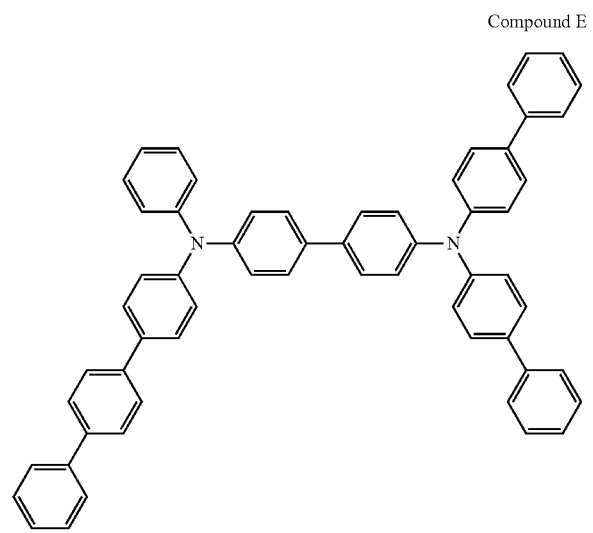

-continued

Compound F

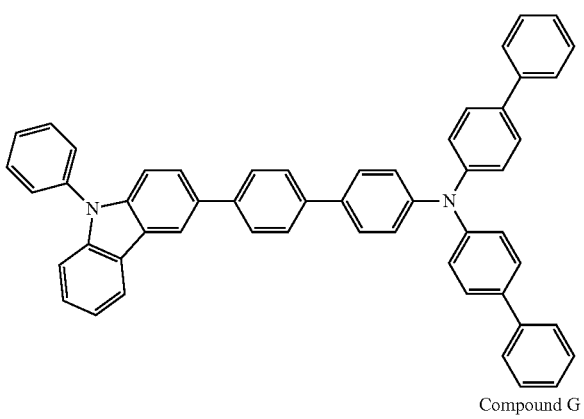

Compound G

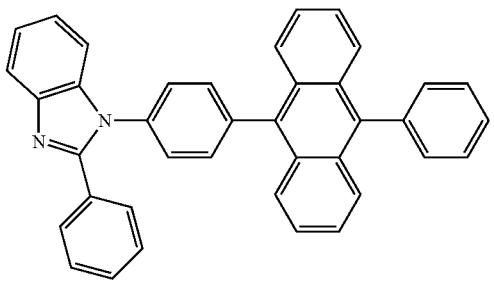

Compound D1

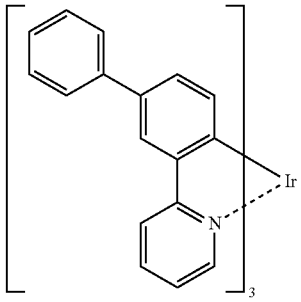

Compound

Measurement of Current Efficiency (Current Efficiency)

The produced organic EL device was caused to emit light under room temperature through DC constant current driving (current density: 10 mA/cm$^2$), and then its spectral radiance spectrum at the time was measured with a spectral radiance meter (CS-1000 manufactured by KONICA MINOLTA HOLDINGS, INC.). Its current efficiency (unit: cd/A) was calculated from the resultant spectral radiance spectrum. Table 1-2 shows the current efficiency thus calculated together with a value for the voltage applied at the time of the measurement of the current efficiency.

Example 1-3

An organic EL device of Example 1-3 was produced in the same manner as in the organic EL device of Example 1-2 except that the compound 3 was used instead of the compound 2 as a phosphorescent host material for the light emitting layer of the organic EL device of Example 1-2. Then, its current efficiency and voltage value were determined. Table 1-2 shows the results.

TABLE 1-2

|  | Host material | Voltage (V) | Current efficiency (cd/A) |
| --- | --- | --- | --- |
| Example 1-2 | Compound 2 | 4.1 | 67 |
| Example 1-3 | Compound 3 | 4.3 | 65 |

Example 2-1

(Production of Organic EL Device)

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes, and was then subjected to ultraviolet (UV)/ozone cleaning for 30 minutes.

The glass substrate with the transparent electrode line after the cleaning was mounted on the substrate holder of a vacuum deposition apparatus. First, the following electron acceptable compound (A) was deposited from the vapor onto the surface on the side where the transparent electrode line was formed so as to cover the transparent electrode. Thus, an A film having a thickness of 5 nm was formed. NPD as a first hole transporting material was deposited from the vapor onto the A film so that a first hole transporting layer having a thickness of 85 nm was formed. Subsequently to the formation of the first hole transporting layer, the compound 1 obtained in Synthesis Example 1-1 as a second hole transporting material was deposited from the vapor so that a second hole transporting layer having a thickness of 10 nm was formed.

A host compound (BH) and a dopant compound (BD) were co-deposited from the vapor onto the hole transporting layer so as to have a thickness of 25 nm. Thus, a light emitting layer was obtained. The concentration of the dopant compound (BD) was 5 mass %.

Subsequently, the following compound (ET1) having a thickness of 20 nm and the following compound (ET2) having a thickness of 5 nm were deposited from the vapor onto the light emitting layer so that an electron transporting/injecting layer was formed. Further, LiF having a thickness of 1 nm and metal Al having a thickness of 80 nm were sequentially laminated so that a cathode was formed. Thus, an organic electroluminescence device was produced.

[Chem. 58]

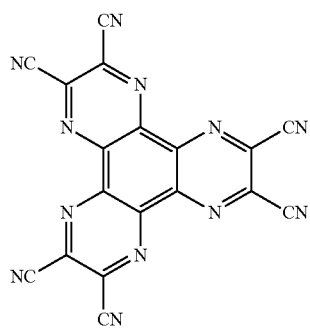

(A)

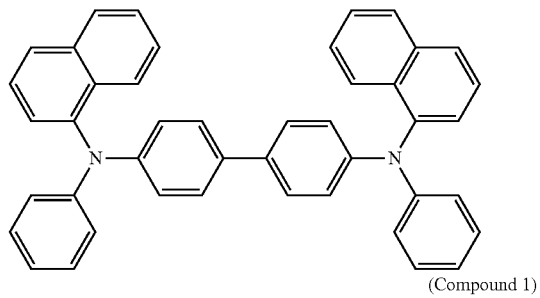

NPD

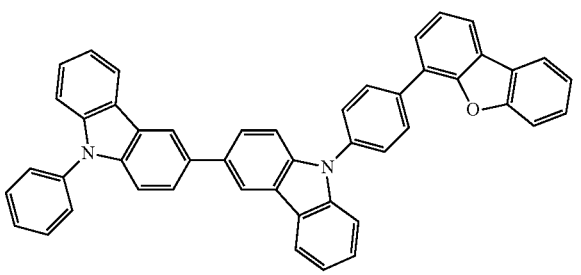

(Compound 1)

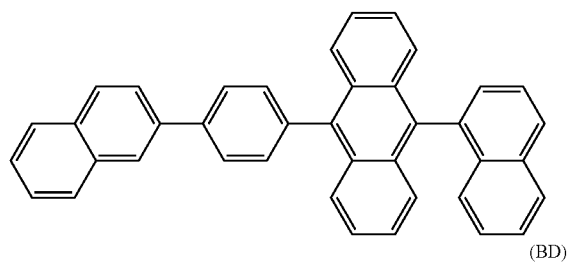

(BH)

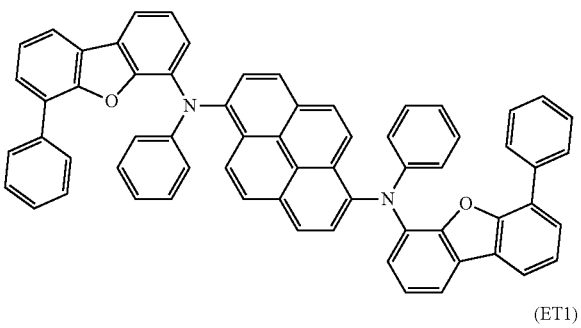

(BD)

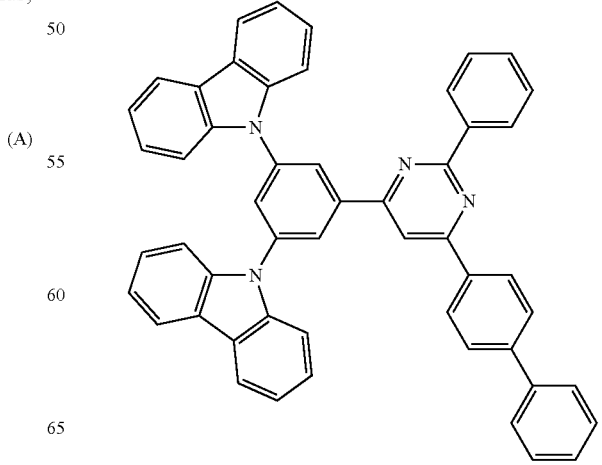

(ET1)

-continued (ET2)

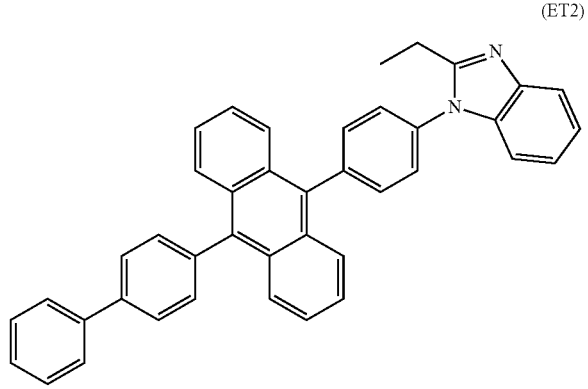

(Evaluation of Organic EL Device for its Light Emitting Performance)

The organic EL device produced as described above was caused to emit light through DC current driving, its luminance (L) and current density were measured, and its current efficiency (L/J) and driving voltage (V) at a current density of 10 mA/cm² were determined. Further, the lifetime of the device at a current density of 50 mA/cm² was determined. Here, the term "80% lifetime" refers to a time period required for the luminance to attenuate to 80% of the initial luminance at the time of constant current driving. In this case, the term refers to a time period required for an initial luminance of 20,000 cd/m² to attenuate to 16,000 cd/m². Table 2-1 shows the results.

Comparative Example 2-1

An organic EL device was produced in the same manner as in Example 2-1 except that the following comparative compound 2-1 was used instead of the compound 1 as the second hole transport ing material in Example 2-1. The resultant organic EL device was caused to emit light through DC current driving, its luminance (L) and current density were measured, and its current efficiency (L/J) and driving voltage (V) at a current density of 10 mA/cm² were determined. Further, the lifetime of the device at a current density of 50 mA/cm² was determined. Table 2-1 shows the results.

[Chem. 59]

(Comparative compound 2-1)

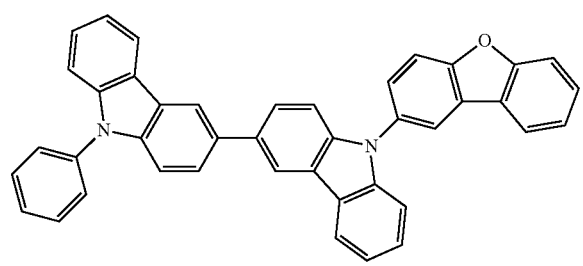

TABLE 2-1

| | Hole transporting material | Results of measurement | | |
| --- | --- | --- | --- | --- |
| | | Current efficiency (cd/A) at 10 mA/cm² | Driving voltage (V) at 10 mA/cm² | 80% lifetime (hour(s)) |
| Example 2-1 | Compound 1 | 8.2 | 4.0 | 225 |
| Comparative Example 2-1 | Comparative compound 2-1 | 7.4 | 4.0 | 20 |

INDUSTRIAL APPLICABILITY

The present invention can be utilized as an organic EL device having a long lifetime and high current efficiency, and capable of low-voltage driving needed for a reduction in power consumption, and a material for an organic EL device for realizing the device.

REFERENCE SIGNS LIST

1 organic electroluminescence device
2 substrate
3 anode
4 cathode
5 phosphorescent light emitting layer
6 hole injecting/transporting layer
7 electron injecting/transporting layer
10 organic thin-film layer

The invention claimed is:
1. A biscarbazole derivative, according to formula (1):

(1)

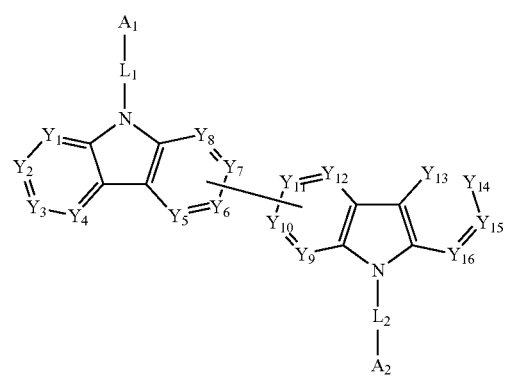

wherein:
one of $A_1$ and $A_2$ represents a substituted or unsubstituted dibenzofuranyl group or a substituted or unsubstituted dibenzothiophenyl group;
the other of $A_1$ and $A_2$ represents a substituted or unsubstituted aromatic hydrocarbon group having 6 to 30 ring carbon atoms;
$Y_1$ to $Y_{16}$ each independently represent C(R) or a bond to a carbazole skeleton;
R represents a hydrogen atom;
$L_1$ and $L_2$ each independently represent a single bond or a substituted or unsubstituted phenylene group; and
when $Y_6$ and $Y_{11}$ are bonded to each other, the following conditions (i) and (ii) are satisfied:

(i) when $A_1$ represents a dibenzofuranyl group or a dibenzothiophenyl group, $L_1$ represents a substituted or unsubstituted phenylene group; and
(ii) when $A_2$ represents a dibenzofuranyl group or a dibenzothiophenyl group, $L_2$ represents a substituted or unsubstituted phenylene group.

2. The biscarbazole derivative according to claim 1, wherein the derivative is a compound according to formula (2):

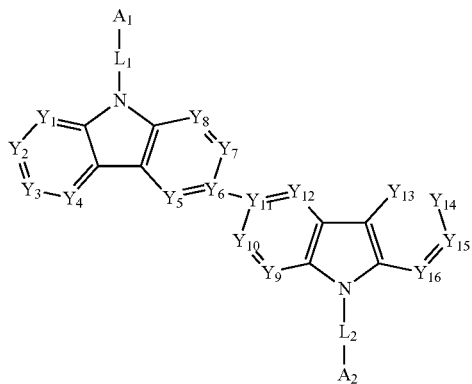

(2)

wherein $A_1$, $A_2$, $Y_1$ to $Y_{16}$, $L_1$, and $L_2$ each have the same meaning as in formula (1).

3. The biscarbazole derivative according to claim 2, wherein:
$A_1$ represents an unsubstituted dibenzofuranyl group or an unsubstituted dibenzothiophenyl group; and
$L_1$ represents a substituted or unsubstituted m-phenylene group or a substituted or unsubstituted p-phenylene group.

4. The biscarbazole derivative according to claim 2, wherein:
$A_1$ represents an unsubstituted dibenzofuranyl group or an unsubstituted dibenzothiophenyl group;
$L_1$ represents a substituted or unsubstituted m-phenylene group or a substituted or unsubstituted p-phenylene group; and
-$L_2$-$A_2$ represents a phenyl group, a biphenyl group, a terphenyl group, or a naphtyl group.

5. The biscarbazole derivative according to claim 1, wherein the derivative is a compound according to formula (3) or (4):

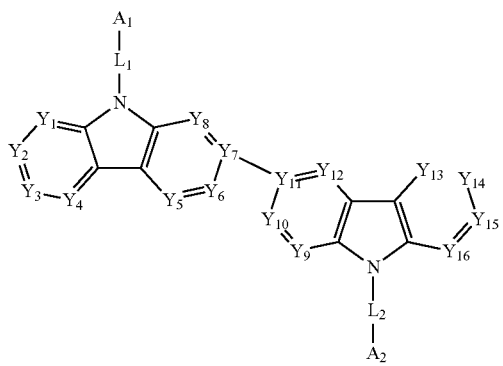

(3)

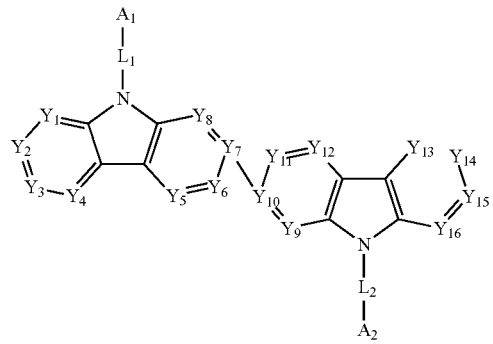

(4)

wherein $A_1$, $A_2$, $Y_1$ to $Y_{16}$, $L_1$, and $L_2$ each have the same meaning as in formula (1).

6. The biscarbazole derivative according to claim 1, wherein $A_1$ represents an unsubstituted dibenzofuranyl group or an unsubstituted dibenzothiophenyl group.

7. The biscarbazole derivative according to claim 1, wherein $A_1$ represents a 4-dibenzofuranyl group, a 2-dibenzofuranyl group, a 4-dibenzothiophenyl group, or a 2-dibenzothi ophenyl group.

8. The biscarbazole derivative according to claim 1, wherein:
$A_1$ represents an unsubstituted dibenzofuranyl group or an unsubstituted dibenzothiophenyl group; and
$L_1$ represents a substituted or unsubstituted m-phenylene group or a substituted or unsubstituted p-phenylene group.

9. A material for an organic electroluminescence device, comprising the biscarbazole derivative according to claim 1.

10. The biscarbazole derivative according to claim 1, wherein the biscarbazole derivative is selected from the following compounds:

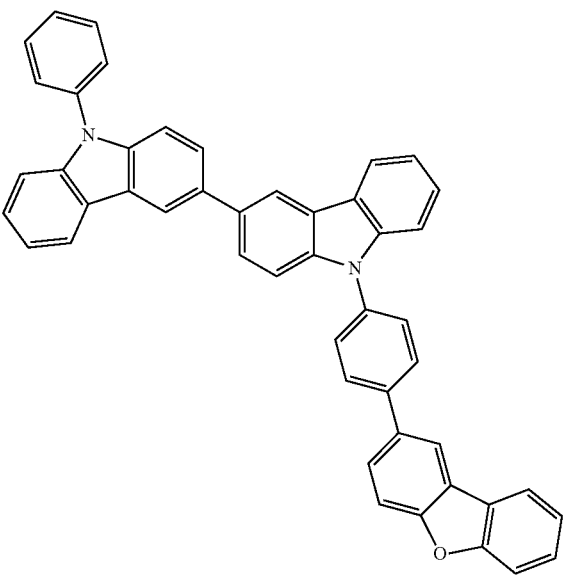

195
-continued
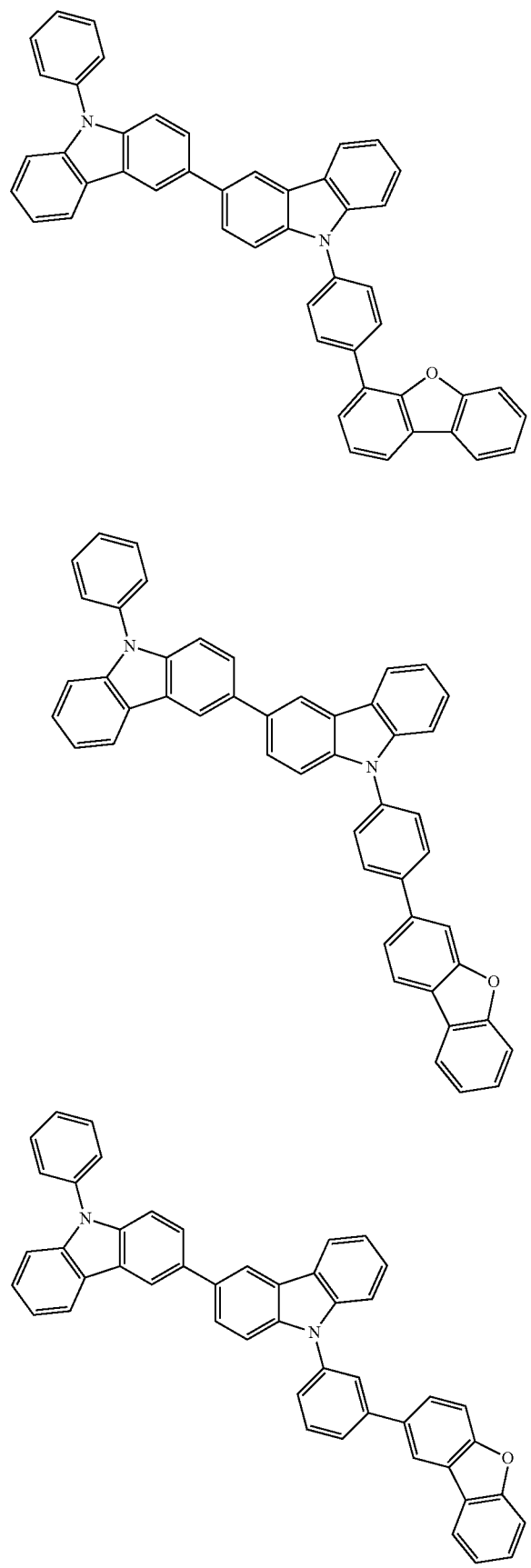
196
-continued
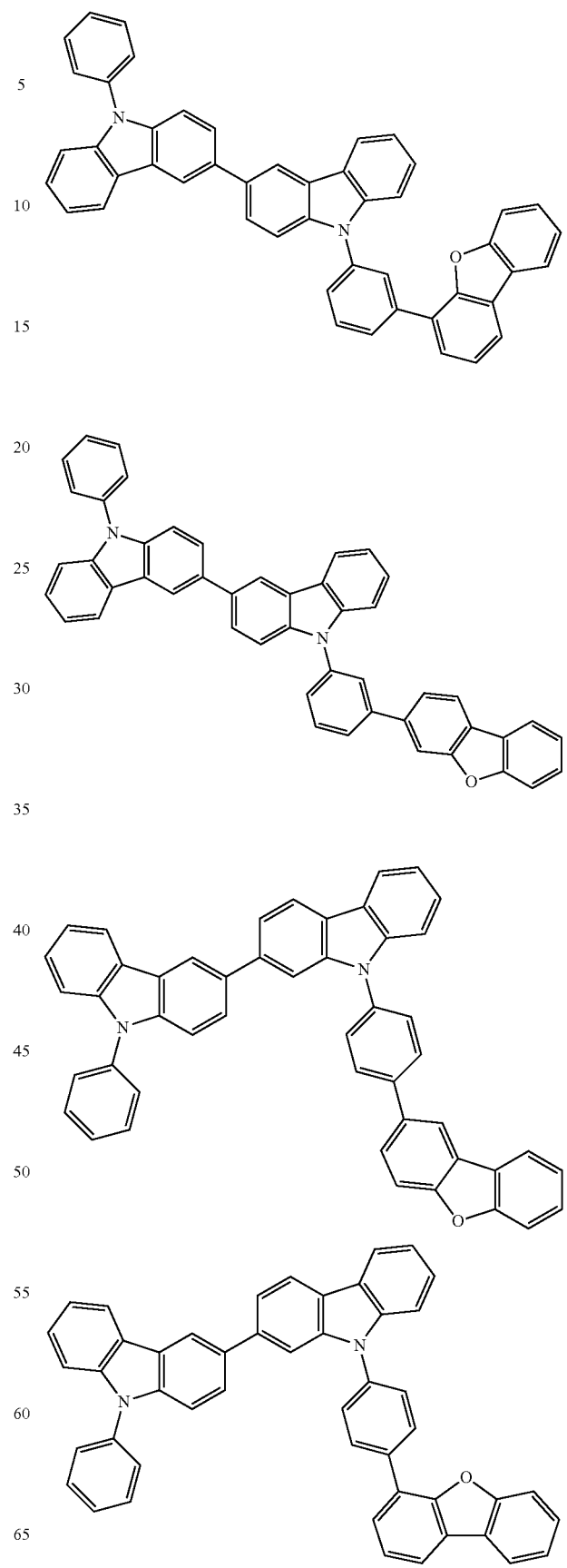

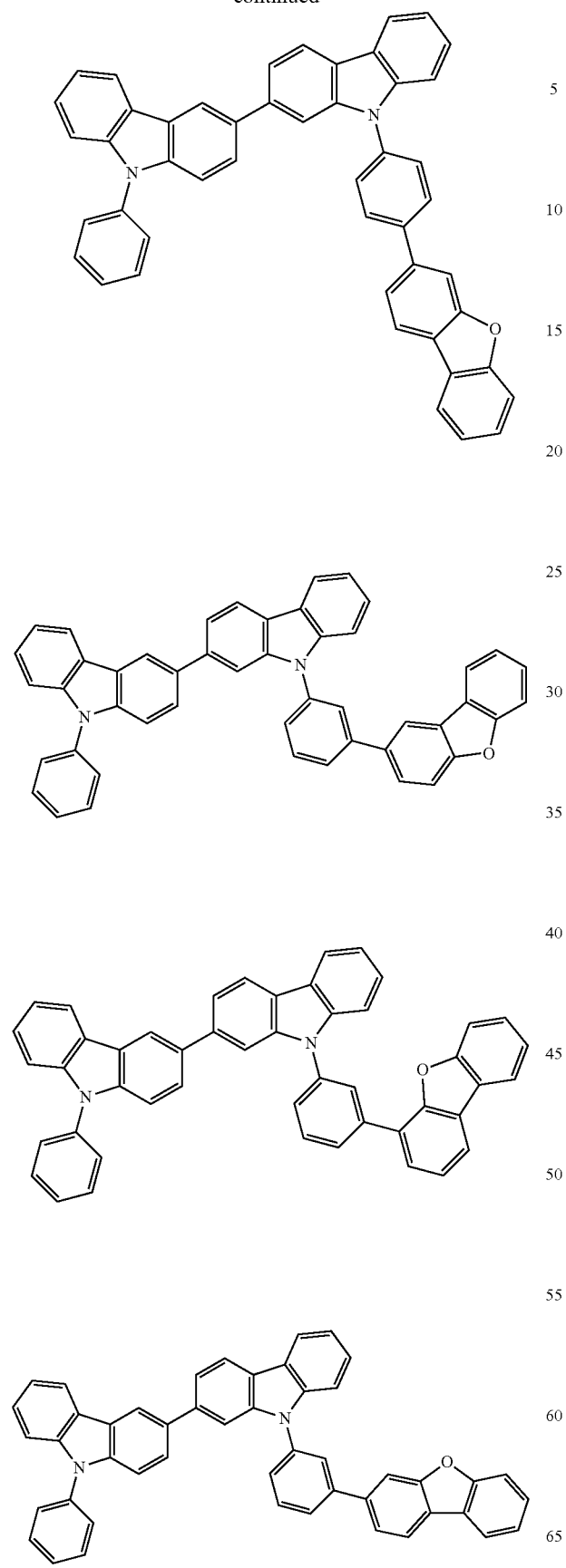
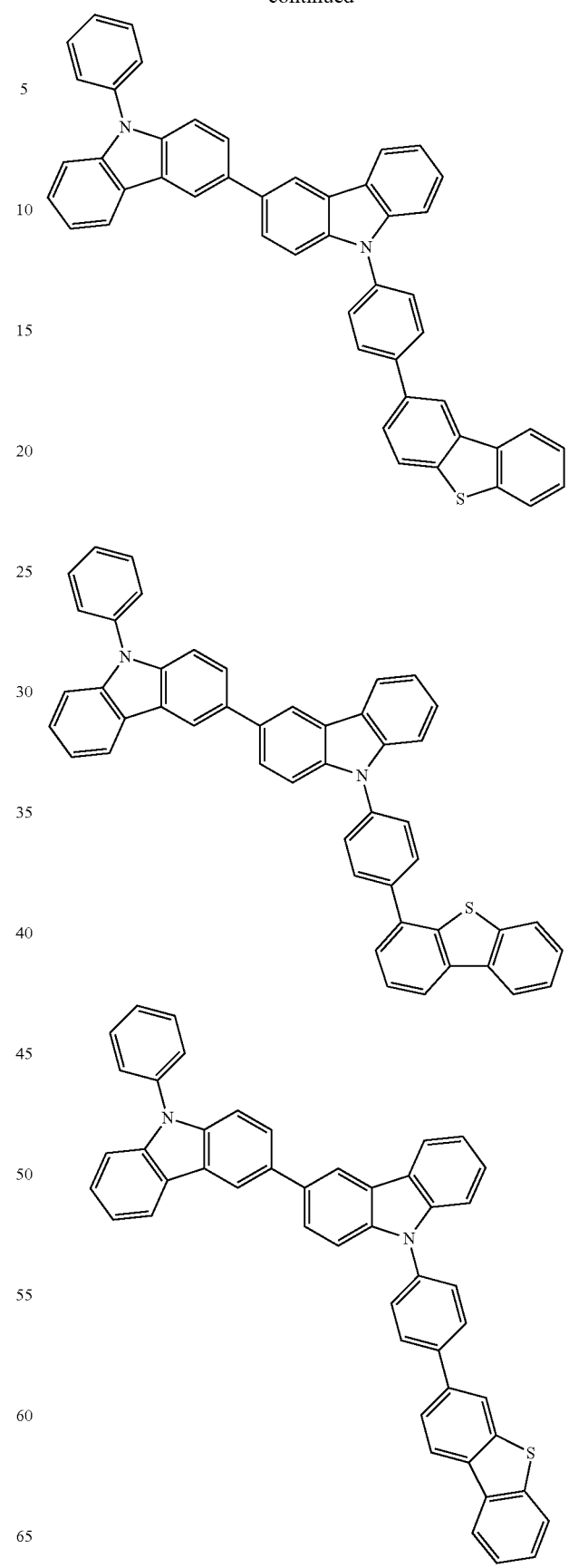

-continued

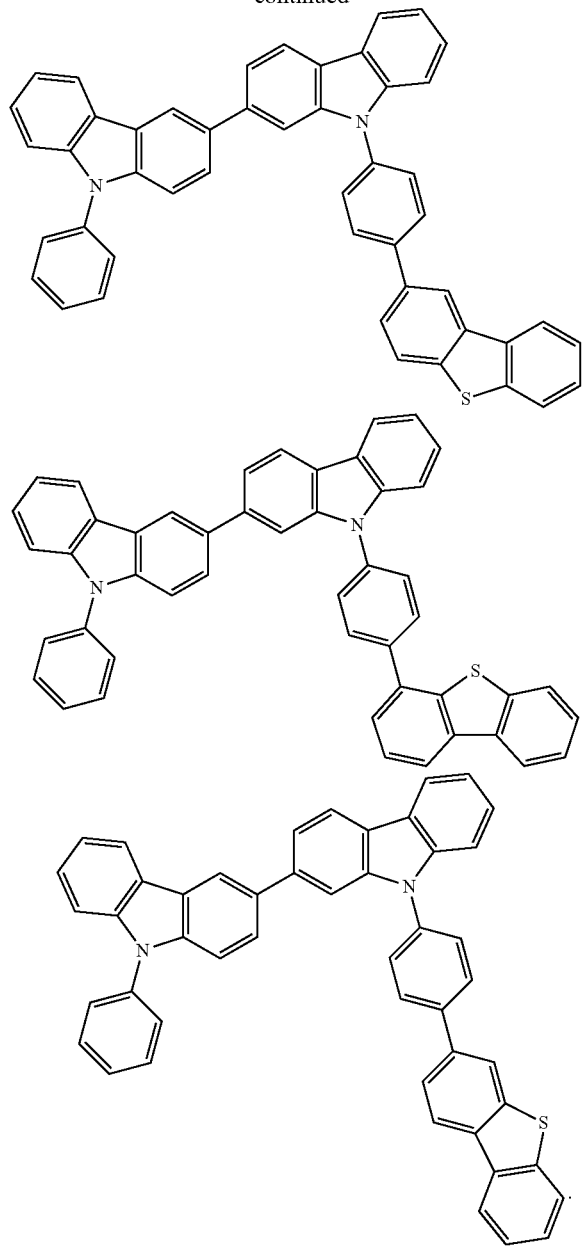

11. The biscarbazole derivative according to claim 1, wherein the biscarbazole derivative is the following compound:

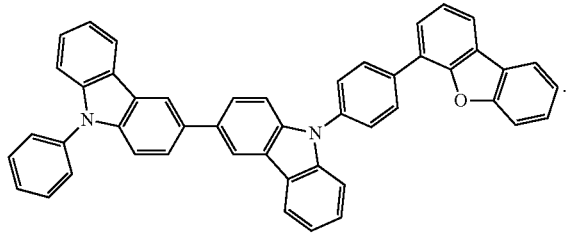 [SMILES: c1ccc(-n2c3ccccc3c3cc(-c4ccc5c(c4)c4ccccc4n5-c4ccc(-c5cccc6c5oc5ccccc56)cc4)ccc32)cc1]

12. An organic electroluminescence device, comprising a plurality of organic thin-film layers including a light emitting layer between a cathode and an anode, wherein at least one of the plurality of organic thin-film layers comprises a biscarbazole derivative according to formula (1):

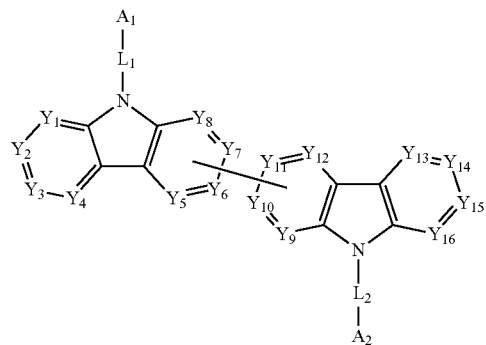
(1)

wherein:
one of $A_1$ and $A_2$ represents a substituted or unsubstituted dibenzofuranyl group or a substituted or unsubstituted dibenzothiophenyl group;
the other of $A_1$ and $A_2$ represents a substituted or unsubstituted aromatic hydrocarbon group having 6 to 30 ring carbon atoms;
$Y_1$ to $Y_{16}$ each independently represent C(R) or a bond to a carbazole skeleton;
R represents a hydrogen atom;
$L_1$ and $L_2$ each independently represent a single bond or a substituted or unsubstituted phenylene group; and
when $Y_6$ and $Y_{11}$ are bonded to each other, the following conditions (i) and (ii) are satisfied:
(i) when $A_1$ represents a dibenzofuranyl group or a dibenzothiophenyl group, $L_1$ represents a substituted or unsubstituted phenylene group; and
(ii) when $A_2$ represents a dibenzofuranyl group or a dibenzothiophenyl group, $L_2$ represents a substituted or unsubstituted phenylene group.

13. The organic electroluminescence device according to claim 12, wherein the derivative is a compound according to formula (2):

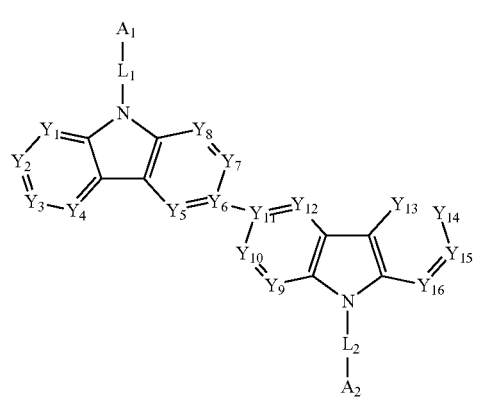
(2)

wherein $A_1$, $A_2$, $Y_1$ to $Y_{16}$, $L_1$, and $L_2$ each have the same meaning as in formula (1).

14. The organic electroluminescence device according to claim 13, wherein:

$A_1$ represents an unsubstituted dibenzofuranyl group or an unsubstituted dibenzothiophenyl group; and $L_1$ represents a substituted or unsubstituted m-phenylene group or a substituted or unsubstituted p-phenylene group.

15. The organic electroluminescence device according to claim 13, wherein:

$A_1$ represents an unsubstituted dibenzofuranyl group or an unsubstituted dibenzothiophenyl group; and $L_1$ represents a substituted or unsubstituted m-phenylene group or a substituted or unsubstituted p-phenylene group; and $-L_2-A_2$ represents a phenyl group, a biphenyl group, a terphenyl group, or a naphtyl group.

16. The organic electroluminescence device according to claim 15, wherein a hole transporting layer is provided between the anode and the light emitting layer, and the hole transporting layer comprises the biscarbazole derivative.

17. The organic electroluminescence device according to claim 12, wherein the derivative is a compound according to formula (3) or (4):

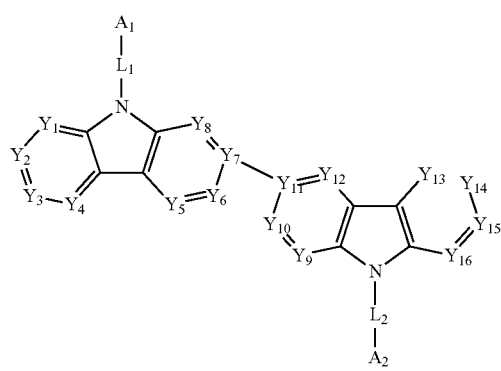

(3)

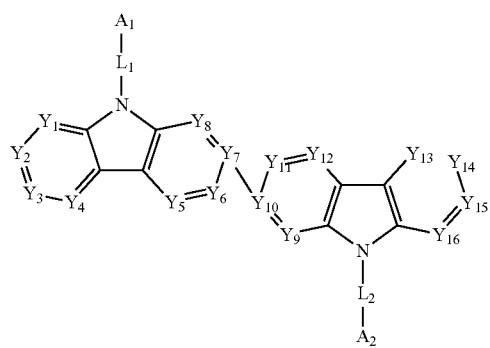

(4)

wherein $A_1$, $A_2$, $Y_1$ to $Y_{16}$, $L_1$, and $L_2$ each have the same meaning as in formula (1).

18. The organic electroluminescence device according to claim 12, wherein $A_1$ represents an unsubstituted dibenzofuranyl group or an unsubstituted dibenzothiophenyl group.

19. The organic electroluminescence device according to claim 12, wherein $A_1$ represents a 4-dibenzofuranyl group, a 2-dibenzofuranyl group, a 4-dibenzothiophenyl group, or a 2-dibenzothiophenyl group.

20. The organic electroluminescence device according to claim 12, wherein:

$A_1$ represents an unsubstituted dibenzofuranyl group or an unsubstituted dibenzothiophenyl group; and $L_1$ represents a substituted or unsubstituted m-phenylene group or a substituted or unsubstituted p-phenylene group.

21. The organic electroluminescence device according to claim 12, wherein the light emitting layer comprises the biscarbazole derivative.

22. The organic electroluminescence device according to claim 21, wherein the light emitting layer comprises a phosphorescent material.

23. The organic electroluminescence device according to claim 22, wherein the phosphorescent material comprises an ortho-metalated complex of a metal atom selected from iridium (Ir), Osmium (Os), and platinum (Pt).

24. The organic electroluminescence device according to claim 12, wherein an electron injecting layer is provided between the cathode and the light emitting layer, and the electron injecting layer comprises a nitrogen-containing ring derivative.

25. The organic electroluminescence device according to claim 12, wherein a hole transporting layer is provided between the anode and the light emitting layer, and the hole transporting layer comprises the biscarbazole derivative.

26. The organic electroluminescence device according to claim 25, wherein a hole injecting layer is provided between the anode and a hole transporting layer.

27. The organic electroluminescence device according to claim 12, wherein the device is capable of fluorescent emission in use.

28. A lighting apparatus, comprising the organic electroluminescence device according to claim 12.

29. A display apparatus, comprising the organic electroluminescence device according to claim 12.

30. The organic electroluminescence device according to claim 12, wherein the biscarbazole derivative is selected from the following compounds:

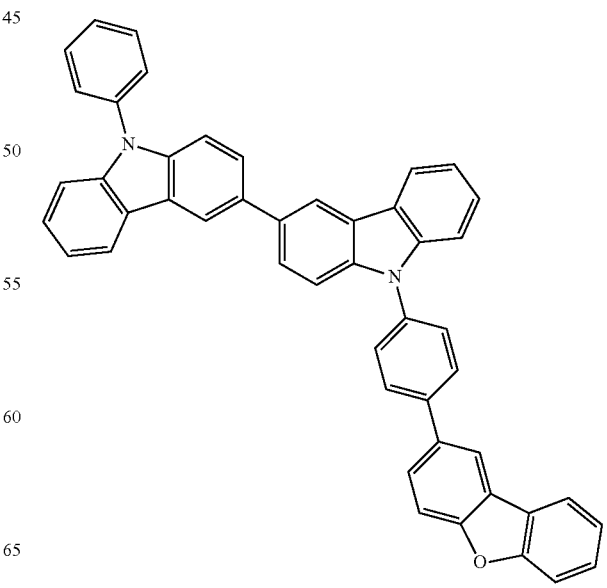

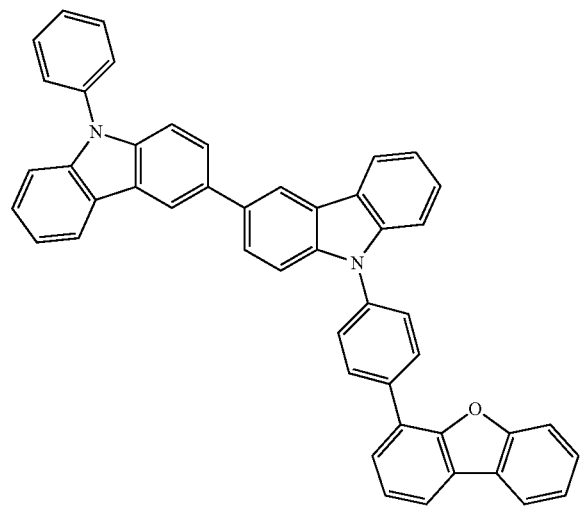
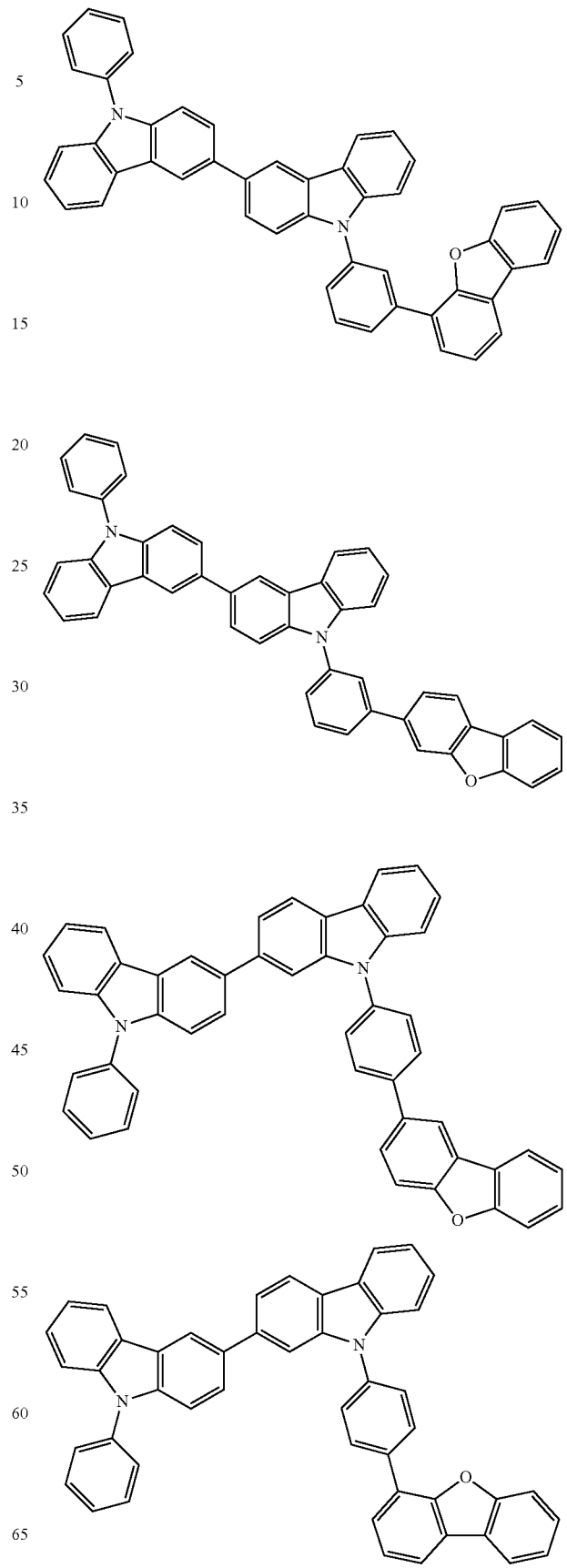

205
-continued
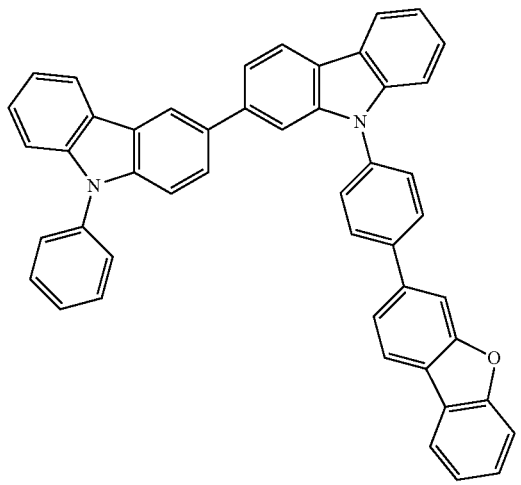
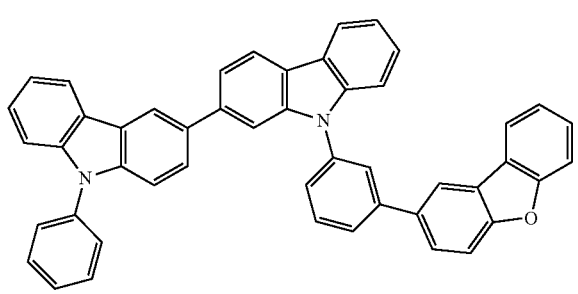
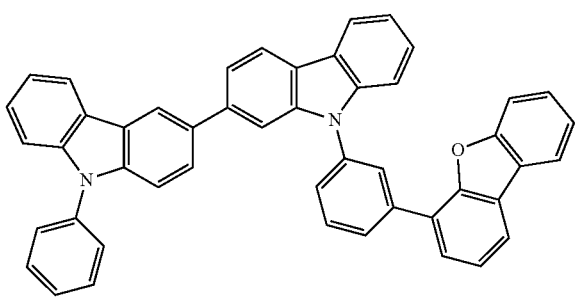
206
-continued
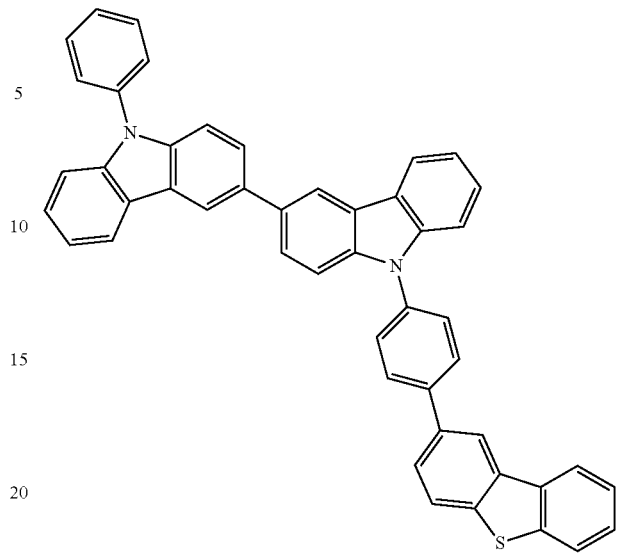
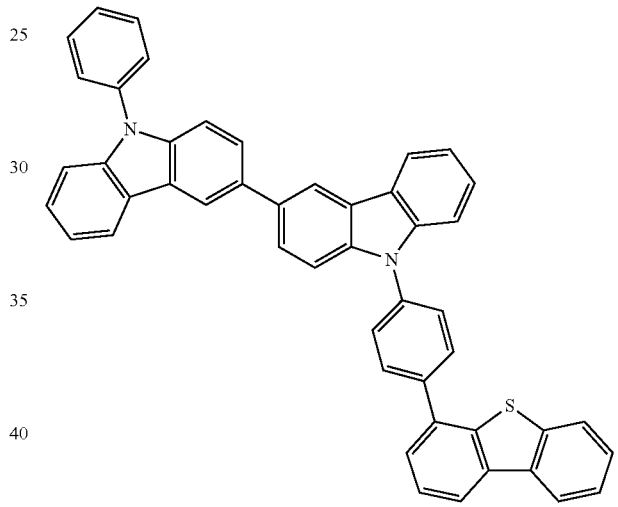
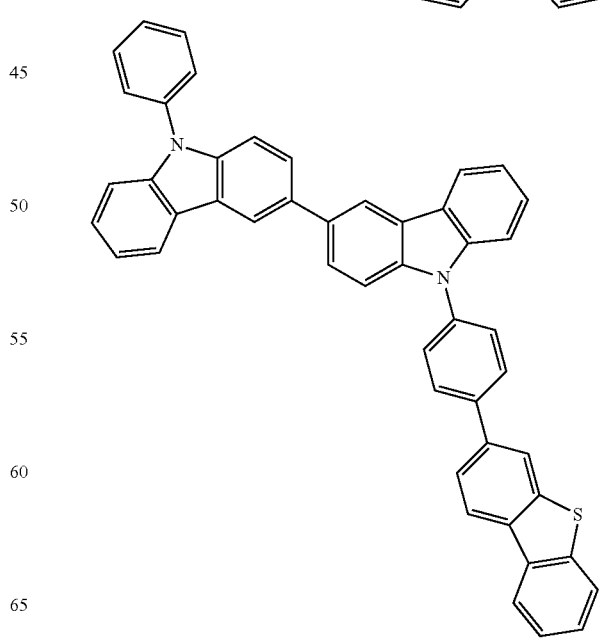

207
-continued
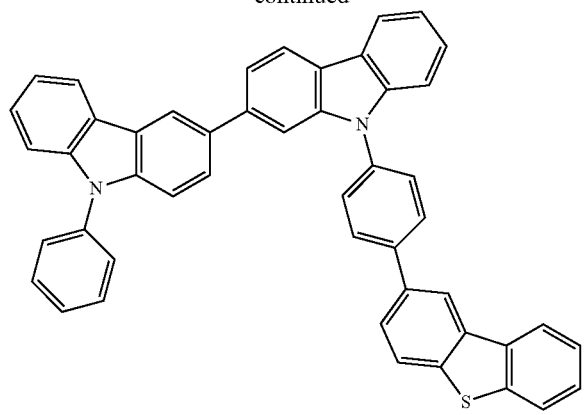
208
-continued
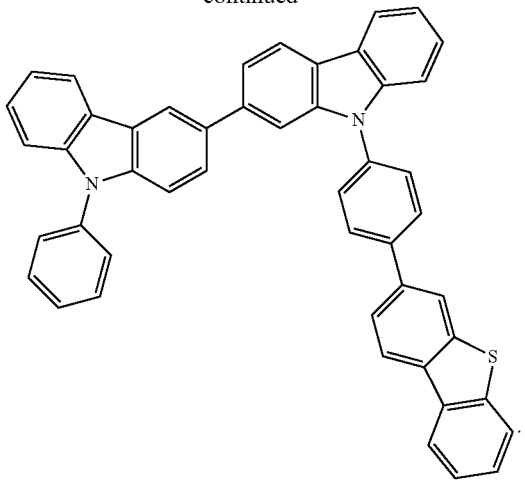
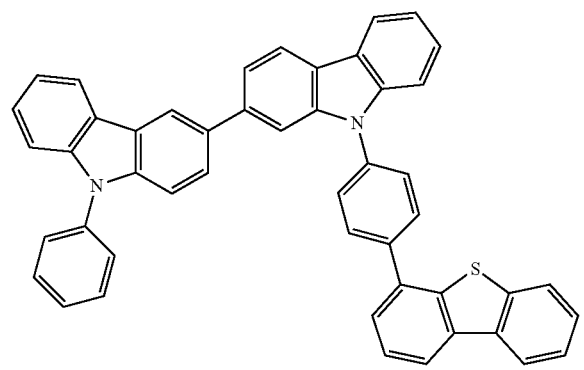
31. The organic electroluminescence device according to claim 12, wherein the biscarbazole derivative is the following compound:
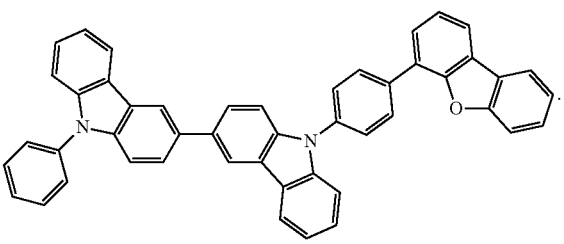 [SMILES: c1ccc(-n2c3ccccc3c3cc(-c4ccc5c(c4)c4ccccc4n5-c4ccc(-c5cccc6c5oc5ccccc56)cc4)ccc32)cc1]
* * * * *